United States Patent
Mond et al.

(10) Patent No.: US 10,821,173 B2
(45) Date of Patent: *Nov. 3, 2020

(54) MULTIMERIC FUSION PROTEIN VACCINE AND IMMUNOTHERAPEUTIC

(71) Applicant: The Henry M. Jackson Foundation for the Advancement of Military Medicine, Inc., Bethesda, MD (US)

(72) Inventors: James J. Mond, Silver Spring, MD (US); Clifford M. Snapper, Potomac, MD (US); Xinle Cui, Gaithersburg, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,025

(22) Filed: May 4, 2018

(65) Prior Publication Data

US 2018/0303931 A1  Oct. 25, 2018

Related U.S. Application Data

(63) Continuation of application No. 14/416,780, filed as application No. PCT/US2013/052270 on Jul. 26, 2013, now Pat. No. 9,962,436.

(60) Provisional application No. 61/675,948, filed on Jul. 26, 2012.

(51) Int. Cl.
| | | |
|---|---|---|
| A61K 39/245 | (2006.01) | |
| C07K 14/005 | (2006.01) | |
| A61K 39/12 | (2006.01) | |
| A61K 39/21 | (2006.01) | |
| A61K 39/00 | (2006.01) | |

(52) U.S. Cl.
CPC .......... *A61K 39/245* (2013.01); *A61K 39/12* (2013.01); *A61K 39/21* (2013.01); *C07K 14/005* (2013.01); *A61K 2039/53* (2013.01); *A61K 2039/55505* (2013.01); *A61K 2039/55561* (2013.01); *A61K 2039/57* (2013.01); *A61K 2039/70* (2013.01); *C07K 2319/00* (2013.01); *C12N 2710/16234* (2013.01); *C12N 2740/15022* (2013.01); *C12N 2740/15034* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,200,577 B1 * | 3/2001 | McLauchlan | C07K 14/005 424/204.1 |
| 6,432,679 B1 | 8/2002 | Mond et al. | |
| 6,749,857 B1 | 6/2004 | Peters et al. | |
| 7,144,991 B2 * | 12/2006 | Goshorn | B82Y 5/00 530/391.7 |
| 7,449,188 B2 | 11/2008 | De Filette et al. | |
| 7,541,180 B2 * | 6/2009 | Valiante | C07K 14/005 435/320.1 |
| 7,994,293 B2 | 8/2011 | Valinate | |
| 2005/0003403 A1 | 1/2005 | Rossi et al. | |
| 2008/0260769 A1 | 10/2008 | Capecci et al. | |
| 2009/0186025 A1 | 7/2009 | Colaco | |
| 2010/0098718 A1 | 4/2010 | Valiante | |
| 2011/0293704 A1 * | 12/2011 | Holst | A61K 39/0011 424/450 |

FOREIGN PATENT DOCUMENTS

| | | |
|---|---|---|
| EP | 1982993 | 10/2008 |
| JP | 2008-263983 | 11/2008 |
| JP | 2012-509071 | 4/2012 |
| WO | 2005/014838 | 2/2005 |
| WO | 2010/002818 | 1/2010 |
| WO | 2010/057501 | 5/2010 |
| WO | 01/02440 | 1/2011 |

OTHER PUBLICATIONS

Little et al. (Microbiology 1996, vol. 142, p. 707-715).*
Arai et al. (Protein Engineering, 2001, vol. 14, p. 529-532).*
Trinh et al. (Molecular Immunology, 2004, p. 717-722).*
International Search Report dated Dec. 3, 2013 from International Application No. PCT/US2013/052270, pp. 1-12.
De Filette, Marina et al. An Influenza a Vaccine Based on Tetrameric Ectodomain of Matrix Protein 2. The Journal of Biological Chemistry, Apr. 25, 2008, vol. 283, No. 17, pp. 11382-11387.
Fiers, Walter et al. Soluble recombinant influenza vaccines. The Royal Society, Phils. Trans. R. Soc. Land, B (2001) 356, 1961-1963.
Weissenhorn, Winfried et al. Assembly of a rod-shaped chimera of a trimeric GCN4 zipper and the HIV-1 gp41 ectodomain expressed in *Excherichia coli*. Proc. Natl. Acad. Sci., Jun. 1997, vol. 94, pp. 6065-6069.

(Continued)

*Primary Examiner* — Agnieszka Boesen
(74) *Attorney, Agent, or Firm* — MH2 Technology Law Group, LLP

(57) ABSTRACT

The present disclosure provides fusion proteins that incorporate unique mechanisms for multimerizing antigens to enhance their immunogenicity. The fusion proteins comprise at least two antigens, or other vaccine related proteins, separated by a linker sequence and an oligomerization domain. When expressed, the fusion protein forms a muKimeric protein complex, This approach can be used to muHimeri?.e a single antigen/protein or to create multimers comprising two or more different antigens/proteins. Also provided are nucleic acids encoding the fusion proteins. Yet another aspect is directed to methods of inducing or suppressing an immune response in a subject by administering to the subject a vaccine composition comprising a fusion protein or nucleic acid encoding the fusion protein, optionally without using an adjuvant.

15 Claims, 11 Drawing Sheets

Specification includes a Sequence Listing.

(56) References Cited

OTHER PUBLICATIONS

Development of a prophylactic vaccine against Epstein-Barr virus (EBV). Uniformed Services University of the Health Sciences, Institute for Vaccine Research, Printed Mar. 27, 2012, pp. 1-5. http://www.usuhs.mil/pat/ivr/ivrproject3.html.
Supplementary European Search Report dated Mar. 8, 2016 from European Patent Application No. 13823370.5, pp. 1-8.
Cui et al., "A novel tetrameric gp3501-470 as a potential Epstein-Barr virus vaccine", Vaccine, May 9, 2013, vol. 31, No. 30, pp. 3039-3045.
Japanese Office Action dated May 17, 2016 from Japanese Patent Application No. 2015-524466, 6 Pages (including English translation).
Yang et al., "Highly Stable Trimers Formed by Human Immunodeficiency Virus Type 1 Envelope Glycoproteins Fused with the Trimeric Motif of T4 Bacteriophage Fibritin", Journal of Virology, May 2002, vol. 76, No. 9, pp. 4634-4642.
Bird et al., "Single Chain Antigen-Binding Proteins", Science, Oct. 21, 1988, vol. 242, No. 4877, pp. 423-426.
Dempsey et al., "C3d of Complement as a Molecular Adjuvant: Bridging Innate and Acquired Immunity", Science Jan. 19, 1996, vol. 271, pp. 348-350.
Kortt et al., "Single-chain Fv fragments of anti-neuraminidase antibody NC10 containing five- and ten-residue linkers form dimers and with zero-residue linker a trimer", Protein Engineering, 1997, vol. 10, No. 4, pp. 423-433.
Robinson et al., "Optimizing the stability of single-chain proteins by linker length and composition mutagenesis", Proc. Natl. Acad. Sci. USA, May 1998, vol. 95, pp. 5929-5934.
Chichili et al, "Linkers in the structural biology of protein-protein interactions", Protein Science, 2013, vol. 22, pp. 153-167.
Chen et al., "Fusion Protein Linkers: Property, Design and Functionality", Adv Drug Deliv Rev., Oct. 15, 2013, vol. 65, No. 10, pp. 1357-1369.
Klein et al., "Design and characterization of structured protein linkers with differing flexibilities", Protein Engineering, Design & Selection, 2014, vol. 27, No. 10, pp. 325-330, 2014.
Van Rosmalen et al., "Tuning the Flexibility of Glycine-Serine Linkers to Allow Rational Design of Multidomain Proteins", Biochemistry, 2017, vol. 56, pp. 6565-6574.

* cited by examiner

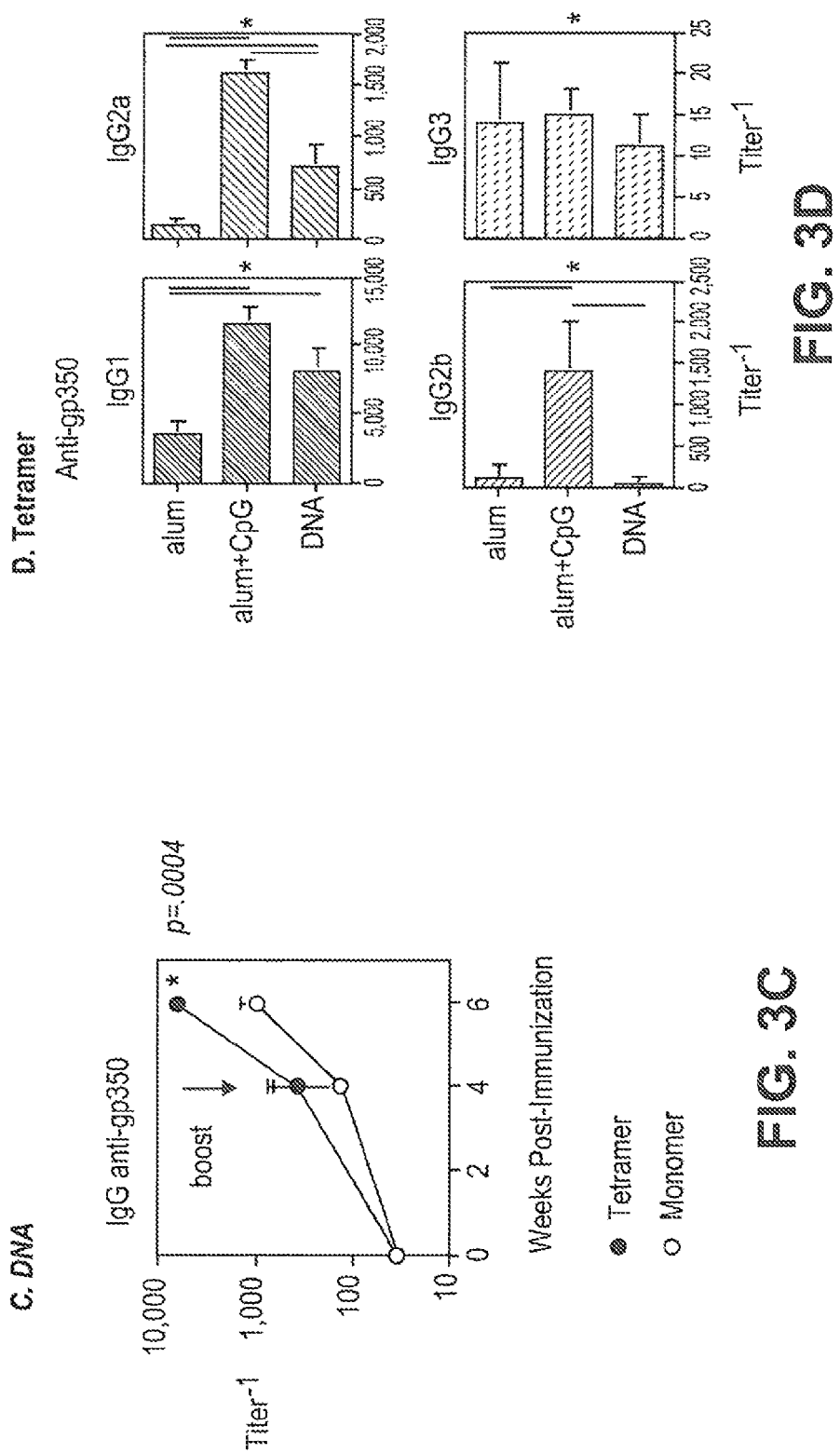

SEQUENCE LISTING

<160> NUMBER OF SEQ ID NOS: 19

<210> SEQ ID NO 1
<211> LENGTH: 907
<212> TYPE: PRT
<213> ORGANISM: Epstein-Barr virus

<400> SEQUENCE: 1

```
Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240
```

```
Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
            500                 505                 510

Val Thr Thr Pro Thr Pro Asn Ala Thr Ser Pro Thr Pro Ala Val Thr
        515                 520                 525

Thr Pro Thr Pro Asn Ala Thr Ser Pro Thr Pro Ala Val Thr Thr Pro
    530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
                565                 570                 575

Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
        595                 600                 605

Pro Asn Ala Thr Gly Pro Thr Val Gly Glu Thr Ser Pro Gln Ala Asn
    610                 615                 620

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
                645                 650                 655
```

```
Ile Thr Ser Ser Ser Thr Ser Ser Met Ser Leu Arg Pro Ser Ser Asn
            660                 665                 670

Pro Glu Thr Leu Ser Pro Ser Ser Asp Asn Ser Thr Ser His Met
    675                 680                 685

Pro Leu Leu Thr Ser Ala His Pro Thr Gly Gly Glu Asn Ile Thr Gln
690                 695                 700

Val Thr Pro Ala Ser Ile Ser Thr His His Val Ser Thr Ser Ser Pro
705                 710                 715                 720

Glu Pro Arg Pro Gly Thr Thr Ser Gln Ala Ser Gly Pro Gly Asn Ser
                725                 730                 735

Ser Thr Ser Thr Lys Pro Gly Glu Val Asn Val Thr Lys Gly Thr Pro
            740                 745                 750

Pro Gln Asn Ala Thr Ser Pro Gln Ala Pro Ser Gly Gln Lys Thr Ala
        755                 760                 765

Val Pro Thr Val Thr Ser Thr Gly Gly Lys Ala Asn Ser Thr Thr Gly
770                 775                 780

Gly Lys His Thr Thr Gly His Gly Ala Arg Thr Ser Thr Glu Pro Thr
785                 790                 795                 800

Thr Asp Tyr Gly Gly Asp Ser Thr Thr Pro Arg Pro Arg Tyr Asn Ala
                805                 810                 815

Thr Thr Tyr Leu Pro Pro Ser Thr Ser Ser Lys Leu Arg Pro Arg Trp
            820                 825                 830

Thr Phe Thr Ser Pro Pro Val Thr Thr Ala Gln Ala Thr Val Pro Val
        835                 840                 845

Pro Pro Thr Ser Gln Pro Arg Phe Ser Asn Leu Ser Met Leu Val Leu
850                 855                 860

Gln Trp Ala Ser Leu Ala Val Leu Thr Leu Leu Leu Leu Leu Val Met
865                 870                 875                 880

Ala Asp Cys Ala Phe Arg Arg Asn Leu Ser Thr Ser His Thr Tyr Thr
                885                 890                 895

Thr Pro Pro Tyr Asp Asp Ala Glu Thr Tyr Val
            900                 905

<210> SEQ ID NO 2
<211> LENGTH: 658
<212> TYPE: PRT
<213> ORGANISM: Epstein-Barr virus

<400> SEQUENCE: 2

Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125
```

-continued

```
Asp Val Tyr Phe Gln Asp Val Phe Gly Thr Met Trp Cys His His Ala
    130                 135                 140
Glu Met Gln Asn Pro Val Tyr Leu Ile Pro Glu Thr Val Pro Tyr Ile
145                 150                 155                 160
Lys Trp Asp Asn Cys Asn Ser Thr Asn Ile Thr Ala Val Val Arg Ala
                165                 170                 175
Gln Gly Leu Asp Val Thr Leu Pro Leu Ser Leu Pro Thr Ser Ala Gln
            180                 185                 190
Asp Ser Asn Phe Ser Val Lys Thr Glu Met Leu Gly Asn Glu Ile Asp
        195                 200                 205
Ile Glu Cys Ile Met Glu Asp Gly Glu Ile Ser Gln Val Leu Pro Gly
    210                 215                 220
Asp Asn Lys Phe Asn Ile Thr Cys Ser Gly Tyr Glu Ser His Val Pro
225                 230                 235                 240
Ser Gly Gly Ile Leu Thr Ser Thr Ser Pro Val Ala Thr Pro Ile Pro
                245                 250                 255
Gly Thr Gly Tyr Ala Tyr Ser Leu Arg Leu Thr Pro Arg Pro Val Ser
            260                 265                 270
Arg Phe Leu Gly Asn Asn Ser Ile Leu Tyr Val Phe Tyr Ser Gly Asn
        275                 280                 285
Gly Pro Lys Ala Ser Gly Gly Asp Tyr Cys Ile Gln Ser Asn Ile Val
    290                 295                 300
Phe Ser Asp Glu Ile Pro Ala Ser Gln Asp Met Pro Thr Asn Thr Thr
305                 310                 315                 320
Asp Ile Thr Tyr Val Gly Asp Asn Ala Thr Tyr Ser Val Pro Met Val
                325                 330                 335
Thr Ser Glu Asp Ala Asn Ser Pro Asn Val Thr Val Thr Ala Phe Trp
            340                 345                 350
Ala Trp Pro Asn Asn Thr Glu Thr Asp Phe Lys Cys Lys Trp Thr Leu
        355                 360                 365
Thr Ser Gly Thr Pro Ser Gly Cys Glu Asn Ile Ser Gly Ala Phe Ala
    370                 375                 380
Ser Asn Arg Thr Phe Asp Ile Thr Val Ser Gly Leu Gly Thr Ala Pro
385                 390                 395                 400
Lys Thr Leu Ile Ile Thr Arg Thr Ala Thr Asn Ala Thr Thr Thr Thr
                405                 410                 415
His Lys Val Ile Phe Ser Lys Ala Pro Glu Ser Thr Thr Thr Ser Pro
            420                 425                 430
Thr Leu Asn Thr Thr Gly Phe Ala Asp Pro Asn Thr Thr Thr Gly Leu
        435                 440                 445
Pro Ser Ser Thr His Val Pro Thr Asn Leu Thr Ala Pro Ala Ser Thr
    450                 455                 460
Gly Pro Thr Val Ser Thr Ala Asp Val Thr Ser Pro Thr Pro Ala Gly
465                 470                 475                 480
Thr Thr Ser Gly Ala Ser Pro Val Thr Pro Ser Pro Ser Pro Trp Asp
                485                 490                 495
Asn Gly Thr Glu Ser Thr Pro Pro Gln Asn Ala Thr Ser Pro Gln Ala
            500                 505                 510
Pro Ser Gly Gln Lys Thr Ala Val Pro Thr Val Thr Ser Thr Gly Gly
        515                 520                 525
Lys Ala Asn Ser Thr Thr Gly Gly Lys His Thr Thr Gly His Gly Ala
    530                 535                 540
```

```
Arg Thr Ser Thr Glu Pro Thr Thr Asp Tyr Gly Gly Asp Ser Thr Thr
545                 550                 555                 560

Pro Arg Pro Arg Tyr Asn Ala Thr Thr Tyr Leu Pro Pro Ser Thr Ser
                565                 570                 575

Ser Lys Leu Arg Pro Arg Trp Thr Phe Thr Ser Pro Val Thr Thr
            580                 585                 590

Ala Gln Ala Thr Val Pro Val Pro Pro Thr Ser Gln Pro Arg Phe Ser
        595                 600                 605

Asn Leu Ser Met Leu Val Leu Gln Trp Ala Ser Leu Ala Val Leu Thr
    610                 615                 620

Leu Leu Leu Leu Leu Val Met Ala Asp Cys Ala Phe Arg Arg Asn Leu
625                 630                 635                 640

Ser Thr Ser His Thr Tyr Thr Thr Pro Pro Tyr Asp Asp Ala Glu Thr
                645                 650                 655

Tyr Val

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caccatggag gcagccttgc ttgt                                              24

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agatctttag gatacagtgg ggcctgtgc                                         29

<210> SEQ ID NO 6
<211> LENGTH: 114
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccaccatgg agacagacac actcctgcta tgggtactgc tgctctgggt tccaggttcc       60
actggtgacg cggcccagcc ggccaggcgc gcgcgccgta cgaagctcgc cctt            114
```

```
<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaatggtga tggtgatgat gggtggatac agtggggcct gt                          42

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccatcgatgg ctagctagcg gtggatacag tggggcctgt                             40

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggaggcag ccttgcttgt                                                   20

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcaaccaaaa gctaacggta aaattattaa attttagttc agttatacct ataaatttag       60
aatttgcttt tatatactgg gtggatacag tggggcctgt                            100

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttttgctca acagctcttc cactttatct tccagctgtt tcatgcgttc taaatgacta       60
gcagatactt taggaaccct caaccaaaag ctaacggtaa                            100

<210> SEQ ID NO 12
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

-continued

```
ctagctagcg gtggcggagg gagtggtggc ggagggagcg gtggcggagg gagtatggag      60
gcagccttgc ttgt                                                        74
```

<210> SEQ ID NO 13
<211> LENGTH: 108
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
ccatcgattc aatggtgatg gtgatgatgg ctagtgcgtt cgcccaccag ctttttcaga      60
cgcgccactt cgttttccag atgatagttt ttgctcaaca gctcttcc                  108
```

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5

<210> SEQ ID NO 15
<211> LENGTH: 172764
<212> TYPE: DNA
<213> ORGANISM: Human herpesvirus 4

<400> SEQUENCE: 15

```
agaatttgtc ttgctctatt caccgttact tttcttcttg cccgttctct ttcttagtat      60
gaatccagta tgcctgcctg taattgttgc gccctacctg ttttggctgg cggctattgc     120
cgcctcgtgt ttcacggcct cagttagtac cgttgtgacc gccaccggct tggccctctc     180
acttctactc ttggcagcag tggccagctc atatgccgct gcacaaagga aactgctgac     240
accggtgaca gttcttactg cggttgtcac ttgtgagtac acacgcacca tttacaatgc     300
atgatgttcg tgagattgat ctgtctctaa cagttcactt cctctgcttt tctcctcagt     360 cttttgcaatt tgcctaacat ggaggattga ggacccacct tttaattctc ttctgtttgc    420
attgctggcc gcagctggcg gactacaagg catttacggt tagtgtgcct ctgtgatgga     480
atgcaggttt gacttcatat gtatgccttg gcatgacgtc aactttactt ttatttcagt     540
tctggtgatg cttgtgctcc tgatactagc gtacagaagg agatggcgcc gtttgactgt     600
ttgtggcggc atcatgtttt tggcatgtgt acttgtcctt atcgtcgacg ctgttttgca     660
gctgagtccc ctccttggag ctgtaactgt ggtttccatg acgctgctgc tactggcttt     720
cgtcctctgg ctctcttcgc caggggggcct aggtactctt ggtgcagccc ttttaacgtt    780
ggcagcaggt aagccacacg tgtgacattg cttgccttt tgccacatgt tttctggaca     840
caggactaac catgccatct ctgattatag ctctggcact gctagcgtca ctgattttgg     900
gcacacttaa cttgactaca atgttccttc tcatgctcct atggacactt ggtaagtttt    960
cccttccttt aactcattac ttgttctttt gtaatcgcag ctctaacttg gcatctcttt    1020
tacagtggtt ctcctgattt gctcttcgtg ctcttcatgt ccactgagca agatccttct   1080
ggcacgactg ttcctatatg ctctcgcact cttgttgcta gcctccgcgc taatcgctgg   1140
```

```
tggcagtatt ttgcaaacaa acttcaagag tttaagcagc actgaattta tacccagtga      1200
gtatctattt gttactcctg tttagttgaa gaaaacaagc tattggattg taacacacat      1260
tttacgcttt gttccttaga tttgttctgc atgttattac tgattgtcgc tggcatactc      1320
ttcattcttg ctatcctgac cgaatggggc agtggaaata aacatacgg tccagttttt       1380 atgtgcctcg gtggcctgct caccatggta gccggcgctg tgtggctgac ggtgatgact      1440
aacacgcttt tgtctgcctg gattcttaca gcaggattcc tgattttcct cattggtaag      1500
tgtgacacca acaggtgttg ccttgttatg tcaccgttct gacacatgac ttacatgggt      1560
ttggcttttg taggctttgc cctctttggg gtcattagat gctgccgcta ctgctgctac      1620
tactgcctta cactggaaag tgaggagcgc ccaccgaccc catatcgcaa cactgtataa      1680
aggtaagtat tattaaattt tagagacact atcacgtgta acttgacgtg caaggatgga      1740 ggatagggc agggaaacgc aaatgccggt tgcccggtat gggggcccgt ttattatggt       1800
aaggctcttc gggcaagatg gagaggcaaa catacaggag caaaggctat atgagctact      1860
ctctgacccc cgctccgcgc tcggcctaga cccggggccc ctgattgctg agaacctgct      1920
gctagtggcg ctgcgtggca ccaacaacga tcccaggcct cagcgtcagg agagggccag      1980
agaactggcc ctcgttggca ttctactagg aaacggcgag cagggtgaac acttgggcac      2040
ggagagtgcc ctggaggcct caggcaacaa ctatgtgtat gcctacggac cagactggat      2100
ggcaaggcct tccacatggt ccgcggaaat ccagcaattc ctgcgactcc tgggcgccac      2160
gtacgtgctt cgcgtggaga tgggcaggca gtttggcttc gaggtgcata agaaccggcc      2220
ctccttccgt cagttccagg ccatcaatca tcttgtcctg tttgacaacg cccttcgcaa      2280
gtacgattcc ggccaggtgg cggcgggctt ccagagggcc cttctggtgg ccgggccaga      2340
gaccgctgac acgaggccgg acctccgcaa gctgaatgag tgggtgtttg gtggcagggc      2400
tgctggtggc agacagctgg ccgacgagct aaagatcgtg tccgcgctgc gagacactta      2460
ctcgggccac ttggtccttc agcccacgga gacccttgac acatggaagg tgttgagcag      2520
ggacacacga accgctcata gtttggagca cggattcatt catgccgcgg ggaccatcca      2580
ggccaactgc ccacagctgt ttatgagacg ccagcacccc ggcctctttc ccttcgttag      2640
tgcaatagca tcatcgctgg gctggtacta ccagaccgcc accggccccg gagcagatgc      2700
cagggcggcg gcccggcgtc aacaggcctt tcagaccagg gcggcggctg aatgccatgc      2760
caaaagcggg gtgccggtcg tggccggctt ctataggacc atcaacgcca cgctcaaggg      2820
aggagagggc ctacagccca ctatgtttaa cggggagctg ggggccatca agcaccaggc      2880
acttgacact gtgaggtatg actacggcca ctatctcata atgttggggc cattccagcc      2940
atggagcgga ctgacggccc ctccgtgccc ttacgccgaa agttcatggg cacaggcggc      3000
cgtgcagacg gccctcgagc tgttctcggc cctgtacccg gccccgtgca tctcgggcta      3060
cgcgcgcccc ccgggcccca gtgctgtgat cgagcatctg gggtccctag tcccaaaggg      3120
gggtctgctg ttgtttctgt ctcacctacc ggatgatgtt aaggacgggc tcggagaaat      3180
ggggccggcc agggccacgg gacctggaat gcagcagttt gtcagcagct acttcctcaa      3240
ccccgcctgt tccaacgtct tcattacagt gaggcagcga gggaaaaga tcaacggccg      3300 taccgtcctc caagcgctcg gacgcgcatg cgatatggca ggctgccagc actatgtgct      3360
gggctccacg gttcccctcg gtggactcaa ctttgtcaac gacctggcgt ccccggtttc      3420
caccgccgag atgatggatg atttctctcc cttcttcacc gtggagtttc cccgattca       3480 agaggagggc gcacgttctc cggtaccctt agatgtggac gagagcatgg acatctctcc      3540
```

```
gtcttacgag ttgccctggc tctcgctgga gtcatgcctc acaagcatcc tgtcacaccc    3600
caccgtggga agcaaggagc acttggtcag gcacacggac agggtcagcg gaggacgcgt    3660
ggcacagcag cccggggtag gtccccctgga cctgccgctg gcggactacg ccttcgttgc    3720
ccacagtcag gtctggacca ggcccggtgg ggctcctccc ttgccctatc gtacctggga    3780
tcgaatgaca gagaagctgc ttgtctccgc aaagcccggc ggagagaacg ttaaggtttc    3840
aggtaccgtg attacattgg gagaacaggg gtacaaagtg tcgttggatc tgagggaggg    3900
aaccaggctg gcaatggctg aggcgctgct gaatgcagca tttgccccaa tcttggatcc    3960
ggaagacgtc ttgctcaccc tgcatctaca cctggatccg cgccgggcag acaactcggt    4020
cgtgatggag gctatgacgg cggcgagtga ctacgcgcgt ggcctgggcg tgaagctgac    4080 cttttggctcg gcctcctgcc ccgagaccgg ctcgtccgcc tccagcttca tgactgtggt    4140
ggcctctgtc tccgcccag gggaattctc gggtcctctg atcacgccag tgcttcagaa    4200
gacgggcagt ctcctgattg cggtgcgttg cggggatggc aagatccagg agggtcgct    4260 gtttgagcag ctctttagcg acgtggccac gaccccacgg gcgcccgagg cgttgtctct    4320
gaagaatctc ttccgggcag tccagcagct ggtcaagagc ggcatcgtgc tgtcagggca    4380
tgacatcagc gacgggggcc tggtgacctg cctggtggag atggccctgg ccgggcagcg    4440
gggagtgacc atcactatgc cggtggcctc cgactacctc ccggagatgt ttgcagagca    4500
ccccggcctg gtgtttgagg tggaggagcg cagcgtgggt gaggtgctgc agaccctgcg    4560
ctccatgaac atgtacccgg cagtcctcgg tcgagtgggc gagcaaggtc cagatcaaat    4620
gtttgaggtg cagcacggcc cagagacggt gttgcgccag tcgctgcgcc tgctgctggg    4680
aacctggtcc tcctttgcca gcagcagta cgagtgcctg cgaccagatc ggattaaccg    4740
gtccatgcac gttccgact acggctataa cgaagcactg gcagtctccc cgttgacagg    4800
aaagaatctc agcccacgcc ggctggtgac agagcctgac ccacgatgtc aggtggccgt    4860
gctatgcgcc ccgggcacca ggggccatga agcctcctg gcggccttca cgaatgccgg    4920
atgcctgtgc cgacgggtgt tctttcgcga ggttagggac aacacgttcc tcgacaagta    4980
cgtgggtctg gccatcggag gagttcatgg ggccaggac tctgccctgg caggccgtgc    5040
caccgtggcg ctgattaatc gttcccccgc cctgcgtgac gctattctaa agttcctcaa    5100
caggccagat acgttctcgg tggccttggg ggagctgggg gtgcaagttt ggctggcct    5160 gggggccgtg gggtcaacag ataatccacc cgccctggc gtggaagtta atgtccagag    5220
atcacctctg attctggccc ccaacgcctc tggcatgttt gagtcccgct ggctgaacat    5280
tagcatcccg gcgaccacca gctctgtcat gctgcgtggc ctccggggct gcgtcctgcc    5340
ttgttgggtg caaggctcgt gcctgggcct gcaatttact aacctcggga tgccatatgt    5400
tttgcagaat gcccaccaga tcgcctgcca cttccacagc aatggcacgg acgcctggcg    5460 cttttgctatg aattatccaa gaaaccccac ggagcagggc aacattgcag ggctctgttc    5520
acgcgatggt cgtcatctgg ctctcctgtg tgaccccctca ctttgtacag acttttggca    5580
atgggagcac attccccccg cctttgggca ccccacgggg tgctcccccct ggacacttat    5640 gtttcaagca gctcacctat ggtcactcag gcacggtcgc cctccgagt gaccagtcac    5700 cttccagact atgcatacac tgaatttagc ctgatattgt cccccgagcc ccgggcccag    5760
ccctcctcag aaaactctgc atggagaagc tggacgtgaa ccttccccc ccccccgacc    5820 tgtgtgctgt atttacaaac actacaataa acccaatgtg caaatgtggt ttgtatggct    5880
```

```
actttgtgtt cctaaaaaat gcaacaatag aagtggaaac cctcagtcac gggacattaa   5940
cctcaaccac aaaatggggg ttggagaaag taaccacata tactgagat  gattcatggg   6000
ctgggggttc ccggacaata cacccatctg gagttcaact taattacatg gtagataaat   6060
taagagtccc tcctcaccac tcgaaactat ggcagacatt ctataagata acgaggagag   6120
atgaggtgag ggcagaggac attgggcagg tgtgggccac ggggcagctg gccatatccc   6180
ccgcaccaca gaagtgtaag caaagtgaag ggctcggaag gcaggcgggg cctagcaatg   6240
tcacagctaa atgcccacca gggcacacac tcaagcgggg tctcggagct cctaggtcag   6300
accacgaaag gtcagcctgc aaggtggatg gcgtgttttc tgaggttatc cccgctacgt   6360
gcagtgctgg gtgagagaga ccctagaatg tgtcgaaatg accaagcgtc cccgcagcgg   6420
ggctcccaac acgggttccc agagagggta aaagagggggg ccataaagcc cagggtgtaa   6480
aacaccgacc gcgccaccag atggcacacg tgggggaaat gagggttagc ataggcaacc   6540
cccgcctaca caccaactat agcaaacccc gccccgtcac ggtgacgtag tctgtcttga   6600
ggagatgtag acttgtagac actgcaaaac ctcaggacct acgctgccct agaggttttg   6660
ctagggagga gacgtgtgtg gctgtagcca cccgtcccgg gtacaagtcc cgggtggtga   6720
ggacggtgtc tgtggttgtc ttcccagact ctgctttctg ccgtcttcgg tcaagtacca   6780
gctggtggtc cgcatgtttt gatccaaact ttagttttag gatttatgca tccattatcc   6840
cgcagttcca cctaaacggg gcttaacgtt gcatcccaga agatgcacac gtaacccgc    6900
ctacaaccgt gacgtggctg tttaccagca tatatagagt tacggttcac tacatcaaac   6960
aggacagccg ttgccctagt ggtttcggac acaccgccaa cgctcagtgc ggtgctaccg   7020
acccgaggtc aagtcccggg ggaggagaag agaggcttcc cgcctagagc atttgcaagt   7080
caggattctc taatccctct gggagaaggg tattcggctt gtccgctgtt tttttgtggc   7140
tagttttgca cccacaacat gtaagggccc gctacccta  caacacaaaa caaactatct   7200
ccactaacca tccttttgcc aatcaattct gtgacgggt  ttcctggaca cccagtctta   7260
gttcaggtag acacccagtt atgcagtgcc accaattcca accattttta aacctcctgg   7320
aattctatca ttaaacggca tgcaggaaaa ggacaagcag cgaaaattca cgccccttg    7380
ggaggtggcg gcatatgcaa aggatagcac tcccactcta ctactgggta ttatatgctg   7440
actgtatatg cattaggata gcatatgcta cccagatata gattaggata gcatatgcta   7500
cccggatata gattaggata gcatatacta cccaaataga gattaggata gcatatgcta   7560
cccaaataga gattaggata gcatatgcta cccggatata gattaggata gcatatacta   7620
cccaaataga gattaggata gcatatgcta cccaaataga gattaggata gcatatgcta   7680
cccggatata gattaggata gcatatgcta cccaaataga gattgggata gcatatgcta   7740
cccggatata gattaggata gcatatgcta cccaaataga gattaggata gcatatgcta   7800
cccggatata gattaggata gcatatgcta cccaaataga gattgggata gcatatgcta   7860
tcctaatctc tatctgggta gcatatacta tcctaatctc tatatgggta gcatatgcta   7920
tcctaatcta tatctgggta gcatatacta tcctaatctc tatatgggta gcatatgcta   7980
tcctaatcta tatctgggta gcatatgcta tccatcgcaa cattagccca ccgtgctctc   8040
aacgacctcg tgaatatgag gaccaacaac cctgtgcttg gcgctcaggc gcaagtgtgt   8100
gtaacttgtc ttccagatcg cagcaatcgc gcccctatct tggcccgccc acctacttat   8160
gcaggtattc cccggggtgc cattagtggt tttgtgggca agtggtttga ccgcagtggt   8220
tagcgggggtt acaatcagcc aagttattac accccttagtt tacagtccaa aaccgcaggg   8280
```

```
cggcgtgtgg gggctgacgc gtgcccccac tccacaatttt caaaaaaaag agtggccact    8340
tgtctttgtt tatgggcccc attggcgtgg agcccgtttt aattttcggg ggtgttagag    8400
acaaccagtg gagtccgctg ctgtcggcgt ccactctctt tccccttgtt acaaatagag    8460
tgtaacaaca tggttcacct gtcttggtcc ctgcctggga cacatcttaa taaccccagt    8520
atcatattgc actaggatta tgtgttgccc atagccataa attcgtgtga gatggacatc    8580
cagtctttac ggcttgtccc cacccccatgg atttctattg ttaaagatat tcagaatgtt    8640
tcattcctac actagtattt attgcccaag gagtttgtga gggttatatt ggtgtcatag    8700
cacaatgcca ccactgaacc cccccgtccaa atttattct ggggggcgtca cctgaaacct    8760 tgttttcgag cacctcacat acaccttact gttcacaact cagcagttat tctattagct    8820
aaacgaagga gaatgaagaa gcaggcgaag attcaggaga gttcactgcc cgctccttga    8880
tcttcagcca ctgcccttgt gactaaaatg gttcactacc ctcgtggaat cctgatccca    8940
tgtaaataaa accgtgacag ctcatggggt gggagatatc gctgttcctt aggacccttt    9000
tactaaccct aattcgatag catatgcttc ccgttgggta acatgtgcta ttgaattagg    9060
gttagtctgg atagtatatg ctactacccg ggaagcatat gctacccgtt tagggttaaa    9120 aaggggggcct tataaacact cttgctaacg ccctcttgag ggtccgctta tcggtagcta    9180
cacaggcccc tctgattgac gttggtgtag cctcccatag tcttcctggg cccctgggag    9240
gtacatgtcc cccagcattg tgtaagagc ttcaaccaag agttacacat aaaggcaatg    9300
ttgtgttgca gtccacagac tgcaaagtct gcttcaggat gaaagccact cagtgttggc    9360
aaatgtgcac atccatttat aaggatgtca actacagtca gagaacccct ttgtgtttgg    9420 tcccccccccc gtgtcacatg tggaacaggg cccagttggc aagttgtacc aaccaactga    9480
agggattaca tgcactgccc cgcgggaaat acgtcctacc caggaacccg aaacagtgtt    9540
tcccagaagc tgtaaaaata gaacgccctg gaactgcccc actgtgcaat gcagctttta    9600
gccatgccat gctctataaa tcacttccct atctcaggta ggcctgcaca ccttaggtat    9660
ggagcgaagg ttagtggtca ctctgcagtg cctggtgctg ctttacctgg cacctgagtg    9720
tggaggtaca gaccaatgtg acaatttttcc ccaaatgttg agggacctaa gggatgcctt    9780
cagtcgtgtt aaaacctttt tccagacaaa ggacgaggta gataaccttt tgctcaagga    9840
gtctctgcta gaggacttta agggctacct tggatgccag gccctgtcag aaatgatcca    9900
attctacctg gaggaagtca tgccacaggc tgaaaaccag gaccctgaag ccaaagacca    9960
tgtaaattct ttgggtgaaa atctaaagac cctacggctc cgcctgcgca ggtgccacag    10020
gttcctgccg tgtgagaaca agagtaaagc tgtggaacag ataaaaaatg cctttaacaa    10080
gctgcaggaa aaaggaattt acaaagccat gagtgaattt gacattttta ttaactacat    10140
agaagcatac atgacaatta aagccaggtg ataattccat accctggaag caggagatgg    10200
gtgcatttca ccccaacccc ccctttcgac tgtcatttac aataaaatga aacctttat    10260 tcttgattgc ctcttgtgtt cttgccgccc aggtaccttc ctgtgttctc cccacgggaa    10320
aaagaatagc ttctgcagaa ggccattgac gcaagttttg cccgtgggga ttacccgacc    10380
cggccactta cagcacattt tgttctaggt ccatcttagg agcccgggcc agcattctat    10440
cagcttaacg ggaagagaag tggggagggc actcgcccac taaccttaac acctgcagcc    10500
tacaaaagta cactagctgt ttgctctatt cgccactaga gaccgccaag atgcgaaact    10560
gcaggcccgg gcccaggcct tgtagggcag acggttaggc tgacaagggg acaagtgtgg    10620
```

| | | | | | |
|---|---|---|---|---|---|
| caggtgggcg | ggaaggggca | caagaatgac | ggcgaaactg | gaccacggtc | cacccccgccc 10680 |
| tcaagcgtcc | gggagccagg | cggttcggtt | aaggagggcg | gccttgcgaa | caatcattag 10740 |
| tagctaccaa | caagggcccc | cagatgcccc | ccaccagtca | ccccggccgt | gtccactcac 10800 |
| atattccact | cttatttta | aattaatgtg | tcccaattag | aaacccaagc | gcagaaatta 10860 |
| gttgagaggc | tagtgtttta | aacatgcacc | ctaggccagc | cagagataat | gtcacaagac 10920 |
| tatcaagttg | gtgtaaacac | gccgtgggaa | aaaatttatg | gttcagtgcg | tcgagtgcta 10980 |
| tctttggaac | agtagaaaat | tgaaccttgt | tggcgggaga | aggcataacg | ccttatctgg 11040 |
| gaggagcgac | ggattatagc | caataagaga | gctcaagacg | cagggctcgc | aaagtatagt 11100 |
| ggccccgtgg | gaccttagag | gtggagcaac | gtctaaagtg | gtaataacac | caggcggggc 11160 |
| tgggcaaagg | ggtcctacgg | gcgggattaa | ttacgccttg | cttacgcaag | ctcagttaat 11220 |
| tcgcccacga | cttgaaaaat | gtagccctta | accaattggc | ggcccctaag | gggggacta 11280 |
| aggtcccact | acaaaaactc | tgtgttctgc | tgcaaatttt | agataagatg | gcatagagac 11340 |
| aaggacaccg | aagaccccca | gagccctcat | cgcagggttc | ttaccatgcg | gccatgtagg 11400 |
| cccacttaac | actacaagac | ctacgcctct | ccattcatca | tgtaacccac | aaatcatcta 11460 |
| aaccgtaagt | ctaagggcct | cctgaggttt | tctcaggagg | ccctaatgta | taattaatca 11520 |
| tgcatttgat | tttaaaaaag | taggttacac | tcattttagg | ccagacttta | tttgcagatt 11580 |
| aataatttat | gtgattctcc | ttccctctag | gactgaagaa | acagcctcct | gcacgtgagc 11640 |
| atgtatctga | ataattatt | atgtcataag | tgtaatgatt | agaaagtcat | aaacccacttt 11700 |
| cccttacat | gaatctgggc | actgaatttt | ggggtacttc | taaagactaa | cgtgttcgat 11760 |
| ttcggggtca | cttcccctt | tataagtgtg | tgaacagtga | tttcagtaaa | acctaagaga 11820 |
| tatttggtgt | cacttccgca | ttttaagttt | cagaaaattt | taaaattaaa | attgaaatttt 11880 |
| ctctcaaaat | aattccaatg | aaaacttcaa | agaatcttat | gtatgtaatt | cttttgcccc 11940 |
| aaactgggct | tcagatgcct | tctattgcac | tctcacaaaa | acattctgga | cacatgtgcc 12000 |
| agacgcctgg | gcctctaagg | ccctcgggtc | ccctggacc | ccggcctcag | caaccctgct 12060 |
| gctcccctcc | tgccacccca | gcctccccc | ctccccgtcc | cccttcgctc | cttatcctcc 12120 |
| cccggtcccc | agtagggccg | cctgccccc | tgcacccagt | acctgcccct | cttggccacg 12180 |
| cacccccggc | caggccacct | tagacccggc | caagccccat | ccctgaagac | ccagcggcca 12240 |
| ttctctctgg | taacgagcag | agaagaagta | gaggcccgcg | gccattgggc | ccagattgag 12300 |
| agaccagtcc | aggggcccga | ggttggagcc | agcgggcacc | cgaggtccca | gcacccggtc 12360 |
| cctccggggg | gcagagacag | gcagggcccc | ccggcagctg | gccccgagga | ggcgcccgga 12420 |
| gtggggccgg | tcggctgggc | tggccgagcc | cgggtctggg | aggtctgggg | tggcgagcct 12480 |
| gctgtctcag | gaggggcctg | gctccgccgg | gtggccctgg | ggtaagtctg | ggaggcagag 12540 |
| ggacggccta | ggcccgggga | agtggagggg | gatcgcccgg | gtctctgttg | gcagagtccg 12600 |
| ggcgatcctc | tgagaccctc | cgggcccgga | cggccgccct | cggccccca | gacagacccc 12660 |
| agggtctcca | ggcagggtcc | ggcatctcca | ggggcagcag | gctcaccacc | acaggccccc 12720 |
| cagacccggg | tctcggccag | ccgagccgac | cggcccgcg | ccgggcgcct | cctcggagcc 12780 |
| agccccgggg | gttggttctg | ccctctctc | tgtccttcag | aggaaccagg | gacctcgggc 12840 |
| accccagagc | cctcgggcc | cgcctccagg | cgccctcctg | gtctccgctc | ccctctgagc 12900 |
| cccgttaaac | ccaaagaatg | tctgaggga | gccaccctcg | gggcccaggc | ccagagtcc 12960 |
| agaggtcagg | ggcacctcag | ggtgcctccc | cgggtcccag | gccagccgga | gggacccccgg 13020 |

```
cagcccgggc ggccccagag gccggttcct cgccccttcc ccgggcttca gagcccaggg    13080
tgtcccccag aagggaccct aggcgtcccc tctcctcccc tccaggcccg agcctctccc    13140
tcgcggagag gggcctcttc gagccctcaa gtccagtccc accgagaccc gagtggcccg    13200 gatccccac  cggcccttct ctttccccct actcctctcc aaccttcgct ccaccctaga    13260
ccccagcttc tggcctcccc gggtccacca ggccagccgg agggaccccg gcagcccggg    13320
cgagtcgcct tccctctccc ctggcctctc cttcccgcct cccacccgag ccccctcagc    13380
ttgcctcccc accgggtcca tcaggccggc cggagggacc ccggcggccc ggtgtcagtt    13440 cccctgcag  ccgcccagtc tctgcctcca ggcaagggcg ccagcttttc tcccccagc     13500 ctgaggccca ggctcctgtg cactgtctgt aaagtccagc ctcccacgcc cgtccacggc    13560
tcccaggccc agcccgtcc  accctcccc  acgttggaca ggccctctgt ccacccgggc    13620
catccccgcc ccctgtgtc  caccccagtc ccgtccaggg gggactttat gtgacccttg    13680
ggcctggctc cccatagact cccatgtaag cctgcctcga gtaggtgcct ccagagcccc    13740
ttttgccccc ctggcggccc agcccgaccc ccgggcgccc ccaaactttg tccagatgtc    13800
caggggtccc cgagggcgag gcccagcccc ctcccgcccc tgtccactgc cccggtcccc    13860
ccagaagccc ccaaaagtag aggctcaggc catgcgcgcc ctgtcaccag gcctgccaaa    13920
gagccagatc taaggccggg agaggcagcc ccaaagcggg tgcagtaaca ggtaatctct    13980
ggtagtgatt tggacccgaa atctgacact ttagagctct ggaggacttt aaaactctaa    14040
aaatcaaaac tttagaggcg aatgggcgcc attttgtccc cacgcgcgca taatggcgga    14100
cctaggccta aaaccccag  gaagcgggtc tatggttggc tgcgctgctg ctatctttag    14160
aggggaaaag aggaataagc ccccagacag gggagtgggc ttgtttgtga cttcaccaaa    14220
ggtcagggcc caagggggtt cgcgttgcta ggccaccttc tcagtccagc gcgtttacgt    14280
aagccagaca gcagccaatt gtcagttcta gggagggga  ccactgcccc tggtataaag    14340
tggtcctgca gctatttctg gtcgcatcag agcgccagga gtccacacaa atgtaagagg    14400
gggtcttcta cctctcccta gccctccgcc ccctccaagg actcgggccc agtttctaac    14460 ttttcccct  tccctccctc gtcttgccct gcgcctgggg ccaccttcat caccgtcgct    14520
gactccgcca tccaagccta ggggagaccg aagtgaagtc cctggaccag cccggcccgg    14580 gcccccggt  atcgggccag aggtaagtgg actttaattt tttctgctaa gcccaacact    14640
ccaccacacc caggcacaca ctacacacac ccacccgtct cagggtcccc tcggacagct    14700
cctaagaagg caccggtcgc ccagtcctac cagagggggc caagaaccca gacgagtccg    14760
tagaagggtc ctcgtccagc aagaagagga ggtggtaagc ggttcacctt cagggtaag    14820 taacctgacc tctccagggc tcacataaag ggaggcttag tatacatgct tcttgctttt    14880
cacaggaacc tgggggctag tctgggtggg tttaggctgc ctcaagttgc atcagccagg    14940
gcttcatgcc ctcctcagtt ccctagtccc cgggcttcag gcccctccg  tccccgtcct    15000 ccagagaccc gggcttcagg ccctgcctct cctgttaccc ttttagaacc acagcctgga    15060
cacatgtgcc agacgcctgg gcctctaagg ccctcgggtc ccctggacc  ccggcctcag    15120 caaccctgct gctcccctcc tgccacccca gcctcccccc ctcccgtcc  ccttcgctc     15180 cttatcctcc cccggtcccc agtagggccg cctgccccc  tgcacccagt acctgcccct    15240
cttggccacg caccccgggc caggccacct tagaccggc  caagcccccat ccctgaagac   15300 ccagcggcca ttctctctgg taacgagcag agaagaagta gaggcccgcg gccattgggc    15360
```

```
ccagattgag agaccagtcc aggggcccga ggttggagcc agcgggcacc cgaggtccca   15420
gcacccggtc cctccggggg gcagagacag gcagggcccc ccggcagctg gccccgagga   15480
ggcgcccgga gtggggccgg tcggctgggc tggccgagcc cgggtctggg aggtctgggg   15540
tggcgagcct gctgtctcag gaggggcctg gctccgccgg gtggccctgg ggtaagtctg   15600
ggaggcagag ggacggccta ggcccgggga agtggagggg gatcgcccgg gtctctgttg   15660
gcagagtccg ggcgatcctc tgagaccctc cgggcccgga cggccgccct cggcccccca   15720
gacagacccc agggtctcca ggcagggtcc ggcatctcca ggggcagcag gctcaccacc   15780
acaggccccc cagacccggg tctcggccag ccgagccgac cggccccgcg ccgggcgcct   15840
cctcggagcc agccccnggg gttggttctg ccnctctctc tgtccttcag aggaaccagg   15900
gacctcgggc accccagagc ccctcggccc cgcctccagg cgccctcctg gtctccgctc   15960
ccctctgagc cccgttaaac ccaaagaatg tctgagggga gccaccctcg gggcccaggc   16020
cccagagtcc agaggtcagg ggcacctcag ggtgcctccc cgggtcccag gccagccgga   16080
gggacccccgg cagcccgggc ggcccagag gccggttcct cgccccttcc ccgggcttca   16140
gagcccaggg tgtcccccag aagggaccct aggcgtcccc tctcctcccc tccaggcccg   16200
agcctctccc tcgcggagag gggcctcttc gagcccncaa gtccagtccc accgagaccc   16260
gagtggcccg gatcccccac cggcccttct cttccccct actcctctcc aaccttcgct   16320
ccaccctaga ccccagcttc tggcctcccc gggtccacca ggccagccgg agggaccccg   16380
gcagcccggg cgagtcgcct tccctctccc ctggcctctc cttcccgcct cccacccgag   16440
cccccctcagc ttgcctcccc accgggtcca tcaggccggc cggagggacc ccggcggccc   16500
ggtgtcagtt cccctgcag ccgcccagtc tctgcctcca ggcaagggcg ccagctttc   16560
tccccccagc ctgaggccca ggctcctgtg cactgtctgt aaagtccagc ctcccacgcc   16620
cgtccacggc tcccaggccc agcccgtcc acccctcccc acgttggaca ggccctctgt   16680
ccacccgggc catccccgcc cccctgtgtc caccccagtc ccgtccaggg gggactttat   16740
gtgaccnttg ggcctggctc ccatagact cccatgtaag cctgcctcga gtaggtgcct   16800
ccagagccccc ttttgcnccc ctggcggccc agcccgaccc ccgggcgccc ccaaactttg   16860
tccagatgtc caggggtccc cgagggcgag gcccagcccc ctcccgcccc tgtccactgc   16920
cccggtcccc ccagaagccc ccaaaagtag aggctcaggc catgcgcgcc ctgtcaccag   16980
gcctgccaaa gagccagatc taaggccggg agaggcagcc ccaaagcggg tgcagtaaca   17040
ggtaatctct ggtagtgatt tggacccgaa atctgacact ttagagctct ggaggacttt   17100
aaaactctaa aaatcaaaac tttagaggcg aatgggcgcc attttgtccc cacgcgcgca   17160
taatggcgga cctaggccta aaaccnccag gaagcgggtc tatggttggc tgcgctgctg   17220
ctatctttag agggaaaag aggaataagc ccccagacag gggagtgggc ttgtttgtga   17280
cttcaccaaa ggtcagggcc caaggggggtt cgcgttgcta ggccaccttc tcagtccagc   17340
gcgtttacgt aagccagaca gcagccaatt gtcagttcta ggggagggga ccactgcccc   17400
tggtataaag tggtcctgca gctatttctg gtcgcatcag agcgccagga gtccacacaa   17460
atgtaagagg gggtcttcta cctctcccta gccctccgcc ccctccaagg actcgggccc   17520
agttctcaac tttttcccct tccctccctc gtcttgccct gcgcctgggg ccaccttcat   17580
caccgtcgct gactccgcca tccaagccta ggggagaccg aagtgaagtc cctggaccag   17640
cccggccggg gcccccggt atcgggccag aggtaagtgg actttaattt tttctgctaa   17700
gcccaacact ccaccacacc caggcacaca ctacacacac ccacccgtct cagggtcccc   17760
```

```
tcggacagct cctaagaagg caccggtcgc ccagtcctac cagaggggggc caagaaccca   17820
gacgagtccg tagaagggtc ctcgtccagc aagaagagga ggtggtaagc ggttcacctt   17880
caggggtaag taacctgacc tctccagggc tcacataaag ggaggcttag tatacatgct   17940
tcttgctttt cacaggaacc tgggggctag tctgggtggg tttaggctgc ctcaagttgc   18000
atcagccagg gcttcatgcc ctcctcagtt ccctagtccc cgggcttcag gcccctccg    18060
tccccgtcct ccagagaccc gggcttcagg ccctgcctct cctgttaccc ttttagaacc   18120
acagcctgga cacatgtgcc agacgcctgg gcctctaagg ccctcgggtc ccctggacc    18180
ccggcctcag caaccctgct gctccctcc tgccacccca gcctcccccc ctcccgtcc     18240
cccttcgctc cttatcctcc cccggtcccc agtagggccg cctgccccccc tgcacccagt  18300
acctgcccct cttggccacg caccccgggc caggccacct tagacccggc caagcccat    18360
ccctgaagac ccagcggcca ttctctctgg taacgagcag agaagaagta gaggcccgcg   18420
gccattgggc ccagattgag agaccagtcc aggggcccga ggttggagcc agcgggcacc   18480
cgaggtccca gcacccggtc cctccggggg gcagagacag gcagggcccc ccggcagctg   18540
gccccgagga ggcgcccgga gtggggccgg tcggctgggc tggccgagcc cgggtctggg   18600
aggtctgggg tggcgagcct gctgtctcag gagggggcctg gctccgccgg gtggccctgg   18660
ggtaagtctg ggaggcagag ggacggccta ggcccgggga agtggagggg gatcgcccgg   18720
gtctctgttg gcagagtccg ggcgatcctc tgagaccctc cgggcccgga cggccgccct   18780
cggcccccca gacagacccc agggtctcca ggcagggtcc ggcatctcca ggggcagcag   18840
gctcaccacc acaggccccc cagacccggg tctcggccag ccgagccgac cggccccgcg   18900
ccgggcgcct cctcggagcc agccccgggg gttggttctg ccctctctc tgtccttcag   18960
aggaaccagg gacctcgggc accccagagc ccctcgggcc cgcctccagg cgccctcctg   19020
gtctccgctc ccctctgagc cccgttaaac ccaaagaatg tctgagggga gccaccctcg   19080
gggcccaggc cccagagtcc agaggtcagg ggcacctcag ggtgcctccc cgggtcccag   19140
gccagccgga gggaccccgg cagcccggcc ggccccagag gccggttcct cgcccctccc    19200
ccgggcttca gagcccaggg tgtccccag aagggaccct aggcgtcccc tctcctcccc    19260
tccaggcccg agcctctccc tcgcggagag gggcctcttc gagccctcaa gtccagtccc   19320
accgagaccc gagtggcccg gatccccac cggcccttct ctttccccct actcctctcc    19380
aaccttcgct ccaccctaga ccccagcttc tggcctcccc gggtccacca ggccagccgg   19440
agggaccccg gcagcccggg cgagtcgcct tccctctccc ctggcctctc cttcccgcct   19500
cccacccgag cccctcagc ttgcctcccc accgggtcca tcaggccggc cggagggacc    19560
ccggcggccc ggtgtcagtt cccctgcag ccgcccagtc tctgcctcca ggcaagggcg    19620
ccagcttttc tcccccagc ctgaggccca ggctcctgtg cactgtctgt aaagtccagc    19680
ctcccacgcc cgtccacggc tcccaggccc agcccgtcc accctccccc acgttggaca    19740
ggccctctgt ccacccggggc catccccgcc cccctgtgtc caccccagtc ccgtccaggg   19800
gggactttat gtgaccccttg ggcctggctc cccatagact cccatgtaag cctgcctcga   19860
gtaggtgcct ccagagcccc ttttgccccc ctggcggccc agcccgaccc ccgggcgccc   19920
ccaaactttg tccagatgtc caggggtccc cgagggcgag gcccagcccc ctcccgcccc   19980
tgtccactgc cccggtcccc ccagaagccc caaaagtag aggctcaggc catgcgcgcc   20040
ctgtcaccag gcctgccaaa gagccagatc taaggccggg agaggcagcc ccaaagcggg   20100
```

```
tgcagtaaca ggtaatctct ggtagtgatt tggacccgaa atctgacact ttagagctct    20160
ggaggacttt aaaactctaa aaatcaaaac tttagaggcg aatgggcgcc attttgtccc    20220
cacgcgcgca taatggcgga cctaggccta aaaccccag gaagcgggtc tatggttggc     20280
tgcgctgctg ctatctttag aggggaaaag aggaataagc ccccagacag gggagtgggc    20340
ttgtttgtga cttcaccaaa ggtcagggcc caaggggggtt cgcgttgcta ggccaccttc   20400
tcagtccagc gcgtttacgt aagccagaca gcagccaatt gtcagttcta ggaggggga    20460 ccactgcccc tggtataaag tggtcctgca gctatttctg gtcgcatcag agcgccagga    20520
gtccacacaa atgtaagagg gggtcttcta cctctccta gccctccgcc cctccaagg     20580 actcgggccc agtttctaac ttttcccct tccctccctc gtcttgccct gcgcctgggg    20640
ccaccttcat caccgtcgct gactccgcca tccaagccta ggggagaccg aagtgaagtc   20700
cctggaccag cccggcccgg ccccccggt atcgggccag aggtaagtgg actttaattt    20760
tttctgctaa gcccaacact ccaccacacc caggcacaca ctacacacac ccacccgtct   20820
cagggtcccc tcggacagct cctaagaagg caccggtcgc ccagtcctac cagagggggc   20880
caagaaccca gacgagtccg tagaagggtc ctcgtccagc aagaagagga ggtggtaagc   20940
ggttcacctt caggggtaag taacctgacc tctccagggc tcacataaag ggaggcttag   21000
tatacatgct tcttgctttt cacaggaacc tggggctag tctgggtggg tttaggctgc    21060
ctcaagttgc atcagccagg gcttcatgcc ctcctcagtt ccctagtccc cgggcttcag   21120 gcccctccg tccccgtcct ccagagaccc gggcttcagg ccctgcctct cctgttaccc    21180
ttttagaacc acagcctgga cacatgtgcc agacgcctgg gcctctaagg ccctcgggtc   21240
cccctggacc ccggcctcag caaccctgct gctcccctcc tgccaccca gcctcccccc   21300 ctcccgtcc cccttcgctc cttatcctcc cccggtcccc agtagggccg cctgcccccc   21360
tgcacccagt acctgcccct cttggccacg caccccgggc caggccacct tagacccggc   21420
caagccccat ccctgaagac ccagcggcca ttctctctgg taacgagcag agaagaagta   21480
gaggcccgcg gccattgggc ccagattgag agaccagtcc aggggcccga ggttggagcc   21540
agcgggcacc cgaggtccca gcacccggtc cctccggggg gcagagacag gcagggcccc   21600
ccggcagctg gccccgagga ggcgcccgga gtggggccgg tcggctgggc tggccgagcc   21660
cgggtctggg aggtctgggg tggcgagcct gctgtctcag gaggggcctg gctccgccgg   21720
gtggccctgg ggtaagtctg ggaggcagag ggacggccta ggcccgggga agtggagggg   21780
gatcgcccgg gtctctgttg gcagagtccg ggcgatcctc tgagaccctc cgggcccgga   21840
cggccgccct cggccccca gacagacccc agggtctcca ggcagggtcc ggcatctcca   21900
ggggcagcag gctcaccacc acaggccccc cagaccagg tctcggccag ccagccgac    21960 cggccccgcg ccgggcgcct cctcggagcc agccccggg gttggttctg ccctctctc    22020 tgtccttcag aggaaccagg gacctcgggc accccagagc ccctcgggcc cgcctccagg   22080
cgccctcctg gtctccgctc ccctctgagc cccgttaaac ccaaagaatg tctgagggga   22140 gccacccctcg ggcccaggc cccagagtcc agaggtcagg ggcacctcag ggtgcctccc   22200
cgggtcccag gccagccgga gggacccggg cagcccgggc ggcccagag gccggttcct   22260 cgcccttcc ccgggcttca gagcccaggg tgtccccag aagggaccct aggcgtcccc    22320
tctcctcccc tccaggcccg agcctctccc tcgcggagag gggcctcttc gagccctcaa   22380
gtccagtccc accgagaccc gagtggcccg gatccccac cggcccttct ctttcccct    22440 actcctctcc aaccttcgct ccaccctaga ccccagcttc tggcctcccc gggtccacca   22500
```

```
ggccagccgg agggaccccg gcagcccggg cgagtcgcct tccctctccc ctggcctctc    22560
cttcccgcct cccacccgag cccccteage ttgcctcccc accgggtcca tcaggccggc    22620
cggagggacc ccggcggccc ggtgtcagtt cccctgcag ccgcccagtc tctgcctcca     22680
ggcaagggcg ccagctttc tccccccage ctgaggccca ggctcctgtg cactgtctgt    22740
aaagtccagc ctcccacgcc cgtccacggc tcccaggccc agcccgtcc acccctcccc    22800 acgttggaca ggccctctgt ccacccgggc catcccgcc ccctgtgtc caccccagtc     22860 ccgtccaggg gggactttat gtgacccttg gcctggctc ccatagact cccatgtaag     22920 cctgcctcga gtaggtgcct ccagagcccc ttttgccccc ctggcggccc agcccgaccc    22980
ccgggcgccc ccaaactttg tccagatgtc caggggtccc cgagggcgag gcccagcccc    23040
ctcccgcccc tgtccactgc cccggtcccc ccagaagccc ccaaaagtag aggctcaggc    23100
catgcgcgcc ctgtcaccag gcctgccaaa gagccagatc taaggccggg agaggcagcc    23160
ccaaagcggg tgcagtaaca ggtaatctct ggtagtgatt tggacccgaa atctgacact    23220
ttagagctct ggaggacttt aaaactctaa aaatcaaaac tttagaggcg aatgggcgcc    23280
attttgtccc cacgcgcgca taatggcgga cctaggccta aaaccccag gaagcgggtc     23340 tatggttggc tgcgctgctg ctatctttag aggggaaaag aggaataagc ccccagacag    23400
gggagtgggc ttgtttgtga cttcaccaaa ggtcagggcc caaggggggtt cgcgttgcta   23460 ggccaccttc tcagtccagc gcgtttacgt aagccagaca gcagccaatt gtcagttcta    23520
gggaggggga ccactgcccc tggtataaag tggtcctgca gctatttctg gtcgcatcag    23580
agcgccagga gtccacacaa atgtaagagg gggtcttcta cctctcccta gccctccgcc    23640
ccctccaagg actcgggccc agtttctaac ttttccccct tccctccctc gtcttgccct    23700
gcgcctgggg ccaccttcat caccgtcgct gactccgcca tccaagccta ggggagaccg    23760
aagtgaagtc cctggaccag cccggccggg gcccccgt atcgggccag aggtaagtgg      23820
actttaattt tttctgctaa gcccaacact ccaccacacc caggcacaca ctacacacac    23880
ccacccgtct cagggtcccc tcggacagct cctaagaagg caccggtcgc ccagtcctac    23940 cagaggggc caagaaccca gacgagtccg tagaagggtc ctcgtccagc aagaagagga     24000
ggtggtaagc ggttcacctt caggggtaag taacctgacc tctccagggc tcacataaag    24060
ggaggcttag tatacatgct tcttgctttt cacaggaacc tggggggctag tctgggtggg   24120 tttaggctgc ctcaagttgc atcagccagg gcttcatgcc ctcctcagtt ccctagtccc    24180
cgggcttcag gcccctccg tccccgtcct ccagagaccc gggcttcagg ccctgcctct    24240
cctgttaccc ttttagaacc acagcctgga cacatgtgcc agacgcctgg gcctctaagg    24300
ccctcgggtc cccctggacc ccggcctcag caaccctgct gctcccctcc tgccacccca    24360 gcctccccc ctccccgtcc cccttcgctc cttatcctcc cccggtcccc agtagggccg     24420 cctgccccc tgcacccagt acctgcccct cttggccacg cacccgggc caggccacct     24480 tagacccggc caagcccat ccctgaagac ccagcggcca ttctctctgg taacgagcag    24540
agaagaagta gaggcccgcg gccattgggc ccagattgag agaccagtcc aggggcccga    24600
ggttggagcc agcgggcacc cgaggtccca gcacccggtc cctccggggg gcagagacag    24660
gcagggcccc ccggcagctg gcccgagga ggcgcccgga gtggggccgg tcggctgggc     24720
tggccgagcc cgggtctggg aggtctgggg tggcagcct gctgtctcag gagggccctg     24780
gctccgccgg gtggccctgg ggtaagtctg ggaggcagag ggacggccta ggcccgggga    24840
```

```
agtggagggg gatcgcccgg gtctctgttg gcagagtccg ggcgatcctc tgagaccctc    24900
cgggcccgga cggccgccct cggcccccca gacagacccc agggtctcca ggcagggtcc    24960
ggcatctcca ggggcagcag gctcaccacc acaggccccc cagacccggg tctcggccag    25020
ccgagccgac cggccccgcg ccgggcgcct cctcggagcc agcccccggg gttggttctg    25080
cccctctctc tgtccttcag aggaaccagg gacctcgggc accccagagc ccctcgggcc    25140
cgcctccagg cgccctcctg gtctccgctc cccgttaaac ccaaagaatg    25200
tctgagggga gccaccctcg gggcccaggc cccagagtcc agaggtcagg ggcacctcag    25260
ggtgcctccc cgggtcccag gccagccgga gggaccccgg cagcccgggc ggccccagag    25320
gccggttcct cgcccttcc ccgggcttca gagcccaggg tgtcccccag aagggaccct    25380
aggcgtcccc tctcctcccc tccaggcccg agcctctccc tcgcggagag gggcctcttc    25440
gagccctcaa gtccagtccc accgagaccc gagtggcccg gatcccccac cggcccttct    25500 cttccccct actcctctcc aaccttcgct ccaccctaga ccccagcttc tggcctcccc    25560
gggtccacca ggccagccgg agggaccccg gcagcccggg cgagtcgcct tccctctccc    25620
ctggcctctc cttcccgcct cccacccgag cccctcagc ttgcctcccc accgggtcca    25680
tcaggccggc cggagggacc ccggcggccc ggtgtcagtt cccctgcag ccgcccagtc    25740 tctgcctcca ggcaagggcg ccagcttttc tccccccagc ctgaggccca ggctcctgtg    25800
cactgtctgt aaagtccagc ctcccacgcc cgtccacggc tcccaggccc agcccgtcc    25860 accctcccc acgttggaca ggccctctgt ccacccgggc catcccgcc ccctgtgtc    25920 caccccagtc ccgtccaggg gggactttat gtgaccttg ggcctggctc ccatagact    25980 cccatgtaag cctgcctcga gtaggtgcct ccagagcccc ttttgccccc ctggcggccc    26040
agcccgaccc ccgggcgccc ccaaactttg tccagatgtc cagggggtccc cgagggcgag    26100 gcccagcccc ctcccgcccc tgtccactgc cccggtcccc ccagaagccc caaaagtag    26160 aggctcaggc catgcgcgcc ctgtcaccag gcctgccaaa gagccagatc taaggccggg    26220
agaggcagcc ccaaagcggg tgcagtaaca ggtaatctct ggtagtgatt tggacccgaa    26280
atctgacact ttagagctct ggaggacttt aaaactctaa aaatcaaaac tttagaggcg    26340
aatgggcgcc attttgtccc cacgcgcgca taatggcgga cctaggccta aaaccccag    26400 gaagcgggtc tatggttggc tgcgctgctg ctatctttag aggggaaaag aggaataagc    26460
ccccagacag gggagtgggc ttgtttgtga cttcaccaaa ggtcagggcc caaggggggtt    26520 cgcgttgcta ggccaccttc tcagtccagc gcgtttacgt aagccagaca gcagccaatt    26580
gtcagttcta gggaggggga ccactgcccc tggtataaag tggtcctgca gctatttctg    26640
gtcgcatcag agcgccagga gtccacacaa atgtaagagg gggtcttcta cctctcccta    26700
gccctccgcc ccctccaagg actcgggccc agtttctaac ttttttcccct tccctccctc    26760 gtcttgccct gcgcctgggg ccaccttcat caccgtcgct gactccgcca tccaagccta    26820
ggggagaccg aagtgaagtc cctggaccag cccggcccgg gccccccggt atcgggccag    26880
aggtaagtgg actttaattt tttctgctaa gcccaacact ccaccacacc caggcacaca    26940
ctacacacac ccaccgtct cagggtcccc tcggacagct cctaagaagg caccggtcgc    27000
ccagtcctac cagaggggc caagaaccca gacgagtccg tagaagggtc ctcgtccagc    27060
aagaagagga ggtggtaagc ggttcacctt caggggtaag taacctgacc tctccagggc    27120
tcacataaag ggaggcttag tatacatgct tcttgctttt cacaggaacc tgggggctag    27180
tctgggtggg tttaggctgc ctcaagttgc atcagccagg gcttcatgcc ctcctcagtt    27240
```

```
ccctagtccc cgggcttcag gcccccctccg tcccgtcct ccagagaccc gggcttcagg    27300
ccctgcctct cctgttaccc ttttagaacc acagcctgga cacatgtgcc agacgcctgg    27360
gcctctaagg ccctcgggtc cccctggacc ccggcctcag caaccctgct gctcccctcc    27420
tgccacccca gcctccccc ctcccgtcc cccttcgctc cttatcctcc cccggtcccc      27480
agtagggccg cctgcccccc tgcacccagt acctgcccct cttggccacg caccccgggc    27540
caggccacct tagacccggc caagcccat ccctgaagac ccagcggcca ttctctctgg     27600
taacgagcag agaagaagta gaggcccgcg gccattgggc ccagattgag agaccagtcc    27660
aggggcccga ggttggagcc agcgggcacc cgaggtccca gcacccggtc cctccggggg    27720
gcagagacag gcagggcccc ccggcagctg gccccgagga ggcgcccgga gtggggccgg    27780
tcggctgggc tggccgagcc cgggtctggg aggtctgggg tggcgagcct gctgtctcag    27840
gaggggcctg gctccgccgg gtggccctgg ggtaagtctg ggaggcagag ggacggccta   27900
ggcccgggga agtggagggg gatcgcccgg gtctctgttg gcagagtccg ggcgatcctc    27960
tgagaccctc cgggcccgga cggccgccct cggccccca gacagacccc agggtctcca    28020
ggcagggtcc ggcatctcca ggggcagcag gctcaccacc acaggccccc cagacccggg   28080
tctcggccag ccgagccgac cggccccgcg ccgggcgcct cctcggagcc agccccgggg   28140
gttggttctg cccctctctc tgtccttcag aggaaccagg gacctcgggc accccagagc   28200
ccctcgggcc cgcctccagg cgccctcctg gtctccgctc ccctctgagc ccgttaaac    28260 ccaaagaatg tctgagggga gccacccctcg gggcccaggc cccagagtcc agaggtcagg   28320
ggcacctcag ggtgcctccc cgggtcccag gccagccgga gggaccccgg cagcccgggc   28380
ggccccagag gccggttcct cgcccctcc ccgggcttca gagcccaggg tgtcccccag    28440
aagggaccct aggcgtcccc tctcctcccc tccaggcccg agcctctccc tcgcggagag    28500
gggcctcttc gagccctcaa gtccagtccc accgagaccc gagtggcccg gatccccac    28560 cggccctctt ctttccccct actcctctcc aaccttcgct ccaccctaga ccccagcttc    28620
tggcctcccc gggtccacca ggccagccgg agggaccccg gcagcccggg cgagtcgcct   28680
tccctctccc ctggcctctc cttcccgcct cccacccgag ccccctcagc ttgcctcccc    28740
accgggtcca tcaggccggc cggagggacc ccggcggccc ggtgtcagtt cccccctgcag   28800 ccgcccagtc tctgcctcca ggcaagggcg ccagcttttc tcccccagc ctgaggccca    28860 ggctcctgtg cactgtctgt aaagtccagc ctcccacgcc cgtccacggc tcccaggccc    28920
agccccgtcc acccctcccc acgttggaca ggccctctgt ccaccgggc catcccgcc     28980 cccctgtgtc caccccagtc ccgtccaggg gggactttat gtgacccttg ggcctggctc    29040
cccatagact cccatgtaag cctgcctcga gtaggtgcct ccagagcccc ttttgccccc    29100
ctggcggccc agcccgaccc ccgggcgccc ccaaactttg tccagatgtc caggggtccc    29160
cgagggcgag gccagccccc ctcccgcccc tgtccactgc cccggtcccc ccagaagccc    29220
ccaaaagtag aggctcaggc catgcgcgcc ctgtcaccag gcctgccaaa gagccagatc    29280
taaggccggg agaggcagcc ccaaagcggg tgcagtaaca ggtaatctct ggtagtgatt    29340
tggacccgaa atctgacact ttagagctct ggaggacttt aaaactctaa aaatcaaaac    29400
tttagaggcg aatgggcgcc attttgtccc cacgcgcgca taatggcgga cctaggccta    29460 aaaccccag gaagcgggtc tatggttggc tgcgctgctg ctatctttag aggggaaaag    29520
aggaataagc ccccagacag gggagtgggc ttgtttgtga cttcaccaaa ggtcagggcc    29580
```

```
caaggggtt cgcgttgcta ggccaccttc tcagtccagc gcgtttacgt aagccagaca    29640
gcagccaatt gtcagttcta gggaggggga ccactgcccc tggtataaag tggtcctgca    29700
gctatttctg gtcgcatcag agcgccagga gtccacacaa atgtaagagg gggtcttcta    29760
cctctcccta gccctccgcc ccctccaagg actcgggccc agtttctaac ttttcccct    29820 tccctccctc gtcttgccct cgcgctgggg ccaccttcat caccgtcgct gactccgcca    29880
tccaagccta ggggagaccg aagtgaagtc cctggaccag cccggcccgg ccccccggt    29940 atcgggccag aggtaagtgg acttaatttt tttctgctaa gcccaacact ccaccacacc    30000
caggcacaca ctacacacac ccacccgtct cagggtcccc tcggacagct cctaagaagg    30060
caccggtcgc ccagtcctac cagaggggc caagaaccca gacgagtccg tagaagggtc    30120
ctcgtccagc aagaagagga ggtggtaagc ggttcacctt caggggtaag taacctgacc    30180
tctccagggc tcacataaag ggaggcttag tatacatgct tcttgctttt cacaggaacc    30240
tgggggctag tctgggtggg tttaggctgc ctcaagttgc atcagccagg gcttcatgcc    30300
ctcctcagtt ccctagtccc cgggcttcag gccccctccg tccccgtcct ccagagaccc    30360
gggcttcagg ccctgcctct cctgttaccc ttttagaacc acagcctgga cacatgtgcc    30420
agacgcctgg gcctctaagg ccctcgggtc ccctggacc ccggcctcag caaccctgct    30480
gctcccctcc tgccacccca gcctcccccc ctccccgtcc cccttcgctc cttatcctcc    30540
cccggtcccc agtagggccg cctgcccccc tgcacccagt acctgcccct cttggccacg    30600
caccccgggc caggccacct tagacccggc caagcccat ccctgaagac ccagcggcca    30660
ttctctctgg taacgagcag agaagaagta gaggcccgcg gccattgggc ccagattgag    30720
agaccagtcc aggggcccga ggttggagcc agcgggcacc cgaggtccca gcacccggtc    30780
cctccggggg gcagagacag gcagggcccc ccggcagctg gccccgagga ggcgcccgga    30840
gtggggccgg tcggctgggc tggccgagcc cgggtctggg aggtctgggg tggcgagcct    30900
gctgtctcag gaggggcctg gctccgccgg gtggccctgg ggtaagtctg ggaggcagag    30960
ggacggccta ggcccgggga agtggagggg gatcgcccgg gtctctgttg gcagagtccg    31020
ggcgatcctc tgagaccctc cgggcccgga cggccgccct cggccccca gacagacccc    31080 agggtctcca ggcagggtcc ggcatctcca ggggcagcag gctcaccacc acaggccccc    31140
cagacccggg tctcggccag ccgagccgac cggcccgcg ccgggcgcct cctcggagcc    31200
agccccgggg gttggttctg ccctctctc tgtccttcag aggaaccagg gacctcgggc    31260
accccagagc ccctcgggcc cgcctccagg cgccctcctg gtctccgctc ccctctgagc    31320
cccgttaaac ccaaagaatg tctgagggga gccaccctcg gggcccaggc cccagagtcc    31380
agaggtcagg ggcacctcag ggtgcctccc cgggtcccag gccagccgga gggacccggg    31440
cagcccgggc ggccccagag gccggttcct cgcccttcc ccgggcttca gagcccaggg    31500 tgtccccag aagggaccct aggcgtcccc tctcctcccc tccaggcccg agcctctccc    31560
tcgcggagag gggcctcttc gagccctcaa gtccagtccc accgagaccc gagtggcccg    31620
gatcccccac cggcccttct ctttcccct actcctctcc aaccttcgct ccaccctaga    31680
ccccagcttc tggcctcccc gggtccacca ggccagccgg agggacccg gcagcccggg    31740 cgagtcgcct tccctctccc ctggcctctc cttcccgcct cccacccgag cccctcagc    31800 ttgcctcccc accgggtcca tcaggccggc cggagggacc ccggcggccc ggtgtcagtt    31860 cccctgcag ccgcccagtc tctgcctcca ggcaagggcg ccagcttttc tcccccagc    31920 ctgaggccca ggctcctgtg cactgtctgt aaagtccagc ctcccacgcc cgtccacggc    31980
```

```
tcccaggccc agccccgtcc acccctcccc acgttggaca ggccctctgt ccacccgggc   32040
catccccgcc ccctgtgtc cacccagtc ccgtccaggg gggactttat gtgacccttg    32100
ggcctggctc cccatagact cccatgtaag cctgcctcga gtaggtgcct ccagagcccc   32160
ttttgccccc ctggcggccc agcccgaccc ccgggcgccc ccaaactttg tccagatgtc   32220
caggggtccc cgagggcgag gcccagcccc ctcccgcccc tgtccactgc cccggtcccc   32280
ccagaagccc ccaaaagtag aggctcaggc catgcgcgcc ctgtcaccag gcctgccaaa   32340
gagccagatc taaggccggg agaggcagcc ccaaagcggg tgcagtaaca ggtaatctct   32400
ggtagtgatt tggaccccgaa atctgacact ttagagctct ggaggacttt aaaactctaa  32460
aaatcaaaac tttagaggcg aatgggcgcc attttgtccc cacgcgcgca taatggcgga   32520
cctaggccta aaaccccccag gaagcgggtc tatggttggc tgcgctgctg ctatctttag  32580
aggggaaaag aggaataagc ccccagacag gggagtgggc ttgtttgtga cttcaccaaa   32640
ggtcagggcc caaggggggtt cgcgttgcta ggccaccttc tcagtccagc gcgtttacgt  32700
aagccagaca gcagccaatt gtcagttcta gggagggggga ccactgcccc tggtataaag  32760
tggtcctgca gctatttctg gtcgcatcag agcgccagga gtccacacaa atgtaagagg   32820
gggtcttcta cctctcccta gccctccgcc ccctccaagg actcgggccc agtttctaac   32880 tttttccccct tccctccctc gtcttgccct gcgcctgggg ccaccttcat caccgtcgct   32940
gactccgcca tccaagccta ggggagaccg aagtgaagtc cctggaccag cccggcccgg   33000
gccccccggt atcgggccag aggtaagtgg actttaattt tttctgctaa gcccaacact   33060
ccaccacacc caggcacaca ctacacacac ccacccgtct cagggtcccc tcggacagct   33120
cctaagaagg caccggtcgc ccagtcctac cagagggggc caagaaccca gacgagtccg   33180
tagaagggtc ctcgtccagc aagaagagga ggtggtaagc ggttcacctt caggggtaag   33240
taacctgacc tctccagggc tcacataaag ggaggcttag tatacatgct tcttgctttt   33300
cacaggaacc tggggggctag tctgggtggg tttaggctgc ctcaagttgc atcagccagg   33360
gcttcatgcc ctcctcagtt ccctagtccc cgggcttcag gccccctccg tcccgtcct   33420 ccagagaccc gggcttcagg ccctgcctct cctgttaccc ttttagaacc acagcctgga   33480
cacatgtgcc agacgcctgg gcctctaagg ccctcgggtc ccctggacc ccggcctcag    33540 caaccctgct gctcccctcc tgccaccca gcctccccc ctcccgtcc ccttcgctc       33600 cttatcctcc cccggtcccc agtagggccg cctgccccc tgcacccagt acctgcccct   33660
cttggccacg caccccgggc caggccacct tagacccggc caagcccat ccctgaagac    33720 ccagcggcca ttctctctgg taacgagcag agaagaagta gaggcccgcg gccattgggc   33780
ccagattgag agaccagtcc aggggcccga ggttggagcc agcgggcacc cgaggtccca   33840
gcacccggtc cctccggggg gcagagacag gcagggcccc ccggcagctg gccccgagga   33900
ggcgccggga gtggggccgg tcggctgggc tggccgagcc cgggtctggg aggtctgggg   33960
tggcgagcct gctgtctcag gaggggcctg gctccgccgg gtggccctgg ggtaagtctg   34020
ggaggcagag ggacggccta ggcccgggga agtggagggg gatcgcccgg gtctctgttg   34080
gcagagtccg ggcgatcctc tgagaccctc cgggcccgga cggccgccct cggcccccca   34140
gacagacccc aggtctccca ggcagggtcc ggcatctcca ggggcagcag gctcaccacc   34200
acaggccccc cagacccggg tctcggccag ccgagccgac cggcccgcg ccgggcgcct    34260 cctcggagcc agccccgggg gttggttctg cccctctctc tgtccttcag aggaaccagg   34320
```

```
gacctcgggc accccagagc ccctcgggcc cgcctccagg cgccctcctg gtctccgctc   34380
ccctctgagc cccgttaaac ccaaagaatg tctgagggga gccaccctcg ggcccaggc    34440
cccagagtcc agaggtcagg ggcacctcag ggtgcctccc cgggtcccag gccagccgga   34500
gggaccccgg cagccgggc ggccccagag gccggttcct cgcccttcc ccgggcttca     34560
gagcccaggg tgtcccccag aagggaccct aggcgtcccc tctcctcccc tccaggcccg   34620
agcctctccc tcgcggagag gggcctcttc gagcccctcaa gtccagtccc accgagaccc  34680
gagtggcccg gatccccac cggcccttct cttttcccct actcctctcc aaccttcgct    34740
ccaccctaga ccccagcttc tggcctcccc gggtccacca ggccagccgg agggaccccg   34800
gcagcccggg cgagtcgcct tccctctccc ctggcctctc cttcccgcct cccacccgag   34860
cccctcagc ttgcctcccc accgggtcca tcaggccggc cggagggacc ccggcggccc   34920
ggtgtcagtt cccctgcag ccgcccagtc tctgcctcca ggcaagggcg ccagcttttc    34980
tccccccagc ctgaggccca ggctcctgtg cactgtctgt aaagtccagc ctcccacgcc   35040
cgtccacggc tcccaggccc agcccgtcc acccctcccc acgttggaca ggccctctgt    35100
ccacccgggc catccccgcc cccctgtgtc caccccagtc ccgtccaggg gggactttat    35160
gtgacccttg ggcctggctc cccatagact cccatgtaag cctgcctcga gtaggtgcct   35220
ccagagcccc ttttgccccc ctggcggccc agcccgaccc ccgggcgccc ccaaactttg   35280
tccagatgtc caggggtccc cgagggcgag gcccagcccc ctcccgccca agctgctttg   35340
attcctggga tattttgggg aatggtgtta actttctccc cttgtatttg ctattcaatc   35400
aacctgattc cccctgctca tacctccact cacaaccaag ccactacggc cacgtccaca   35460
acctcccgca caggtaagtg cttttccatt tttagcccca gcccgcctc tataagttct     35520
aggcaaacct ccaatcacca gccaccttcc aatgtagtct cttagagagt ggctgctacg   35580
cattagcgag agatttgacc cacacccagt agccacccga cgccaatctg tctacataga   35640
agaagaagag gatgaagact aagtcacagg cttagccagg tgatttgtga atttcagttt   35700
atttactttc ttccaatcaa gctttcccag cctccgcttc tcaggtccca gttatgggtt   35760
ttccatgggg gacctagtat ccgttctatt agattaactc gcaagatact aaaattaacc   35820
aaggtcagcc caagtgacgc gtgttatgcc aggctgccca ccctgaggat ttcccccaaa   35880
aatgggctgt tagtagggtc ctcctacccc ctctttaggc caggtgtgtt attttgttgt    35940
gttagtgcta tgtaatgtgt tgccgccagg tggcagcttg tttgtagatg tgcagcgccc   36000
cttaatggta ggtctgcttt agggctgcca ggtggcgcaa actaggatta attcacctgt   36060
atccctttcc ctccacccgc agtaactcag cgctggcgtg tgacgtggtg taaagttttg   36120
cctgaacctg tggttgggca ggtacatgcc aacaaccttc taagcacccg cgcttgtgtt   36180
ttgctttatc tgctgccatc atgcctacat actatcttgc gttacatggg ggacagtcat   36240
ataatctaat tgttgacact gatatgtctg gaaacccgtc actctccgta attcccacga   36300
atccttacca ggaacaacta tcaaataatc cattaattca actacaaatc gttgtcgggg   36360
aaaacactgg ggcacccgca ccgccccaac caccccccc acccccctcca cctcctccac    36420
ctgagcgcag ggatgcctgg acacaagagc ccttaccact ggatatgaat cccctgggca   36480
gtgacgccag tcaaggccct ctggcatctt ccataagaat gctttgcatg gctcaatacc   36540
ttcttagaaa cgcacggggc caacaaggcc ttcttaggcc actaggacca caaacacgct   36600
ctcaggtcac cttggaacgt caacctgtcc acaaccctcg ccaggaggca cccatcattt   36660
tgttacagag tcccgcgccc ccccgattca caccagtgcc catggtagcc ttaggacata   36720
```

```
ctcttcaacc cacaccacca ccaaggccta ctcttcctca acccagaata ccactgataa    36780
taccaccaag gcatactaat caaccagcca caacaccacc cacggcgcca caaaggctca    36840
cactagggca tcaactaagt ctaccaccgc atcctccccc gcatcagagc accccacatt    36900
gtagttctga tagtacagga ctccctccac ctcccacatc ttacagcatt ccttctatga    36960
cattatcccc cgaaccattg ccgccaccag cagcaccagc acaccccctt ccaggtgtca    37020
tttatgacca acaagcactt cctccaactc cagggccacc atggtggcca cctgtccgcg    37080
accccacgcc aaccactcag actccaccaa caaatacgaa acagggcccg gaccagggcc    37140
agggaagggg caggtggcgg ggcaggggca gaagcaaggg caggggcaga atgcacaaac    37200
ttcctgaacc acggagacca gggccagaca cttccagtcc tagtatgcct caattaagtc    37260
cggttgtcag tcttcatcag ggacaggggc ctgagaactc accaaccccc ggcccgtcta    37320
cggccggccc cgtctgtaga gtgacacctt cagcaacccc tgacatttca ccaatacatg    37380
aaccagagtc ctctgatagt gaagaacccc cctttctctt ccccagtgat tggtatcctc    37440
caacgttaga acctgcagaa ttagatgaaa gttgggaggg catttttgaa acaacagaat    37500
ctcatagctc tgatgaagag aatgtagggg ggcctagtaa aagacctcgc acctccactc    37560
agtaaaagac cttactctct ccagtaatca atgtatccca aataaatgtt aatgattttg    37620
ttcttaacta ttgacccgcc tgtcattcta ttaattaaac aagggaagct atgtttagct    37680
attccaccaa cactgcacca atggacagcc aaaattggtg ccttgctcac agctcttttt    37740
gccagtggct tacagcccag taggcagctc agaaaagttt agctattcca ccaacccggc    37800
cccaatgaat gcttgccaaa attggggcct tgctctcagc actttgccag cgacttatag    37860
catggtaggc cgctcaactc ggcctgtctt actgccagc ctactctcca cttccagtcc    37920
atgttcgcac tcctatgcat ttccttccct cccacttta tcccagtccc aacccaaaac    37980
cacacacaac acatagaatt gttagtttaa acagtttatt gatacatggc tgcttttagc    38040
ctaattgtgt attgctctcg ttgccaaaac ctggtgtaag ggccggcacc cgcaacatgg    38100
ggaaaacata accgccgcca tcccatgggg agggtagagg cggttgacat gtaggtgagt    38160
agtgtaagaa gcatggcgaa gtagacaggt tacttttaga gtgtagtgta cagggccggg    38220
cgcaacagtg ccaccaaccc ggggtctgag cattccatgg gcagcaggga cactgcacta    38280
ccgccaggtc caggggcagc cggggttcct ggcgctccgg ggggcagcca ggcggccgcc    38340
ggtgggtccg ctgggccgct gccccgctcc gggtggggg tggccccgct gggcaccgct    38400
gcgccgccgc caggtccagg ggcagccggg gttcctggcg ctccggggc agccgggcgg    38460 ccgccggtgg gtccgctggg ccgctgcccc gctccgggtg ggggtggcc ccgctgggca    38520 ccgctgcgcc gccgccaggt cctggggcag ccggggttcc tggcgctccg ggggcagccg    38580
ggcggccgcc ggtgggtccg ctgggccgct gccccgctcc gggtggggg tggccccgct    38640 gggcaccgct gcgccgccgc caggtccggg gcagccggg gttcctggcg ctccggggc    38700 agccgggcgg ccgccggtgg gtccgctggg ccgctgcccc gctccgggtg ggggtggcc    38760 ccgctgggca ccgctgtgcc gccgccaggt cctgggcag ccggggttcc tggcgctccg    38820
ggggcagccg gcggccgcc ggtgggtccg ctgggccgct gccccgctcc gggtggggg    38880 tggccccgct gggcaccgct gcgccgccgc caggtccagg ggcagccggg gttcctggcg    38940 ctccggggc agccgggcgg ccgccggtgg gtccgctggg ccgctgcccc gctccggtg    39000 ggggtggcc ccgctgggca ccgctgcgcc gccgccaggt cctggggcag ccggggttcc    39060
```

```
tggcgctccg ggggcagccg ggcggccgcc ggtgggtccg ctgggccgct gccccgctcc    39120 gggtggggggg tggccccgct gggcaccgct gcgccgccgc caggtcctgg ggcagccggg   39180
gttcctggcg ctccgggggc agccgggcgg ccgccggtgg gtccgctggg ccgctgcccc    39240
gctccgggtg ggggtggcc ccgctgggca ccgctgcgcc gccgccaggt ccaggggcag     39300
ccggggttcc tggcgctccg ggggcagccg ggcggccgcc ggtgggtccg ctgggccgct    39360
gccccgctcc gggtggggg tggccccgct gggcaccgct gcgccgccgc caggtcctgg     39420
ggcagccggg gttcctggcg ctccggggc agccgggcgg ccgccggtgg gtccgctggg     39480
ccgctgcccc gctccgggtg ggggtggcc ccgctgggca ccgctgtgcc gccgccaggt    39540 cctgggcag ccggggttcc tggcgctccg ggggcagccg ggcggccgcc ggtgggtccg    39600
ctgggccgct gccccgctcc gggtggggg tggccccgct gggcaccgct gcgccgccgc    39660
caggtccagg ggcagccggg gttcctggcg ctccgggggc agccgggcgg ccgccggtgg    39720
gtccgctggg ccgctgcccc gctccgggtg ggggtggcc ccgctgggca ccgctgcgcc    39780
gccgccaggt cctgggcag ccggggttcc tggcgctccg ggggcagccg ggcggccgcc    39840
ggtgggtccg ctgggccgct gccccgctcc gggtggggg tggccccgct gggcaccgct    39900
gcgccgccgc caggtcctgg ggcagccggg gttcctggcg ctccactgca cctggaatgc    39960 agggtgggg cgtggtcccc tggaccccag ccccgccgat ccctccccca gggcgtaccc    40020
ggcttgcctg gttctgggc tcctctgggg gtcgctgcat ccgccggtag ggttcgaatg    40080
ggcgtggtcc gcttgctctg ctggcccggt acgcctggat tgccggctgg gggctggggt    40140
cccgggacgc cccctccctg ctcccacccg gttccctccc caggggcgtg ccccgcttgc    40200
ctggtcctgg agctcatccg gggatgctgc atccgctagt ccgacctggg tgggtgcggt    40260
ccgctggccc caccctgggg gtcgccgccg ggtctgctgg tccggtgcac ctgaaaggca    40320
gggggggggc agtgagggag gggcgtggtc ctgggacccc gcgccgactg gcaggggtc    40380 cccatggcac aggcctaggg gtccagggg cagccgcggc ccagcgcgcc ccgttcacgg    40440
gggaggaccg cggccgagcc accaggggcc cggcggggt ggggggtgcg ctcccaggcc    40500
ggaccctggt gccaggcagg gaccccgcgc caccccgcttc atggggggg aggccgccgc    40560 aaggacgccg ggccggctgg gaggtgtgca cccccgagc gtctggacga cgctggcgag    40620
ccgggccggc tcgccttctt ttatcctctt tttggggtct ctgtgtaata ctttaaggtt    40680
tgctcaggag tgggggcttc ttattggtta attcaggtgt gtcattttag cccgttgggt    40740
ttcattaagg tgtgtcacca ggtggtggt acctggaggt tattctattg gataacgag    40800 aggaggaggg gctagaggtc cgcgagattt ggggtaggcg gagcctcagg agggtcccct    40860
ccatagggtt gaaccaggag ggggaggatt gggctccgcc ccgatatacc tagtgggtgg    40920
agcctagagg taggtatcca tagggttcca ttatcctgga ggtatcctaa gctccgcccc    40980
tatataccag gtgggtggag ctaggtagga ttcagctagg ttcctactgg ggtaccccc    41040 taccctacct taaggtgcgc caccttcct ccttccgttt taatggtaga ataacctata    41100
ggttattaac ctagtggtgg aatagggtat tgcagctggg tatataccta taggtatata   41160
gaacctagag gaagggaacc ctatagtgta atccctcccc ccctaccccc ccctcccttt    41220
acggttgcct gagcccatcc cccaccccag cacccggg tgacgtggca cccgcgtgc      41280 cttactgact tgtcacctt gcacatttgg tcagctgacc gatgctcgcc acttcctggg    41340
tcatgacctg gcctgtgcct tgtccgtgg acaatgtccc tccagcgtgg tggctgcctt    41400
tgggatgcat cactttgagc cactaagccc ccgttgctcg ccttgcctgc ctcaccatga    41460
```

```
cacactaagc ccctgctaat ccatgagccc cgcctttagg aagcaccacg tcccggggac   41520
ggaaggggac ttggggtgat tttctatgtg ggggtggaaa tatgagcaag aataaggacg   41580
gctccttatt aacctgatca gccccggagt tgcctgtttc atcactaacc ccgggcctga   41640
agaggttgac aagaagggtc aaggtttcgt ctgtgtgttg aagggcaggg gctgttgggt   41700
gcatctggaa cggcttacct cgggtaactg tttgccatta aaaggttggg gattaggttt   41760
agccccttta gctgccattt cgaaccgggg tgtgcagatg caggtctccg ggtgggcagg   41820
cagtacgaga tgtcacgttg tgttgtcttt cctcccaccc ctgtcctggc tgtggcaaat   41880
gcgaccctca tagagttgtg tttcaggtct gtgtcctgtt ttgcggtggg ttatttcccc   41940
cctcagtgtt cgccagctta tttccccagt ccccacgtac tggggcctgt ggacacctga   42000
gggagcggcc gttggtgggc atgtgttgga attgctccca ccctcaattt tcgcttgcct   42060
tcttcccttg ttaacctgat agcatagcct ctaggtttcc ttgtaggtct gtttgggttt   42120
gttggttcac gtggtgctaa cttgaatttt ttggttttct agttccctct taattacatt   42180
tgtgccagat cttgtagagc aagatggcct attcaacaag ggagatactg ttagccctgt   42240
gtatacggga cagtcgtgtg catggaaatg gtaccctgca tcctgtgttg gagctagcag   42300
caagagaaac acctctccgc cttctcgccag aggacactgt agttctgcgt tatcatgtgt   42360
tgcttgagga gataattgaa cgaaattcag agacatttac agaaacttgg aacagattta   42420
taacacacac cgaacatgtg gacctggatt ttaactcagt attttagag atatttcacc   42480 gtggagaccc aagccttggg cgcgcgttgg cctggatggc ctggtgcatg catgcctgca   42540
ggacattgtg ttgtaaccag tctactcctt actatgttgt ggacctgtca gttcgtggga   42600
tgttagaagc cagcgaaggc ctggatggtt ggattcatca acagggcggc tggtctacat   42660
taattgaaga caacattcct ggatccagaa ggtttagctg actttgtttt cttgctggac   42720
tgactttgag tctgttagtt atatgtagtt atttatttat ctccagagga agacactaat   42780
ctatacattt tctcagcact ttatatgaat cagggtcatt gggcctgcgg ggaactgagc   42840
cagtaggata ttaggcaagg gtgacacagt gcccatgcat tataatttaa ccaaacagtg   42900
gtcgtgagtt ttaggccggc catggggggct acaagaata acatgccaat gacccggccc   42960
ccactttaaa attctgttgc agcagatagc tgatacccaa tgttatcttt tgcggcagaa   43020
attgaaagtg ctggccatat ctacaattgg gtgtcctagg tgggatatac gcctgtggtg   43080
ttctaacggg aagtgtgtaa gcacacacgt aatttgcaag cggtgcttca cgctcttcgt   43140
taaaataaca caaggacaag atactaaaga aataactgag gtgagtgtgg gaagatggga   43200
atactatgtg ttatgttaac gggtgagagc ctatactgca gcccagactc ggggggagga   43260
ggaaatggta agagttatac tctacttatc ttttttgaca ctacatttaa ctgttatgta   43320
acaatgtttg cttattttca tgttcaataa acgctatgtt aatgatgaag aacctgtgtt   43380
ctttggaagt gggcccaatg gggtagtagg ttttgggagg gtgccgtgct agatatttca   43440
actgccacag acccattttt gtcccacctg ttaccacatt ctaggtcctg catccagtgg   43500
gccaggtgtc tcaccatggc tctttctagg tggataccac agtccaggcc cccaaggcta   43560
ccgtgctaat tacctcctca tgtccacccc caccctgtgt tactgtcgcc tgattatcct   43620
ggcttagcag cctccaagtt ttacaagacg tcccattgcc ctgcccttgg tccaagtctc   43680
gcctgttttc agcagcctgt tgtagcctgc ccccaagttt cgcaggtttc ccccatgctt   43740
ccacccgtta acccaatagc atgacagcca atccaacacg aggcaagttt taagagttaa   43800
```

```
aagcaactac tgtttatttt ccaaaatgag ctgggtatag ttgatgatct gtaggcgcag    43860
ctcatcccca cattccaggt ccttgatggc ctcgtagatg gcatcttcgt cgacattgac    43920
agccttctca tataccgtgt ctctggggct gacctttata cagaaggcgt ccctactag    43980 gtccacggcc agctcgtagg tggggcctat gttttcacat aacagtttca agcaggtctc    44040
tgggatgtga agggaggtgc cctggagcag gagatgcatg attaggcgcc cttttccatt    44100
tgtgctgaag atggggcaga tggtgccaca aaagtgtccg gtgaccaggt aagcgtagag    44160
aaggctgggt tgggaaagtc cagcctttac tgcactggga gagctgctga gcagagacac    44220
atagaaggtc ttgttgggta ttatcttgtg gacattgttg aagaaggaga gctgggtgga    44280
gctaaactcc tgaggcacat gaacctggga cctattgatg cagatctcgc agtgagaccc    44340
cagagtcagg ctgtggccga agggagacag gcgaaggcag cgcccggggg agagagtgca    44400
cagtgacagt gggagaaaca cggcctctga gacatgtatg ggggtgttca tctcacgcag    44460
aaaatctttg cccagctcaa agttggcaga gattcccctg aagaagtccc gtagtgaaaa    44520
atgggatctg tctacaccat gtctggtgtg ccgggaacat attgatcggg ccacactgcc    44580 aacccttttcc attcttccca gctctgagcg agattttcca cacctggaca ccgacttcac    44640
gctatgcgcc gaggcctttg aggccgtgta gtttctgtgg tgcggatgca ttaggcggcg    44700
caatgcggga tctgccggtc gctgttggcg tgcattcacg gcatctgggg tgaccggggc    44760
catcgggttt acttttcaca cgtagacctg ggaagtttga taggactgta ccaggtcaag    44820
gccgtggatg cgcaggacca cgtccagttc cttagtgaca tccacgagga ttgttttgcc    44880
cactctggcc acttgtgtgg atttaaatat gtacacaagc gtaattaacg agtcacagac    44940
cccctgttcc agattctgac cggctgcaag cgctgcctta aaggcctgga agctgggtgg    45000
gtaaatctga ccaaacagca cgctcggatt cgtgatgctg tggttgatgg cacacagggg    45060
gtcgcagaac aggtgcttgt ggaagtcttg cggggtgcac atctgcagcc aggcccttag    45120 cctgggcat ggcacatcca gcagcgtgtt ttgggtcttg atgaggaaca cgatcctgtc    45180
taggattttg atgttgttgc cgaacgagtc aagaatcagg ctcttgaagc ggtcaagggt    45240
gtccttggcg tccgggtggg ccccgaggct ctcgcagagt gggcagatgg tccgtgaggc    45300
attcttgtgc cttagtccaa acatgggggc caggaggcag gggccctgcg aatggtcgcc    45360
agcctccggt ctggtgatgg ccagggccaa ctccgccagc tcatcgccgc tgtattccgc    45420
gtttaaaccg atagcatggt ggcctggccc cccgagcagg tccgtcccct gccacgtacc    45480
taatagtagt ccacagtagt cggccttggt tgtaattttta ggagagagtc ctccctttctc    45540 ggccctgaga aatggatgct gaactcggtt tctggtaggc aggtggcagc acagggcggt    45600
gtacaggccc ctgccgacgt cccctgggac atcctgggaa tctttgcagg ttctgggtcc    45660
agggagggta agaaaagtgg gggtggttct gggccacatg gacttgaagc agaagttggc    45720
cggggactgg ccggtgagga tggatttcag aaactccaat ttgtagtagc cgaggttggc    45780
atttctaatc atgtcagaag aggacacagg gaggaagcac cggcaaatgt aaaagtgaag    45840
ctggatgtca atggcaagaa tcctggaggg catgaagagg gaatccaacc ccccggccat    45900
ggggaagtat tttatcagga tgtgtaaaaa gtccatgcct gtgatgaggc tagagatcca    45960
ggctcgtggg gcatttagac agtagtagca gagcagggca tagtcctcaa agaaggccac    46020
gggggcatct gagtgattga ccagggtgtc gagcagatca caaactcggc aggtgctggc    46080
tggagagagg gactcgtagg tgtggacgag tggtgggtag gctatgcctt cttccgcgtt    46140
ggctggaaga taggagtggg ccatcaaaag gccgactgcc tcgaactggc ttttcagatt    46200
```

```
gtccacggtc cagggcacaa agtcctccat ctttggagtt ctgcccgcga tctgtgccac   46260
ctctgttacg ccactcctcg tgagggggca gctggacagt cttttccgg tcagggggtt   46320 tggctcgttt gcgctcgtga ctttgtgagc catgacacat ctgggtggca aggtgaggtc   46380
ttctgggttt ttaataccgg ggtcggcacc agtttctggg acaccgccac aaggacaagg   46440
tgggctagca agttctcgag tctacgaaga ctccggggc agtcttttga gtttctcgcc   46500
tatgatccac cccaatctcg ccccctaat tgcgccatct gcctacgcga ggctgaacct   46560
cctgaatcac tgcatctttc ttgaggcgtt taaagaagag aatagtggcc agggcctcgg   46620
tggggtccag cgtgaggtct tatttttgaa aagggatatt ataaaacagg tcattgctcg   46680
gattgtggca gccgatagca ccctagatct agtgaatcat ggcgagcccg aagagaggc   46740 tcctagacga gctcaataac ttaattgtgt catttctgtg tgactctggg tctctggaag   46800
tggagagatg ctccggggcg catgtgttct ccaggggcag ctcccaaccc ctctgcaccg   46860
tgaagctgcg ccacggacag atttaccacc tggagtttgt ctacaagttc ctggcctta   46920 agctgaagaa ctgcaactac ccttcctcgc ccgtgtttgt gatatccaac aacggcctgg   46980
ccaccaccct gaggtgcttt ttgcacgagc cgtcgggtct cagatcgggc cagagcggcc   47040
cttgcctggg tctctcaacg gatgttgacc taccaaagaa ctccatcatt atgctgggcc   47100
aggatgactt cattaagttc aaaagccccc tggtcttccc tgctgagctt gatctcctga   47160
aatctatggt ggtctgccgg gcctacatca cggaacaccg gacgacgatg cagtttctgg   47220
tgtttcaggc cgccaacgcc cagaaggcct cgcgggtcat ggatatgatt agtgatatgt   47280
ctcagcaact gtctcggtct ggtcaagtcg aggatacggg cgccagagtc acaggtggag   47340
gaggtcccag gcctggcgtc acgcactcgg ggtgtcttgg ggactcacac gttaggggc   47400 gcggtggttg ggacttggat aacttttcag aagctgagac cgaagacgag gcgagttacg   47460
ctccttggag ggacaaagac tcgtggtcgg aatccgaggc ggcgccgtgg aagaaggaac   47520
tcgtgaggca ccccatccgc aggcaccgga cacgcgagac tcgccgtatg cgcgggagcc   47580
attcacgggt ggaacacgtg cccccgaga cccgggagac ggtggtgggg ggagcatggc   47640
gttattcttg gcgcgccaca ccttatctgg cacgggtgct ggctgtcacg gccgtggccc   47700
tgctcctgat gtttctgagg tggacctgac gttgcaggcc cttggggagc ggggttctc   47760 caggctcctg gatctggggc tggcctgcct ggatctgagc tatgtggaaa tgaggaatt   47820 tgtggtttgg ggcaggcccc cagcttctga ggcggctgtg gcctctacgc caggctcgct   47880
tttccgaagc cactcgtccg cctactggtt gtcggaggtg gagaggcccg ggggccttgt   47940
ccgctgggcc aggtcacaga ccagcccctc atccctgacc ctcgcgcccc atcttggccc   48000
gtccctcttg tccttttcag tggtcaccgg tggtgggtgt ggagccgtgg ccttttgcaa   48060 cgccttttc ctagcttatt ttttggttgt gcggtctgtt ttccccgcgt tttccgatag   48120
aatagctgcc tggatctgcg cccagtcccc tttctgcgaa acacccggg ccgtggccag   48180 gggttaccga ggcctcgtga agaggttctt ggcattcgtg tttgagcgta gtagctatga   48240 ccccccttg ttgaggcaaa actctaggcc tgtggagcgc tgctttgcca tcaagaatta   48300
tgtcccgggc ctggactcac aaagctgtgt gacggtcccg agcttctccc gctgggccca   48360
gtctcacgcc agcgagctcg atccccggga gattcgcgac agagttacac cagcgactgc   48420
accttcgttc gtggctgatc atgcctcggc tctattggcc tccctccaga agaaggcctc   48480
cgacaccccc tgtgggaatc ccattcagtg gatgtggtac cgcctgttgg taaactcgtg   48540
```

```
cctgaggagt gcccactgtc ttctgcctat acctgccgtc tctgaggggg ggagaaagac    48600
gggcggggc gtaggggagg atctcgtggg ggccggggg ccctgcctga gccgggatgt     48660
tttcgtggcg atcgtaagcc gcaatgttct ctcgtgtctg ctgaacgtgc ctgccgcggg   48720
tccccgggcc tacaagtgtt tcagatccca cgcctccaga ccggtgtctg gcccggatta   48780
ccctcccttg gccgtgtttt gcatggactg cggttactgc ttgaactttg gaaagcagac   48840
aggtgtagga ggcaggctca attcctttag acccactctc cagttttatc cccgtgacca   48900
gaaggagaag catgtgctga cctgccatgc cagcggccgt gtgtactgct ccaactgcgg   48960
ctctgcggcg gtgggctgcc agaggctggc tgagccaccg agcgcccgct cgggctggcg   49020
gccccgaatc cgggcagtgc tgccgcacaa cgcggcctac gagctcgacc gtggctcccg   49080
cctcttggat gccatcatcc cctgcttggg acccgaccgc acttgcatgc ggccggtggt   49140
cctgcggggg gtgacggtca ggcagctcct gtatttaact ttgcggacag aggccagagc   49200
cgtttgctcc atctgtcagc aacgccaagc tccagaggac gcccgcgacg agcctcacct   49260
gttctcctcc tgtttagagg tagaattgcc acctggtgag cggtgtgcgg gctgccgtct   49320
ctatcagacg cgttatggca cgccggctgc ccaagcccac cctccagggg aggctggagg   49380
cggattttcc agacagtccc ctgcttccta aatttcaaga gctgaaccag aataatctcc   49440
ccaatgatgt ttttcgggag gctcaaagaa gttacctggt atttctgaca tcccagttct   49500
gctacgaaga gtacgtgcag aggacttttg gggtgcctcg gcgccaacgc gccatagaca   49560
agaggcagag agccagtgtg gctggggctg gtgctcatgc acaccttggc gggtcatccg   49620
ccaccccgt ccagcaggct caggccgccg catccgctgg gaccggggcc ttggcatcat    49680
cagcgccgtc cacggccgta gcccagtccg cgacccctc tgtttcttca tctattagca    49740
gcctccgggc cgcgacttcg ggggcgactg ccgccgcctc cgccgccgca gctgtcgata    49800
ccgggtcagg tggcggggga caaccccaag acaccgcccc gcgcgggca cgtaagaaac    49860
agtagagggc acgaaacatg gtgtatgcac tttattaata aacaattaca gatacaaaaa   49920
cttgagtctc tcgaggtctg cgatgaggcg gtgggtggaa cgctccagct tgcggcgaag   49980
ctggctcacg aagcgagaca gtactcggct agcctgacta agggtgaggc tataacgcag   50040
gtcctgttcc ggggcggcgg tggatagaga ggaggggat ccggagggga ccactaggtc    50100
gccgaggtc gaccctcctg tcaccactc cctgataatg tcttcaatag acagaaattg     50160
ggtgaccact gagggagtgt tccacagtaa tgttgtctgg tcgctagatg gcgcgggtga   50220
ggccacgctt tgcgaaaacg aaagtgcttg aaaaggcgcg ggatagcgtg cgctaccgga   50280
tggcgggtaa tacatgctat ccttacattt tggcatttg ggcagctggg aggcggcgga    50340
tggggtgct tctttcgca cggtgtatgt ttggggaccc gcatgccggt actgggatag     50400
gcgcacctcg ggccgcgcgc caggctccga gccggaatgc attgggggca atgggattgc   50460
gggggattgt tgctgtctgc tcctgacagg gagagacacg cgcggcggag atgcagccga   50520
cggcggggcc gcggtgggct gccccgagg acggcgccg gccgccagcg ccccccgtggc    50580
ctttggcacg ggcctggcac ccaccgcttt aattgtgggg gtgggcaggg cagctgcatc   50640
ttggggcctt tgtgcttgcg ttttttgggg gcgcggtgcc aatgcaccaa ctgggtgtgt   50700
cgccggggcg gccaagccgg accccagggc gggtgcctgg gggatgggaa agccggacgg   50760
cgcttctccc gggtcgaacg ctggagtagc ggaggctgct gcgccggcgg ccaccacggg   50820
cgcacggggt gcgcagccga cggccgtggg gaggcgggtg gcggagggcc gaatctccgc   50880
ggcttcttcc cggccccct gctgtttctt ctcccgttgc atgatagaat ggccatagggg   50940
```

```
tgggtcctga gaggaggctt gtgtgtcctg gggctggagc ccaaaagtcg ttaaagacgc    51000
tgctgatggt gtgggagcta tgcctcccgt cgactggccg ggcttgtagg gggctgaggg    51060
tggataactg ggcttctgtg aaggcaccaa ccctggaatc tggatggtat gtttcttctg    51120
tgaccccgag gcagtcgatg gtgtagagtt tggagacaat gtgtagacga tgggcccttg    51180
ttcagaagcc cagggacttg agggggggctg ttgtggtgct ggttggggaa ggagctccag    51240
ggaatctttg ggccatggcc ttggggaggt tcccggagac cggtctgggc tctcggaagc    51300
cctcgtttcg gccccgaaat agggccttgc catcaatcgg gggcctggga gagtgatggg    51360
ggcggccaat cccggggtaa ctgtcacgtc ccggggggag gaggtaggag acagccagtc    51420
cctgggcctg ccaggggcca ccttctctaa gaggggggctc tgtgggctgg gagggccaga    51480
ggcctcagat tcagcagtag tgctcccctc ttcccccctgg tccgtctccc ctcctcccaa    51540
ctgctggagc cggtcggagg aggccggggt gttatctgct gactgaaacc cgtccccgct    51600
gaccagtccg tgccccaccc ttgggggaa accggagaac agctcctgga cgttgcgtgg    51660
attcggggga agctggtatc caaccggcag tggaggatct tcgtgctcgt agaaggaggg    51720
gttgagtaca tcggtcggcc atcgtgaggc cccggccgcg ttaaagtaga actgcacgtc    51780
cggcagattg tgccgatagg tgaaacactt ccagatgatg ttttttctgt tggccaggat    51840
ggccacggtg gggggcctgg cctccttagg tttggcggcc ctggcctcgg tgagaagctc    51900
gcgtagccac acggcctggc gtgcaaagat ggacatctct ggctcgaaag actcggagta    51960
gccgtccagg tcctgcagaa aattcagcga gatggtctcc accagggacc ggaagggctc    52020
agagtgcccg tcgcagtaga ggaggggagc aacgaccctg acctgtccca gggtcttcag    52080
gttaaacaga tattgagagg agacaaagag agttaggggc cgaccgagga aggccgccgc    52140
cacggccgcc tcaaaaacgg agacggggat ggtgtcaccg gagcccctct taggaccggt    52200
aatgggagtg ccataaggca taagatttct cagggcccgg ccggtaacgg tgccgtagga    52260
agacggggtt tcgcggggga cctcgagtcc ctccgccctg gggagctctt ctccgcgtgt    52320
ataggcctgc ttcacaaagt cgcgcaggta gtcctgaaat gcgaccgggc cctccagcgg    52380
gcgcaatgag tgccagagct gctgaaggggc ctcggggggcg aagcaccggc gtgcgaggag    52440
cagcatgcag gctcgggcgc gggccgtact ttggttgtgg accaggccca agaactcggg    52500
gtgcggccag agggcggccc gggtatccat ctcctcccag gcgtcctgga agaagatgaa    52560
gccggtgggt ggaccggcga tgcggtggcg ggtgaggcgg cgcgcgtctt ccccgtcgtt    52620
gctgccgcgg gtggttgagg gcatgccccc cctcccggag gctggactcc tgaccagcct    52680
gtaggtgagg accgagtccg acaggaggtc tcccaaaccc ccatctctcg ctagagccga    52740
gaccaggccg agtcctgcgt agaacgatgg ggcgcccagg aaggcggcag cgtaggccgg    52800
atgtgtgccg accagcagcg ccatcatctc ccgttgttcc aatagaataa cttcccggtc    52860
tgtggccggg gctggataag gggggtgatt cctagaggcg atgagactgg cgtgcgctaa    52920
aagcgtcatg gccacaatgg ggttgtctgc caggtcttcc atcagggctt tgggcgcaga    52980
gacgtattcc cgaagcagct ccccggcgtt ggactccacg tcgggccagg tgtcccagta    53040
ggagtcggcg gcgcggcgc tgaggcgggc ggaagctaca ctggccaggg ttcttctcct    53100
cctctcttgg tcatcctgcg ggggaccaat agcttggggg cgtccggctg gggtcaggga    53160
aaaggcctct gggttctcca gcacggtggg catgacatat tccagaaagt tgtgtagac    53220 ggggatgtag ttgagcggct cctgggtgtc tgcggagacg taggccgggt taaggggtc    53280
```

```
gcagggagac tctgtttcca gccagagggt gccggcgtat ttcgccggcc ctgccgccgc    53340
cagaaattgt gcccgccggg tcggggctcc attgccccat ccagttggtg gtgccgaaat    53400
cgtgatgagg aggggcaggt tgttggtcaa gggatgctta acgaaaacgg taggctgggc    53460
ggtctcgtaa aaagccagga aactctgctt ggccgaggca tagcgcagca gcttgtcctt    53520
gaggagtgca tactgggagc cagccgaggc cccaagcgcc aggcccctgg cagcctccac    53580
cacgatcttg agctggcgcg ggtcggtgtg gcccctggcc tgggtgacca gatcctgcag    53640
cgttccctgc agctgggact cttcctgggc ctcctggatg atggcctcca gtcgggagag    53700
gcgccttttc cagtctgcga cggtctcctt gccccccgcg accgcttgg ggtccaacgt     53760
ggccagagcc aacctcagct cctccatgcc atccatggag ttctgggcca tgccctcgac    53820
ttccaggagc cgtgttagct catgaatttc accgtcagcc gcagcggcta ggttcagcca    53880
ggcacccaca cccccagcta aggccagggc tccttcggaa agacccgca ctgcctcgca     53940
gatgccccgg atccacttgg cggctgccag ggatttccgg tagggccacg agccgttccc    54000
ggccgctgcc cgggccaggg cggcctcgag gggagcctgg acaggggctt tgggcgggga    54060
ggggagcagg ctccggagtt catcgtcggg ggcttcgtcg cgtgacctgg agaggacggc    54120
ctccagagcc gtgtgaaagc cccgccgagt gcttgccgcc atctcgtggg ccttcgccat    54180
cagggtctgg ctctcccgga cctgctcttc cagcgcccgg acctcggccg cctcggcctc    54240
ggtcagcagc tctgagaaga agtccccgt ggcctggagg agatcgtccc gctctcgcct     54300
tgtcagcagc tggggcttct taggccagag cgccgagtcc gaggccagcc tgggcggggc    54360
ggttgcctgg gggatagttg gaggaggagg caggttagcc tggcctgggt cattagtggc    54420
ttcgggtagc gtccgatcca cgtactcgct cacgatggcc gtcagggcag cctcggctga    54480
tcgtcttttt tccagaagcc cggccagccc ccgctcgtac tccgcgtagg gggcctccag    54540
atccgtgttg accaccgctg atttcatgtc cggggactgc agggcctggc gcgtctgcgc    54600
gagggccgaa cggatggcat cggccgccgt cctggcacga aagagggccc cggccgcttc    54660
ctccgctcct cgcccctcctc ctccttcttt ggcggtagcc gcgggggtgg cgggccaagc    54720
gtccagtctg gccagagggc cggtctcgat ctccgtgaac cagccgggtt ccacggcctc    54780
cattctctcc gccgcaccac catcgtccac gagcagggat cgcagtctct ccctcctcac    54840
cctcgttatt cccaatagca tagcggcaag gatctgtgtg agggagtcca agatgtccgt    54900
gtttctggct actgccgccg ctgctgccgc ggctgagtcc gtattgtctg gcagcaggga    54960
ggccagcagg gtgttccagt catcgggcga agtgggagcg ggctctgggc gtgccccag     55020
cgccttccta attctggccc aggcctcatt cgcctctcgc gctcgccgct cccgcctctc    55080
cttgtcttcc tgttctcgga gcttctcctt ttccttgcgc ccggtctcca taagctgccg    55140
cagcttcttc tcatactgtc gcttgagctc tttgttgggg gcagtgtcca gaaaggcctc    55200
gagctgttcc tcggtggcgg gcttaaagcc ttcggcctcc aggcgccagg cctgcacctc    55260
cttctgtctg agctgatcgt tgttgttatt cttcaatttc tgcaggtaac ttaggaagcg    55320
tttcttgagc ttccctggga tgagcgtttg ggagagctga ttctgcagcc cagagagtag    55380
tctcagggca tcctctggag cctgacctgt gaccgtcgca tcatagaccg ccagtagacc    55440
tgggagcaga ttcaccgccg cggccgtctc ctttaaggtg ctgtgagtag caaaattctg    55500
caaggccact aggcgcgctg gctccagcgt cagccggttg cccatctcga atgtgtgcag    55560
ggcctctgag accatggggt ccaggatgcg gtcaatgcca cctgcacct cagggtcaag     55620
gaccggcaag tcacgataga ggtggtctat gctctcctcg aaggaggcaa tgtagttatc    55680
```

```
gatggtgtag aaggtgatgg atttcaggat gttcatcagg tacttttggg agcggacaat   55740
ctgctgtata gtgtcacgta ggcggatgta cgtggggttc tttgcggccc cgactatcga   55800
ccctgcattt gcgatgtact tttctatgac ggggatggtg agggccgcgg tgtcggccag   55860
tggtggcgtg gcttcggggt tgtcgtggtt ggcggtgtc gcagagggag aggcgggaga    55920
gatgggggcg cctggggccg aggccacacc ggccaggccc aacattgcct cgatgtcgtc   55980
caggatggtc cggaggcgct tttcgttttc tctggtggtc tcgagctcct tctgtttttt   56040
cgcgactgtc tcaaactctg aagggggc aatgctgggg tcgtcctcct caactcgctc     56100
caggggccag gggataccgc tcatatcact aagggcggtg cccaggtaga ggagctcgcg   56160
atagtcccat tcaatggacg tgtaccggat gtttaggaga ggcagggagg cgatgatctg   56220
gcatgtgtgc cgcaggtgtg tcaggaggtc gtcaaaatcc atcaccgttg ggaggcttgg   56280
gtcctcaagg taggagagat aatcggaggc cgccgaggcc accttgtccc tgatgtccgc   56340
cgtacacctg cgcacgtgca gggccgcatt cttggaccgg acgggcacgt tgtggacaaa   56400
ggggggcact gaggcggcgg gaggggcccc atactctatc gctgtcaaca gcgccaaaaa   56460
gcggacgtcc tcctcatcta ccccagcctg ttgtctggcc acggccgttc gggcggcctc   56520
cgccagggat aggaggcgct tccagctctc gtcgtccagg accaagggga catccacgtg   56580
cgggcccctg tagatggaat gatcctcggg ttctcctcct ccttcctccc cctcctgatc   56640
tccgcccgag agcaggtcgg tcaggcgtct acgggccgcc tccaggtcaa attttccgtc   56700
gccgctctcg gccagctggg gaatttcagc cagcatctta gcaccggcat ctacacggac   56760
cgcgtccttc gtggccaggg acggcaggca ggcctccagc tttgcggcca ggtgctcatg   56820
gaactctccc gctcttccct tgttttctga tagcatgttt gcgaggtttt ggatgttaag   56880
ttcggaagtg agcagttgct ccaggtccag cgtggggacc tgcagatgtc ccgaccagtc   56940
ctttaagaat tccagcagat ttagcacagc cgatcggtcc ctactcctta ttagcccctg   57000
ctcgaggacc actgtcacaa gaagatagtc tatcatgctc aaggcatctg cctctggcac   57060
ttccctgtta gaggccgggt cgtagacgat ggcctgttcc tggtaggtat gtccggctat   57120
tctcgcaatg ttgctctcga ggggcacaaa gtccatctca ggagtctcta tgtcaaaggt   57180
ggtctgatag tattggctcc tggcggtgtc cagtgtgatg ggggacgtgg gggcactgga   57240
tcccgattcc aggctgttgg agaacacttc atcttcaaac atgtcttcat cctctgtggt   57300
ggggatatcg gaggctaagt cgctctccgc ttcttcagag tcggacatgg ataggaaagg   57360
ctcctctagg tcagacaggt agcggacgag gccagaaccc ccagatgcat catccccaaa   57420
ggagggctgc tgcccgaagg gaggtgatgg ggatatctcc gttccagccc tgtcagcggc   57480
cgagggattg ttttttttctg gttcgagtgt cgtggctgat ggtgggagct gctgagcatg   57540
aggaggagcc ggggtagctg atggcagggg ctgctgctga ggaggaagag gagaaggagc   57600
ccgggcggct gacggcgggg gctgctgctg aggaagaagt ggagagggag ccggggcggc   57660
tgattgcggg ggctgctgct gagttggagg aggagaagga gccggggcgg ctgattgcgg   57720
gggctgctgc tgagttggag gaggagaaag agtcgtggcg gtggggctg ctgctgcagt    57780 cggggaaggg gatggggtgg tcagagggat ttctgggttc gagggagctg cctgtggcag   57840
agggatgggt atttgcaaag ggaggcgagg agatggagtg actgaaggag cgatagttga   57900
gactggcgcg gggcggggtg tcgggaggc gggtggtgat tggtgaggga tggggattac    57960 tggagggga aggcgagctg ctgaagggg gcgatggggc ggaacgtggg tgcgtggcag     58020
```

```
ctgatcatcc tctgtgtcag tggtggagga cagagggagg cggcggccgg aggtgggctt    58080
cttgtggggg ctatctttgc ccaatcccctt tttcctcttg ggagtctgag gcgctgcgcc    58140
gcccgacgcc cttggtggcg tggagggagc ggggaccccg ggggtgtgac ctaggccggg    58200
gatggggatg aagaggggag ggctggaggc cggggccgcg gaggccgggg ccgcggaggc    58260
cggggccgcg gaggccgggg ccgcagaggc cggggccgca gaggccgggg ccgcggaggc    58320
cggggccgca gaggccgggg ccgcagaggc cggggccgca gaggccggag acgacggcgg    58380
ggagttggtc tttgcaggac tatacctggc ggcagggaat gagtcggatg tgaaagatcg    58440
agagggcagt ggcctgaggt tatacggtat tattcgccgt tcaaacggta gcatgacggg    58500
agggctgcta tcagcaccgg gcgtccccgc cgcctcccca tcactggaca caagctcggg    58560
ccccaccagg tcaaagccgc tgccgttggc ctcataaaag tcatacacgc catagtgttc    58620
cagcataaag atgcggggt cctctgtctc aaaggcctcg ggtagaaaat agagatgcac    58680
gcaagtgtac tgggccctg gtgccccac gtactgcagg atgtcgtgcg cataggtgct    58740
gactctgaca tgggcggggg tgcccggggc cgcatccttc tggcagtggg ggtcaaacaa    58800
gtagaaggag ccatctgtct cgatgatgat ggccccgcg tagatgtcgc agatgtagag    58860
gatgaactgg gccaccccgt tgtaactgcc gtgcaggacc tcggcaggg actgaacaac    58920 tgccgagttt gcgatctggg cagggaatag gacgaggcca aagatctccg ccgagcggta    58980
tatgtgcacg cgcccaccgc ccctcaggac cacggagctg ggcacgtccg tcaactgggc    59040
catctcgtgc cccttgagga tgccgctctg gcgcatgagg gcatccagcc gcgcccctc    59100 gtccaggacc tcgtccagct cagggcggga ggtcagggg cggccggcca ggaagctctt    59160
gaccaggtag aggacgcagt tgctgacgca ctggatgccg gcaaagcggc caaacttgca    59220
gtgggcctgg ttgcacgagg ccgtgcctag gatgcgagg gccgagcctc cactcccgcc    59280
cccgggggca ttcacatcca tggtcctgat tccgcgcacg gggccggttc cccgggtgcg    59340
ctggctttgc ccccagtcgc cgttactcat cttcggcggt ggggcgggga ggacgccttg    59400
tcgcccccct tctggtccgg ggtcttacgc ggctggcggc ggcagccgcc gagagataag    59460
gggggtacgt gtgtgcctcc gcctctcctc tgtctgggcc gccgccgcg cttgcccgcc    59520 ttgaaggaga gggggtagtc cgcggactgc gtctgcgggg gcaggaggtc tcaaccttct    59580
gggctcgggc cgcggtgtcg atatccgatg gcctttccct gtcttcctcg tatgctcctt    59640
ctcctcctcc tcccggcacg ccctgagat ctgcctcccc tccctctccc tcgtcctggt    59700
cggaaaagtc tgaggaggag aaggagaatg ggggaggagtc caaaacggca cgccacctgc    59760
cgtggggcgg tggtgacagg tcccggctgg cccggcgctt gctcgcgttc ctgccgttac    59820
ccaggagaat ggccgcgagt ttttgggcgg ggaggatgcg gaatggcggg ggcgtttgtc    59880
ccacgggtga gggggaatcg tcggttaggg ccggcacgag gtggtgggtc tggacccggg    59940
ccgtgcgagc aaaggcggcg agaaccgagg ggcttctggg ggtgactgtg atctgttccg    60000
gatttaggtc catggcgggt gtgtatgttt taataggggt ggtctctggc gcggcaggat    60060
gatggtcgag gacgtccacc agggccttgc agatgctctt gcctagatac aggatgtcgt    60120
ccatgctgag gggaggtggg gtgtctgctc ccccctgcgg aagccgcctg ggtgcggggg    60180
tgaagacagg tggtgggcgg gcgtctcgcc ggactatggc ctcggcacgc tcggcgtcga    60240
tggcgggtgg ctggaacagg cgggcgaatg tgtaatcccg gaaccggtag gcgacgctgc    60300
gcctgagggc gcccgtcagg ctgtatccca gctccagggc gtgctccacc cgctcgttga    60360
gctcctcgag atccggacgc aggggctcgc tggtgtgggc ccagagggg tgatccgcga    60420
```

```
tgccccggct ctccctgagg gccggcacca ggaggcgcct tctgagggtg gccgtgtcgg    60480
ccgtggccag ggcccacctg gcggcggcgt cccggcacac atcctggatg ccctccacga    60540
cgctctttag cgtctggagg tccgtggagt agtggcgggg ggaggatgaa acgctctttt    60600
ccttcaccgc taccaccgcc tcctcctcct cttccgtcgc cagagggatc tgcaccctcc    60660
cggtctctgc gtcgtacagg agcgggcggg agcacagcct ccaagctgcc cccgtcaagc    60720
gcgagatgtc ctccgagagg gtctcacccg agaccagaaa gcggcgggtg ccaggccca    60780 acgactccgc cgtcgtgctg tatctcaggg tgaagaggag tgaaaagagg gaggtgggcc    60840
aggcaagcgg tggtgcttcc gccgcccgct ctgaagctga gatagtctcg gagatgatgc    60900
ctgagacctc tcggacggcg tccatgatcc taaggactgc gtcgtgggac gacagccccc    60960
agggcccccc gccctcttcg tcttctgcac cctcggctcc tgcgtcccg gccttgcctt    61020 cccccctctaa gttgaggggg cgcagtccga ccgcctgggg ggactcccca ggcatcggag    61080
gggccccgtc atagatctcc cagacggtgg cgtatatgag ctcgagagga cggcgggccc    61140
gggtcagctc gggggaaggg agggccaggt cgctgccgaa ggagaccagc cagcgcaggg    61200
cggccagaga gcgggttttg ggcagctcgt tggagaggac ccggcgaagg gcgggccaga    61260
tttggaactc gatgaaggcg gccgggaaga aggggctgcg gacataggcc ggatccgcgc    61320
gcgccgtttg gccggccctc agggaccggc agtatgcctc gacgtctgtc cgcggggccg    61380
ccgccaccgc cgccgtccac tgccttctcc cctgctcgcc ggggagtagg ggggcttac    61440 aggggagggc cggagccggg gccggggcct gccacaggcg gctgtagcgg acccatagca    61500
gagacctgag gagttcggat gaaaggtccc ccgccacctg ctcatactcg gccgcgggag    61560
gagggacgat gaagatgcgc agaggggtta cggcgtccca agggtccgcc gccgccccca    61620
cacccacagc cgtcgcggcg ggggcggcgg cgggcgtaga ggggccgctg gtgcgccggg    61680
ctcgtctgtc cacggcctcg gcctccgccc tcaggtaggc cgcccgggcc acacgggcga    61740
agcggctcgt ggggctcgcg gtgggcagca gtcggaaaaa gtgcagggca aagcccgata    61800
gactctctag gagggcggcg gtggcctcga gccacctcca ccgcgagcgg gacacccggg    61860
gcacagaggc cagcatcatg gcgtagtccc ccgccacggt ctcgttgagc ccggccgaga    61920
gcagaaccgt ggccacctgc tcgatggcgg ctggagagaa ggatgcccgg ctccccgccg    61980
cctcctgcac acgagcggcc agggcctcca tctctgccgc catcccggcc aggaaggcct    62040
cgatgaccga gtctgggacg ccgtaagtct ggtcccagag cagggcctcg tacacatagt    62100
cgtaaaagag ggccctgag ggctccaaaa gccgagccg gcggcgtca aaggccagga    62160 cgggcacagc cgcgacgggg ggcgtttgtc ccccgctggc ctccgcgtac acgcccagga    62220
tctctaccgc ccgccgccgg gccagggca gtgaggccac cacgctggaa agtgactcgg    62280
ggcggtgaaa gagaccgcca ccgccgcttt cttcacccctc tcccccgccg gccccgcccc    62340
cactgtgctc caccagctcc acggccatgg ccttgatgtc cgcggccgtg ggctgacct    62400 gccctgcagc cgcccagggg tagcggttgg tctccgcgta tacggtgacc agccatctcc    62460
ccagcgtcgt tttcgccgcg ttaaaagcgt agaatgacag cccctcccgc gggaaggcgt    62520 cccaccggc cagataagtg tcggccacca gctcttccac gaaggcaaag gtggccgttg    62580
ggccagagac cgcgagcacc tcccgctgc cctcttcgat gatgcgccgg tacgtggccg    62640
ccagggcccg ggtctctgcg atgagccgag agccgtccag cggatcgtcg gtggccgag    62700 aggctgtcgt gggggggcagt gaggaggcca gcacgtccag ggccgcctcc agatggccga    62760
```

```
ggccgaagct gcgcctggaa aaggaggccg cccggagtag gtagtaggcg tggtggcgga   62820
ggaccgccgc cgggtaagcg tggccgctca tgagggtgag agtatttaaa aaatcgcgca   62880
ccagcaccgg ctgggccaaa tctcccagtc caaagatccc cagctccaga ggcatcagcg   62940
cgcgcaggcg ggcagcgggg tcgtccccag acagcagcaa ctgacgcgtc acgcgggcga   63000 gcccccgtc cacctctgcc aggggcggct gggcgtctgc ccctccgcta ccgccgccgc    63060
tgtcactctc catagcggac gccatgaagg tccaggggtc cgtcgatcgc cgccgtctgc   63120
aacgccgaat cgcggggctg ctgcccctc cggcccggcg tctaaatatt tcccgggggt   63180
ccgaattcac gcgggacgtt cgtgggctgg ttgaggaaca cgcgcaggcc tcctcgctga   63240
gtgcggcggc cgtctggcgc gcagggctgc tggccccggg ggaggtggcg gtcgccgggg   63300
gtggcagtgg agggggggagc ttcagctggt ctggtggcg gccgccagtc tttggggact   63360
ttctgataca cgccagctcc ttcaacaacg ccgaggcaac tggaacgccc cttttccaat   63420
tcaagcagag tgacccgttc tcgggcgtcg acgcggtatt cactcctctc tccctgttta   63480
tcctaatgaa tcacggccgg ggtgtagccg cccgggtcga gcaggtggg ggcctgacgc   63540 ggatggccaa cctgctgtac gacagccccg caaccctggc tgacctggtc ccggactttg   63600
ggcggctggt ggccgaccgc cgcttccaca acttcatcac ccctgtgggc ccctggtgg   63660 agaatataaa gagcacctat ctgaataaaa tcaccacggt ggtccacggg cctgtggtca   63720
gcaaggccat ccctcgcagc accgtcaagg tgacggtgcc ccaggaggcc tttgtggatc   63780
tggacgcgtg gctctccggc ggcgccgggg gtggcggtgg aggatgcttc gtcgggggc    63840 tgggcctgca gccgtgcccc gccgatgcgc gcctctatgt cgctctgacc tatgaggaag   63900
ccgggccgcg gtttacgttt tccagtcgt cccgcggcca ctgtcagatc atgaatatct    63960
taagaattta ttactcacca tccatcatgc accgctacgc tgtggtccag cccctacata   64020
tagaggagct gaccttcggg gcggttgcct gtctggggac atttagtgct actgacggtt   64080
ggaggaggtc tgccttcaat taccgtggct ctagcctccc cgtggtggag attgacagct   64140
tttattccaa cgtctctgac tgggaggtga ttctctagac ttaacgggag gaaacaggag   64200 gaggagggg acaagagcac aaaagtggtt cagtggacac ccaccacaca gcatggcaac   64260
gaccagtcat gttgagcatg agctcctctc caaattgatt gatgagttaa aggtcaaggc   64320
caactcagac cccgaggctg atgtcctggc agggcgcctg ctccaccgcc ttaaggccga   64380
gtcagttaca cacacagtag ccgaatatct ggaggtcttc tctgacaaat tctacgatga   64440
ggaattcttc cagatgcacc gggatgagct ggagacccga gtctctgctt tcgcgcagag   64500
cccggcctac gagcgcatcg tctccagcgg ctacctgtcg gccctgcgct actatgacac   64560
ctatctgtat gtggggcgca gcggggaagca ggagagtgtg cagcactttt acatgcggtt   64620
agccggcttc tgtgcctcaa ccacctgcct ctacgcgggt ctcagggcag ccctgcagcg   64680
ggccaggccg gagattgaga gtgacatgga ggtgtttgat tactactttg agcacctaac   64740
ctcccagacg gtgtgctgct ccacgccctt tatgcgcttt gccggggtgg aaaactccac   64800
tctggccagc tgcatcctca ccaccccga cctcagctcc gagtgggacg tgacccaggc   64860
cctctatagg cacctgggc gctacctctt tcagcgagcc ggggtgggtg taggggtgac   64920
gggggctggc caggatggga aacacatcag cctcctgatg aggatgatca acagccacgt   64980
ggagtaccac aactacggct gcaagcggcc ggtcagcgtg gcggcctaca tggagccctg   65040
gcacagccag attttcaagt ttttggaaac gaagctgccg gagaaccacg agaggtgccc   65100
gggcatcttt acggggctct ttgtccccga gctcttcttc aagcttttta gggacactcc   65160
```

```
ctggtcggac tggtacctgt ttgaccccaa ggacgccggg gacctggaga ggctctacgg    65220
ggaggagttt gagcgcgagt actatcggct ggtgacagcg ggcaagtttt gtgggcgggt    65280
ctccatcaag tccctgatgt tctctatcgt caactgcgcc gtcaaggccg gcagcccctt    65340
catccttttg aaggaggcct gcaacgccca cttttggcgc gacctgcagg gcgaggccat    65400
gaacgctgcc aacctgtgcg ccgaggtgct gcagccctcg aggaagtctg tggccacctg    65460
caatctggcc aacatctgcc tcccgcgctg cctggtgaat gcgcctctgg cggtgcgggc    65520
acagcgggcc gacacgcagg gggatgaact cctgctggcc ctccctcgac tctcagtcac    65580
cctacctgga gaggggcag tcggtgatgg attctcgcta gcccgcctca gagatgccac    65640
ccagtgtgcc acctttgtgg tggcctgctc cattcttcag ggatccccca cttatgattc    65700
cagggatatg gcctccatgg gcctcggggt gcagggcctg gccgatgtct ttgcggacct    65760
gggctggcag tacactgacc ctccctctcg ctcgttaaac aaggaaatat tcgaacatat    65820
gtactttacg gccctctgca ccagtagtct gattggactt cacaccagga agattttttcc    65880 gggtttcaaa cagagcaagt atgccggggg gtggtttcac tggcacgatt gggcaggaac    65940
agacctttct attcccaggg aaatttggtc tcgcctctct gaacgcattg tgagggatgg    66000
gcttttcaat tcacagttta tcgccctgat gcccacctca ggctgtgccc aggtgacggg    66060
ctgttcggac gccttctacc ccttctatgc caatgcgtcc accaaggtca ccaacaagga    66120
ggaggccctt aggccaaacc ggtcttttg gcgtcatgtg cgtctggatg acaggggaagc    66180 tttgaatctt gtcgggggcc gtgtctcctg cctcccggag gctctgcggc agcgctacct    66240
gcgtttccaa acggcctttg attacaacca ggaggacctg attcagatgt cccgggacag    66300
ggcccccttt gtggaccaga gccaatctca cagcctgttt ttgcgtgagg aagatgccgc    66360
gcgggccagc acgctagcca acctactggt gcgcagctac gagctgggcc tgaagactat    66420
catgtactat tgtcgcattg agaaggccgc cgatctgggg gtgatggagt gtaaggccag    66480
cgcggctctg tcggtgccgc gggaggaaca gaatgagcgg agtcccgctg agcagatgcc    66540
gcctcgtccc atggaaccgg cgcaggttgc ggggccggtt gacatcatga gcaagggccc    66600
aggggaggga ccaggtgggt ggtgtgtgcc cggggggattg gaagtgtgct ataagtaccg    66660
tcagctcttc tcagaggatg atctgttgga gactgacggt tttactgaac gagcctgtga    66720
atcttgccaa taaacgttta ttgccatgtc caagttgttg tacgtgcgtg atcatgaggg    66780
ctttgcctgc ctaacggtcg aaacccaccg caaccgctgg ttcgcggctc acattgtcct    66840
caccaaggac tgcgggtgtc tcaagctact caatgagagg gacttggagt tttacaagtt    66900
cctctttacg ttcctggcca tggccgagaa gcttgtgaac tttaacattg atgaactggt    66960
caccagcttc gagagccacg acattgatca ctactacacc gagcagaagg ccatggagaa    67020
cgtccacggg gagacttatg ctaacatttt aaacatgctc tttgatgggg acagggcggc    67080
gatgaacgcc tacgcagagg ccatcatggc cgacgaggcc ctgcaagcca agatttcctg    67140
gctccgtgac aaggtggcgg ccgccgtcac cctgccggag aagattcttg tgttcctgct    67200
gattgaaggc atcttcttca ttagctcctt ctacagcata gccctgctgc gggtccgggg    67260
cctaatgcct ggcatctgcc tggccaataa ctacataagt agggatgagc tgctccacac    67320
ccgcgctgcc tccctgttat acaatagcat gacagccaag gctgaccgac caagggccac    67380
ctggatccag gagctgtttc gcactgcggt ggagtagag actgccttca tcgaggctcg    67440
tggagagggg gttaccttgg tggatgtgcg agccataaag cagtttctgg aggccacggc    67500
```

```
cgatcgcatc ctgggtgaca ttggtcaggc tcccttgtat ggcacaccac cccccaagga   67560
ctgcccgctc acctcatgac ctagcatcaa gcaaactaat ttctttgagc aagagagttc   67620
cgattacacc atgctggtgg tagatgacct ttgagtcagg gtggctactt gctcaggttt   67680
ctgggcataa attctcctgc ctgcctctgc tctggtacgt tggcttctgc tgctgcttgt   67740
gatcatggaa accactcaga ctctccgctt taagaccaag gccctagccg tcctgtccaa   67800
gtgctatgac catgcccaga ctcatctcaa gggaggagtg ctgcaggtaa accttctgtc   67860
tgtaaactat ggaggccccc ggctggccgc cgtggccaac gcaggcacgg ccgggctaat   67920
cagcttcgag gtctcccctg acgctgtggc cgagtggcag aatcaccaga gcccagagga   67980
ggccccggcc gccgtgtcat ttagaaacct tgcctacggg cgcacctgtg tcctgggcaa   68040
ggagctgttt ggctcggctg tggagcaggc ttccctgcaa ttttacaagc ggccacaagg   68100
gggttcccgg cctgaatttg ttaagctcac tatggaatat gatgataagg tgtccaagag   68160
ccaccacacc tgcgccctga tgccctatat gccccggcc agcgacaggc tgaggaacga   68220
gcagatgatt gggcaggtgc tgttgatgcc caagacggct cctcgttgc agaagtgggc   68280
acgccagcaa ggctcaggcg gcgttaaggt gacactcaat ccggatctct acgtcaccac   68340
gtatacttct ggggaggcct gcctcaccct agactacaag cctctgagtg tggggccata   68400
cgaggccttc actggccctg tggccaaggc tcaggacgtg ggggccgttg aggcccacgt   68460
tgtctgctcg gtagcagcgg actcgctggc ggcggcgctt agcctctgcc gcattccggc   68520
cgttagcgtg ccaatcttga ggttttacag gtctggcatc atagctgtgg tggccggcct   68580
gctgacgtca gcggggggacc tgccgttgga tcttagtgtt attttattta accacgcctc   68640
cgaagaggcg ccgccagta cggcctctga gccagaagat aaaagtcccc gggtgcaacc   68700
actgggcaca ggactccaac aacgcccag acatacggtc agtccatctc cttcacctcc   68760
gccacctcct aggacccta cttgggagag tccggcaagg ccagagacac cctcgcctgc   68820
cattcccagc cactccagca acaccgcact ggagaggcct ctggctgttc agctcgcgag   68880
gaaaaggaca tcgtcggagg ccaggcagaa gcagaagcac cccaagaaag tgaagcaggc   68940
cttaaccccc ctcatttaac accatgttct cgtgcaagca gcacctgtcc ctgggggcct   69000
gtgtcttctg tctcggcctc ctggccagca cccccttcat ttggtgcttt gtctttgcca   69060
acctgctctc tctggagatc ttctcaccgt ggcagacaca cgtgtacagg cttggattcc   69120
cgacggcatg cctaatggcc gtcctctgga cgctggtacc cgccaagcac gcggtgaggg   69180
ccgtcactcc agccatcatg ctgaatattg ccagcgcctt gatcttcttc tcccttagag   69240
tctactcgac cagcacgtgg gtttctgccc cctgtctctt tctggccaac ctgcctctct   69300
tatgcctgtg gccccggctg gccatcgaga ttgtttacat ctgcccggct atacaccaaa   69360
ggttctttga acttgggttg ctcttggcct gcaccatctt tgccctgtcc gtggtctcca   69420
gggcccggga ggtgtcggct gtcttcatgt ctccattttt catctttctg gctttgggct   69480
ctggaagcct ggccggtgct cggcgtaacc agatttacac ctcgggtctc gagcggagac   69540
gcagcatttt ctgcgcccgg ggagatcatt cggtggcatc cctgaaggag accctccata   69600
aatgccgtgg ggatctgctg gccatctctg ccttgaccgt tcttgtcgtc tgtgtgatga   69660
ttgtgttgca tgtgcacgca gaggtgttct ttggactctc tagatacctg cccctctttc   69720
tctgtggggc gatggcctcc gggggggctgt acctgggcca ttccagcatc attgcatgtg   69780
tcatggccac cctctgcacc ctgtcatctg ttgtggtata tttcctccat gaaacccttg   69840
gacccctggg caagaccgtg ctgtttatct caatctttgt ctattacttt agcggggtag   69900
```

```
cggccctgag cgcagctatg cgctacaagc ttaagaagtt tgtgaacgga ccctggtcc    69960
atctccgtgt ggtatacatg tgctgttttg tctttacttt ttgtgaatat ctgttggtga    70020
cattcattaa atcctaacga ccggagtcct gtctctttgt gttcttgggg acttgagtt     70080
agctgtcttt cctcttatta cattgggcta acgggaggaa atgaacccag ggtggcagt    70140
ggatggggtc atttatgggc aaaactcaca ggacatgttt ggggagttag cattggcgtc    70200
gggaaacaca gctctggcag ttataaccgc accagctaac aggacatgtt tgggggagtt    70260
ggcattggcg tcaggagaca cggctctgtc agttatcacc gtaccatgag tgccatgtgt    70320
gtccagtgcc taatcaccgt tcctcatttt gtgtgcctcc tcaaatgttc cagaagtcgg    70380
ccacagggga ggtggctgaa ttagggcctt ttccctcatt cccccatgag acccacgtgg    70440
caggcctagg ggctacattc gcctcccacg tttcccttcg cgtgaggcat ccgatatgac    70500
tgaattttcg cagtctcttt tccctcttcc cttgttattc ccatagaatt acagtgaggt    70560
tacacaggtg gagattcagt ttaaccattt attgatttaa tccaggaaca aaaaacagtc    70620
ctagtgaccc agtgcccgga gagagaatgg ccctgacaag tcggctgcat gatgcacttc    70680
ggcagtcacg tgtgtgagtc tccacggcct ctgtcaaaag ggagcttagc gtgccagggt    70740
tgtaattctt gatgtagtgg cccaggaatt caacttcatc gtgtctccgt ctgcagttgg    70800
cgttaatgta ggctggggct actgccgcat atgctgccaa gagacagagg ggctgcttca    70860
catatgagct gctcagggtc tccaccacct tgttttgacg ggccgtggca caggtgatgt    70920
agaagagttg cttcacaaag ttgtagtctc gcgtgttagg aaggaagcag ggtgccagct    70980
ctttgagctt ggtcaggatc accttgctaa gactcatggc gcaggccagg aggatgtctt    71040
ccgcgggagc tagggcagg tcgccgtggt aggtgatctc ctggagccaa agatggtct    71100
cttctagcat ggccaccagg gtgcagagcc ccgcgttctg gatcgcctgc atgcgtgcat    71160
ccagccatgt gtccttgttg gttgacttgg tgaaaaactc acgtagtgtc ttgtagctcc    71220
tgcgcagctc gtgtctgggt tgcactttct gccaggctcc aatctctgga tgggcggcca    71280
ccgccagcat cgactgtagg aacgggtctt ggatgggctc tagggtcaga gaggccaggg    71340
ggctgggcaa ggtgacaaat gtaatcttgg agacaggctt aaccagactc atgtcaaacc    71400
acggtttgtt gggcaggggc ctctggctgc gttcttgcct cgcctgcttc cttgtgctcc    71460
tgccggcccc tcgagattct gaccggggac ctctggttgc tctgttgctt cggggagctc    71520
ttggagacct cggtgctcta ggcaccctgg ggcccttgg ggctctgggc gctcttgctc    71580
ccgggggcag gtgtcggcgc ttgccataac tttcatcggt gcagccatgg acctctccgc    71640
gtcgcctttt gtggcctctg gtgtaagagg agttgccagt ctcctccttc tcgtcctcgt    71700
ccctgcacag gggtgagcga tgcaatgtga ctgtcttgtc ctgtaggtcc acttctttc     71760
tgggaatcac aaacgatgcc gaggtagggg ttatgaccac gctggagggc cgtgcaggta    71820
tggtgtgggc cggagttgga tcttcatcct cctcctctga ggatgaaatc tctccatctg    71880
tggagtgttc ttcgctgccc tccatagggt ccatatcgca gtctgtgttg gtgtctgaga    71940
ccgcttcgag ttccagaatg tggctctctg cagaggggag acaaaaggtg gagactgcct    72000
tgagcacctc tgtctcaggc accggatgcc cccggctcca cggccccggc cactggccgg    72060
tgtagcttct tacctgcggg atcctcgttg gaggaaatgc tgctagttcg ggagagtctc    72120
tgagaaggaa ccatcttgtc tgtctctacg acgggctagc tgggatgtag tgctgtcttg    72180
actggcctca gccctatta tgattctgga ggcgggcacg ctgatggaga aatgggcggt      72240
```

```
cggttgattg gccccacagc gaccggcgaa gcactgactc atgaaggtga ccgtgatggc    72300
ctgtgatgtg tagtagagta ccagaaacac cctcacattc ttggagctgg ccctgtgggt    72360
atgcctcagg cacgcaaagt tcctgccccg ggcatggcac acctgaacta agtttggccc    72420
ggtttgctca aacgtgacat ggagaaactg ggggaatttg tcttctggca cagctgttgc    72480
cagggtgctc atgagcgagg gccagatgca ggagctgacc caggcgacga gatccaggcc    72540
cagatgtccc tctatcatgg cgcagacatt ctccacggtg gggggcaggg tctcgcgggt    72600
cctctggatt agatagtcac gcccatcatc cgcgatgtgg tagcagaagg ttttgggggc    72660
cggccagccc acgtgcagtg agtgatgtaa gaggttttga atgttgaggg cattcttaac    72720
atagctgtgc ttgtcttcct cttccggatg acagacaaag aggcgcagct gccggctaag    72780
accaccgccc ctgtccacct tgtaggtatg cggcagccgg atgcaccgcc cggcgtgata    72840
cacgccgctg tcaaaaagcg gggccccaat ctctttgatc ttgtgacgca tgcggcgcag    72900
gcaggccgtt aggcccatga gcttctgcag cacagacaca aaccctggta ctgcgcttgt    72960
tcccacaata gcatggcctc taggtagggg ggtgatgacg cgaaagccca gttttcccgt    73020
gcatatgcaa aaggggagca catcttccat attatccggg tcggcgggtg gacaagctga    73080
tttgaaaaaa tagactgggt ggggccctgga cactggaccc aggcggcgca tgaggcgcag    73140
tacctcacgc cgcacggtcc ggcacaggtc atagatttcc tccagcgacc aggggccccc    73200
cttgatcttt agatccaggt ccaggaccag gttgcagacc ggaagccggg gattaaagta    73260
ttcatgccgg gagacaaaga gctgctcgct caggctgttc tgtgaatagt acactggggt    73320
gtaggagagg gccctggtga gacacgtgtc tgggaggcgg cagttggtcg gggtggagac    73380
gacctccgcc aggtgggacg agaagggtc agcggctgtc attacaaagt agtgcctgtc    73440
tgcaaaatgg cagaggaaga ccggtagccg ctgcacccttt cgaaggacgg tgggtgggag    73500
gaattgttcc ttgggattcc actggccccg gcaggtggcc tggccggcca agcatagaaa    73560
cccttgaagc gtgggggggt atgtgggacc ctcatccgcg tgccagcgcg cgagctccac    73620
cagctcccgg gccacgtcca cactgagccc ggcccaagcc cgcatgagtc cgtcatcggg    73680
gtcggggtcc cacgtgtatg gggccggggg ctccatgcgg attttcagct gctggacacg    73740
cacatgctca gccaggtaag tctcccgggt gaagtaggtg cgcatgtgct ccgcaaagcc    73800
cctgtccagg agcgagggga gcacgacgcc ccccgaaggc agacacccaa tttctcccac    73860
gctcgttaac tgagagtatc gcttaaaggt tccctcgttg aagcactgtg cgtgggccaa    73920
atagacgtag cgcacgagat cggccgaggc caggggaagg cgcccctgt aggcgtctat    73980 cgtccttgcc acagcgcgga tctctcgtga gtcccgccgc agcttctcgt gtgcaaagtg    74040
ggcaaaagcc tcggtctgct ccgcccatgc cgaggagcca aagacctccc ccagctcggc    74100
cagggacgtg acggcggcca ggctctgacc agactcggaa gtaaatagct ccgtgaggtg    74160
cgccagggtc tcaatcgtac aaggaatgcc ccaaaaatag taagcagccg tgactagcac    74220
gaactgggcc tcgtgggagc caaaggtgct aatgaaccac ctggccgaga tgttaacgcg    74280
gtagatgcgg cgcagacagc ccacgatctt gggacgcagc cacgccacgc ggcctctggc    74340 atcccctgt ggctgcttct tagcgctcag tgtgagcagt tccacgaggg gcgtgagcga    74400
gcgcagggcc cccgcgcgat ctaggtaggt ggatagacgg tccgcggtga gcggcgtgag    74460
gccgcgcagg aaggggaagg cctcctccgc cggcaggtgc agcgtcagaa ccaggccgca    74520
gcggctctgt gaggtcagcc gcttcttggg caggtgaagc tgcagttcca cgagagaacc    74580
cgccacgtgg tggaggggcg aggcgttgtg gcacaaacaa aacaggcgga agccctcgtc    74640
```

```
aggccgcgag aggatggcat cgaggatggc ctccgcaatg tcagtgtttg aggccacaag   74700
ggccttgatg acgacggggg cggacattat ttaagaccgg gaggccccaa cggcgggcta   74760
aacagaacga tggccttcta tctcccagac tggtcgtgct gcgggctctg gctctttggc   74820
cggcccagga atagatacag ccagctccct gaggagccgg agacctttga gtgcccggac   74880
cgctggcgag ccgagataga tctgggcctg cccctggtg tgcaggtggg agatttgcta    74940
agaaatgagc agacgatggg ctcactgaga caggtttatt tgctcgccgt tcaagccaat   75000
agcatcacgg atcacctgaa gcgctttgac gccgtccgcg tccctgagag ctgtcgtggg   75060
gtggtggagg cccaggtggc caagcttgag gccgtgcgct cagtcatctg gaataccatg   75120
atctctctgg ctgtaagcgg catcgagatg gacgagaatg ggctcaaggc cctgctggac   75180
aaacaggctg cgacagcct ggccctgatg gagatggaga aggtggccac ggcgctcaag    75240
atggacgaga ccggtgcctg ggcgcaagag atctcggccg ttgtctcatc ggtgaccgcc   75300
ccctcagcct cggccccttt catcaactcc gcctttgagc ccgaggtgcc caccccgtc    75360 cttgcaccgc ctcccgtggt gcggcagccg gagcactctg ggcccacgga gctcgcgtta   75420
acgtagcaac cagactccac accaaataaa cattttattg gtaaaacaag ggatatgaag   75480
gtgtcattga cccgaggatc caaaccccct cccctgtctc ccctcgagcg cctcgctcag   75540
cccactatca cccatggcca ggcccggcac ctcctcgaag gcgcagctgg cccacctaaa   75600
gagagatctg gggccaagga cccccgcgtc actgtggggg ctgtagaagg aggtgaggtg   75660
gtgcttgtga aggtaaacaa gctgacagaa gcgccggtac ttgttaagga acacggtctg   75720
gtcactaaag ttggtcaggc tgacgtccac cccaccccgg cgccacctgc agggcttcac   75780
tagaataccc tgcatggcca ggcccgacct gccaaagatt gtcggcctgt ggtgagggat   75840 agaaggggg ggcacggtga gtgtcactga gacggtctga tggggaaga gggccaggtc     75900 ctttggcaaa gagacgtcca ggcccacgtc cccggggtac tgggggtggt tgatgggacc   75960
cttgtcctcc tccatctggg gggtggcata tctgaaggca gccaggtgga ttttgagctc   76020
cgatggacgc agcgtggagt tgtagcgccg ctgattctgg aggattagcc ggagttcccc   76080
cgtgtagccg ggatcgatga tgccaacatg agacgtgacc ggacgggagg tgctgcccca   76140
cagcatgagc ccatgaccct cgggtgggcg ggcatagagg cctaggtcca cagttgtggt   76200
cttcatcggg cgcagcagga tggtggtctt gttgaccaag gtgagccgcc ctacactagc   76260
ctgctggagc aacagcttgt cattctggaa ggcgtagcgt atgtgtggac aggcctccat   76320
ggtgatgatc taacagacag ggacggcggc gctatatata agagcccaag acccggctct   76380
ctttactgcg aaatggggaa ggtcctaaga aagccgtttg caaaggctgt gccactgctc   76440
ttcctcgccg ccacctggct tctgaccggg gtgctgccgg ccggcgcttc cagtcccaca   76500
aacgcggcgg cggcttccct gactgaagcc caggaccagt tctactccta cacatgtaat   76560
gcggacacat tctcgccttc tttgaccagc tttgcctcca tctgggcact tctgacgctt   76620
gtcttagtca ttatagcctc agccatctac ctgatgtacg tctgctttaa caagtttgtg   76680
aacacgctgc tgacggatta gatggggata tttaaagggg gcagcaatct cggctgtctg   76740
tacttcttct ctgctcgtta aaccaatagc atgtcagctc cacgcaaagt cagattgcct   76800
tctgttaagg ctgttgacat gagcatggaa gacatggccg cccgcctggc tcgcctggag   76860
tctgagaata aggctctgaa gcaacaggtc ctcaggggg gtgcctgtgc ctcgtctacc    76920
tctgttcctt ctgctccagt gcctccgcct gagccgctta cagctcgaca gcgagaggta   76980
```

```
atgattacgc aggccacggg ccgtttggcg tctcaggcta tgaagaagat tgaagacaag    77040
gtgcggaaat cagttgacgg tgtaactacc cgcaatgaaa tggaaaatat attgcaaaat    77100
ctgaccctcc gcattcaagt atctatgttg ggtgcaaaag gccaacccag ccctggtgag    77160
ggaacacgac cacgagaatc aaacgaccct aacgccaccc gacgtgcccg ctcccgctcc    77220
cggggacgtg aagcaaagaa agtgcaaatt tctgattaat aaatctttat tgactttata    77280
cataggtctc ggcgtcatca tatggtgggg tggtgtaggt atgggatgtc gacaagttac    77340
gcctgaaggc gcagtccgcc atgaccagca gcagcagaag ggtcagcaca gccagagagg    77400
cccactgcag tactagcatg gagaggtttg agaatctggg ctgggacgtt ggcgggacag    77460
gcacggtggc ttgggctgtg gtaaccggtg ggctcgtaaa agtccagcgg ggccgcagtt    77520
tgctagaagt gctgggaggt agataggtgg tcgcattgta tctcgttctt ggcgtagttg    77580
aatcaccgcc gtaatctgtg gtgggctctg tacttgtccg ggctccatgt cctgtggtgt    77640
gctttccacc ggtggtagaa ttggcctttc cacctgttga ggtgaccgtg gaaccgccg    77700 tcttttggcc actgggggcc tggggcgacg ttgcattttt gggggcgtg cctttggtga    77760 cattaacctc ccccggtttt gtggatgtgg aactgtttcc agggcctgac gcttggctgg    77820
tggtgcctgg gcggggcgct ggcgaactgg tggacacatg atgtgtgctg gtagaggctg    77880
gtgtcacctg tgttatattt tcaccacctg ttgggtgagc ggaggttagt aaaggcatat    77940
gtgacgttga attgtcactg gtggaggggc tgagtgtctc tgagattgaa ctgggtctca    78000
gtgacatgga agaggttgaa cttgaagtta tgttatgttg cctgtggta acagcactgg    78060 ttgcattttt tggtgggctg gtaactactg gggtggaact tgttcctcct aatgtgtggt    78120
tggtggtatt tgcctgtgga cttgtttctc ccacggtagg gctggtggca tttggggttg    78180
gggtagtcac tgctgaggtg ggacttgttt ttcccaaggt ggggatgtg gcatttgggg    78240 ttggggtagt cactgctggg gtggggctgg tggcatttgg ggttgggta gtcactgctg    78300 aggtgggact tgttttccc aaggtggggc tggtggcatt tggggttggg gtagtcactg    78360
ctggggtggg gctggtggca tttggggttg gggtagtcac tgctgaggtg gggctggtca    78420
tgtcgggggc cttactttct gtgccgttgt cccgtggaga tggacttggt gtcaccggtg    78480
atgcgcctga cgttgtgccg gctggtgttg ggctggtgac atccgcggtg gatacagtgg    78540
ggcctgtgct tgcaggtgcg gtgaggttgg taggcacgtg agtagagctg ggtagacctg    78600
tcgttgtatt gggagcagca aatccagttg tattcaaggt aggggaggtg gtggtgctct    78660
cgggtgcctt ggagaatata accttgtggg ttgttgtggt ggcattggta gccgttcgtg    78720
tgataatgag tgtcttgggg gccgtgccaa gacccgagac agtaatgtca aatgtccgat    78780
tgctcgcaaa tgcaccagaa atattttcac aacccgaagg tgtccccgag gtgagagtcc    78840
atttgcactt aaagtcagtt tcagtgttgt ttggccaggc ccaaaaggca gtcactgtaa    78900
catttggcga gtttgcgtcc tcagaagtga ccattggcac tgaataggta gcattgtcac    78960
ccacatatgt gatgtctgtg gtgtttgtcg gcatgtcctg tgaagctgga atctcatcag    79020
agaacacaat gttggactga atgcagtaat ctccccgct cgccttcggt ccattcccag    79080
agtaaaacac gtacagtata ctgttattgc caagaaatcg tgacactgga cgtggtgtca    79140
gacgcaggct gtatgcatac cctgtaccag gtattggggt ggccacggga ctcgttgatg    79200
tgagaattcc gccgctggga acatggctct cgtatccact gcaggtgatg ttaaatttgt    79260
tgtctccggg cagaacttgt gaaatttcgc catcctccat aatacactca atatctatct    79320
cattaccgag catttctgtt tttacgctga aattcgagtc ttgagctgat gttggcaaac    79380
```

```
ttaagggtag cgtgacatcc agcccctgtg cccttactac tgccgttata ttggtagaat    79440
tacagttatc ccactttatg tatggcactg tttctggtat taggtatact gggttttgca    79500
tttctgcatg gtggcaccac atggtgccaa acacatcttg aaagtagaca tctacagatt    79560
ccaggcttac ttgttgctcc tctccggtgg tgatgttaat tggaagcttc ttagaccgca    79620
tagttagagc caattctcct gcaccaagga gctccagtag aaagagattg gtggcatttt    79680
ctgagccacc aaatgcacct cgaggttggt agacagcctt tgtatggggt gtcagcaggc    79740
caaagtcaag attaagttta tgcttttttgc ccccgacatc gaaattgata gttgcattga    79800
catctgccgt gcaaacattg cacgctgggt aaaatgggaa ttccagaatc tcaacattga    79860
aaaaaccagg atcatcacgc gtgagttgga taaggctctg gatggtgtac tgacacacaa    79920
gcaaggctgc ctccattgtc tcagcaccga tttctaggca gcaccctctt taataggtgc    79980
aaggggggtg cggtgttggt gagtcacact ttcgttgcag acaaaatgga caaggacagg    80040
ccgggtctcc cggccccgga tgacaacata aagaagtac catctacctc gggtgttcag    80100
gaacgggcgt ctgagggaga ttgggaaaat gtcctcatag agatatcaga tagcagctca    80160
gaagaggaag cagaagatgc ccacctggag ccatcccaga ggggtaaaaa gagaaaacgg    80220
gtcgatgatg atgccggtgg ttcagctcca gcacaacacg tgccccccc tcagctggat    80280 caccctggtc gagaagccat tctctacagg tttccgctag atttaagaag gtttattcaa    80340
gcaattggag ccgcagctac ggtgagcttc cctatggccc aggtgtgtga tgtgtgtttt    80400
tgcccatcgc acaacaaggt aagtgatttg ttgccgttgg tttcagcacc ccgacacgcg    80460
agccatagac cagttttttcg gatcccagat ttcaaatacc gacctgtacg taatgtatgc    80520
catggccatt cgacaggcca ttagagatcg tcggaggaat ccagcttctc gtagaagtca    80580
ggtcaaatgg agaatgacca ccctggccgc tggttggcct atgggttacc aggcatacag    80640
tagctggatg tacagctaca ccgatcccca ggtgactgcc acgatcatac atctgcaggc    80700
gactcttggg tgcgcaagtg gccgtaggtg tcatgtgacc ttttctgccg gcacctttag    80760
gccgccgcga tgtagtcccg gggatcgcca gtggttgtat gttcagagcc gcgtgggtga    80820
ccttgtgcag agttctaatc catgctacag tattttcttt gactacatgg ccatacatag    80880
gagcctcacg aaaatctggg atgaagtggt aacacctgat cagcgtgtta catttatgga    80940
attcctgggc ttttttgcaac gcacggagtt ggtctacatc aagagctttg tcagctatgc    81000
cttgggcacc actagtatcg aaacaccgtg gatggatgag aatcctagca cagagacggc    81060
acaggcttgg aatgccggct tgctccgggg gcgtgcgtac gggcaagact tgcttagaac    81120
tgaaggagaa catggcgaag gtgctacctg tgaaacacgg gaagaaagtg aggacacaga    81180
gagcgatggg gatgatgaag aacttcctcg tgtagtgtcc agggatggaa ctaagcacag    81240 acgacccct atatttttaa gacgcctgca caggttgctg ttgatgagag cgggcaaagg    81300
aaaggaacgg gccagggaga cactggcgaa ggccctagg cgcacttatg gcacacctag    81360
gccgccagtt cagaaaccaa gaccagaggt cccgcaaagc tatgagacag ctaccagtca    81420
cgggtcggcg caagtcccag aaccccacc cacccaccca ttacatcagc aacacagcat    81480
ggccccgtgt atggtagctc agaacccacg tgcacccta ggggaccaac tcccaggtgt    81540
tcctaaagat ggacgagggg cgtgtgcacc ggtacccgcc ctggccgggc ctattgtccg    81600
gccctgggag tcatccctgt tacagtctcc gggaagggcc tttgcacccg ttagcccaca    81660
acccatgcca gtagaacccg tccctgtccc tactgtggca cttgagcgac cagtttgtcc    81720
```

```
cgcacctcct gagattgcta tgcagggccc gggggaacct tctggcatta aacgcacacg   81780
ggagcgttgg aggcccgcac cgtggacgcc aaacccaccc cgctctccca gtcagatgtc   81840
cgtgcgtgac cgtctggctc gtttgcgtgc tgaggcacag gcccgtcagg ctagtgttga   81900
ggtgcagccc acccagttga cccaagtatc ccctcagcaa ccaatggaga ggccgttgga   81960
accagagcag cagatgttcc ctggttcccc ctttagccag gtcgctgatg ttgcccggga   82020
atctggggta cctgcaatgc agcctcagta ctttgacctc cccttaactc aacccattag   82080
ccagggggca cccgcggccc cgttgagggc tagtatgggc ccggtacctc cggtaccggc   82140
aacacagcca cagtattttg acatcccctt aactgaaccc attaaccagg ggcatccgc    82200 ggcccatttt ctccctcagc aaccaatgga ggggccgttg gtacccgagc ggtggatgtt   82260
ccaaggtgcc accctgagcc agagtgttag gccaggggta gcgcagtcac aatattttga   82320
cctcccctta actcaaccca ttaaccatgg ggcacccgca gcccatttcc tccatcagcc   82380
accaatggag gggccgtggg tacccgagca gtggatgttc caaggtgccc ccctagcca    82440 aggcactgac gtggtccaac atcagctgga tgatttgggg tatccactcc atgatctcaa   82500
ccatcccggg gttccgtgt ctcctgccgt taaccaatat catttcagcc aggctgcctt    82560
tgggttacct attgatgagg atgagagtgg cgagaggtcc gatacctccg agccgtatga   82620
agctcttgat tgtcaatcc atggcaggcc ctgccctcag gccccgaat ggcctgttca     82680 aggggagggt ggccaggatg ccaccgaggt tcttgatttg tcaatccatg gcaggccccg   82740
ccctcggacc cccgagtggc ctgttcaagg ggagagtggc cagaatgtca cagaccatga   82800
acctagaagg gtggtggtgt cagctattgt tcacatgtgt caggatgacg agtttccgga   82860
tctacaagat cctccagatg aggcctaagc aaaggtgtag aagtgtgtcc ccctccattc   82920
cacccactga tatacgcccg acaataaagt tgatgatatt gaattccaca cctactcgtg   82980
tttgtgattt tatttcatat tccatgagag agacctcgca tatttgcaga gggtcactga   83040 aacatttttat cttaaaacag ttacacctga aaaatgaaga aagcgtggct cagcagagca   83100
cagcaagccg atgccggggg ggcatctggc tccgaggacc caccagatta tggagatcaa   83160
ggtaatgtgc aacaggtggg atctgatcct atttcacctg cgattggccc cttttgaactc   83220 tctgcggcca gtgaggatga tcctcaatct gggccagtgg aagagaattt agatgccgct   83280
gcaagagagg aagaggaacc tgatgagcag gagcacaatg gtggtgatga tcccttggaa   83340
gtccatactc ggcagcctag atttgtggat gtgaacccaa cgcaggctcc agtgatccaa   83400
ctagtccatg ctgtttatga ttccatgttg gtaagaggca cctagaacat ttccagatgt   83460
ttagcttgga tattttggcc agtcttaatt tattgtcatt ggtttcagca atcggacctc   83520
cggtctctag gcagtttatt ccttgagcaa aacctgaaca tcgaagagtt tatatggatg   83580
tgcatgacag tgcgtcacag atgtcaggcc atcagacaaa aaccattacc gattgataag   83640
cagaggcggt ggaagctcct gtcaccttac agaacctggc gtatgggtta ccgtacgcaa   83700
accctcaatg taaacagttt tgagacaggg ggagataaag tccacccact ccttgtgact   83760
gctacgctag gatgtgaaga gggcctgcgg catgcaataa cttacagtgc tggcattgta   83820
cagctaccac gaatgtcaga ccaaaaccaa aagatagaaa cagccttctt gatggcacgt   83880
cgtgctaggt cactttcggc agaaagatat actttgttct ttgatttagt atcctctgga   83940
aacaccctgt atgccatatg gattgggctg gcacgagaa accgagttgc atttgtcgag   84000
tttgtaggat ggctatgtaa gaaggaccac actcatatac gtgaatggtt ccgccagtgc   84060
accgggagac cctcaccatc caagccatgg atgagagcgc atcccgtcgc cgttccttat   84120
```

```
gacgatccat taacaagtga ggagactgac ctggcctatg cccgtggact ggccatgagt   84180
atcgaggctg ctagactgcc agatgatcca ataattgttg aggatgacga tgaaagtgag   84240
gaaattgaag ataaatgtga taaggatgaa gaggaaagtg gaacggaaga tgttacaagc   84300
ataccgcaaa cactgccgca cagtccaaca gtatacggca ggccctcggt gttttaccga   84360
aagccagata ctaaatcaac caaaaaatgc agggccatag tgactgacct tagtataatc   84420
aaggtcattg aagatgaaca cagaaagaag aagacagcca gaacagagca accaagagcc   84480
aagcctgatt cccctgcccc cacagtggtc cttcggcgac cacccacgca aaaggtgact   84540
ggccctgccg gttcactgag tgtccaggct cagctggagc catggcaacc tttgtcctgg   84600
ccacatgaga caagagttat acttcacgga ccacccacgc agggtgacca agcacacggt   84660
tccatgctag accttcttga aaaggacgac cagcacatgg agcagcaggt tatggcaacc   84720
ctactgccac cagaaccaca ccagccccgg tctgggagaa gagccccttg tgtctacacc   84780
gctgacctag acatagaaag tgatgagccc gccacgtcag agccggttct tgatcagcta   84840
ctgcccgccc caggacttgg acctcttgca attcaaccat taacgtcccc caccacgtct   84900
caactccgca gttcagcacc gagccacgca caaactccat ggccggttac ccacccaagt   84960
cagactccag gtggcccaac gacacagtcc ctggcaccgg aaacagaagc cccgcgccag   85020
tggccaatgc cactgcgacc tatccctctg caccccttgc ggatgcagcc aatatcattt   85080
aatcctgcag tgagacccac tccccatcag ccacctcagg tggagcccac tttctatcag   85140
tccacttggg tgaaaccccc tcaacaatac cagcctcaga tggggcacat tccatatcag   85200
ccccgaccaa cgggtcactc tactatgctc cggccccagt gggcacccac caccatgcag   85260
ccaccaccaa gggcgcccac tcccatgccg ccacctcagg ggccaccac cgctatgcag   85320 aggcctcagg gggcgcccac tcccatgccg ccacctcagg gacacccac cgccatgcag   85380 aggcctcagg gtgcgcccac tcccatgccg ccacctcagg gacacccac cgccatgcag   85440 aggcctcagg gtgcgcccac tcccatgccg ccacctcagg gacacccac cgccatacag   85500 aggcctcagg gtgcgcccac tcccatgccg ccacctcagg gacacccac cgccatgcag   85560 aggcctcagg gggcgcccac tcccatgccg ccacctcagg gacacccac cgccatgcag   85620 aggcctcagg gggcgcccac tcccatgccg ccacctcagg ggccaccac cgccatgcag   85680 aggcctcggg gggcgcccac tcccatgccg ccacctcagg ggccacccac cgccatgcag   85740
aggcctcagg gggcgcccac tcccatgccg ccacctcagg ggccacccac cgccatgcag   85800
aggcctcggg gggcgcccac tcccatgccg ccacctcagg ggccacccac cgccatgcag   85860
aggcctcagg gggcgcccac tcccatgccg ccacctcagg ggccacccac cgccatgcag   85920
aggcctcggg gggcgcccac tcccatgccg ccacctcagg ggccacccac cgccatgcag   85980
ctgtcaccaa gggcacttac cggccagaag gggccagcaa agcacattct gcgccagttg   86040
ttaacggggg gcgtcaagag tgggagacca tcacttaagt ttaaggctgc ccttgagcgt   86100
caagccgctg cgggcttgcg accttcacca gggtctggaa cgggtgccaa gattgtgcag   86160
gcacctgttt tctatccacc cgtcctacag cccatacaag ttatgtggca agtgggttcc   86220
tcaaaggccg tggccgcctc aacggtgaca caggcaccca cggaatatac cggggaaagg   86280
aggttagggg ggcctatgtc tcccactgat attccgccgt ctaaacgggt gaagaaaaag   86340
gcctatccag agcgcaagac gccgcatggg gggccctcac actcttccac cgttatgtgg   86400
gagaatgtca gccagggaca acagcagact ctggagtgcg gaggaactga taaacaggaa   86460
```

```
aggaacatgt tggggatggg ggacattgca gtttcttccc cttcctcttc tgaaacatcg    86520
aatgatgagt gatttcaacc acgtaacaag aactgggatg aaccctcggg cagtatcaga    86580
ctgcggggag gggcagtgat aagtcatgac aatttagat gaggtagaca ttttgcatat     86640
tttcagaccc accatggaat catttgaagg agagggggac tctatacagt cacctgacaa    86700
tgcgcgggga gatgatgtac agaatactgg tgagcatatt caggaccccg ggccggggcc    86760
ttcaaccggc ggggcttctg agggattggt gcagaacgag ccggactcaa gagatcaaca    86820
gtcccggggg cagagaaggg gtgatgaaaa cagaggctgg atgcagcgca tcaggcgaag    86880
gcggagaaga cgggccgcat tgtccggcca tcttttagac atggaagaca atgtgccgcc    86940
gtggtttcct ccacacgata tcacaccata tgtcgcaagg aatatcaggg acgctgcctg    87000
ccaggctgtc aaggtgagca tgcctctaac tgggttcatg ggggccatct aaggcccacg    87060
tgtgacccat gtttccatta attttagcac tcgcacctgc aagcgctatc aaacctgata    87120
ctcgatagtg gtttagacac acaacacctc ttgtgcttcg tgatggcagc caggcagcgt    87180
cttcaggaca ttcgacgtgg acccttggtt gtagaggag gtgttggttg gcgacattgg     87240
cttctgacat ctcccagccg atcctggtcc atgggatatc gcacagcaac actacgcaca    87300
ttaactcccg tgcctaacag ggttgggct gacagcatca tgttaactgc cacgtttgga     87360
tgccaaaatg gggcactagc tataaacacc ttctccgcca ccgtgtggat accacccct     87420 gctggaccaa gagagcaaga aagatacgct cgggaagccg aggtgcgctt ccttcgtggt    87480
aaatggcaga ggcggttccg aagaatcttt gatttgatag aactgtgtgg ctctctgcac    87540
cacgtctggc aaaacatgct gcagaccgag gagaaccttt tagatttcgt gcgtttcatg    87600
ggtgtcatgt ccagctgcaa tagttcatct gtgaattact ggtttcacaa gacaatcgga    87660
aactttaagc catattaccc gtggaatgca ccacctaatg aaaatccata tcacgcacgg    87720
agaggcataa aagaacaagt aatccagaaa gcatttctaa aggcacaaag acagggttta    87780
tcaatgttag caacgggagg tggacccaga ggtgatgcta ctagtgaaac gagcagcgat    87840
gaggataccg gtagacaggg ttcggatgtg gagctagagt catcggacga tgagctgcca    87900
tatatcgatc ccaacatgga gccagttcag cagaggcccg tcatgtttgt gagccgtgtg    87960
cctgtaagga aaccgaggac actgccgtgg cctacaccca agacgcaccc agtgaagcgc    88020
acaattgtta agacctccta tagatctgat gaggcagaag aagcacagag cacccctgaa    88080
aggccgggcc cttccaaaca accatcagag cccgtggagc ccgcccacac aaccccagcg    88140
gggaggtcaa cggtgattct ccacgaacca cctcgagagc ccgaagctgt ttccttcaag    88200
cctccgccac caccttcccg gaggagaagg ggagcgtgtg ttgtatatga cgatgatatc    88260
atagaggtga ttgatgttga aaccaccgaa gaggagacga cgtcaatgca aagacagcct    88320
ccgctcgggc aacaaccgcc cccccccgtg atttctaccg ggagtgccat gtcttccagt    88380
cacacggatc catcagtaac acagccaagt aagccacatc ggaaacctca agacggattt    88440
caacgttcag gccgacgtca aaaacgagcc atgcctcccc cagtgagtcc ttctgacgct    88500
gggcctcctt ccaccaggcc tcgtgtcatg gcgcctcctt ccaccgggcc tcgtgtcatg    88560
gcgactcctt ccaccgggcc tcgtgacatg gcgcctcctt ccaccgggcc tcgtgacatg    88620
gcgcctcctt ccaccgggcc tcgtgacatg gcgcctcctt ccaccgggcc tcgtgacatg    88680
gcgcctaccg tcgtacatat gtttacgagg agcgcctgc tcacccagtc caccggccct     88740
gcacctcgga gcttctggga aatgcgggcc ggccgtgatg ctcccaaaat tcaacaagaa    88800
ccaagttcac aacagcagcc agccactcag tctacaccgc cttgccaatc atgggtccca    88860
```

-continued

```
tctgtctatg tcctcccggc agtggatgct ggtaatgccc agcccctaca aatatcacac    88920
ttgagctcca tgtcgcccac gcagccgata tcgcatgaag aacaaccccg gtatgaggat    88980
cctgacactc ctctggattt gagtttacat ccagatactg caactctgcc gcccacccag    89040
gatttatacc ctggacgcga ggatctgcag gccacccagg ctccataccc gggatacgag    89100
gagccacggc cccccaggc tccttttgta ggtgactatg gttttgttca aattccctcg     89160
gctcaatggg agccacaccc ctctcagggc acataccagg gccacattga tccccagctt    89220
ccggctgctc tagatttagg gccagagcag ccccggttcc cacaagatcc atatgtgtat    89280
tccgggggcc aattgtcttc atgtccaggt tatgcaggtc cctggccctc gaggcctcaa    89340
catccaagat ataggcacac cttggcattg tggcctcgag aacccaggca tgggcactct    89400
cagggcccat ggaaaccctg gtcagcacat ctcccacctc agtgggatgg atctgcagga    89460
catggccagg atcaggtctc ccagttccca catctgcatt cggagacagg cccaccacgt    89520
cttcaacttt catcggtgcc acaggtgctg taccgcagc cactggtctc atcctctgca     89580
ccatcgtggt catctcccca gccccgagcc cccatacgcc ccattccaac aagattcccc    89640
cctcccccta tgccgttaca agatagcatg gccgtgggt gcgactcatc aggtacagca     89700
tgcccaagca tgccctttgc cagtgattac agtcaaggtg catttacccc actggacatt    89760
aatgccccca cgccaaaaag tcctcgagta gaagaaagtt ctcacggacc cgcccggtgt    89820
tcccaagcta cttctgaagc acaggagatt cttagtgaca attctgagat ctccgtgttc    89880
ccaaaagatg caaagcagac tgactatgat gcatccactg aaagtgagct agattaaggg    89940
gatccaaggt gacccctgtt agctatttga tctttgactg acacataaac atggtttaag    90000
gaatgaacac tcatggtgtg agactggaac tgtactaaat ttgctgacat atgtacaatg    90060
agagccaaaa atttgataaa ccttaaaagt ccccccatct aatgatgtcc agttcccttc    90120
tcccaccctg tacaccccga cccaaaggga ctcaatggca ttcagatttc tagttaccac    90180
aggtagaata tcgggcgttg gcccataaaa ataagtgcat ggatatagct ctgcacaggc    90240
ttggaaacac ccattccagg tgtgcttctt tttggtgaaa taaaaacagc gttctttata    90300
tgaaaatgtg tattctcttg tgttgcagta tgtacagtta gctttggtat agttttgggg    90360
tacctgaaac gtgtgcaggg tgggtgtcca atgtggcagt tttatctctt tgtccccata    90420
ctcctgctcg gccgtcttgt taaagttaac cggcggtgga ggatccaccg gccagacctc    90480
tacatttggt ttgggtaccc aggtgatggc cgctgccgac acccgccctc ctcctcttac    90540
cctgggtggc aaaaagtatg ccaggagtag aacaataaca agtgcgatgg cggtaaacaa    90600 tggcacctc acctgcttaa acgaaaccat ggcaaccact tcaaagagag ccaacaggaa    90660
gatatttatt aatattccat tagtaaacga ggcgtgaagc aggcgtggtt tcaataacgg    90720
gagttagaaa tttaagagat cctcgtgtaa acatctggt gtccggggga taatggagtc      90780
aacatccagg cttgggcaca tctgcttcaa caggaggcgc agcctgtcat tttcagatga    90840
tttggcagaa gccacctgcg gacaaaaatc aggcgtttag atgggggcatt ttatgtttgg    90900 gccattagcc acctgggcat tcgtgttact gtatactgac ctcacggtag tgctgcagca    90960
gatgcttaaa cttggcccgg cattttctgg aagccacccg attcttgtat cgctttatat    91020
ctagttcaga atcacattcc tccagctgcg agcaagggaa tgcgttacta caagtggtgc    91080
ctagtcagtt gaaacaggcc ccaccgtccg ctgccgccct ccttgagccc caccatccgc    91140 tgccacccctc tttgagcccc accgtccgct gccaccctct ttgagcccct tcttaccgat    91200
```

```
tctggctgta gtggtttcct tgtacgtcgt gccggggcag ccgctggtgc aggctgtgga    91260
gcaccaatgt ctgctagctg ttgtccttgg ttagccccgg gacaagcaaa caccactgct    91320
gctgctggtt gaacagtaga attgtctcca ggttgaggtg cttctccccc ggcttggtta    91380
gtctgttgat tctgggttat gtctgagact gggaatagct gaggtgctgc ataagcttga    91440
taagcattct caggagcagg ctgaggggca ggaaaccacg acccagttgg agcggctgaa    91500
acatgatagg cagtgagctg gccttgtggc agaggctctg gcagcaccgg ccacagcaca    91560
caaggcaaag gagcttgtga tggccctccc aggtcctgat agactctggt agcttggtca    91620
aaagcttgta caaaaggcac ctggtatggg tcaggtgtaa attttacatc ttcagaagtc    91680
gagtttgggt ccatcatctt cagcaaagat agcaaggtg gccggcaagg tgcaatgttt     91740
agtgagttac ctgtctaaca ctccccttt aaagccaagg caccagcctc ctctgtgatg     91800
tcatggtttg ggacgtgcta aatttaggtg tgtctctgag gcacattagc aatgcctgtg    91860
gctcatgcat agtttccaaa agaggaggag gcagttttca gaagtgtcta aaataagctg    91920
gtgtcaaaaa tagacagccc agttgaaata tgcatggcat gcagcagaca ttcatcattt    91980
agaaatgtat ccaagatttc attaagttcg ggggtcaggg gggagtccag attcaaatcc    92040
tctgtcatgg actctagtgt tgtggtcagt tcgtccaaat ggccacgagg gggcgggtgg    92100
ttcaggtcca tctgtccaca tatggctgct tcctccttct ggggaataac agtgtcagcc    92160
atctccctta gggccttcac ggcctgactg gtttcctcat cagggtcctc caacagatga    92220
cttgcctcgg gggttactgc gggggccggg tcaagtggcc ggggcactgg ggctggcgtt    92280
agggatccga ccggttcatg gacaggtcct gtggggtgg gagccaaaga ggcaggcagg     92340
ggccggttgg cccacgggga tccgggtgga tggaagggcc tgatcctctt tggctgacac    92400
acctctcgcc cctcgaacac gtcagatatg gcactgcccg cttccggctt tggcaggaac    92460
ataccttccc ggctatccct gaggcccttc ttcctttaa cgggaggaag aaaggtgggc     92520
tttgaggggt gggggaatat gggtctctca tcgctctctt ggtggaccgc tgctatccaa    92580
ggctgttcag gttcctccgc gttggaagga catggagttt gaccacggtt gggcctggat    92640
gtccggcgcg actttggggc ccgcaggcgc ggggcctcgg ccctggcctc ttcccgctcg    92700
ctctgctcgg tgtcactgtt gcccgagtca ctgctgctgg aactgctgtc accgcagtcg    92760
gcgctttggg caccgggctt caggggcatg gtcgggctcg ggagactttc gagttcatct    92820
gtaaaagcat gaaactgtcc ggactccgag tagcgggcct cggtgtgaga ggcaccccca    92880
tcattcccca tgagctcctc gtccatcctg tcggctccgg acacgaggat aggagtttcc    92940
actgccttgg acttggttga cagcaggcac gcgggaagca cgccgctcac gtagctcctc    93000
tgtccggcgt ggctggagta ggaggccggg ggcagtgtct taatcagagc cctgacatcc    93060
ttaacatcgt ccgtcagatg gcctgtcttg gacgagacca tagtctggaa catctcctcg    93120
aggacgggat aggtgaacac ccacttgcaa aaggccttga acttggagct taggaggcct    93180
tccttctcca tcctgttcag gtgttccact acctgcttgc cggaggccat gatggccgcg    93240
cggtccacgc ccagcacctt gctgtaggtg taggcccgca cccgactgtg ttttaggagc    93300
ttgtacatag cggtgcctat ggtggcagga atcatcaccc ggttgctggg ggcctggatg    93360
aagaatctgt cagtgaccac tatcaggtgg tctaacacgt agcgcatcac tatagggcac    93420
gcgatggaac atgcgtcgtt gccggcattc tcagcccgtc ttcttaccct gttgtttcgg    93480
agaatggccc aaaaattgca gatgttgagc gtggccatta gcccgcccca ttctcgcccg    93540
tgggccttgg cctcatttat aaatgccttg catattttgt aggatctcag agtaatctcc    93600
```

```
acactcccgg ctgtaaattc cttgttgagg acgttgcagt agtcagagac cagagagccc   93660
agctgctttt tgatttcagg agttagcctc agaaagtctt ccaagccatc cttttaggc    93720 ctcatggcta gtagtaacag aggaaatgcc cgaccattaa aatctttcct ccatgagctt   93780
tacctgaaac actatcccga agtggggat gtggtgcatc tactgaacac catcggggtc    93840
gactgcgacc tcccacctag ccacccactc ctgacagccc agaggggct gttcctggca    93900 agagtcttgc aggctgtaca gcagcacaag ctgctggaag acaccatcgt ccccaagatc    93960
ttaaagaagc tggcttattt cttagagctg ctaagctact actcccccaa ggatgaacag    94020
cgtgacatcg ccgaggttct tgaccacctc aagacgaatc gggacctggg gctggacgac    94080
agactctggg ccctgattag gaaactgcgc caagacagac accatgcctc tgtaaatgtc    94140
ctcatgccag gaagcgacta cacagccgtg tcgctgcagt actacgacgg catctccata    94200
ggtatgagga aggtaatcgc ggatgtctgc cgcagtggct atgcctccat gcctccatg     94260 acggccacgc acaacctctc ccaccagctc ttgatggcgt ccgggcccag tgaggaaccg    94320
tgcgcctggc gcgggttctt taaccaggtc ctcctctgga ctgtggccct ctgcaagttt    94380
cgcagatgca tttactataa ctacattcag ggatctatag ccaccatctc ccagcttctg    94440
cacctcgaga tcaaggccct ctgcagctgg ataatatccc aggatggcat gcgcctcttt    94500
caacacagca ggcctctcct caccctctgg gagagcgtgg ccgcaaatca ggaggtcacg    94560
gatgccatta ccctgcctga ctgcgctgaa tacatagacc tactaaagca cacaaaacat    94620
gtcttagaaa actgttctgc catgcaatac aaataaattt ctcttacctg cgtctgtttg    94680
tgtagtgagg tgttgtgtcc tgtatggtat tctactttaa aaatgccggc tgacatggat    94740
tactggtctt ttatgagcca ttggcatggg cgggacaatc gcaatataaa accctgacca    94800
tcacatgggg cattaggcga ctctgcatca gcatcgctta agtatgagtg ggcagcagag    94860
aggctcggtt attttggttc ctgaacatct ggctggggca ttaactaagc ttatgagcga    94920
ttttatcaca ggacaagatg tcactctttc tggaggaaat attgcagtca aaattcgcga    94980
tgctataaac cagaccccg ggggtggtga tgtagctata ctttcttccc tgtttgcttt     95040
atggaatgcc ctcccaacat ctggtagaca atcctccagg gacgatttaa tcccagccgc    95100
cgtgcaggcc ttaaccacgg cccacaactt atgtctgggt gttattccag gtgagacctc    95160
acacaaggac acacccgagt cattgctccg ggctatcgtg acgggtctcc aaaaattgtg    95220
ggtggattcg tgcggatgtc cagagtgcct acaatgtctt aagggattga aggcaattaa    95280
gcccggcctt tatgaaatcc ctaggataat accacacact aagcagtgta gtcctgtcaa    95340
tctcctgaac atgttggtcc acaagcttgt ggctttacgt ggtcatgtgc agcttgcata    95400
cgacgcccgt gtcctgacgc ctgactttca cgaaatccct gacctcgatg actccgatgc    95460
tgttttcgca cgcaccttat tggcagcctt atttcacctc aatatgttct ttattctcaa    95520
agattacata acacaagact ccatgagctt gaagcaggcc ctcagtggtc attggatgtc    95580
tgccacgggc aaccccctgc ctgcagcacc ggaaaccctg cgagactact ggaagctttt    95640
ccgaaattcg gataatcact tttatctccc gacgacaggg cctttaaaca ccttcaaatt    95700
tcccgaagag cttctggggc gcgttgttgt gattgattcc tctttgtgtg ccgccagtca    95760
cgttcaggac gttatcaccc gtggtgttgg ggcgggtgtt cctcgtcctc agttttggc    95820 cctgcctccg gccccatccc gtaagcccca gcagacatgc tctcagttaa cgagcagagg    95880
aaatgaaagc tcacggcgaa acttgggcca gcccggggg acctcccctg ctgttccccc     95940
```

```
agtttgcccc atcgtttccc tgacggcctc aggggccaag caaaaccgcg ggggcatggg     96000
gtccttgcac ttagccaagc ctgaggaaac ctcccccgcc gtctcccag tatgccccat      96060
cgcttcccca gcggcctcca ggtccaagca gcactgcggg gtcactggat cctcacaggc     96120
cgcacccagc tcttcttccg ttgccccagt agcatctctg tctggtgacc ttgaagagga    96180
agaggagggg tcccgagaat ccccatccct accgtccagc aaaaaggggg ccgatgaatt    96240
tgaggcctgg cttgaggctc aggatgcaaa ttttgaggat gttcagcgag agttttccgg    96300
gctgcgagta attggtgatg aggacgagga tggttcggag gatggggaat tttcagacct    96360
ggatctgtct gacagcgacc atgaagggga tgagggtggg ggggctgttg gaggggcag     96420
gagtctgcac tccctgtatt cactgagcgt catctaataa agatgtctat tgatctcttt    96480
tagtgtgaat catgtctgac gagggaccag gtacaggacc tggaaatggc ctaggacaga    96540
aggaagacac atctggacca gacggctcca gcggcagtgg acctcaaaga agaggggggg    96600
ataaccatgg acgaggacgg ggaagaggac gaggacgagg aggcggaaga ccaggagctc    96660
cgggcggctc aggatcaggg ccaagacata gagatggtgt ccggagaccc caaaaacgtc    96720
caagttgcat tggctgcaaa ggggcccacg gtggaacagg agcaggagga ggggcaggag    96780
caggaggggc aggagcagga ggggcaggag caggaggggc aggagcagga ggggcaggag    96840
caggaggggc aggagcagga ggggcaggag caggaggggc aggagcagga ggggcaggag    96900
caggaggggc aggagcagga ggaggggcag gagcaggagg ggcaggagca ggaggggcag    96960
gagcaggagg aggggcagga gcaggaggag ggcaggagc aggaggaggg gcaggagcag    97020
gaggaggggc aggagcagga ggaggggcag gagcaggagg aggggcagga gcaggaggag    97080
gggcaggagc aggaggaggg gcaggagcag gaggaggggc aggagcaggc ggggcaggag    97140
caggcggggc aggagcagga ggaggggcag gagcaggagg aggggcagga gcaggaggag    97200
gggcaggagc aggaggaggg gcaggagcag gaggaggggc aggagcagga ggaggggcag    97260
gagcaggagg aggggcagga gcaggaggag gggcaggagc aggaggaggg gcaggagcag    97320
gaggaggggc aggagcagga ggaggggcag gagcaggagg aggggcagga gcaggaggag    97380
gggcaggagc aggaggaggg gcaggagcag gaggaggggc aggagcagga ggaggggcag    97440
gagcaggagg aggggcagga gcaggaggtg gaggccgggg tcgaggaggc agtggaggcc    97500
ggggtcgagg aggtagtgga ggccggggtc gaggaggtag tggaggccgc cggggtagag    97560
gacgtgaaag agccaggggg ggaagtcgtg aaagagccag ggggagaggt cgtggacgtg    97620
gtgaaaagag gccaggagt cccagtagtc agtcatcatc atccgggtct ccaccgcgca    97680
ggcccctcc aggtagaagg ccattttcc accctgtagc ggaagccgat tattttgaat    97740
accaccaaga aggtggccca gatggtgagc ctgacatgcc cccgggagcg atagagcagg    97800
gccccgcaga tgacccagga gaaggcccaa gcactggacc ccgggggtcag ggtgatggag    97860
gcaggcgcaa aaaaggaggg tggtatgaa agcatcgtgg tgaaggaggt tccagccaga    97920
aatttgagaa cattgcagaa ggtttaagac ttctcctggc taggtgtcac gtagaaagga    97980
ctaccgagga tggaaattgg gtcgccggtg tgttcgtata tggaggtagt aagacctccc    98040
tttacaacct caggcgagga attggccttg ctattccaca atgtcgtctt acaccattga    98100
gtcgtctccc ctttggaatg gccctggac ccggcccaca acctggccca ctaagggagt    98160
ccattgtctg ttatttcatt gtctttttac aaactcatat atttgctgag ggtttgaagg    98220
atgcgattaa ggaccttgtt ttgccaaagc ccgctcctac ctgcaatatc aaggtgactg    98280
tgtgcagctt tgacgatgga gtagatttgc ctccctggtt tccacctatg gtggaagggg    98340
```

```
ctgccgcgga gggtgatgac ggagatgacg gagatgaagg aggtgatgga gatgagggtg   98400
aggaagggca ggagtgatgt aacttgttag gagacgccct caatcgtatt aaaagccgtg   98460
tattcccccg cactaaagaa taaatcccca gtagacatca tgcgtactgt tggtgtattt   98520
ctggccacct gtcttgtcac cattttcgtc ctcccaacat ggggcaattg ggcataccca   98580
tgttgtcacg tcactcagct ccgcgctcaa caccttctcg cgttggaaaa cattagcgac   98640
atttacctgg tgagcaatca gacatgcgac ggctttagcc tggcctcctt aaattcacct   98700
aagaatggga gcaaccagct ggtcatcagc cgctgcgcaa acggactcaa cgtggtctcc   98760
ttctttatct ccatcctgaa gcgaagcagc tccgccctca cgggccatct ccgtgagttg   98820
ttaaccaccc tggagactct ttacggttca ttctcagtgg aagacctgtt tggtgccaac   98880
ttaaacagat acgcatggca tcgcgggggc tagacctctg gctggatgag cacgtgtgga   98940
agaggaaaca ggagattggt gtgaaaggag aaaatctcct tctccccgac ttatggctag   99000
atttcctaca actcagcccc atcttccagc gcaagcttgc tgccgttatt gcctgtgtcc   99060
gacgactgcg gacacaggcc accgtctacc cggaggagga catgtgcatg gcctgggccc   99120
gcttttgcga cccctctgat attaaggtgg ttattttggg ccaggacccc tatcacgggg   99180
gtcaagcaaa cggcctggca ttcagcatcg catacggctt tccagtcccc cccagcctga   99240
ggaacatcta cgcggagctg caccggagtc tgccggagtt ttctccccca gatcacggct   99300
gtctagacgc gtgggcctcc caggggggtgt tgctactcaa caccatcctg accgtgcaaa   99360
agggcaagcc cggctcgcac gcagacattg gctgggcgtg gtttactgac cacgtaattt   99420
cattgctctc tgagcggtta aaagcgtgcg tgtttatgct gtggggtgcg aaggcgggag   99480
acaaagcttc actaatcaac tccaagaagc atctggttct gacctctcag catccctctc   99540
ccctggccca gaacagcacc cgaaagagtg cccagcagaa gttcctgggc aacaaccact   99600
ttgtcctcgc taacaacttt ttgcgtgaga aggggctcgg tgagatagat tggaggctgt   99660
agaggggtca tcactatggc catgtttctg aagtcgcgtg gggtccggtc ttgcagggac   99720
cggcgcctct tgtcggacga ggaggaagag acttcacaga gcagcagcta cactctgggg   99780
tctcaggcct cccagtctat ccaggaggag gacgtgagtg acactgatga gtctgactac   99840
tcagatgaag acgaggagat tgatttggag gaagagtacc ccagtgacga agacccatct   99900
gagggcagtg atagcgaccc ctcgtggcat ccttcagatt cagacgagtc tgactacagc   99960
gagagcgacg aggatgaagc aaccccccggc tctcaggcct cacgatcttc aagagtctcg  100020
ccatctaccc aacagtcttc aggtctgaca cccacgcctt cgttctcccg accacgcacc  100080
cgggcacctc cgaggccgcc ggctcccgcg ccggtcaggg gacgggcctc agcacctccc  100140
aggccaccag cccagttca gcaatccacc aaagacaagg gtccccatag acctacgcga  100200
cctgtactta gaggcccagc tccacgccgc cccctccac cttcaagtcc aatacatac   100260 aataaacaca tgatggaaac cacccccccc attaagggca ataacaacta caattggcca  100320
tggctgtaaa taaaatgtca taacctggag tctgcatgtc tgttgtttta ttcagtaaac  100380
cagtagtgcg cgtgagttct ttagggcatc cacgatgtag ccgctcgcgg ggttcccctc  100440
cccagtgatc atctcggata gggattcct gtccatgacc acgcaattag agtgccggc   100500 ccgggacagc gccacataca catggccggg tttgatgttt ctgtggctgc cgaagcagat  100560
ggcgactttg tttagggaca gaccctgggc cttggctatg gtcatggcca gctttgagct  100620
aatgccatag tcacggatgc tgcagaggtt cagggacttg tcctctatcg tctcatacag  100680
```

```
cttgttagta ttgtgttcca ggcagcacac gaagcctgcc tcatccttga ccattagcct   100740
gggcatgcgt gaactgccag cgtcctgagg ctgctgcttt cctcggatgc caaagaagac   100800
gttgagatgc gtgtagccca gaagcgtgta gttctcggtg gtggaggcgt agtccaggag   100860
gccgtgaagg agaggctcgt ctgaggtgaa ctctatgttg tcgcgaatca gcatgttgtt   100920
ggtaaatgtg cagaagggga ggtccctgaa ctcccttctg ccatagcgga cggccacatc   100980
caggcattgc ctgaaatagg ccctgaggtc attatatatg tttaacaggg agcagagggg   101040
ggcagaattt gcggccgggg gagccagtac tcgggcatag aagacagcgg cggggctccg   101100
ctccccatcc caggcaacct ccagcggcag ttcacccagc tccatcccag cagtcacctc   101160
cggatcccac gtacgcccgg gcaggggcac agcaccaagc tccgccacgt attcccgtt    101220 ttcacagaga gaatgtcctc cgtggctaaa agcgtagatg ccgccgtaga tgagtcgggc   101280
caggaagctg tagacatact cgggctgctc atgcccgtgg gcctcacga agctgtccgc    101340 ctcgagcgtg tccataaagt cccgaaggt gccggtatag ccacagatgg acttttggt     101400 cttgcagttg accgacactg agctgtgctt cacgtaggtg acattgtagg tgaccttgac   101460
ccgttcttca tcctgctcgg ttcccaccgg gaccatgtct tggtcggcga actgcgagta   101520
gttaccgagg cgtgcataat tcttttggag ccaggtgtgg gccgtgaggc ccggaagacc   101580
gaccagggtc ttgtactggg ccaggggctc gaggaagacc tcgcactcca ccgggcaggt   101640
aaacatggtc accccgcccc catctccccc agttccccgc gcggcgcgcc cctgccggc    101700 agtcttgagc gtggcgtgga gggtggtgag gaaggtcttg acctcggcgt gggagaggaa   101760
gagccgggtc cagcccacgt actgcgtggg gtccattatg gccgccctgg ggacgacgaa   101820
gcggtcgacg taggccagga tgtccggcga gagctcgagg ccgtactcga gggtcttcat   101880
gaggtgtcca aactggacgt cggtgcagcg cttgttgttg atgaagaggg cccagttgcg   101940
ggccacgtcc acgtaggtcg cggccctggg gttgcccacc aggaaggtga ggatgttgtc   102000
gcactcgcga atcttgttta cctgggtctc gtggctaaag gaggactgaa aggcgtctgt   102060
ctgggtggga gagcccacgc agacgatgca gggaatgcgg cccggcggt  agagtggggt    102120 gcgcagccag gcgttgaaga accagtagca aaagaccacg gctgttagaa tgtgcacgga   102180
aagcgttcca gcttcgtcca ccacgatcac attggtggtc catagctgcc cctggtgcat   102240
gtctctcagg acctcaaagg cggggccaga gactcccgag tatagccccc tgggcttggt   102300
tcgcctgaac tcggcggcaa tgtcggagag taccggccag tatttggcca tgtcccgccg   102360
ctggagttcc tctagggcgg cgtccgtaga gcgaccatga ctgctgaccc gctgcgtcat   102420
atttatgtgg cggctcttga acccaaaggc gctatagacg gttgggcagt aggctcggag   102480
tgtctgggag aggttctgtg cggccacggt tgtggctccc gtgaccaggc agtccatcgt   102540
gtggtggagg cagctaacgc tggtgctctt gccagccccc gccgttcccg taattacata   102600
ggctgaaaag ggcaggaagg ggggctccga gatctccggg tcaaactcgg gggagaacgt   102660
ctccatatcc gggagttgtt ggacgcggcg cttagccagg gtccctatcc tcctgactat   102720
acgcctcacg gaggcgtctg aggtcatgtt caacatgaac gtggacgaga gcgcctctgg   102780
cgctctcggt cctcggcca ttcctgtgca ccccacgccg gcctcggtcc gacttttga     102840 gatcctgcag ggaaagtacg cctacgtcca gggacagacc atctacgcca acctccgtaa   102900
ccccggagtc ttctcgaggc aggtgtttac ccatttgttt aaacgagcca tctctcattg   102960
cacgtacgat gacgtgctac atgactggaa caagttcgag gcctgcatcc agaagcgatg   103020
gccgagcgat gactcgtgtg cgagccggtt tcgtgagtcc accttcgagt cgtggtccac   103080
```

```
gaccatgaag ctgaccgtgc gtgacctgct gaccaccaac atctaccgag tgctacacag 103140
ccgctccgtg ctctcctatg agcgttatgt ggactggatc tgcgccaccg gcatggtgcc 103200
cgccgttaag aagcccataa cccaagagct ccactccaag ataaagagcc tgagggacag 103260
gtgcgtctgt cggggaattgg ggcatgagag gaccatcagg agtatcggga cggaattata 103320
tgaggcaacg agggaaataa tagagtcgct caactccacg ttcatccccc agtttacgga 103380
ggtgaccatc gagtaccttc cggggagcga cgagtatgtg gcctactact gtggccgccg 103440
catcaggctg catgtgctct tcccccccggc catctttgcc ggaacggtga ccttcgacag 103500
cccggtgcag cgcctatacc agaacatttt catgtgctac cgcacgctgg agcatgccaa 103560
gatctgccag ctcctgaaca cggcccctct caaggccatc gtgggccacg ggggcgaga 103620 catgtacaag gacatcctgg cccatctgga gcagaactca cagcgcaagg accccaagaa 103680
ggagctgctg aacctgctgg tcaagctctc ggagaacaag accatcagcg gggtcacgga 103740
cgtggtggag gagttcataa cggatgcctc caacaacctg gtggaccgca accgtctatt 103800
tggccagccc gggggagacgg ctgcgcaggg cctaaagaaa aaggtctcca cacggtggt 103860 caagtgtctg actgatcaga taaacgagca atttgaccag attaatggcc tagagaagga 103920
gagggagctc tatctaaaga agatccgctc catggagtct cagctgcagg cctccctggg 103980
tcccggcggc aacaacccag cggcgtcagc ccccgccgca gttgcggcag aagccgcgtc 104040
tgtagatata ctgacgggca gcaccgcctc cgcaatcgaa aagctgttca actcccgtc 104100 cgccagcctg ggtgccaggg tgtctggtca caatgaaagc atcctaaaca gtttcgtttc 104160
tcaatacatc ccccttcgc gggaaatgac taaggatctg actgaactt gggaaagcga 104220 gctgtttaac accttcaagt taacacccgt ggttgataat cagggcagc gtctctacgt 104280 cagatactcg tcagacacga tctctatatt attgggcccc ttcacctatc tggtggcaga 104340
gctttcaccg gtggaactcg tgacagatgt ctacgccacc ctaggcatcg tggagatcat 104400
cgacgagctc taccggagca gtcgcctggc catctacatc gaggacctcg gtcgaaaata 104460
ctgccccgcg agcgcgaccg ggggagatca tggcatccgg caagcaccat cagcccgggg 104520
ggacgcggag cctgaccatg caaaaagtaa gcctgcgcgt gacccccgc ctggtgctgg 104580 aagttaaccg ccataacgcc atctgcgtgg ccaccaacgt ccctgagttc tacaatgcca 104640 gggggggacct taacatccga gacctccggg cccacgtcaa ggccccggatg atctcgtccc 104700 agttttgcgg ctacgtcctc gtgagtctgc tggactccga ggaccaggtc gaccacctca 104760
acatattccc ccacgtgttc tccgagagga tgatcctgta caaacccaac aatgtgaacc 104820
ttatggagat gtgcgccctg ctctcgatga ttgagaatgc caagagcccc tccataggcc 104880
tctgccggga ggtgctgggt cgcctgaccc tcttgcactc caagtgcaac aatctggact 104940 ctctgttttct gtacaatggg gccaggacgc tgctgtccac cctggtcaag taccacgacc 105000
tggaggaggg ggctgccacc cccgggccgt ggaatgaggg cctgagtctc tttaagctgc 105060
acaaggagct gaagcgcgcc ccatccgaag cccgggacct catgcagagc ctctttctga 105120
cctcggggaa gatgggggtgc ctggccaggt cacccaagga ttactgcgcg gatctaaaca 105180
aggaggaaga tgccaactcg ggcttcacat ttaacctgtt ttatcaagat tctttattga 105240
ccaagcattt ccagtgccag accgtcctcc agaccttgag acgcaagtgc ctcgggagtg 105300
acacggtctc aaaaataatt ccctagaata aactgagaac agtcatcagt aaatctgtct 105360
ctcgcgtgat ttccatagga atggtgtagc cggggtggag ggccgatatc acatcaagca 105420
```

```
gaaaggccat aatctctcga aagtaggcgg tggggctgag accatgctca gtggccgtct   105480
ggcaggggc cgggcgcgct ccgtccttgt ccaggagaca cacgtggctt ccagagaggc    105540
gcagcccagc cctccgcagc cgctgaagcc aggctcgcgg aagagcccaa aacctgtttc   105600
ggcgccgccc gggggccagt ctccgggtca ggtcgcggac cagggtcaac aggtggtcgt   105660
gggatggcgg ggccttgtct gcctcgggtc tcgccgctag ttggtccagg gtccaggaga   105720
aggcttcgtg ccaaaccaaa aagggccccg agtgctccct acatccaccc acgtaaagat   105780
cccctgaaa gatggccatc agtaggcacc cgggcccgcg tcgagccttc acccgaatgt    105840
gtctgcgggc cacggtggcc tctccaccca tcacatcccg gtcgagccgg ctggcatcct   105900
ccgagtcttt cacgccttgc aggaaagcct aggagataca gcaacagaaa gctattagcc   105960
ggtggttccc ccaccatcat tcttcctgtt aacgggaaga ataagagttg gcaaacccc    106020
gggggccgcg ctctcccacc cagccccgct tctcacctgt gctagtggct cctctgaagg   106080
atgggcggag gttggtgcca caaagcccag gatgaactcg tctgcataag cccaggtcag   106140
tcctaggtca gcggccgcgt gtaggagaac ccgggtgacg gcggtgtaga ggcccccgag   106200
tgcccgtcgc gtgtctgagg tgccatagcg gtgaagggcc cgcagccagg tttgcgcgtc   106260
ccgcgcctgc cctccgccat caggcgttcc cacggggggcg cccctggcag agaggtggca   106320
gcgggccaat tcgtagagcc accaagtggc atcagcctca aggatggctg tggcctccgc   106380
gcgcccgacc accgtcgtct cgtcctcccc ccctccctcg ccgccttccc gcgtgcaaac   106440
gtggcgaggg ttaatctcct ttcgggtcgg gggccagatt tgttgtagga gcagcgagcc   106500
gcgtcgttgc cctgaccgcg cgtcgaggcc caggagggcg tctgccaggg gcgtcccaga   106560
gactcccagg ttcaggtcca gtagcaggag accctcgctg tgtggcgccc ggtgccagaa   106620
ggccggcctc gcccgtccca cataatggat gggcaggaag ggaaagcccg ggacataggg   106680
ctggaaatct gagccccctg ggcagagttc ggggtccagg aggtagaaga tgggcttggt   106740
gcctctgtgg ttggcgtagc aggaggcata gatactgcgg aggaaggcgt agagcccgcc   106800
cccggccata ctccaagagt tgacaagcca ggactcgaat cccccagccg gctcaagaat   106860
tttcaggctg acgcggtgcc gtcggcgtc cccaccacgg ccggtggccc cgtcggacga    106920
caccagatct acttcataag tgaccggtcg caggatgtcc ctaaagggga cgggagaggg   106980
gtcgtcggga gtctcggtgg aataggtgaa aacatcccca cgcggtgtcc tgatgtatac   107040
gtccaactgt ccgggagact cagagtgcct ctgagcatgg gggcatgtct gttcccctc    107100
catctcggac ccgaagccat caacaggtgg gggttgttgg tcccgcccat catccccga    107160
gcagctttgg cagaccacct gtgctggaaa gagaggctgg aagatgaggc cctgctcatc   107220
ctccaccctg gcggcggaca agagtctgcg gtctcgggtt ctaaatgaaa ggtcaaatag   107280
gtccttctcg gcggcatcgg cgagcatagc aatgagcccc ccgctgcgcc tgagctcccg   107340
ctcccatcgc aaaagttga gttcggtagt cgagggcgcg ttgaccacgg ggggctccag    107400
ggagcctcca agcggcggct ggcaggcctg caccacgatc agagtctcaa cgtcctccct   107460
tttgatgggc acgatgccca cgacccaaat cgcccaccac cgccctgcgg tctgggtgac   107520
attataaaag gtaaccgagc tgacgcgggc cctgacgctc tccgcgggtg tttccatcat   107580
tgtttgagat ctgaggagga ctggaccctt taaaacatcc ggtcacgccc tttgcaaatt   107640
atttaaaagg tgaatgctca actgagacca tcgcaatcat gaagtcctcc aagaatgaca   107700
cgttcgtcta tagaacgtgg ttcaaaacgc ttgttgtgta ctttgtgatg tttgtcatgt    107760
cggcggtggt ccccatcacc gccatgttcc ccaacctggg gtaccccctgc tactttaacg   107820
```

```
cactggttga ttacggggca cttaacctga ccaattacaa cctggcccac cacctgaccc  107880
ccacgctcta tctggagccg ccggagatgt ttgtctacat cacactggtc tttatcgcgg  107940
actgcgtggc tttcatctac tacgcctgcg gcgaggtggc gctaatcaag gcccgaaaaa  108000
aggtctcggg tcttacagac ctctcggcct gggtctcggc agtgggctcc ccgaccgtgc  108060 tgttttggc catcctcaag ctctggtcca tacaggtctt catccaggtc ctttcctaca  108120
agcacgtctt tctctcggcc tttgtgtact ttttgcactt tctggcctca gttctacacg  108180
cctgcgcatg tgtgactcgc ttctccccgg tctgggtggt caaggcccag gacaactcta  108240
ttccccagga caccttcttg tggtgggtgg tcttctacct gaagcccata gttacaaacc  108300
tgtacctggg gtgccttgcc ctggagacgc tggtcttctc gctcagcgtg ttcctggccc  108360
tgggcaacag ctttactttt atggtggggg acatggtgct gggagccgtg aacctcttcc  108420
tcgtcctgcc catattctgg tacattctga cggaggtgtg gctggcctcc ttcctgcggc  108480
acaactttgg cttctactgc ggcatgttca tcgcctccat catcctgatc ctgcccttgg  108540
tcaggtacga ggccgtcttt gtctccgcca agctgcacac cactgtggcc atcaatgtgg  108600
ccatcatacc tatcctgtgc tcagtggcca tgctcatcag gatatgccgg atttcaaaa  108660 gcatgcgcca gggcactgac tatgtccctg tctcggagac ggtggaactg gagctagagt  108720
cagagccgag gcctaggccc tcgcgcacgc catcacccgg gcgcaaccgc cgccgctctt  108780
ctacgtcctc atcttcctcc aggtcaacca ggagacagag gcccgtctct acccaagccc  108840
tcatctcctc cgttttaccg atgacgacga cagcgagga ggagatcttc ccctaatgca  108900
ataaaaactt aaaacactga ggttactttc ccgtcattct ttcgggggaa cgaggggagg  108960
cgggaattgg gttaagatag gggcgaaggg tgggggtggg tgcaagaatt ggggctggga  109020
atggagaggg gagtgggcta ggtgccgaca ccggggtgcc aagataatgg attgagtaag  109080 catgggggctc tgatcgggtc cgccgggttc tcaggggtgt agtgggtggg cattgcatat  109140
ttttgccgcg gtgctgttgg gccttggact cggggtgatc atccgtacca tcacccgcac  109200
ccgcacccca gtccacagcc accggccaag gtcctgggcc tcccaccacc gttatgcctc  109260 ccccttttacc cattaattac aagagatgtt agtttggttt tttatttggc aaaaacagca  109320
attcatcatt ttcagagtcc tcatcatatt cgagcccctc gttggtttcc ccgcaggccc  109380
tcccttcttc ggccgctatt agcttagtag tctccaggtt aaactcctca tagtcattat  109440
acaggttgat tattccccg tccacgtcgc ctatggagtt gactcgtcgt cggcaaagag  109500 accagaggc acccatggcg cggtgtcaaa agtattgtct gcgtacgctt tccaggagcc  109560
agccgcggtg ctcaaggtct tacggatgac agagtccggc aggaccacgg tgtcaccag  109620 caccgccacg ggaatctcca ccgaggcgtc cagaagcagg tctgagccga gcgtgcaggt  109680
cgccgggtct agaggcgacc gttttcgaaa gaaggccgtc acaatgttca cccggggtga  109740
gcagtctctc ccgggcttgc caccccact gtggcggacg tagtctccaa caattttgta  109800
ttggaggagc acctggtaga agtagttgtg ccgtggattg atgaagatgt tgactgggac  109860 ccggtctttta ataccaatgc gcccccgcatt ttcgcttggg tccgtcatta cgtagagcat  109920
agactccacc ccctgttgg cagctaggct gtctgccacc aggtcatgac cggggcccag  109980
tttgcgctta cggacatctt taagattcca ggcctcatcc tgcgtcaaca gatagtcacc  110040
ctccgaggga aaccgcccat ccgggacgta ctccacggta ggacgagcta tagaattgat  110100
aaatctgata aatgacctct tgcatggcct cttgtaaagc gcagtgtagg atgggtagat  110160
```

```
ggggtcaaat tctgacttgg aaaagaggta cttgaagcgg cacttaatct cataaatgca   110220
gctccggtcg gtgaacagta taaagtctcc ctgtgactcc acattgacgc aaagatccag   110280
agacacccca aaaatgccat ccgtgggact aatcataaag ccaaattgac ggttggcgga   110340
tgcgtccccg cagatgagct tacagacaat gtccttgacc gtgtcctcac accgcaggcc   110400
aaaggccaca ggtcccccaa agtagtgatt tgtggagatg ggagctggct caaacacctt   110460
ggtgggtcca ttcttaatgg tggagagcag cttggaagag gaaattatgc catttcgcaa   110520
tatgtcccac atcaggttct cagactgccc cctggtcatg gactccacgt acgagcagag   110580
aacagtcctc tgctcgtcgg tggcctcctg tagcccccag taaatggatt tcagggaggg   110640
accgtcctgg ctgtcattct cttggactaa cgaggagaca aagtcacaga agccagtttc   110700
accagagaac tcttgtattt gttcacagag gcaatagaga tagacatagc gcatggccgg   110760
catctgaggt ggacggtcaa ggttacggac aaaggcctca gtctccggac tgcggaggaa   110820
gcgggcaaac gtgtaggagg tcatctcctc catgggatcc tcgagctcat ccacgtcggc   110880
catctggacc aaagaagtcg tctgccaaga gttcagctac cagacctgga agatgagggt   110940
gctcaaaccg tgggcgacag ttgaagaagt agctctcctt gaacctcttt ttaaggctcc   111000
ggcaccactg caagaattga ctcatatgct ccgccgtgac atccacgcac ggactctcgc   111060
cacacgaggt caggcccatg tctaagttca ggttccacat ctgcgacagc acctccaaca   111120
gcaccacctt tggggctgca aattgcaaaa agtagagcgg gtcggatcgg tcaaatccca   111180
tgtcagggtt ggggtagggg attttgtggg tggagtcagc gaggtgcatg ataccataga   111240
gcagcgagta gccgagcgac tgcagatcca ggcgaagggc cgtctgcgcc ccacggggc   111300 cacacgccga ggggtcaggg atgtgcccag ccccctcaa gatgtagcac ttgctcaaaa   111360
ggcagagggg cttataggtg tccttggcta tagaaaatgg ttccctctgg caatagaggc   111420
gatagagctg ccggccctta gaagacttta gccgcacatc cagcatcttg ttgcggtcgt   111480
ggagggaagc agtcccataa tcagtcagga ccagcctacc catgccccac atggtgtctg   111540
tgaaatccac caggatgttg ctggggctaa tgtccgaatg aagaggccg cagtgccgat   111600 tcagaaagta aacggcatct ttgaggccct gaaagccccg caccagggc tcaatactac   111660 catcatgcca gtggccataa tcctggagac tgcatctgaa ctggggcata acagggcgt   111720 ggcaggacgt gcaggccgac aggtagtcca ccagggcctt gtcctgccca tcctcggcg   111780 tggccttccc aatctgaatc atgtcacaca ccatgagctc gtgatacagc tccgtcacag   111840
agtcatagag tttgaccgtg gcattatctg catgtgcata cacggcccg tagctccccc   111900 gccccagcag atactcgcag gtaatgggga ggtgatcaca gcgcgtcatg ttctccggca   111960
gctttacata gagggtctcc gtcatgtcat caatgttggt caccttcagg tgtttgtgct   112020
gaaaggtgaa gtaatcaatg acagtcacct tccccaaaaa ggcctgggtc tctcgagggg   112080
gttctgggga gacactcaac tcgccactgc tggaggagtt cgtcgggctc aactccgcag   112140
ccatattcac atccatgttc ctcaaatggc tcgagggcct gtcgcagctc gtctctggcc   112200
tcaagctcct gctcacggag ctcctccacc cgctctagct gcttgtagtt gattttggga  112260
aattgagtct tggtcgcggt gaccaccctc tgataggtag aaattagctg tttgactca   112320 aacgtctccc ttgcgcggcg cagggactct aaggcacccc gagcagatgt aaactgtgtt   112380
tcaaacagag cgtggtccct cccaaatctg tcacgtgcgc tcacagccgc tctctttct   112440 accgaggctc ttagttgctg ggccaccaga tctcgcttag aactactcat cttcataagt   112500
caccatgtcc gcaactatgg agcccagatc atacgtgggg tagagtacgg tagttccagt   112560
```

```
ggaggcttcc cggtaatttc ccacagcgtc caccatatat ctttctgcct ctcccgttag   112620
aattaggcaa ggatcatacg tgtccaccgg ccttttatac tgagcgttta ggttttgttt   112680
atgtagcaag cacaaaaggc acacacgagt gatgcaaaag ggttcctgag gcagcaggca   112740
gagctgtttt gccattttat tcaggcggct aacgtcaaag ggaggagcta tatcctcacc   112800
cttccagtca cgcacgtcca agtacagggc atacacacac ctggtgaggt gtgccaggaa   112860
tgcctctatg ttggcacatg gtgtataaac cgcagtgggt agcagaatag ggcccctctt   112920
gccccgtgct gcagcgtaaa cacagtgacg ctcttcgcag tgggacctgg ggccgtagaa   112980
gagggcccac atccaaggga gtgggtcttc aggcaccagg gaggtccagg tatgggagtg   113040
ggccaatatt tgcaaggcct gacctataac ctcatctttg ttccaggcca gcgcaattcg   113100
cataaggtcc ccatcaaaca cctcaaaaca cagacccatg cccatttcag gctgagaggg   113160
ctccatccgg ctcgaccacc cttgtccacc aaactgccat tcttctggta aacggggatt   113220
gaggggcaag agctccaaag ccaggctcga gaagtcatag tcatcctcgg ccacacggcc   113280
ggagctccgg gcctcgtgcc agggcctgtt gtcctggggg aggatattgg acacgagcag   113340
gaagctcttg agtggcgtct ccaccagctt aaattgctcg ggcgtgtcct ggcaggcctc   113400
cagtgccagt tccagacact gcccatacct gcgggcgagc atcgggtcat cgggcatatc   113460
ggccttgacc gcgttgaaca tgctgtatgc ctcgcagcgc ggccgtctga ccgagaacct   113520
aagaaacgcc ctgcagcagg atagcaccac gcaaggctgc ctgggtgccg agaccccgag   113580
tattatgtac acgggggcca agtcagacag gtgggctcac cctctggtgg cacaattca    113640 cgccagtaat ttatattgcc caatgcttcg agcatactgc cgccactatg gccccaggcc   113700
cgtgtttgta gcttctgatg aatcattacc catgttcggt gcgagccccg cccttcacac   113760
cccagtccag gtccagatgt gcctactacc agagctacgc gacacgttac agcgcctgct   113820 gccccaccc aatcttgaag actccgaggc cttgacggaa ttcaagacca gcgtgtcctc    113880
tgcccgtgcc atccttgagg accccaactt tttggagatg agagagtttg tcaccagcct   113940
ggccagcttc ctgagtggtc agtacaagca caagcccgcc cgcctagaag cattccagaa   114000
acaagtagtg ttacattctt tttattttct gatctcaatc aaatctttag agattacaga   114060
caccatgttt gacatctttc aaagtgcttt cgggttggaa gaaatgacgc tggagaagct   114120
gcacattttt aagcaaaaag ccagcgtgtt tcttatcccc aggcgccacg gcaagacctg   114180
gatagtcgtg gccatcatca gcctcatcct ctcgaatctc tccaacgtgc aaataggcta   114240
cgtggctcac cagaaacatg tcgcgtccgc cgttttcact gaaattattg acaccttgac   114300
caagagcttc gactccaagc gtgtagaggt caacaaggag accagcacca tcacgtttag   114360
gcacagtggg aaaatctcca gcaccgtaat gtgtgccacc tgcttcaata agaatgtaag   114420
acctgacgtt tcagtacttg gcaattgtag agcatagccc ggctgtaaag gtcagaaaat   114480
cgcagcaggg tccaaggttg tgctgtacat gggacctctt tcccattagc aagaacccc    114540 tgcaggacgc gtgacatgtc cgggtgcatt ttgggtgggt taaatctcag tcccaccaca   114600 aaggggggcat cctccggttt gaacatcaga cccaacaaag cccgatgccc agttatgggt  114660
acgtagtcgt tgttcagggc cgtgcatggt agcagacaag gacaggtgcc agatgtgcct   114720
gggctatcgt cctccgtcca gccacgcagg atgttcacgt gggcccccggc accatagcat  114780 gtcacacatt ccccgttatc acatctggtt agcaggttga taaatgggt cagtgatgga    114840 aaggttggca tattggggca gcacatcagc atgtccatgt taacgaaaaa catgtacagg   114900
```

```
gcccctkctg catccagge accacccogt eccagtggga tgatctccga gggtgtgata  114960
tcttgcagtt cttctactgt tttaacggcg gttgaggtgg taaagacgtg ggccgtggtc  115020
agatctgtgc aggtgactac agggtttccc ctaatctcca caggcaccgc ctcacccacg  115080
gcatctgaga ataccccaaa gtacatgaga gtcaggctgt gtggcccctg gactgcctta  115140
gtgaagagaa cctcgggcct ggccacggtg gctagggttc cattgatgta gacggtcaca  115200
taggtgggct tcttcttggg cttcagcaca atgagggtaa cattcatgta ggttttagga  115260
ggtccggcta tctgaggcac gtacacagct gacacggcgg ttgtggccgt atagactttc  115320
atctggggcg tagaggcatc gctcagcacc cagaggcact ccttgttgag gaacttgcga  115380
agctgttccc ggctactgtt cgcggcggat gccatgacgt gccagaatat atcccctctc  115440 ctcggggtg agtgccaatt ggcctttaat aacaaagccc ccaggcagca ccaaaaatgc  115500
ctgcccgtcc gatgtggtgg ccaggtggac gcagtgcccg tcagttccaa gggctactag  115560
ctgggaagca gccccaacca gcccaccggg gggcctggag tcgatcacct tacccccaggc 115620 cgaggcccct tcctcataca gcgggtggct atctatccat aggcaggcat ccggcgtctt  115680
tggtgcattg gagatagctt tcacccaaca actttcccaa ctaacccgtg tctggacagt  115740
gaagaacgct tccctgatca ggtctgaatt tttatagata cgggagtagg aggtgggaat  115800
aacaactggg atttcttgtt gtgctgtcca ggcctgcatg gccagttttt ccctgaagct  115860
agcagaaatt ctgagggcca ctgaaatgag gaagcgaaac tccctctctg gagctcccaa  115920
aattgaaacc tcagcaagat ctgttgctgg ggaggcatgg gtgacagctg tcatcctgtg  115980
cagtctgccc tgggcactca gctctggata tgtgacaaca tagagagcgt gggggctaaa  116040
aatatgagca attcccctga ccagggccct ggactcacga atggcccgac gggtcttaga  116100
gaaagaaaca ggcaccctcg agagtgcccc cgacccgacc cccacagtgc cgccagtccc  116160
tgctcggcct ccgccgcctt ccccaccggc gctgccccgg atgttgctgg ggttctcgag  116220
ggctgggtgg tgcttggaca cagaggtctc agcagccgcc ttggtctcgg ccccggcccc  116280
aagtctgagc cccaggcaaa gggccggact cccagcgtgg cccaacctct gctcccctct  116340
attctcctct tgcgttatct ccaatagaat ttgcttgagg tcatacgttt tagggtgctc  116400
gacctgggcc gcggccatcg gcatatgctc tatacccgcc cctccggggg gcccaggatc  116460
tataggtatg ggctgcatag ccgcagcaga ctcctggacc ccagaggcct ctctgatcag  116520
atgcccgtcg gtcagagccc ttttggcccc ctcaaagaga gacaggtaat aaatctgtag  116580
ctccccaacc agccctcctt catcgtaaaa tcgaagggcg gccacgtgga aggggttgta  116640
gagctctgga aggccctcct cgcagtacac tggcacactg gtaaacgtgc cccgatggct  116700
aggccgtccg ggcagcatgc cccgagcagc aaacacgcgg cagaccctcg tgagacccgt  116760
ccggtcactg aagagagtct ggcaccaggc ccctcgcag tttggcacgc gattgggggca  116820 aagtctgccc ataaccgtgt cgggaacaaa taggtgcacg aggaggggggg tcccgaggcc  116880 actcaacact tggttgtcaa tgtggacatc catagctctc tcatgcgttt ggctacagca  116940
tcatagcgct tgtttctggt ggatttaaat aacagggccc cgtagacagt cttttgtgag  117000
taaatagaga tgatgacatg gatgtagaga ctgaggacca catccaccac cttctcggag  117060
gaggcccccc taaacagcat caggcagcaa gggaacacaa aggaaaccag ggccgggatg  117120
tgaggcctca gcgcccoctc ctgatcaaag agggcctcgc tgaccccgga gatgacattc  117180
tcattcagaa agtagtgata gaggtgattg accacagtct taaccaggcc ctggacttgt  117240
tcaggctccc acttgtcccg ctggtcctgt gtgtcttgtc ggatctcggt ccagggcctc  117300
```

```
agcgccggct ggaaatgcgg ccccatgtag ttgcctgtaa gggcgcacac cactccctca   117360
tgggtctcaa tcagggtgca ctcgctggat ccatcacata cgtggtactc gccacagccc   117420
cagcaggcaa acacggaggc catgctctca ggtaacggga gatggaactc cagcttacta   117480
tacgagcaca ggtggcgagg attgggctca tccgtgcccc cctcccccg cgggaggctc    117540 aatcggcctt ggtctgacat tccaccccgg ccaggtccag gagggtgcaa atattctcca   117600
ggcgctgcac ctcagagacc tcctgctcaa agaggcctcc caccgccacg tagacgcggg   117660
ccaccgtccg gggaaggtca gtggggtccc agctcagcaa ttgtccaaat tctgtctccc   117720
caatagtgac tcgcttctta tcctgtcttt cagagcatcc gggggcagac atttcacctc   117780
ttgtttgtgg acgaggctaa ctttatcaag aaggaggccc tgccggcgat cctgggcttt   117840
atgcttcaga aggatgccaa gattatcttc atctcgtctg tgaactcggc tgaccaggcc   117900
accagctttc tttataagct gaaggatgct caggagcggc tgctgaacgt ggtaagttat   117960
gtgtgtcagg agcatcggca agattttgac atgcaggaca gcatggtctc atgcccctgc   118020
tttcgcctgc acatcccgtc ctacatcacc atggacagta acatccgagc aaccaccaac   118080
ctctttctgg acggggcctt tagcaccgag ctgatgggtg acacctcctc gctgagccag   118140
ggtagcctga gccgcactgt gcgtgacgat gccatcaacc agctggagct ctgccgggtt   118200
gacaccctca cccccgagt agccggacgc ctagcctcct ccctctacgt gtacgttgat    118260
ccggcctata ccaacaacac atccgcatca ggcaccggaa tcgccgccgt gactcacgac   118320
agggcggacc ctaacagggt catcgtcctg ggcctggaac acttcttcct caaggaccta   118380
acaggggacg ctgccctcca gatcgccacc tgcgtcgtgg ccctcgtctc ctcgatcgtc   118440
accctgcacc cccacttgga ggaggtgaag gtagccgtgg agggcaacag cagtcaggac   118500
tctgcggtgg ccattgcctc aatcattggg gaatcctgcc ccctccctg cgccttcgtg    118560 cacaccaagg acaagacgtc cagcctgcag tgggccatgt acctcctgac taatgagaag   118620
tcaaaggcct ttgagaggct catctacgca gtgaacacgg ccagcctttc tgccagtcag   118680
gtcaccgtct ccaacaccat ccagctctcc ttcgatccgg tcctctatct catctcccag   118740
atcagggcca tcaagcccat ccctctccgc gacggtacct acacctacac cggcaagcag   118800
cgcaacctct ctgacgacgt gctggttgcg ctagtcatgg ctcattttct cgcaacaaca   118860
cagaagcaca cgttcaagaa agttcattaa actttattga ctacaccagt cccttgtaaa   118920
gcgacgggtc tcgcgtgacg gcattcgtga gcagggcttc gtccagggc ttgttcttgg     118980 cggacatcat tagcccagcc gcaaatatca gaattagcat cagaaaagtg agccccacaa   119040
acaccagtgt ccagagagga agaccgtaag ataaagatgg ctgcctctca tctggaacgg   119100
tgggaagctc agcagttgtt tttgtggcat tggacgtccc tttggaggac agcgtggggg   119160
ccaaggtggt agcgttggta atacgggtag tagcactggt ggtggtggag gacctggtgg   119220
tgacattgct agtcacaccc gtggaggttc ctgttccggc ctcggtggca gtgatgttct   119280
gtgcagtaac cttagtggtg acattgatgg tggatgcgtt ggaagttgtt gggactggtg   119340
tgacagttgt cccagtggat gtcaccgtgg ttgtgttggt gctcaggata gcagttgtgg   119400
ttataggggc gctggtcgtg gtcaaggtcg tagactggtt tgtgctagga cccgatgccg   119460
acggtgatgg tgtagtcaca gccgttgtgc ctgtcacgtt ccccgccgag gccgtcgaac   119520
tgccactaga tgtccagata aggcttgtct cacagatgag tatcatggcc aggacagcgc   119580
ctgccttgtc tctggcgtgt gccatcgcgt ctggacgcag aaggcctccc ggcctctttt   119640
```

```
atagctagtc tccacaccca atactctact gaaccatcac atacatgacc tcctcgaggt    119700
atgcagggaa tgagcggtcc gtgagccggt caacacgaca ttgcttccgt ttcatgcctc    119760
cagctgcccc tgaccagtta ggacccttga cggatgtctt taacggcgcg gtgcagttgg    119820
tcaccaatga cggcctaaag gccaacacat ccttgaagca gggcgtagga atggtaccaa    119880
actcggggcc cacccccatca aagacataat atgtctcata gtggcagtga tgatgcatca    119940
ccaccacagc actcgccagg accctctgca tatcttgtac aaggcgcctt tcaactcggc    120000
cactggctct ggtgacgtta aatgtcctgt tcctattagt cacagcctgt agatttgggc    120060
acccagactc aaaaagtgca gctacatgaa gggcagccgc ctcaaatcca ccatgacccc    120120
catggctgtc cgtgttgttg gggtaataag tcacattgtt aatgaccacg gccgggataa    120180
gggtgtaaac cttgcagaat ggattggtcg gacacccata agacaggggc accccaaaat    120240 cacgccccctt accccgaagc accttggccc ccaccggcat aaagctgggc aaaaagagtg    120300
ggttaaaacc aaaggcgagt agggccagga acgccaaata gcagcagtaa tagatgaaaa    120360
caaagctcag catgaaacag cgtggaggct cagctagggt ctctgcctct ccatcataga    120420
catcttcctt gaatctcatt ctctcaccgc atacctcgct cttcatccag gaggggggcca    120480 tggctgccat tctaccagtt aacgaggaga gagagagtag gtccgcggaa attggtgccc    120540
ctctctgccc tcctgacgag gccatggtgt catccatctc cgcagtccgt tcttcagctt    120600
tggcattggt ccgggtccgg gtggtctgat tttgattctg atcctgggta ttggtcttgg    120660
tctctcctcc cccattggca tggattggca taggtgggtg tggctcaggc tcaggttccg    120720
gccctgggac ggcagcagcc gccgggacgg tgaagtcgtg gaaggtagag gcccgtccct    120780
cccgaggtcg tggggccgga gccttataaa agacttccac cctctccccg ctggccaaga    120840
cacgccgctc gtgaccacg ccatcttcct cccggctgat tgtgtggctg acggtgccgt    120900
gttccaccgc cacttgttca tcgaccatgg tacccccttt atcttaacca gcaagtggcc    120960
gtcagggtct cttgagagta tgccgctgtg gccaagcgag gccccaaatt aaatagtgat    121020
gccaaagact gtaggtaggt catcatcaca cgcatgcgtg ataaatcatc cgccactgac    121080
aggtcatcca ggtctatccg ggctatctca tccggcacca tttcctggaa gagattcaag    121140
aggtcgtaat gctcatgccg gataaggcct cggaccaggc gcatactggc cctgggcagc    121200
agggtcacca tgatgcaaaa gtagagactc agattgtcca gcagggccaa gccaagggc    121260 cctggcacct ccgggagggc caactcgtag tggtgcccca ggtatgaaac agagccaaga    121320
tgcatgtgta catcgagcat gtctgcgttc ccgggagcct gcatgacaac ccgggagtac    121380
acgttaaaca ggagaatctt ctgcagcacc tcctctgcta tgggcgtagg cagcaccatg    121440
gggaaaacaa tgtccacatc attggactct aacttcacgg tggcatgctc tcgtccaaat    121500
accgggggca taacactgag gctcccggtc ccatgccact ggaaaaaggg ctggtacttg    121560
ttcttaatgg cgtaggtctg acctggaaca atcttggtga gtatcaaact gtccacgcta    121620
acctcatcca gcacggccag ggtgcaatca gacaggtagt tgtacatgga cacgtagtcc    121680
gggaccgtct ctagagagta cacctgaccc aagcccaatc cctgcacatt ctgcgtcccg    121740
tgagtggaag ccaggggtaa gatgcagcca atcctctgtt gcatcttggc aatctcatcg    121800
gtatacagac gagaggagag agacactacc actttcaaat ccatctttat tgacaattat    121860
caaaaaacca ccttatttcc aaactttaat attcttcgta ccggcgccac ctcttcaatt    121920
atatagtgtc cgtaatggat gggggcgtgg gtctgtttga cagacataaa ctcatcgatg    121980
agtgcccggg aggaggctga gagtgcgggg aatgcctcct gcagaaagct gcagggctgc    122040
```

```
tccagaaaca cgtcagtgcc agcaatcact acaaactgca cctctgtgtt gctggtggct   122100
gggtgccctc caagtcgctg gctgtactcg ttgaccatgt tgtagagtcc cctgttgttg   122160
cgcagaagct cctccttgtt gaaaaatgcc cggcaggggc tgtagaggcc cgggacggcc   122220
gtctggcgat aggaggagtt gtacatgatg tcacccagag aacccagctg agatgcccag   122280
ggattcacag tgctccggta ttcataggcg gcatccgggc gagaatggtc atagatgagc   122340
ccctcggcaa cctcctgatt gtagttttca caggagacca cacaggcggc ccgtcccctt   122400
ggagagttgg acttttgaaa ataagccacg tctgccgtga ccggtgttac gataatctca   122460
caggtggcct gctggccgtg gcagagtcct ggagctccat taacattagt catacctgcc   122520
aggtatgtcc tggggtcccg aagcagcgtc ccattgcgct gagcgcccac cttggccttg   122580
atgtagtcat tgacttgctg gttgccaaag gcctcggccg gaaagacgct aaagaagtct   122640
tgggtgtgga tacccatgtc agtagtgatg gccgccaccc tggccggcgt catggtcgag   122700
ctataactaa gcccggtgtc gatggaggcc atctcgtgat gcacctcaaa ggttaccgcg   122760
tccaccctgg cctcccggcg gctaacattt ggggtcccaa tgaacatgga tgttgaggcc   122820
ctggagctaa acaatatgtt ttcagagagg atctcatcgg tcctgaccac ggtcatggcc   122880 accctgggt ggatcttgag cttggcctgg gcaatatagg ccatggggga catcttgatg   122940
tgcatggcgg tcattccact gattgaaacg agggaaggaa gacattcggc cgcgtatttg   123000
cccatgggcg agcggtgcca ctcccggtac tctgcaaaga gctgctctgg ccggttgaag   123060
gcttccacgg cccgctgctg aggattgcgc ataacaaagg tggcaacatc ctggtgcatg   123120
gtggcagcca ctcgcgggtc cccgtaaaac atatggaaag gaatggcgtg aaagagacac   123180
tgggtgacgg cccgggtcct ctcggagaag gcaaaggcca ccagcccgtt caccaaaaca   123240
gtctgctctg tccgcttgtc ggcgggattc ggggccagct gctgcgtaac gtcattgtcc   123300
accgacacgc gcacggtgcg ggtgaaagtg gggcaggtca tgaatgaggc gctgaggtcc   123360
ctgatcatgc ccacggtggg gcggaggtcg gagatctcca gcagatccct gagcgtccca   123420
ttctccaaat tgtcgagtat gtcctcgtcc ctggtaaaat gatggctgaa ggctggcccg   123480
ttgtaggcca gggtctgggc cacgtgctga agtccaccc cgaggccgca catgtgggca   123540
ttggtgcagg tcgggaggaa aacgtagtaa aagatctttt ccagcacatc cgcatgcccc   123600
tcatctacat aagggcctag gtgcagacgg aaatcgtggt cgtggtctcc gttaacccgg   123660
tagccgtaca aggccacaaa ttgggcagcc atctcatcca tgtttccaac cctctcaata   123720
aactggggcg cggccagggt gtcagcgtaa acctcatttc cgataataat ctgggggcc   123780 cggtcactaa cggtgagaag atgggtgaaa atgtctgtgt aggccaccgg ggggagcagg   123840
ttagggtcca ggagtgcgca gacatactga cccacgctct catcccccac aacatctgac   123900
ccggccaggc gcatcagggc ctgctctagg gctataagtt ccccatagat ttttctatac   123960
atggaatagg cctccttgga gatggcgtta tttcccaggt ggcggcagat gaacttgatc   124020
atggaaaagc tgttcacaaa ggcaagcctc cctgcccgtt cccagtaggt gttgatgcac   124080
agggacacca aaggcacgtt catgacaaac ttttcctcaa acccgtggat catagcctcg   124140
actacgtaga agaaggctgg ataggcagtg tcataggcag tatcctgcac agtctcaata   124200
acggcctgat ccaccacgtg gccagagat gtggcggtct caaactgctg ccccgggcc   124260 tcttggaatg cagctgggc caggggagtc ggcaggttac ccaccattag ccggtgcacg   124320
gccctgtgcc tggccctctc cccggcatcc ctgccaatgt aaatatcata aaggggtgc   124380
```

-continued

```
agctccagcc gcagcaggtc ataattggac gggtggagga agtcttcggt gggcagcccg   124440
cacttgagag ctatatctgt cacgggggct gcatacttgt tatcatagaa ctcgtccaca   124500
ataacaagca cattcatgtg attgggcctc ctgtgttgca gggagtaggt ctcgcgcctg   124560
tctcgcgggg ccggggccgc gttgaggctg tttagggtat gggcgggtgt gtggagtcgg   124620
gggtgacaga gaaccttgag agcattctgt aggttaaacg cgaggagaag gttattcttg   124680
tttacgatcc atgcctccac cggtagctgc tgtgtggggt tgtccagcat tttgatggcg   124740
gcggaggtcg tgtacttggg attgggcata aacaggccca ctgggaaata gtagctgtac   124800
tgcattcttc tgttgagggg gtatgcgggac tgagtgtcat tgtacatctt ttgcaggctt   124860
tccacggcca ccgcgtggtt gcccagcttg atgacggcgg ctgagatcgg cacccggggc   124920
tgatcctcga cccctgcggc cacagccggc aggtcagact tggtgcttcc ggctttttcc   124980
ggtgagtcca cgatcctagc catgaaatgc tcaaacgtac gcatcacgcg cccgtagctc   125040
acggcagtga ccaggttctc cccccgtacc acaaaagaag catagctcga gggcccatg   125100
atctggttgt cggcctcctc acccaggaag gtcaagagtc ggcgcagaac gttgtcggtg   125160
acaataaaca ccccccccac tggctctccc cccttggcgg tcgtgtaggt actgaccccc   125220
ttgagcacgc tctccccgga cacggccgct accatctcag agagacggct cgcacgtac    125280
tgagaaaacc cggagcccat gttctcggcc cggtccagga agaaggagtg ctccagcaga   125340
tgcctcttga acatggcaat gaggtcagac ttgacagtct tggagaaccc cctctcagtg   125400
aaggtaggat ccgccagggt ctgcaggata acatgggag gggcgtggcg aagcttcaca    125460
ctcaggacgt tgttaatgag gcccctctcc agggcatcga ccccaaactg tagggccgag   125520
gccacggtct tgacagcccc cacgtactct gcgtactcga ccggggtctc ggggatacta   125580
tgcaggatct ccagatccag catggacagt tccatttccg tactaatgtg gtgtttgtgg   125640
caatttttga ccacaatgaa tgtccgctgc ttgctgggtc tccttccgtc cccgtgagca   125700
atggtgggga cggagattcg aaattgaatc ttgccatccg tcatacgact caggtctttg   125760
aattccgtgt tcacacagga cacggccagt gccgtctcca ggaagcgaac atattggatg   125820
gcgttcgtgt agaccccgag tagcacctca aacttgatgc ccgcctctct ggcatccttg   125880
cccaccagca ggtcaaagct atgaaacagc ccctcggccg ctgactgccg caggttcgag   125940
agcaggtcgg catccaccgt cagataggg aagggtctgt tttccacacc ctcatttgag    126000
gccatgacac aaggtaagag ggagatgggg ggaggtctcg agggcttctc ttcacagctg   126060
ggtctctttt acgccctggc ctgcaaccgc agcccaccg cacttcccga ggatgctacc     126120
cttctaatca aatggttgga cacggccctg gcagggagg ccaccttta cgcgtgtcgg      126180
gctatgcgtc gtcttctact cggcgttatc cgaataaatg actgccagga gctgccacct   126240
ggtttaataa ttctgagtcc gggcaccgtc cctggcccc ttggagtcca gagtctggag    126300
catacagact gcgaaatatg gtcctctgcc caccctgacc acgctgccca cctcccggtg   126360
cccagggtca tcacatacac cgactgcccg ggttccataa gcacgagctc aatgtttcgc   126420
cttatcatcc gctacttgtc tcatcaccaa tttgagcgct gcttcgagca gttctgccgc   126480
gtggtcccgc gtcgcttcct agggacctgt aagcaaaact ctgcaaagat gctggctcat   126540
ctgaagcagg ttaccaggat cccccctgt ccgcccttca gcgggcggga ggccagactc     126600
aagttccact tcttctcctg gagcacattc atgctgtcat ggccaaacaa tgccacactc   126660
cgggagatca ggacgagggc cgccaccaac ctcacccacc acccacatct agtggacact   126720
ctgtaccacg cctctccgca gaccccattt ctgacacgca gcggtgctct ataccgcttc   126780
```

```
gtcacctgtt gcaactgcac cctgcccaat atctccatcc agcagtgcaa ggccggggac    126840
agaccggggg acctggagat cattctacag agtaacggcg agggaggcc tgcgagcttc    126900
cagttcccct cctccccaac cggcgcccta ttgcgatgca tagttgctgc ggccctgctg    126960
ccagaggtgt ccgtggggca ccaggagctg tctccgctca tgtccagaag ccatggaggg    127020
cagacggatg tcaggtcggg cccggacccg gccggaggc tggtggccct cctgcgaagg    127080
gaagatgggg cacctaagga ccccctctg ggaccgtttg gacaccccg ggggccggc     127140
ccggccaaga gcgaagacga ggagtctgag cgtcgagacg cccctccacc cccgctcgat    127200
ttcagcttcc aagcttcccg gttggtgccc gtggggcctg ggtttcgcct gcttgtgttc    127260
aacaccaatc gggtgatcaa cactaaattg gtgtgctcag agcccctggt gaagatgcga    127320
gtttgcaatg tcccccgcct catcaacaac tttgtagccc gcaagtacgt ggtgaaagag    127380
acggcgttca ccgtcagtct attctttacg gacggggtgg gggccaacct agccatcaat    127440
gtcaatatca gtggcaccta tctgagcttc ctattggcca tgacgtcact gcggtgcttc    127500
ctgcctgtag aggctatttta tcccgcggcc gtgtcaaact ggaactcgac tctagatctc    127560
catgggctgg aaaatcagag cctagtcaga gagaaccgaa gcggggtctt ttggactacc    127620
aactttccct cggtggtgtc ctgccaggac ggtctcaacg tgtcctggtt taaggccgca    127680
actgccacca tatctcgagt gcacgggcgg acattggagc agcacctgat ccgtgaaatc    127740
accccccatcg tgacgcatcg agaggcaaaa atctcccgga ttaaaaaccg gctctttacc    127800
ctgctagagc tacgcaatcg gagtcagatt caagtgctgc acaagcgttt cctggaaggc    127860
ctgctagact gcgcctccct cctgcgcctg gatcccagct gtatcaaccg aatcgcctcc    127920
gagggcctgt ttgatttctc caagagaagc atcgcccact ccaaaaaccg acacgagtgc    127980
gcgcttctgg gtcacagaca ttcggcgaac gtgacaaagc ttgtggtaaa cgagcgcaag    128040
acccgcctgg acatactggg ccgtaacgct aactttttaa cgaggtgtaa gcatcaggtt    128100
aatctaagac agtcacctat tttcctgacc ctcctgaggc acatccgccg acgtctgggc    128160
ctgggccgtg cttccgtaaa acgagagatt acccttctcc tggcccacct gcgcaaaaag    128220
acagccccca tccactgccg tgatgctcaa gtgtaagcag cccggggccc gcttcattca    128280
cggggccgtg cacctgccat cgggacagat tgtcttccac accatccaca gccccactct    128340
tgcctcggcg ctgggactgc ctggggaaaa tgtacccatc ccggccctct tccgtgcctc    128400
gggcctcaac gtccgtgaga gcctgcccat gaccaacatg agagcaccga tcatctcgct    128460
ggctcgcctc atcctggccc ccaacccta tatcctagag ggacagctga cggtgggcat    128520
gacacaggac aacggcattc ccgtgctttt tgccaggcct gtcattgagg taaaaagcgg    128580
gcctgagtcc aacattaaag cctcctcgca acttatgata gcagaagact cctgcctgaa    128640
tcagatcgcc ccctttttccg catcagagca ccccgccttc tccatggttg agtccgtaaa    128700
acgagtccgg gtcgatgagg gagcaaacac ccggcgcacc atccgggata ttctggagat    128760
ccccgtgact gtgctctcat ccctgcaact gtctcccacc aagtccatcc tgaaaaaggc    128820
accggagccc ccacctccgg agccccaagc caccttcgat gccgcccct atgcccgcat    128880
cttttacgac atcgggcgac aggtgcccaa gctgggcaat gccccgccg cgcaggtcag    128940
caacgtgctc atcgccaacc gctcccacaa ctctctaagg ctggtgccca atccggactt    129000
gctgcctctc cagcatttgt acctcaagca cgtagtgcta aagagtctga atctggaaa    129060
tatagtgcag gactttgagg ccatcttcac ctccccgtct gataccatca gtgaggctga    129120
```

```
aaccaaggcc tttgagaagc tggtggagca agccaaaaac accgtagaga acatagtctt    129180
ttgcctcaac agcatctgtt ccacctctac actcccagat gtcgtcccg atgtcaataa     129240 cccaaacatt agcctggctc tagagaagta ttttctcatg ttccctccct caggcaccat    129300
tatgagaaat gtcagattcg ccacccccat cgtccggctc ttgtgccaag gggctgagct    129360
tggcaccatg gcacagtttc taggaaagta catcaaggtc aagaaggaaa ctggaatgta    129420
cacactggtc aagctttatt acctgctgcg catctaaagg aaaaacataa caatcttgtg    129480
aaccagaaag atacccagag caaaagcaat aaagtacagg attattgcca aaacaacgtg    129540
tgctctttct tcatacaggc ccgcaatttc catgacagtc ccgttggtgg tcagcagcag    129600
atagtgaacg tggaggttgt caaaatcaaa gtagttggag ctcaagatgg agttttggac    129660
ttcctgggag gtgatgtagg ttgtagtttc caggccttcc ttttcatcat aactgagcag    129720
ggcaaagcca caaaaaatgc aggatttctg cgtcctggta aaattctgga tctttggaat    129780
ctggcggggc tccccagcca cagcaccctg cgaacattta ttcattataa cgggggagag    129840
aaagagagag ctgctgagat aggtggtgct ggcctcgtat agcgccgagc ctcggacctc    129900
acggtcacta gagattatga atgtcacgtt gatgagcggg ataatcatca gaactttgtc    129960
gagcctgtcc acgcatttgt aggcggggag atgccacgca tccctgtctt ctcgctccaa    130020
agagagacgc ccaagaaacc catccacagc atttgaaacg gccgcctggt ccagcattgc    130080
ctcctggggg gccatgctca gcagcttgtc tcgtgtgagg tcaaatcgta ggctgaggta    130140
gcacggtgag aagagcccgc tctccgtccc cagggctagc ccccgcaaaa cctccccaat    130200
ctctagggcc gagcacaggg cggtggacag cagttggtat agggcaaggt tgggcccctg    130260
ggtagtcacg ttcagccgca actcgcgtag caccacgtgg ctgccgataa acagggtctc    130320
tctcatcacg gtatgcaggg gctggaaaag ggggtggcgg ttgtaggccg agagaagcac    130380
agatgtggcg cctccaatga ggccactgta aaccccggcc ttggggtagc cgacggtggc    130440
taacctcagc gcgtactcct gtttctcagt cgtcaggtga ccaagctcct ccatcttgac    130500
cgtggccatc agcacggcgg ccaagcgctc cagcccgtag gattgcatgc ccttgacagt    130560
ggccccataa catatgccga tgatgtcttt caggacagtc agctcaaaga agctcttggc    130620
caaccagcgg aggtccacgc agccattgcc agtctcaccc acggcatgac ccaccttaaa    130680
gaaggccaca gaaacctcaa acatggtagt cagcgtttcc gtgtccagtt ctggctcccg    130740
gcagcctccc ttcatctcca gcaggaccag tttctggaga acgtagcgag cgtagctggc    130800
ggctgtcatg gtgacggctc gggaaaaacat atccttcagg ttgggtacaa agtagttgtg    130860
aaagttggca taatgcacaa aggttgtaac aatcaccagg gaatagtccc cgctttgggc    130920
actggttaag gatgggtaac taaaaggccc cctcagatcc ggcaggtcct tcgtcttgcc    130980
aaagatcagg ctcaacacat gctcatctcc cttctcggtc actcgcttgt aggtgcccat    131040
cagaaattta gaagtcatgg ccccgtgta  ctgaaacttg tccccgttga tggacagggc    131100
cacataagac aagtgacagc gcagctgata aaagacatag ctgtgtggcc gcgtgttggg    131160
cagcatggtg ccaatatagt agaagagctg cttctcaagg ggggcactaa gcatgcaggc    131220
aggggaattc aggccgctaa tgactccggg atggacctta gatgcatcca cttgcatgga    131280
tccttcagag acagcaggga tatcgacagg ctcggccagc gcaataccaa gggtaccaga    131340
cgtcttgtaa attaacttgt agcggttaag catagacgcc aaatcttcgg tgacatttgc    131400
ctctctccac agcgcctctg ggctaaggcc tgggaccttt gccatcagtt cggtccatgg    131460
gatggtgtaa tgcgaagcat gcccctctat gtccaggtgc agcttaacct cgctgagact    131520
```

```
ggcagccccc acctcccata gcaacaccag gcaaaaaaca cagagcaact gcatcctagt   131580
cccgatttcc cctctcaaaa tcagagatca ccttgctcag accagcccaa tcgaaaaact   131640
gagatcgtat tgccggattc ttcaatgcct gcatgtaaat ctccgtccag catccaggta   131700
aatcgtcctg aaactctgag aggtccacaa gcacaaactg aaggtaggct agcgttcggg   131760
tgaacgcaag acaaacttcc aacaacaccg cgtcggctcg gaaaggctgt atgacttcct   131820
taagtacact aaagatgctg ttcttataca gcttctcggc cacaccactt cgaattatgt   131880
gggtgtggct ttgatgacat actgtcgtga ttgttgttag accggcacat accttcacaa   131940
tgtcctcggg ggcaaaatac tgtgttagga gccaggcaca gtaaacggcg tgatatgcat   132000
cgttgacact cttcaggtag ccagcatcca gtcctgactc atgtttcctc cctcgcttct   132060
tcaggcggcg catgttctcc tccacgttta acttcatcca gactatggtg tcccccgggt   132120
ctgcggtaaa cgtggccaaa acttgaataa agtcactata ggagagaagc tggctccgga   132180
gcagcattag agggaaaacc acggaggccg acagcaaatg cgatcatgc aaaatccaac    132240
aatccagggg cgcgactgac ctggcaccag actcggtaac cagcaagctc cgcttcctag   132300
aggccaagac tctgaaaggg gtagtaaatt tcatctggca tgctaaaacc tcagccgacg   132360
tgtcttccct tccatgcctc gcccgagtca cattcttgtg catggcctta atggcatttt   132420
catacacatg agtccagtac cgcatcggtt cagggactac aatggtcagg tccccaaaga   132480
cagccttcaa atgattcagc atagtagtct ttcccacacc aggggcacct tccaaaaata   132540
gggaacaggc aggtttgatt actggtacat gatttgtcag gtgggtcaca attggaaccc   132600
gcgtgctctc cttcctctga gccttggcct ggcgggtgtc ttgggcatca tccagattca   132660
gaacattcat cacactccca cttagccgct tcagctgggc agcatgcttg gataacttac   132720
taaactcacg cccatgggcg gccaggtgtt cgaagagacc agaaggctta cccttgccac   132780
cattcttttg tttaacgcg gaatgagaag agggcctgcg gaaattagac tcatcctcag    132840
actcacagtc agatttgtca tcaagcccaa ggccggccag gccctcctca aagcctttct   132900
ggtacatgaa gctccggctc gtggagtccg cacctccttc tgtgcacgaa gttttgcgga   132960
accaggagaa ggggtctggc gtcttgctgg gccacactc ccggctacgt ggcttcgggg    133020
taggggcagt aggcttttgg tgtgcgggtg ctggtggctg ggctcccctg ggtagggtaa   133080
aggggcacga tgtgtgccgg ctacccggag agtttccagt attagatgtc acggcagcct   133140
gggtccggca cggcaccctc tccccagaca gtccggtcgg agccatcaag gggggccagt   133200
gggtgggcac ctggtagagt ccgtcatcat cttcctcacc tgcccctgag tcactgccgg   133260
ttggggtaag aactgagggg gcaaagtcat caatctcagc gtaaaagttt tcgtgtcttt   133320
cgttttcagg ggactcatcc tcctgacatt ttcgccagcc gccgggcggg ccggcctcct   133380
ttcctggaaa tccagccatg gatcccaccc gaggtctgtg tgccctctcc acgcacgacc   133440
tggcaaaatt tcacagtctc cccccggcta gaaaggcggc aggtaagcga gcgcacctta   133500
ggtgttactc caagctgctc tctcttaaga gctgggagca actagcctct tttttgtctc   133560
tgcccccggg acccacgttt acggacttta gactatttt cgaagtcacc ctgggtcgga    133620
gaatcgcaga ttgcgttgtg gtagctctgc agccttcccc ccgtgttat attgtagaat    133680
ttaagacggc catgagcaac acggccaacc cgcaaagcgt tactcgcaag gcacagaggc   133740
tagagggcac cgcccagttg tgtgactgtg ccaatttct tcgcacgtcc tgccccccg     133800
tgctgggcag tcagggcctg gaagtcttgg cggcgttggt atttaaaaac cagcgatccc   133860
```

```
tgagaacgct ccaggtagag tttccagccc tgggccaaaa gaccctcccc acctccacca   133920
ccggcctgct aaacctcctc tcccgctggc aggatggcgc tctccgggca cgtcttgata   133980
gaccccgccc gactgcccag ggacacaggc cccgaactca tgtgggcccc aagccttcgc   134040
aactcactgc gcgtgtcccc cgaagcgctc gagctggcag agcggaggc cgaaagggcc    134100 aggtcggagc ggtgggacag gtgtgcccag gtgctcaaaa ataggctgct ccgcgtggag   134160
ctggacggca tcatgcgtga ccacctggcc agggcggagg agatccgcca ggacctggat   134220
gctgtagtgg ccttctctga tggcctggag agcatgcagg tcaggtcccc ctccacggga   134280
gggcgctctg cgccagcccc gccctcccca tccccagccc agccgttcac tcggctcacc   134340
gggaacgccc agtatgcagt ctcaatctct cccacggacc cccctctgat ggtggccggc   134400
agcctggctc aaacgctgct tggtaatctg tacgggaaca tcaaccagtg ggtaccgtcc   134460
ttcggaccct ggtacaggac catgtcggct aatgccatgc agcggcgcgt gttccctaag   134520
cagctgaggg gcaacctgaa cttaccaac tccgtctccc taaagctgat gacagaagtg     134580
gtggcggtgc ttgagggcac cacccaagac ttttctcag acgtcaggca cctgccagac    134640
ctccaggctg ccctgatcct ctcggtggcc tacctgctac tccagggggg ctcctcacac   134700
cagcagcgcc cctccctgc ctcacgggaa gagctgctgg agctgggccc ggagagccta    134760
gagaaaatca tcgccgacct caaggccaag tcacccggcg gaaatttat gattttaaca    134820 agcggaaaca aggaagcgcg ccagtcaata gcccctctca accgacaggc ggcatatcca   134880
cccggcacat tcgcggacaa taagatttac aacctgtttg tgggagcggg actactgccc   134940
acgacggccg cgctgaacgt gcccggggcg gcgggtcggg accgagacct ggtgtaccgg   135000
atcgccaacc agatctttgg ggaggacgtg cccccttct catctcacca gtggaacctg    135060
cgcgtaggtt tagccgcact cgaggccctg atgctcgtct acacgctctg cgagaccgcc   135120
aacctggccg aggcggccac ccggcgtcta cacctatcgt ccctgctccc ccaggcaatg   135180
cagcggcgca agcctgccat ggcgtcagct ggtatgccgg gcgccatacc agtccagacg   135240
ctttcccgcc atggggagct cttccgcttc atctgggccc actacgtgag gccacggtg    135300 gcggcagacc cccaggcctc catcagctct cttttccccg gctggtttt gctgccctg     135360 gagctgaagt tgatggatgg gcaggctccc tcccattatg ccataaacct gaccggacaa   135420
aagtttgaca ccctctttga gattatcaac cagaagcttt tatttcacga cccggctgcc   135480
atgctggcgg cacgcacaca gctgcgtcta gccttcgagg acggcgtcgg tgttgccctg   135540
gggcgcccct cgcccatgct gcggcgcgcg gagatcctgg agcgtcagtt ctcagcctcg   135600
gatgactacg accggctgta cttcctgacg ctgggctacc tggcctcccc ggtggcccca   135660
agctgagcca gttcctcgca ctggagtggg tcattggcaa aaaggtaaat aaagtcatcg   135720 cacggggggtt ttgcctcctt ctcgtctctt gtttcgggta ggggagtaag gccgtgccag   135780
gccgccatgc tcagggccac ggcgtgccag aggccctcgt agtcgtgcgc atccgagagg   135840
atggcacggt ccagaagcag atagccggcc aggcagagga aggccacgaa gaggggggcga  135900 aggcgtgccc gaacccgggt ttcatgctcg tctgcacccc agtggacaag gcagtagagg   135960
acacccacca ccaggcggtt agggaggaca ctgccaaggt tgaagagcag atttccgtca   136020
gccagggtga cctggctcag gtccggcgcc ctgcgcagtc caagctgcgc ccacacacat   136080
gcacagacgg cccctgtgac atcaggccgg tcatgcaaaa acagacaaag agaccgtgag   136140
cggttaccgg ggcgcagggc ctctgccggg aagcccaccc gggccagggc ccggtaaagc   136200
aggtaccagt attcatccgg caccttgcgc gccagcacac gattcgtgcg gtttccagta   136260
```

```
tttatcacgg cttcccgcca caggtaaaag ttaacactta gggtcagcag cttggtcagg 136320
gataggtgca aaaacctgag ctcgtcctcg cgcagagcgc aaagcggcca gttctttagc 136380
atcttcagga ggagcccgtg aatcccaggt gtcattcgcg cgtcatcccc gcgcaccccc 136440
agtcccatta acatagcggg cacaatggtg caggcaccgt ctgtatacgt ctgcggcttt 136500
gtggagcgcc cggacgcccc acccaaggac gcctgccttc acctggatcc cctcaccgtc 136560
aagagccagc tccctctgaa gaagcccttg ccactcacgg tggaacacct gccggatgct 136620
ccggtcggct cagtctttgg cctttaccag agccgagcgg gtctctttag cgcagcctcg 136680
attacctctg gggtcttcct gtccctgctg gactcaattt accacgattg cgatattgca 136740
cagagtcagc gcctgcccct ccctcgagaa cccaagttgg aggctctgca cgcctggctc 136800
ccctcactgt cactggcctc cctccaccca gacataccc aaaccaccgc agatggaggc 136860
aagctgtcct tctttgacca cgtgtctatc tgtgccctgg gtcgtcggcg cggcaccacg 136920
gcagtctacg gtacagacct tgcgtgggtc ctgaagcact ttagtgacct ggaaccgtct 136980
atcgccgccc agattgagaa tgacgccaat gccgcaaagc gtgaatccgg atgcccggaa 137040
gaccaccctc tgcccctcac gaagctcata gctaaggcca tcgatgctgg atttctgaga 137100
aaccgcgtgg agactctgag gcaggacagg ggtgtggcca atatcccagc cgagtcgtat 137160
ttaaaggcca gcgatgcccc ggacctacaa aagccggaca aggcacttca gagcccacca 137220
ccggcctcca cagacccaga caccatgcta tcaggtaacg caggagaagg agcaacagcc 137280
tgcggaggtt cggccgccgc gggccaggac ctcatcagcg tcccccgcaa caccttatg 137340 acactgcttc agaccaacct ggacaacaaa ccgccgaggc agacccgct accctacgcg 137400 gccccgctgc cccccttttc ccaccaggca atagccaccg cgccttccta cggtcctggg 137460
gccggagcgg tcgcccggc cggcggctac tttacctccc caggaggtta ctacgccggg 137520 cccgcggcg gggacccggg tgccttcttg gcgatggacg ctcacaccta ccaccccac 137580 ccacaccccc ctccggccta cttttggcttg ccgggcctct ttggcccccc tccaccgtg 137640 cctccttact acggatccca cttgcgggca gactacgtcc ccgctccctc gcgatccaac 137700
aagcggaaaa gagaccccga ggaggatgaa gaaggcgggg ggctattccc gggggaggat 137760
gccaccctct accgcaagga catagcgggc ctctccaaga gcgtgaatga gttacagcac 137820
acgctacagg ccctgcgccg ggagacgctg tcctacggcc acaccggagt cggatactgc 137880
ccccagcagg gccctgcta cacccacccg gggccttacg gatttcagcc tcatcaaagc 137940
tacgaagtgc ccagatacgt ccctcatccg ccccaccac caacttctca ccaggcagct 138000
caggcgcagc ctccacccc gggcacacag gccccgaag cccactgtgt ggccgagtcc 138060
acgatccctg aggcgggagc agccgggaac tctggacccc ggaggacac caaccctcag 138120 cagcccacca ccgagggcca ccacgcgga aagaaactgg tgcaggcctc tgcgtccgga 138180
gtggctcagt ctaaggagcc caccaccccc aaggccaagt ctgtgtcagc ccacctcaag 138240
tccatctttt gcgaggaatt gctgaataaa cgcgtggctt gaaagtaaac tttattgcgt 138300
gttagtacct gtccattcac aggggtatcc agcccttgcg ccgcctcccc cagcccgcca 138360
gccaccccag acaggagatg ataatgatga ggagcaccgg agccaccaca gcacaagtga 138420
ttaggagcag ggccagtgc acccaggtgg tcttagggcg ccagggatcg attggaaaag 138480
ggcccagggt cactggctta tgcgtgggac gtttagaaac aggccgccta tggggcctgt 138540
gactggtgct tgtggtgtgg gagactaatg tggtgggggc tatggtagtg gctgggataa 138600
```

```
cagtaagatg catacgctga gtgagcgtcc ggttggcatg gtattggtcg tcttcttccc   138660
ctgcagagta attgcagtgg accccggagg ccacactgca atttctcagc gtcacattgc   138720
acgtgtagta acctgcatgc gcaagggtca cattggggat tatcagagag acggaggtgt   138780
tggagtcatt tacccattct agggtaaggc tataattgta accccgtta gttatatgag    138840 ttccgttgtt ggaagtagct acggccaagg gcagttgtcc atccccggga gtgtatcccc   138900
ggcccaactc gatccgagag accgactcat tgctaggaac gctgcaggtg agattcactc   138960
tagcacctgc atgggcggtg acattttcaa atttaaccag atctgagaaa aatgcacaaa   139020
cagaccccac acagcagcac aatagaagca ctaaatgagt cattcctaaa ctgtcagttt   139080
taaaactccc tgcttctcag gcctaaatac gtggtggggt gtgcttagga tcactttcat   139140
attctgcaac aacagccata cccggaagag gagctgccgg ttgccatttt tcaagctgct   139200
aaaccacgag tggcagcagg cctaagaagc tcctcagcaa catggagacc tcgaagggaa   139260
actggcagga gcagggagtc acgtaggcac tagcctcttc atgtgaggta agagatcgct   139320
aaaaatggga tcagggtatg taaaccgagt tttgcggggg atggtgagcc agacacggcg   139380
ggtgggggga aggagctgac acgagtgcgt agaaagggcc aaaaatacac cagctataag   139440
gaattgctca gaccaaagtt gttcctcagg tggctttagg cctaatgtag gcaattgcgt   139500
gcctagaaca ttgctaatgt gccctgtgtt tcctgccttc atgcaaatat cctacctccc   139560
ccggcctggt gcaaaatgtc tgcctcagaa tactaacagc taatccaagc taacattcta   139620
tcagtaaacg ggcagaaaac tgataaggac cgcggagttt ggccctccgc ggtgtccggt   139680
ggtcctcaca cgtgccctcc ccccccgggg ccgatggctg aggcccggaa tatgcaagtg   139740
catctttcta accagtaggg gcctccacct aggtgctttg ttaatcttta gtgggaacta   139800
gtgggagtgc tgtgcctagg gtaccccttat cctataggtc ctaccggagc tccttgcctt   139860
gataatccct gtaaacacac accacctaag aacaaggcat cgttaacctt tggtggaacc   139920
tagtgttagt gttgtgctgt aaataagtgt ccagcgcacc actagtcacc aggtgtcacc   139980
ggaggctact tgcctcagtg ccacttttac cttctcaaat ctatacgggg gggggcctc    140040 tgtaacattt ggtgggacct gatgctgctg gtgtgctgta aataagtgcc tagcacatca   140100
cgtaggcacc aggtgtcacc agggctactt gcctcggcat ctcctcaccg gagaaggggt   140160
taacaaaccc gtgggggtc ttagtggaag tgacgtgctg tgaatacagg tccatagcac    140220
cgctatccac tatgtctcgc ccgggctata tgtcgcctta cctcccctat atagtcacga   140280
ccccaccgaa ccaggcatga tgtagaataa aattttatgc atcatcttct aatctgtgcc   140340
gcttggaggg aaacatgacc acctgaagtc tgttaaccag gtcagtggtt ttgtttcctt   140400
gatagagaca caaggactgc cagccccgtt ggggagggg tggtgggtac gggagagttt    140460
gggctcgtct aaacaaagcc tcctctgatg ctctgtggca cctcaaggtg aatatagctg   140520
cccatcgacg tatcgctgga aaccggtggg ccgctgttca cctaaagtga cgcaaggtct   140580
gtcagccgcc agggtccgtt taccaggctt tcaggtgtgg aatttagata gagtgggtgt   140640
gtgctcttgt ttaattacac caagatcacc accctctatc catatcccac aattgataaa   140700
cctccgcatg tccaaccacc acgttgaaca ggatgtggca ccctaagagg acgcaggcat   140760
acaaggttat tacccagtcc ttgtatgcct ggtgtcccct tagtgggacg caggcctagg   140820
tagcatcatt tacactaaaa gcagtgacct tgttggtact ttaaggttgg tccaatccat   140880 aggcttttt gtgaaaaccc ggggatcgga ctagccttag agtaactcaa ggccaagcat    140940
ttcacacctg caaatgcacc atgtaaccac agatctaaac tgaaagttgc agctttagat   141000
```

```
ggcaaggaaa cttgggtttc aggcatagaa agcctggctc actatagcag cccatgtttg    141060
ttccagggtg ggggaaaggc acgtgccctt agaaaactta gctgcaaaaa ttctattgtg    141120
ttgggagagc ctctatatct aaaggccttt cctcccaata caaatgttac taacatctgc    141180
cctctggaga cctgctatgt ggctagactt atggcctacc caagacgttg ggggtctcgg    141240
gtaggccgat tcttccaggc ataggttaca accagtcact gctatcaagc ctactcagtt    141300
cccaacgcag cacataccccc cgcctctcc tgccatgagg actcatggca gtgtttactg    141360
ttctgctttt actcttggac caggccgtca ttctatcaga ataacagggg aagcaatgcc    141420
ccctgcgtca gcgggacacg tgtttctaga atctcggagc caataactac ctgcccctct    141480
aatctgtacg ctgcatgaaa aaccacatac acgtgatgta agtttagcca gtttattgtt    141540
acaccaatgc cccgaaagtc cccccctgtc cctttgggtc tcaggaccca gccctggagc    141600 tcgggggggcg gccgggtggc ccaccgggtc cgctgggtcc gctgccccgc tccggtgggg    141660
ggtggccggc tgcagccggg tccggggttc cggccctgga gctcgggggg cggccgggtg    141720
gcccaccggg tccgctgggt ccgctgcccc gctcccgcgg gggggtggcc ggctgcagcc    141780
gggtccgggg ttccggccct ggagctcggg gggcggccgg gtggcccacc gggtccgctg    141840
ggtccgctgc cccgctccgg cggggggtgg ccggctgcag ccgggtccgg ggttccggcc    141900
ctggagctcg gggggcggcc gggtggccca ccgggtccgc tgggtccgct gccccgctcc    141960 ggcgggggg tggccggctg cagccgggtc cggggttccg ccctggagc tcgggggggcg    142020 gccgggtggc ccaccgggtc cgctgggtcc gctgccccgc tccggcgggg gggtggccgg    142080
ctgcagccgg gtccggggtt ccggccctgg agctcggggg gcggccgggt ggcccaccgg    142140
gtccgctggg tccgctgccc cgctccggcg gggggtggc cggctgcagc cgggtccggg    142200
gttccggccc tggagctcgg ggggcggccg ggtggcccac cgggtccgct gggtccgctg    142260
ccccgctccg gcggggggt ggccggctgc agccgggtcc ggggttccgg ccctggagct    142320
cggggggcgg ccgggtggcc accgggtcc gctgggtccg ctgccccgct ccggcggggg    142380
ggtggccggc tgcagccggg tccggggttc cggccctgga gctcgggggg cggccgggtg    142440
gcccaccggg tccgctgggt ccgctgcccc gctccggcgg ggggtggcc ggctgcagcc    142500 gggtccgggg ttccggccct ggagctcggg gggcggccgg gtggcccacc gggtccgctg    142560
ggtccgctgc cccgctccgg cgggggggtg gccggctgca gccgggtccg ggggttccggc    142620 cctggagctc ggggggcggc cgggtggccc accgggtccg ctgggtccgc tgccccgctc    142680
cggcgggggg gtgccggct gcagccgggt cggggttcc ggccctggag ctcggggggc    142740
ggccgggtgg cccaccgggt ccgctgggtc cgctgccccg ctccggcggg gggtggccg    142800 gctgcagccg gtccgggggt tccggccctg gagctcgggg ggcggccggg tggcccaccg    142860 gtccgctgg gtccgctgcc ccgctccggc ggggggtgg ccggctgcag ccgggtccgg    142920
ggttccggcc ctggagctcg ggggcggcc gggtggccca ccgggtccgc tgggtccgct    142980
gccccgctcc ggcgggggg tggccggctg cagccgggtc cggggttccg ccctggagc    143040 tcgggggggcg gccgggtggc ccaccgggtc cgctgggtcc gctgccccgc tccggcgggg    143100
gggtggccgg ctgcagccgg gtccggggtt ccggccctgg agctcggggg gcggccgggt    143160
ggcccaccgg gtccgctggg tccgctgccc cgctccggcg gggggtggc cggctgcagc    143220 cgggtccggg gttccggccc tggagctcgg ggggcggccg ggtggcccac cgggtccgct    143280
gggtccgctg ccccgctccg gcggggggt ggccggctgc agccgggtcc ggggttccgg    143340
```

-continued

```
ccctggagct cggggggcgg ccgggtggcc caccgggtcc gctgggtccg ctgccccgct 143400
ccggcggggg ggtggccggc tgcagccggg tccggggttc cggccctgga gctcgggggg 143460
cggccgggtg gcccaccggg tccgctgggt ccgctgcccc gctccggcgg ggggtggcc  143520 ggctgcagcc gggtccgggg ttccggccct ggagctcggg gggcggccgg gtggcccacc 143580
gggtccgctg gtccgctgc  cccgctccgg cggggggtg  gccggctgca gccgggtccg 143640
gggttccggc cctggagctc gggggcggc  cgggtggccc accgggtccg ctgggtccgc 143700
tgccccgctc cggcggggg  gtggccggct gcagccgggt ccggggttcc ggccctggag 143760 ctcgggggc  ggccgggtgg cccaccgggt ccgctgggtc cgctgccccg ctccggcggg 143820
ggggtggccg gctgcagccg gtccggggt  tccggccctg agctcggggg ggcggccggg 143880
tggcccaccg gtccgctgg  gtccgctgcc ccgctccggc gggggggtgg ccggctgcag 143940
ccgggtccgg ggttccggcc ctggagctcg ggggcggcc  gggtggccca ccgggtccgc 144000
tgggtccgct gccccgctcc ggcgggggg  tggccggctg cagccgggtc cggggttccg 144060
gccctggagc tcgggggcg  gccgggtggc ccacgggtc  cgctgggtcc gctgccccgc 144120
tccggcgggg gggtggccgg ctgcagccgg gtccggggtt ccggccctgg agctcggggg 144180
gcggccgggt ggcccaccgg gtccgctggg tccgctgccc cgctccggcg ggggggtggc 144240
cggctgcagc cgggtccggg gttccggccc tggagctcgg ggggcggccg ggtggcccac 144300
cgggtccgct gggtccgctg cccgctccg  gcggggggg  ggccggctgc agccgggtcc 144360
ggggttccgg ccctggagct cggggggcgg ccgggtggcc caccgggtcc gctgggtccg 144420
ctgccccgct ccggcggggg ggtggccggc tgcagccggg tccggggttc cggccctgga 144480 gctcggggg  cggccgggtg gcccaccggg tccgctgggt ccgctgcccc gctccggcgg 144540
gggggtggcc ggctgcagcc gggtccgggg ttccggccct ggagctcggg gggcggccgg 144600
gtggcccacc gggtccgctg gtccgctgc  cccgctccgg cggggggtg  gccggctgca 144660 gccgggtccg gggttccggc cctggagctc ggggggggg  gcgctcccag gccggaccct 144720
ggtgccaggc agggaccccg cgccaccgc  ttcatggggg gggaggccgc cgcaaggacg 144780
ccgggccggc tggaggtgt  gcacccccg  agcgtctgga cgcgctggc  gagccgggcc 144840 agctcgcctt cttttatcct gttttttggg gtctctgtgc aataccttaa ggtttgctca 144900
ggagtggggg cttcttattg gttaattcag gtgtgtgatt ttagcccgtt gggttacatt 144960
aaggtgtgta accagctggg tggtacctgg aggtcattct attgggataa cgagaggagg 145020
aggggctaga ggcccgcgag aattgggta  ggcggagcct caggagggtc ccctccatag 145080
ggttgaacca ggagggggag aatcgggctc cgccccgata tacctagtgg gtggagccta 145140
gaggtaggta tccatagggt tccattatcc tggaggtatc ctaagctccg cccctatata 145200
ccaggtgggt ggagctaggt aggattcagc taggttccta ctggggtacc ccctacccct 145260
accttaaggt gcgccaccct tcctccttcc gttttaatgg tagaataacc tataggttat 145320
taacctagtg gtggaatagg gtattgcagc tgggtatata cctataggta tatagaacct 145380
agaggaaggg aaccctatag tgtaatccct cccccccta  ccccccctc  ccttacggtt 145440 gcctgagccc atcccccacc ccagcacccc ggggtgacgt ggcacccgc  gtgccttact 145500 gacttgtcac ctttgcacat ttggtcagct gaccgatgct cgccacttcc tgggtcatga 145560
cctggcctgt gccttgtccc gtggacaatg tccctccagc gtggtggctg cctttgggat 145620
gcatcacttt gagccactaa gccccgttg  ctcgccttgc ctgcctcacc atgcacact  145680 aagcccctgc taatccatga gccccgcctt taggaagcac cacgtccggg ggacggaagc 145740
```

```
tggattttgg ccagtcttaa attttgggga gtggttttgt gtgagccgga agttggcaat   145800
ggggtgaggg tggcgctggt taagctgacg acctcccaag gtctctcacc ctgggtacac   145860
aggtggggcg gcagcctcta actttggctg tggcctctat ttcctcccct tcctagccag   145920
ggccatgtgt tcctgcatgt ctacttgcct cctgtggtgg cagagcttgg ccctgggccc   145980
aacccccgcc ttgggagcct gtaggggcca acacccttgg tttgtttgtg ttcctgtttg   146040
ctggcaactt actggcagcc gagcagattc taatgggcgc ccgccttctt tctctcttgt   146100
tttattaata gaatctcagc caggacctat acctgagact tcaaagtctg gtcctgggtt   146160
ctgagacccc caagatttgt catgcacacc tgcacacctg ttggtattgg gtttctattc   146220
ttgagtgtga agtttgtaa aaaaattcat aaaatgtcac taattcctct tacctgttta   146280
gagtattgtg caattcttca gcctgcctat tttcaatttg cctaaggtgg caatttaaga   146340
tgtggttaat taaccatttt cctgtctgac accactgcat gggcaaccgg gttccatggc   146400
acatttacag ataaacatag atgtcttgtc ttgctcatgt gcagaggagg gggtgttggt   146460
gtgcaatata gtttctggat tccaaaatga gttgggggtg ctattttcac tatggaatta   146520
aattactgac attagacagt ggacaccggg ctatatgtgg ggatgtctgt ggcttgtcat   146580
ttcctcttag aaggtaatcc cccatcttaa cttcccttta aattgtgatg caagccctgg   146640
gttatttata gaatgattat ctaggtttga tagtctgaag gctgggcaga gaatgtttgt   146700
aatttttatt caccttcttt accccccacg agtatccagt tctagaaaat ctcctgatat   146760
cccgggctgc cattattccc ttgagtgtta tagcttcctc ttaacttaag caagagctcc   146820
aggatgttag cttttttggt ggggctggtt gtcaggaaga ggttccagtg ttgtcctta    146880 tttttagatg ttagctttgt gttggggttag tatgggctgg gtattcacta gtgaaggcaa   146940
ctaacacagc tagacgtgct agttgtgccc actggtgttt atccggtccc aaatgtcaca   147000
acagaacaca ggaggctgga tttggcagca gcacgtgtgc ttttgttgat ttttacccctt   147060 gtatcagagt gggggatgct tctggttcct ggtcttctct gtgcacaaaa agggggccaat   147120 ggccacggcc ccgcggcttt ttgtgccggt gcggagccaa tttagcttcc cctcccctta   147180 gcgggggtc tcgcggggtg ccaattgtcg cctgccttcc cctgcttccc cttgttaact    147240
tatagcatga taggtaggtc acctaacgtg gaagcctggt gggtgatcct tcctcggtag   147300
ggagcgctta gggctgttga gctcaacagc cccacctggg taaaatgtat gttctaaaga   147360
gttacccaat tataacaaaa ctgttgtagg gtaacgaaga cctgatggaa gtggtattgt   147420
tgccgttgaa agacgggtgt cctggctcaa gttcgcactt cctatacagt gttaaagcct   147480
tgtatcggaa gtttgggctt cgtcccagtg tactcaataa tgtcgactgc tgcgaaggtt   147540
tggaccgtct tccagtaggt gttggggggtc ccaaatcacg aggttaggca ggtgcactta   147600
gctctttagg agggacccctt aagccaggca atgtagtgcc ccttttttt gcaaattggc    147660 cttattatta aattcttgtt aacactaatt ctgttctatg accctgtgtt tttcagatgc   147720
cgttggacgt gtcactgagc tgattttgga cgcagctact tgacctttgc ccccgtgcct   147780
ccaacgccga taagtgctgc ttccacttttg tgttacaggt gggccaaacc tccagaatat   147840
caagtggtgg ggccttggtg ggctgcataa ggcagtaggt tttaggtgac ctacttggac   147900
catgtggatc cagtgtcctg atcctggacc ttgactatga aacaattctt aaaaaatgca   147960
tcatagtcca gtgtccaggg acagtgcact cggaagtctc atcatctccg tttgtgtgtt   148020
tagtgtggcc agtacggcca ctcctgtgcc acgccctggc atgctgctga catctgggcg   148080
```

```
ccaatttcag cgggccctttt tccccttgt tcaccccata gcaagaaggg taggttacat    148140
gggtattttc ccatcagcac ctgactggcc ggtgtaatta gaggagaggg caacaacgca    148200
aggctgttgt tttatttggg ttacaagagc tgcggtggtc gatgggttca ctgattacgg    148260
tttcctagat tgtacagatg aactagaact gtcacaatct atgggtcgt agacagtgtg     148320
cttaccagac ttccatggaa gatgtgaatt tgctgctagc tatatgggtg gtgctatggg    148380
ctccctaggg actcatgtag tggggctttg tgatagctaa tgaatgtggc agctgttgtt    148440
tgtactggac cctgaattgg aaacagtaac ttggattctg taacacttca tgggtcccgt    148500
agtgacaact atgctgaata tcttgaatat gggaggaggg gggctttggg ttccattgtg    148560
tgcccttttcc tggccaacgt gagggtccta gtgttatagg gcgtggcagt tttcttgagg   148620
gctaataacc cgggtgaggc ggttgtcaca ggtgctagac cctggagttg aaccagtacc    148680
actcggttac aaagtcatgg tctagtagtt gtgaccctgc aaagctacgt ggggatgagc    148740
agccagggac tttggttggc aagcagacag gcggcgcatt ggaacccag aggagtgtcc     148800
cggggccacc tctttggttc tgtacatatt ttgttattgt acataaccat ggagttggct    148860
gtggtgcact ccatctggta aggggctgg tgcggacgcc tgtgtttagt ctatgccaat     148920
gtttacctgc cttgggttac tattccaaac gaccacacct tgaggacac ctggagccct     148980
gatcattctc ggcttttact gccacctggc ttctgttggg tcagacagtt tggtgcgcta    149040
gttgtgtgct tagcagcaac gcacaccagg ctgactgcct tagcagtgtg gcccttatt     149100
gtggcatcct aaggagggat tctggagtgc cttttcgcgtg aagcatgccc tgagacgtac   149160
tcgagttagg acttaatcgc tcctgtgccg ctggatgagg gagcgccaat ttgtacatcc    149220
tagctctggc catagagtta gcccacctt gtgtctccct ttggccttg cggtgccaat      149280
ttccggtggt ttccctttc cgcccgttta tccaatagca tgtaagagag gttgcctaga    149340
tttggcaact ttgagggaac gttccgtgta gctggtgacc taacacccgc ccatcaccac    149400
cggacagatt ctgaacttgt cctgtggtgt ttggtgtggt tttggggtac gcaggagtac    149460
gttggaatgc tttggagccg agagggatgg gcccgcttgt gcgcttatgt gttacacggt    149520
gccaataacc ggcccggtgc ggctgccccg tgacccgtgg gccttacctt cctgccatc     149580
gggggaccct ggtgctaggg tcccttgtgt tgctttctgc cataggggg aaagcatcgc    149640
cttcagaatt ggctgctccg ttggaacatt tgaggcctac tgtatccgtg tcctgacaac    149700
attccccgca acatgacat gggttaattt aaacatgttt tgtttgcttg ggaatgctct    149760
tagggcctgg aagcttgtca ttggattcat cgtttcctga actacaggcg tagggcctat    149820
tgtagcaggc atgtcttcat tcctgcgtac cgaatggcat gaaggcacag cctgttacca    149880
ttggcacctt ttttccatgt aaacctccgt gatcctgggt cctttggaga ctcaagtgtg   149940
aatttgtttt ggtgttcggc gccagggcat ctcgacgttg gaatgtcaac tcaacttggg   150000
cacctcgata accggctcgt ggctcgtaca gacgattgtt tggctctgta acttgccagg    150060
gacggctgac gatgtgttta gtctgccact tgcatccggc gctttggtta cacgggagac    150120
taatgggggg tgtggtatgg cacaggctgg gggtgagtct gggatgtcc ctgggcgttg    150180
ctgcagccca ttcgccctct ggggatgaga tgttcagggg tggccggtac cctacgctgc   150240
cgatttacat aatataaatt gtaaatgctg cagtagtagg gatctggacg cgcgacctgc    150300
tactcttcgg aaacgccaac ccaggagcgt cgcctctggc cccatactcc cgccatgcga    150360
ctgctcgccc cctcccaggc ctccctggtg agccctttgcc gctccccgca ttcctgctttt  150420
cggcgcccct gcggatcccg atgacagcag gcctttcctt cccccgttaa tgaaaagaat    150480
```

```
gacagtgagg ttgtgacaga aggacagctt tattcagttt acagagtgcc ctcggaggct 150540
acgatattcc cgttaaatgt cttgttgatt ctctcaaagg tggggaggga ggagctctcc 150600
acaacaatgt tccctggcag cgtgagcgcg cagccctgcc gttggatgta tcttctcatg 150660
atggtgctga tagaggggtc tccggcgtag atgaaaaagg cctgggccat gctctggccg 150720
gtcacgatcg ttatggggtt gttggaaatg ttccggaccg tcagcttgag ggtctggccc 150780
ggcttccact cctgtgggta gacgtagaag accgggttgg aggagtggga cacgacaacg 150840
gccgtaatct tggagctcag gggggcctcg taggtgttgt tgtattccag ctccgtgatg 150900
aaattaggag gaataatcac aggggagcca aagtagcgga tgtctgtgga ttccccgtcc 150960
cagcgccagt ggctcttagg gtaggggttg taacggaagg caataatcac atcatccaat 151020
agggtcatgc ccaccttgac gttcagcggg ccctctcgtt tcaggtccgg cgtgtccacg 151080
gagactcgga cgtagcccct accgcggcgt atggcgttga ccggacacac cttccccggg 151140
aatgtgtgaa tacgggcgta tgactttaga aatgggggcg tgtgctgcgc cagcaggtaa 151200
ggcaggcact cgtcctggct ggtgacggga gagccactga ggaagatctg gggctcgctg 151260
gtgtttagct tgtccccact ctgggtgcag gagcgtgtca gctgaatgtc gctctgcccg 151320
ggcagaatct gcaggtagag gtaggggttc ttgaccaatc tgatgggcac aatgtaccag 151380
gtaaacttcc ctttctctat gaacaggctg cgcggattca ggacgcttag cacgatgtcc 151440
tggtcagagt gcataacgaa aagggcttg aggaatacct cgttgtcttc cgctccaaag 151500
aacaagaacg caaccgtaaa gtagcggctg ccgtaggtgg tcgtgttgaa ggagaaagaa 151560
ggtaacttga agctgagtat ctggcccacc gaggggcagg gaggcagctc ttggcactgc 151620
gcgtccagct gcaatacctg cttgttggtg acgcgaacgt atgagggaa gatctcgtac 151680
ttccacacgc ctctcatgaa cgacgtgtct ggttttcag tgggccgcag gcggcggagg 151740
ctgttcctga cgacgagcg ccgggacgct agtgctgcat gggctcctcc ggggtaagct 151800
tcggccatgg ccggagctcg tcgacgggca aggtgagagt cgggggggcgg gcgacggtgc 151860
ggccccaata caactctccg ctcgttagct ggtagaatat ccgcccggcg tctaggttgt 151920
cacttcgctc ggccggccag aagagcgcaa gtccaagtct ggtgctgggg ccgatgtgca 151980
gcggtttgtg cccgcagttg tagactgtca ttttttatggg cgagtgggcg gtccacacgc 152040
gcgggcgcag cacccattgg tcgcacgccg cctcctggaa tgtaaacccc cagagagagg 152100
gcgtgccgcc ctggagatgg ccctgtgcca tcacatgtat ttcctccttg ggtggaacga 152160
cggcgtcgtg ctccgggtgg agggggaata gcgtccaggc atctttcagg gtcacgagac 152220
cggggtccat gcttagaaaa cagccctccc gggcggtggg cggcccgggc tccagcagaa 152280
cgtcgcagac ccagccctcc tcggcccgt ccacctgtat gtccaggtgc acggaccgg 152340
aggctgcgtc tcgtgacatg gccaggcctg gtgccagccg accacgtccc gtgtcccagc 152400
cgaggccgcg ccagagcaga gcccgggact gactcagggc cacatcccct cggcccgcgg 152460
acgctgcctc gccagccccc gggccttcat gggcccgctt tctacctctc tccggcaccc 152520
cagcctggtc agccgcagag gaagcatgac cttggggtgg gacggggcag gcgtgatcct 152580
gggcgcaatc tttaccgatc cccacacctt cactccttgt tagtttgata gaatgtcggt 152640
accacgccac gggggcggg cccgcatagg gaaaagccag ggagagcgat atgggcgagg 152700
atgggctcag gcgcccag acacgcaatt tgccccctg gcggccgca gcctgcccct 152760
cggcggcccg tgcccagct ccgtcacggg gggcgcatag gaggggtata tctaggatag 152820
```

```
ccgcacctac acaaatgaga cacagacaca ggtcgtgagg atttaggcaa cgcaggcttg   152880
tctttatagt tacaaacatg ggagcgtgca cctggaagat gcagctgggg tagatcttta   152940
catctttaca gggcgcagcg gccgccagac actgaagggc agagttcacg gcgggcacct   153000
cccagaggga gcccaccagc ccgtacctgg ccacggccag ggcctcgtag ccgagacgg    153060 gcagccggag cttgtggtac tgtccctccg gcaggtggag tgggacacag ttagagaaca   153120
ttagtcccct ggtccctatc tccacccgcc aggcatgtgt gtcagtttgc agggccatcc   153180
tcgcgctcag gtggactggc taggcaccct tctgaagtat ctggcggtga ctgtcacctg   153240
gttcttgaga gagtccataa aatggctgaa gctccaggcg tatagtataa tgagcaacag   153300
ggccagacag gcggcggggc ctgggtagta gcgggcaacg agagactctg tgcaatcaaa   153360
ccccaggctc ccggcctcac ccaggaagag cagcggcagg acagcataa accaggagaa    153420 ggcgcagatg agtccggtga aggtgacgtt gcatatcagg cgcggcttcc ttccgaattt   153480
tgtgcgcaaa agtttccaga tgatgatgac tgtgaggagg acgatcagga ctgccgccag   153540
taggtagcag ccggctttca gtccttggac ggccgtgtgc atgcctttgg tggggccttc   153600
cctgcacatg ttggggcctc tgttgagatt ggcgtcgggg cccatggtaa tgaggaggat   153660
gataatcagc aggagtacca gacaaaacac gcccatcagg tacaggcaca catttctgtg   153720
ggaggttcgc ttgggcgttc ggctgaacaa tgctagggtc ttctccaacg ccatacccaa   153780
gtgagtccat acgagcaca tcaggcccaa gaacatcatg ttctgggtca aaaggcagag    153840
accggtagac gagaactcct gaatcatttt tcccagcacc cagagcagca gttctatgag   153900
aagagctatc agccagacat ccattcggtg aaccaatttt cttacaaaga tgataaacaa   153960
gatgccagcc agtgttagca gaatcagcag gacgagcagc aggcttgtca tgccgctgag   154020
gaaggcgctg taggatttag tgcacgcatc ttccgttgca ttgacggaag tcatgttggc   154080
caccagggtc cccacagtgg acccgggggc catggtggag agcatcttgc tggtcagagc   154140
cagactgggt ggtgtctgca gcaaaagagg aacttgccca ggcagtcagt tattttgcat   154200
gccacctccc tgcctggtgg acttccagac tattttctgc attcgccctt gcgtgtccat   154260
tgttgcaagg agcgatttgg agaaaataaa ctgtgagttt cacagatcca cgggccacgg   154320
tcccctgggg gcttcatgat cccaccgcct ttcccgatga tgatgacaac cgcggctgtc   154380
tgaagcggct gacgaaatcg gttgagattc tgatgagagg cttgggggggg tctttgccct   154440 caaggcgagg ctccttctcc taggaatgcc gagcccctg cactagcttc gctccactgg    154500
ggatctttgc cagccttcat actagattca gcgatccccc ggttgggaat cttcgccagc   154560
cccccgtcct gctatcccgc tcgtcgccgc gcctcccatg ctaagggccc ccttcctttc   154620
ccttgacttt ggggatattc ggagtctgct ctcgccgctc tcttctctcg tttaaacgag   154680
agaatagtag tagggtccag tctcaggccc cctcactttg ggtcttagaa tggtggccgg   154740
gctgtaaaat tctggaggac ggagagggcg ccccggagt tgttatcaaa gaggcactgg    154800
aggatgttgg ccgctccttg gagcagcttg tcgaaataat gatccacggc cacgggaacg   154860
ccgtgccgct cggcgtaggc cgggtcctcg gccatctccg tctttctcgc cccttcact    154920 cccccttgg gctccacaaa gacgtactgg atgcggtcgt ggatctgggg cagttcctcg    154980
ttgcgctcga cgaacttctg gtagacggcc aggtgaggca tctgggtgct cttgtaggct   155040
gagagcttgc ggctgagctc cgttgaaaag cagagctccc ccatgggac cctgccttca    155100 cggaggtctg tgtaggcctg gtttaggatg tcaatgacgg gcaaaaagcc cacaggtagc   155160
ccttgtgtaa atgactcttg gaagggccgg tgggagagga ggctggccgc ctcctttacc   155220
```

```
cgggcatccg ccagcaccag gtcgagcacg cgccggcagc gtgtctgcac aaacttgcag   155280
gccgtcttcc ggacgagctc cacccccttc atcagggtct tgccgtccgt cagcaccccc   155340
acatatctct tctttgtaat cagcatcagg caggagaagg tcttctcggc ctccagggag   155400
atgggggcca caaacaggct ccgggtggtg tgggcggcca gggcctcggc aaagcgcagg   155460
gtctcgctct ctgaaaaccc ccggcactcg ataaacagcg agtccgtgtc cccgtagatg   155520
actcgaagct ggccctcggg gttgaggggc gcccaggcgt ctggggaggg ggccagggcc   155580
tgcaggttgg cggggctcag ggcctccacg aaggccttgg cccgctccaa catcgtgcgg   155640
ccctgcagcg tcaccgtctc ggcgatggag aggcagggaa agaggccgtt ggccaccccg   155700
gtgaagccgt agacggcgtt gcacgtgcac ttgatggcca gctgctgctt gtcgaggatg   155760
gtcctttggc gcggatcctc gcaggccgcc agcagcttct tgatggcctt gcgcttggcc   155820
agccaggagg tcaacagact agccaagaag gactcgtgca cgtgcttctt cacaaagtgg   155880
tagacgcccc ccgtgagcct gaaggactca tagtcttctc ccgggcgcag gccggctagc   155940
ctgtgctctt ctcccggcgt tatcatggta gaataacaga gattatgagc ctgaatgatg   156000
ctcgggtaga ggctggcaaa gtccaccacc agaaccgggg agttgtagaa tccgacagg    156060 ggctggatga cggtggcccc ctggtagccg tcccggtcag aggccagggg catgggcagg   156120
ataaagtttt ccttttgggc ggccgccagg aggcaggaga acacgcggat ctgctgccca   156180
tcgtccagca cccgcctgca ggggatgtga gcgatcttgg caatctctgc cacctccacg   156240
tggatcacga aatggtttag cagatccatg accaggccg agtcctgcac gcagtacatg    156300
ccgagccgcc tgcgcccctc ggggcccgct gcaaagaggc gaggaatctc cttgtaatgc   156360
acatcctcct tcttggcccc cagtaggtgc ctggctactg tgtccagctt gtagtctgag   156420
agactgagct tgtcccggca cacggcgtac atgtctatgg ggatgaggcc ggtgatgcgg   156480
accttggtgt tggcccgcaa gaagcccttg cccgcatcat ggggtcgcct gacctcgcag   156540
acgcccccag ccctaatttt gcccagagag gctgggttga tgctgtagat gtgcctggct   156600
ctgtccagaa tgtagggcca gtcaaagttg gccacgttgt agccggtcac aatctccacg   156660
ctgaggtctc tgatgagctg gaagaaggcg tagagcatgt ccagctccga tgggaactcg   156720
tagacctcaa ccccctctat gtcttcgcag gtgcccagcg tcagcaggat gcgcctatag   156780
cgcccggcct cctcccctgt cgaccagaga acgcaggata tctgcaggat caggtcagcc   156840
tcgttggtgg ccgtggggaa gccctcctcc cctagacact cgatatcgaa ggccagggcc   156900
tggtaggagg gccaggagct gtcttcacgc cggaccgaga ggtcgcccac ctcacagtcg   156960
tactcgagct cggcgtacga gtcccggtgc tggaggcggg ggatggcgcg gcggcagctg   157020
taccagccaa aggtgacaaa gtcattgtcc aggacaaagc ggcgcgtggc atccacgttg   157080
gcctcaaaga tccgacaccc gtgcttgtct tgcagccacg tggccacgtg acacacactg   157140
ttgggatgag agagggtgat cttgtggtag tcgccggcat ggttgccgta gcccataatg   157200
gaacggcgcg tgaccttctc caccgagacc cggcaggggg tcctgcggtc gaaggtgctg   157260
gccttgaggg cgctgaggac tgcaaactcc acgtccagac cctgaggcgc gctggcgtag   157320
aagtaggcct gctgcccaaa cacgttcaca cacacgctgg ccccatcggc cttgcgccgg   157380
cccagtagct tgatgacgat gccacatggc accacatacc cctgtttatc cgatggaatg   157440
acggcgcatt tctcgtgcgt gtacaccgtc tcgagtatgt cgtagacatg gaagtccaga   157500
gggcttccgt gggtgtctgc ctccggcctt gccgtgccct cttgggcacg ctggcgccac   157560
```

```
cacatgccct ttccatcctc gtcaccccce accacegtca gggagtettg gtagaagcac   157620
aggggggget gaggeccceg cacatccace acccctgegg cgcctggtgt ctggaaacac   157680
ttgggaatga gacgcaggta ctccttgtca ggctttttca gaaggccttt attaggtctt   157740
aggaaagggt tatagaagag tcccccagac atggttaaaa ctcagtctct gcctccccaa   157800
gcagtgcggc ggcggtctct ggatcgtgat agcgtcttct gcgtaggcct ggaaaacggt   157860
ccctggctgc ctgcaatgct ctgctggcca ctgagggtcc ggccgccctc tgagctgctc   157920
tcttttgctc ctggttttgc tcatgcagcg ctaacatgat ggcttgtaat tctgtcttac   157980
taatgggatt aatgcctgga ccctcaccag aggcatgttg ctgagcgagc tcgtcgatcc   158040
cggggtagag catctgcacc ggctgctgcg acatctggcg cgtgcgcctc gtgagggaaa   158100
taaccaggat caccacccce gccaccagga ccagaatgag catgccgccg aaggggtttt   158160
tgaagaagga gatgaaacca gagaccaggc tgctaaacaa accccccacc gtgctgacta   158220
ggttggtgat ggactgaccc acgctaccca gactgtccat aagttccccc aggccgtcca   158280
cgaattgatt tcttccgttt gacactgcat tgtccaaatc cttccgcagg ccggcgatgt   158340
tttgcgcctg gaagttgtac tcccggaaga tgccctccag gtcaaagacg ttggaggcac   158400
gctgttcgtc ccgtgagtac agctccaggg aggcaaagtc aatgttctcg atgagggagg   158460
tgtttagtga gatgaaggtc tgcagggtgg caatgccgtc cagctcgatg gttttaaagt   158520
ggtggtagtc gttgtagacg tggatctcgt tgccggactg gaagtagtac tggctggtcg   158580
cctggcacac ctccgtcatc ttttttgtga ggaagatctc gttgtcggtg cccagctgtc   158640
cctcgtaggt cttggtgtcg ttgataaagc tgaaggacac caggggggcgc gagtagcaca   158700
tggtctcgga gccagggacc ctcatgctct tgcgcagggt gacggtggcc tggttaacgg   158760
gcacgcactg ggagactgag atgacatccc ccaggcgctt ggccgccacc gccttaccgt   158820
agatgctgga catgacggtg gtgggattaa tcttggttag ttctctcagc accatgttct   158880
gcctcttctg ctccaggcac caggcccgcg cgaggtctcc cagcatgcgg ttgatctggc   158940
ggcgcaggga atcgtaggca aattggatct ggacggtggc gggattgttg agggtgccca   159000
gggacttccc gggggccgcg gggggcaccg gtgtggtggc attccccgca tcccgcctcc   159060
ggcgcctcag aacggcggcg gaggtgctcc cgcgggccgc gggtggggcg ggggcgatg    159120
gactgctggg gggtgaggaa gtcggagtgg taagctccgt caggttcttg acggtggcca   159180
acgagcgcgg ggtcagaggt agccaagcta ataacaatcc tccgctcgtt ataaaatatg   159240
taatggcttc ctgccccttc gtgtaacgat cctggacggc ctcgtacttc tcatgcatgg   159300
tcttgttcac ctgctcttcg atgcacttga aggcgtccgg gagctctatg cccacggttg   159360
tgttggtcac gaagctagag gtgccctcgt cagtcacaaa atgtattgac ttccctgttt   159420
ctgtggcgat ggtcgagtca aaggtttgcc agtgttgaag cgggcagtag gctgtcctgt   159480
tctcgagctt ccaagatagg gtgtaagtgc ccttgtccag gaaggctcgg cgttcgcctt   159540
gcgggttcgt ccctcggttg tcgtagtcca ctatcttgta gttagttctc acgtggaagg   159600
agtctgcccg ctcatggaag gtttccttat ttttcccgtc atagaaaggg gacatttcca   159660
cagtctgccc ggtggtggtc acaaagaagt cgaaggggct gtttggacttg gccatcatgt   159720
cagttatcag gcagttgacg gtagttcttg ttctgtaagt ccatatcaac cacccggggg   159780
cgtcatagag ctccgtctgg ctggcgtagc ggcgcacccc gttggccagg ccccggtgg    159840
gctttaggtt gacggtgatg ttaactccgt cgcggtctac atacacgcgc gtcagcccat   159900
cttttgtcat cttgaccgcg ttgtagcact ggtagatggt atccatctgg tcagtttcgt   159960
```

```
agctgtcaac ggagaacttc tcctcgtgcc ggttggtcac ggagtccgcg taccagccat  160020
tgtagatgag aatgttggtc actatcttgg tgtaggagcg gaccttaaac gagtagggaa  160080
taatgttgtc tttaaacacc atcaacaggc cctccgtgtg attctcccgc gtgccaaacg  160140
agggacactg gatgtccgag gagaagcgga acaggtcgcc gtggctggag agctcgcaga  160200
ctcggaaagg aaagctggtt tgctgacgcg tggcggtagg ctgcaccgtg gtggcggggg  160260
gtgcgggctg ctctgggtc tgcgcaccga ggcggcacgc cagggcggct agcagcacga  160320
ccacgcttag caccctacgc cgagtcatct ctcatttgga ggtgcaggta gagaagggca  160380
tatagatcct taaatacca cccctgccc ttatacagaa gaattagggg ccggtcagag  160440
tcgtacgtga ggtaaagccc atccggggc agggcctggc cggggctgac cgcgtccgcc  160500
cggcgcagga tcaaggaccg cccccaggtc ttgttgtaga gggacacggt taggacggcc  160560
tcgcgcagcg cccggcacag aatttgctgg ctagatgcca gtgagccccc gggtacgctg  160620
tagaagctgt tgaaggaggt ctctatccag tcgctcggct cgatgcctgg ccatatcagg  160680
gaagtcagga acgccttctg gtgaggcagc gtacctgcgg cgtcacagca gcgagccagg  160740
gccacgttgc tgggtggggg aaagagcccg ctctcctccg ccaggggccc cgtgatgaag  160800
gtgtacaggc tgtgcgtcag cgcgtgcagg tgctccgagc tcagggtctg ggtaaacagg  160860
tgtgttttga tgtacttgga attctcaaag gcggcaccct cgccggcgcg cctgtcctcc  160920
cagggacccg agacgaaggc ccgtctgtag aggaagtggt tgcgcatgcg ggccagctcc  160980
cagtagacca cgtcccccca gacgcgcagg cacagggtct cggtcagggt ctcgctctgt  161040
tgcgccaggc aggactgcag cttggccaga ccctcggtgg ccacctggcg caggtactgc  161100
tccttgcgct tgagcgcgtc cgagagggcg ccggacgggc cgggctctcg tgccccagcc  161160
ggccggggca cctccgggct ctcccgggac gcctcctcct cgcctcggcc caaccgctgc  161220
atggctcggt tgagccgcgt gtagagctcg ttcctctttt gcaggatggc ccggtactgg  161280
gggtgcgccg tgaaggcggc ggcgcagtcc gccttcagcg cctccaccgc gtcgcccgag  161340
gagctgtaga ccccgccgca gaagagccgc tccgtggccc cgggagccac ggcatcaaac  161400
aggtgagtca gccttgcccc cgccagcgcc tcctcgcagg cccgccgcac cagggccagg  161460
cgacgctccc gggcaaacag ggcagagagg cgggaatggc cgccacccct ccctgcccc  161520
gttgcaccga tagcatggcc gccagagttc aatagagga gctccgagag ttccgccacc  161580
tccggggca ctgtcgagaa gacgttgtag gtgtccagcg ctctggtcgc cccctctgcc  161640
tccggccgcc ccgggcccgg gaccgcgcc tcctctgggc cgcccggcct cgccttctcc  161700
tcagcctcca acaggtgccc gagcccagcc tgccggactt cattctcaaa cagtcccgag  161760
accggctccg gattcaccgg caccgccagg tggttacagg agacgtgggt cccctctgcc  161820
gtggaagggt tgccgtggtt gggcagaacc atcagctcgc ccacacagcg ccagcagggc  161880
acagaggtga tgtagaggcg cgggtctggg atgggactta cgcccgaaa gcggcccagc  161940
agatccaggg cccgttccag gctctccagc cccatggtgt gagacatgca ataaaacacg  162000
ctattgattc tcttcattaa aatctctatg tcatttatta ggcacaaact tacatcgact  162060
ttatgccccc cgtaaaactc cacagagtac gcgactgagg gggtgcggag aggcgggacc  162120
cgggtaccct ttctaccagg ggcgagcagc gcggcagagg cctctctcga gttctctagc  162180
aggtgcacca gctccaggga cagggcgctg catgcacgg cattctgccg tctcaaacgg  162240
ggaaggagga tggcctccag ctcggccagc aggccggcgt tgcgcactac cgcagccacg  162300
```

```
tccagactcc gggggtccag ccgggcgcac acgctcagct caaccgccag ggcgtacacc   162360
tggctgtacg ccgccgccag cagccccgac atcgccgccc cagggggtctc tagacctcga   162420 gtccggggag aacggtggcc agacggcgct tgcgtctgcc cccggagccc tgccctcctc   162480
cacccagcag cagcccggcc gaggcctgcg acgcggtgct gaccggctcg ccacgctga   162540 taaagttgtc ctgggctgcc ccgggcccac cccacactcc ctccagaaag tcccgagcgg   162600
cccccgccgt ccactctatc ccgctggagg caatggtcgc cagggtttct aggacgctgt   162660
ccgccaggac ggagaagcgg cccaataagt actccgcgtc gtccctagtc agcgaggcgc   162720
atgcctcgcc catggcatcc acaaggttgc acaccacatc aaacacacag tcttcctcct   162780 gttttttgtga tataatggcc tccaggccag ccctgatgtt ctcaatctca tatgtggtcg   162840
cggcttgggt ccggcgcttc acggtcaacc ctagggtggg ggtggcaaag acaaacttct   162900
tccgcatgga agagcccccg gcctgcttgc gcagcccagc ccgggggcc tgcagcaggt   162960 tcctgtccac gccccggccc ataaagtatc ccaggttccc ggcctggaat atctggttgt   163020
tgccgttgac ccccgtgtac ttgttgatgg tcactggcag cgtgacaacc ggacgggcct   163080
tgcagacctg gctaagacag tctgtggccg cgcagaccac cgtagtcgca gtaagggagg   163140
aggtggcctc cgcgtaggcc gctgccgact ccaccgcccg cgtgcccagt acgtgggggt   163200
agtcacgggc gggcaccgac tgcgtcctcg gcaccagtcc ctgaatcagg ctgatgtaga   163260
actgggtctg gccgcacgcc ttcaggatgg cgttgttgag cctctgcttg gcgtaagtga   163320
ccaggttgcc aggcaccaca tctatgacgt tgctctcttc gtgggcccgg gagccccgt   163380 ccacaaagag ggccaggtca gagtactcct ccgcgctggc cccgctgggg acagggaccg   163440
agcgccgcct ggaaaagttg tgccacaggt acaggcttga gagcttagtg tccgggaata   163500
gggtcttgtg gtaggtgttg aggaatttca tgtagggccc gttgatgatg tagttctccc   163560
tcctggtagt ggacttgatg aagctgttct ggagggcggc attctccccc gtgaagacca   163620
ccctgttctt gatcttgatg ttcctggggc acagcatcag cacctggac atgcgcacag   163680 gcagccgccg gccgtacacc cggccctgca gggccgcgtc caggtctggc aggtcgcagg   163740
tgggctcccc atgcaccacc ttggcctcct tggccgtgag gaccccctg tcgatggcca   163800 ggctcctaaa gttggtgcac agcgtctggt agtgacccctt tagccactct gggggggtct   163860
ggccaagccc gggggttgtca ttctcatagc acatacagat gggcagggag atgtcctgca   163920
ggatggtcag cagtgagcgg taaaacagct gggtgaagat ggggcaggcg ggctgcgcaa   163980
aggggttgca cgagtactgc atcacgtggt agcagctctt gaccaggtcc ttgtaggtga   164040
tgttgttctt ggccatgctg ttcataaact ggaccacttc ggcgtccacc gccgcatcca   164100
cgtccttgaa catcttgaca aagtcacgcg ggccatgggg ctccttctct agctttccct   164160
cagcgtctat gcccagccga gacagccgct ccagcaggtt ctggttcagc tgccagtagg   164220
tgtagcgggg ctcgtcgtcc ggccgctgcc cgtcgtcctc cttatcgatg aagttgagaa   164280
agttgcccaa aaagtccgtc tcgttgtagg agcccgaggc ccccgagatc acatagggt   164340 ccctccgctg cgtggacatg acggggggaa agcggtccct cagcctaaag aagagcgtgt   164400
tcaggcacac ggccggggcc cggccctcgc agagcgagca catggggctg gcggccgccc   164460
ccgccacgta gctgcccgtc tccggcaccg gggtcagaga gctcttctgt ccctggcaaa   164520
actgcaggta gtaggcatag cgggcaagaa ggttgggcga gaaggaggcc gcatagacca   164580
ggtgctccac agcgtagttt cccggaccgt tggttccggt cacgtctggc ccaccccagc   164640
ccgagaagca gggtcggcgg caggggtccc aggtcccctc ctgcagggtc cccaggccgt   164700
```

```
gggtcatgta gaaactgtta aagagactct ccttgccctg accggttgac ttcgagaccc  164760
ccgagacgta gaggacggaa ttggtggcaa agatctgcgt ggacacgtgg ggggccaggc  164820
tggcattata tcggtgtaac gcagccacac gggcctctgg accctcacag tcggcaaaca  164880
ggggccacga gtcgtagttg aggctggccg gggtctcgtg cgaggcctcc agcatggcgg  164940
gcgcgtagct caccgccagc tcgcaggccg cgctgtccac aatcattaag gctcccgagt  165000
ccgggtgact gatggttgag gctgggaact ccttgagggg ggccaccttg gccaccttgg  165060
cctggtcctg caggctctgc ttctccagca gctccaccag cttgcccacc cgtcggacgc  165120
gcagcgcctg cgccagcccg gtgtacagcg cctcgtgcat gcagcggctg aggtccgagt  165180
tgtaaaactg gcggagctgg ggcacgccct ctgggaacac ctccttgtcg tagagcggga  165240
ccctaacgct cgcagactgc ccaccgcta cctcctgttt taacgatgga atggccacca  165300
ggtttccgct gtagagtcgc tccttgaagg cctcggttat tgccaccgcc ccaaggtagg  165360
cagagggatc tagcccttcg gggaagaagt cccccggctc ggagctttcc ctcggtaggg  165420
cgctgtaggc gtcgtatcca aacacctccc tggtctcgcc acagagggcc tcgagacccg  165480
gcccctcaaa gatgggggga accatatggg cattgtggaa cacgtagatg tccctgtgat  165540
aggaggtagc gcgtaggagc ccgcagttgg ggtcgggcct cctgtgcaga gccttgacat  165600
tgatgctgaa gcccggctcc acggtgatgc cacaaaggag cggcaccgtc aggcacctgt  165660
ggcccgcgta gccggtcccc agtgtggcca cctccctaag agggtaggtg gccaggggt  165720 aaaagtagat gtagccgcac ggacccggct ggctctggct gcccagatta tcctcgctag  165780
tctgtgcacc ctgcatgatg cccaaggtat cgccccggcc tcccagtccc acattaaatg  165840 ttacactta ctcatcacgc aacacccact gtttattcat ttacaaagat ttcaggaagt  165900
cagtcaggct ggccagggcc cacgtcacgg ggaactgacg tctcagcgat cttggcatgc  165960
cgcccagcct cgcaaaccag agtctgcgat agagggccag gtagtgggcg attgccccca  166020
gcacgaaggc ggcgctcttg tggtcatcca ggtagtttcg caccgcaaac accactgtgt  166080
agcacagcac caccctgagc cgcgaccagt agtcgtagtg gtcgttgtac actgcgcgca  166140
ggacgctgat gatgagccgt acgtgcgtgt cttgccccc gatgtcggct gtcctgcagg  166200
ccagctccgc gtacagcttc ctatccttcc tcagggaggc cttgatgagc cggcagagga  166260
ccagggctgg caaaggcagg tctttctcat cccgggtgaa caccgcgtac atggccctga  166320
acatgaggta gctggactca gccaccttgt cgtccggcgg cgagggcgcg acccacgcct  166380
cgaccggggt cctcacaaac acagaatctg tagacttggc tggcctcatg gtctcgtcag  166440
gccagctcac gggcttcagg cttatatgat aaaatgggcg tggcagaata gtataagacg  166500
cgaggcctgg gtgaggagag tccagagcaa tggccaggtt catcgctcag ctcctcctgt  166560
tggcctcctg tgtggccgcc ggccaggctg tcaccgcttt cttgggtgag cgagtcaccc  166620
tgacctccta ctggaggagg gtgagcctcg gtccagagat tgaggtcagc tggtttaaac  166680
tgggcccagg agaggagcag gtgcttattg ggcgcatgca ccacgatgtc atctttatag  166740
agtggccttt caggggcttc tttgatatcc acagaagtgc caacaccttc tttttagtag  166800
tcaccgctgc caacatctcc catgacggca actacctgtg ccgcatgaaa ctgggcgaga  166860
ccgaggtcac caagcaggaa cacctgagcg tggtgaagcc tctaacgctg tctgtccact  166920
ccgaaaggtc tcagttccca gacttctctg tccttactgt gacatgcacc gtgaatgcat  166980
ttccccatcc ccacgtccag tggctcatgc ccgagggcgt ggagcccgca ccaactgcgg  167040
```

```
caaatggcgg tgttatgaag gaaaaggatg ggagcctctc tgttgctgtt gacctgtcac  167100
ttcccaagcc ctggcacctg ccagtgacct gcgttgggaa aaatgacaag gaggaagccc  167160
acggggttta tgtttctgga tacttgtcgc aataaacgca cttgcctatt tcaccttgtc  167220
ttagtgtggc atggggggg tggcattgcg ggtggatagc ctcgcgactc gtgggaaaat  167280
gggcggaagg gcaccgtggg aaaatagttc caggtgacag cagcagtgtg tgaagattgt  167340
cacagctgct ggtttggaga aaacgggggt gggcggtgat cagggagaac aattccccgg  167400
ggacacctgc acgagacccc tgcgctctca ggaacttcgc ccaggtctcg ccaattgggg  167460
tgatcctgta gcgccgcggt ttcagcatca caggttattt tgcctgaagc ttgctggggc  167520
gtaaatccct ctcgccttgt ttctcagaga gcatttcagg ccggttttgc agtcgctgct  167580
gcagctatgg ggtccctaga aatggtgcca atgggcgcgg gtcccctag ccccggcggg  167640 gatccggatg gggacgatgg cggaaacaac tcccaatatc catctgcttc tggctcttct  167700
gggaacaccc ccaccccacc gaacgatgag gaacgtgaat ctaatgaaga gcccccaccg  167760
ccttatgagg acccatattg gggcaatggc gaccgtcact cggactatca accactagga  167820
acccaagatc aaagtctgta cttgggattg caacacgacg ggaatgacgg gctccctccc  167880
cctccctact ctccacggga tgactcatct caacacatat acgaagaagc gggcaggagga  167940 aggtaagagt gccatctatc tgtacttta tttattgcat cacaagtcac atcaataata  168000
agggcgccat ctagcgggag atgttatcca caccatccca attcacatct cagggacaac  168060
aggtcaaagt tctttgttga caccccagc gctggctcca ggggtggca gcgttggatg  168120 cagtcctccg catcggggcg gacgcctcct cccaacgcgt ttctgcggat cagtcgctgg  168180
ctggtgggca tcggagtcgg tgggcggtcc tccacgggga cacgctcctt cttggccttg  168240 ttcttgacc ttttggacat tcttctgaag gaacggcgga gagtagcgta gaatccagcc  168300
agtggtctac ccgtcgcat ggtggcttct tagatgagga gcaggcataa aagtccaaac  168360
aggacacaga gtaccaccag gagtagtctt agtctgctga cgtctgggtc ctcggggcag  168420
gggtggctag gcctggtctc cgtagaagag ccgggcaggc cgcaggcaga ggactgctgc  168480
tctagcaaag cacgctccag gacgtgtacc atctcgagag tgaggcacag ctgttttcgt  168540
ggacttttat acagtaagga caaggaaaga aggccagagg aatgtggaaa gatgagcgag  168600
gacaggtgtg gaggttttgg gctagctctt agtttctggg tgtgagagag ggattaaagt  168660
gcttatgcgc aaagaatgtg tcaacaacag gtgttcctgc atctgctggc atgagttagg  168720
tgtggcttgg gctgaatcca aatgtgtatt ggcacaagat ggaaagcaaa gttgctggag  168780
ttactgggtg ggagacaggg atgtatgtgg tcccccgctg gtatgccagt accctgtgga  168840
agtaaggggc ctcatctgcc cggtagttgt gttgtcaga ggtctgatgt gtgtaggagg  168900
ggtgggttca acgcagggc gttggtggcg gagtctggca acgcccgggt cctcttgcta  168960
cctgtgtggt gtgtgaaggg ctgggtaaag gtgtctgcca attctcgcat gtcctccttt  169020 cccccttgttt tgaaatagaa tatgaatgtg gcttttcagc ctagacagac agtgtggcta  169080
agggagtgtg tgccagttaa ggtgattagc taaggcattc ccagtaaatg gagggagagt  169140
cagtcaggca agcctatgac atggtaatgc ctagaagtaa agaaaggtta gtcatagtag  169200
cttagctgaa ctgggccgtg ggggtcgtca tcatctccac cggaaccaga agtacccaaa  169260
agcagcgtag gaaggtgtgg atcaccgccg ccaccgtctg tcatcgaagg cgggccccgg  169320
tcacctcctt tgttttcaac ctcttccgtc aaatttggtg ggcctccatc atttccagca  169380
gagtcgctag ggttatgagg cagcgggtca tgtgggccat tgtcagcagt gttgtcaggg  169440
```

```
tcctgtgggc cattgtcatc agtgttgtca gggtcctgtg ggccattgtc atcagtgttg    169500
tcagggtcct gtgggccatt gtcatcagtg ttgtcagggt cctgtgggcc attgtcagga    169560
ccacctccag gtgcgcctag gttttgagag cagagtgggg gtccgtcgcc ggctccagtc    169620
acgagcaggt ggtgtctgcc ctcgttggag ttagagtcag attcatggcc agaatcatcg    169680
gtagcttgtt gagggtgcgg gagggagtca tcgtggtggt gttcatcact gtgtcgttgt    169740
ccatggtaat acatccagat caaaatcgcc agaaacagga ggagccaaag gagatcaacc    169800
aatagagtcc accagttttg ttgcagatag agagcaataa tgagcaggat gaggtctagg    169860
aagaaggcta ggaagaaggc caaaagctgc cagatggtgg caccaagtcg ccagagaatc    169920
tccaataagt agatccagag acctaagact gcgttgaaaa aagagtgtta gggttggaaa    169980
agtgggggtg tggtaaataa ttcccaggga atgttagatc ttaccaagta agcacccgaa    170040
gatgaacagc acaattccaa ggtacaatgc ctgtccgtgc aaattccaga gagcgatgag    170100 caggaggggtg actggggaaa gaggagaaag tgcgttagag aaggaagagt aagggaaagg    170160
gggtgtgggg caaagggtgt aatacttact catcagtagg agtagacaaa gggctccaag    170220
tggacagaga aggtctcttc tgaagataaa gatgatcaaa attataatta taagtatgag    170280
agcaaaggaa tagaggacaa ggagggctcc tccagtccag tcactcataa cgatgtacag    170340
ccaaaacagt agcgccaaga ggaggagaag gagagcaagg cctagggaag aggagagggg    170400
gggtcctcga gggggccgtc gcgggcccgg tgggccccctc tcaaggtcgt gttccatcct    170460
cagggcagtg tgtcaggagc aaggcagttg aggaaagaag ggggcagagc agtgtgagag    170520
gcttatgtag ggcggctacg tcagagtaac gcgtgtttct tgggatgtag ggccgggggg    170580
atttgcgggg tctgccggag gcagtacggg tacagatttc ccgaaagcgg cggtgtgtgt    170640
gtgcatgtaa gcgtaaaaag gggaagtaga aagcgtgtgt tagtgttaga aaagcgggtc    170700 cccgggggggc aagctgtggg aatgcggtgg gcaagtgcaa caggaaatgg aaaggcagtg    170760
cggcaatcag aaggggggagt gcgtagtgtt gtgggaagcg gcagtgtaat ctgcacaaag    170820
aggcgtgggg cgcgcaacgt tgggaggtcg ttggcggcag gcgggaggcc gtgctttagg    170880
ggggttcagg tgaggcaagg ctgtggggta accgtagggg aggcgggtga ggcggctaag    170940
agggctaagg gtcggcgggt gacgaagcag cagacggcgg atatgggaat ttcagaatga    171000
ggtggcggat tcaggcgaaa agggtgtggg ctgtgcgagt gtcatgaggc aggcgcggaa    171060
agtcgctgcg gcttgctggg gccatgggcc gcgcattcct ggaaaaagtg gaggggggcgt    171120 ggcctgcccc ccgcggcccc ctagccccccc cgcacagagc ggcgcaacgg cgggcggggcg    171180 gcgggggggtc ggggtccgcg ggctccgggg gctgcgggcg gtggatggcg gctggcgttc    171240
aggggaacgg ggggtcggg gggcgcagcg gccgcgcagc catgcgtgac cgcgaggagg    171300
ggacagggtc gcaggggggcg tgtctggtgg gggcgggagc ggggggcggc gcgggagcct    171360
gcacgccgtt ggagggtaga atgacagggg ggcggggaca gagaggcggt cgcgcccccc    171420
gccgcggcag ccaagccccc aaggggggggcg gggcgcgggc agcggagcgt gacgaagggc    171480
cccagggctg accccggcaa acgtgacccg gggctccggg gtgacccagc caagcgtgac    171540
caaggggccg ctgggtgaca cagacaaccc tgacaaaggc ccccaggaa agaccccccgg    171600 ggggcatcgg ggggtgttgg tggggcatg ggggtggggc catgggccgc gcattcctgg    171660
aaaaagtgga gggggcgtgg cctgcccccc gcggcccccct agccccccg cacagagcgg    171720 cgcaacggcg ggcgggcggc ggggggtcgg ggtccgcggg ctccggggggc tgcgggcggt    171780
```

```
ggatggcggc tggcgttcag gggaacgggg gggtcggggg gcgcagcggc cgcgcagcca  171840
tgcgtgaccg cgaggagggg acagggtcgc agggggcgtg tctggtgggg gcgggagcgg  171900
ggggcggcgc gggagcctgc acgccgttgg agggtagaat gacaggggggg cggggacaga  171960 gaggcggtcg cgcccccccgc cgcggcagcc aagcccccaa ggggggcggg gcgcgggcag  172020
cggagcgtga cgaagggccc cagggctgac cccggcaaac gtgacccggg gctccggggt  172080
gacccagcca agcgtgacca aggggccgct gggtgacaca gacaaccctg acaaaggccc  172140
cccaggaaag accccgggg ggcatcgggg ggtgttggtg gggccatggg ccgcgcattc  172200
ctggaaaaag tggagggggc gtggcctgcc ccccgcggcc ccctagcccc cccgcacaga  172260
gcggcgcaac ggcgggcggg cggcggggggg tcgggtccg cgggctccgg gggctgcggg  172320
cggtggatgg cggctggcgt tcagggaac ggggggggtcg gggggcgcag cggccgcgca  172380
gccatgcgtg accgcgagga ggggacaggg tcgcagggggg cgtgtctggt ggggggcggga  172440 gcgggggggcg gcgcgggagc ctgcacgccg ttggagggta gaatgacagg ggggcgggga  172500
cagagaggcg gtcgcgcccc ccgccgcggc agccaagccc caagggggg cggggcgcgg  172560 gcagcggagc gtgacgaagg gccccagggc tgaccccggc aaacgtgacc cgggggctccg  172620 gggtgaccca gccaagcgtg accaaggggc cgctgggtga cacagacaac cctgacaaag  172680 gcccccccagg aaagaccccc ggggggcatc ggggggtgtt ggtgggggcca tgggggggtcg  172740 gatttcgccc ttattgccct gttt                                          172764

<210> SEQ ID NO 16
<211> LENGTH: 706
<212> TYPE: PRT
<213> ORGANISM: Epstein-Barr virus

<400> SEQUENCE: 16

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
                20                  25                  30

Ala Ser His Tyr Thr Ile Pro Trp Thr Glu Leu Met Ala Lys Val Pro
            35                  40                  45

Gly Leu Ser Pro Glu Ala Leu Trp Arg Glu Ala Asn Val Thr Glu Asp
        50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Ile Phe Gly Lys Thr Lys Asp Leu Pro Asp Leu Arg
```

-continued

```
                195                 200                 205
Gly Pro Phe Ser Tyr Pro Ser Leu Thr Ser Ala Gln Ser Gly Asp Tyr
210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
                260                 265                 270

Glu Met Lys Gly Gly Cys Arg Glu Pro Glu Leu Asp Thr Glu Thr Leu
                275                 280                 285

Thr Thr Met Phe Glu Val Ser Val Ala Phe Phe Lys Val Gly His Ala
                290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
                340                 345                 350

Ala Val Leu Met Ala Thr Val Lys Met Glu Glu Leu Gly His Leu Thr
                355                 360                 365

Thr Glu Lys Gln Glu Tyr Ala Leu Arg Leu Ala Thr Val Gly Tyr Pro
370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
                420                 425                 430

Arg Leu Asn Val Thr Thr Gln Gly Pro Asn Leu Ala Leu Tyr Gln Leu
                435                 440                 445

Leu Ser Thr Ala Leu Cys Ser Ala Leu Glu Ile Gly Glu Val Leu Arg
                450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Met Leu Asp Gln Ala Ala Val Ser Asn Ala Val Asp Gly
                500                 505                 510

Phe Leu Gly Arg Leu Ser Leu Glu Arg Glu Asp Arg Asp Ala Trp His
                515                 520                 525

Leu Pro Ala Tyr Lys Cys Val Asp Arg Leu Asp Lys Val Leu Met Ile
                530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
                580                 585                 590

Ala Gly Glu Pro Arg Gln Ile Pro Lys Ile Gln Asn Phe Thr Arg Thr
                595                 600                 605

Gln Lys Ser Cys Ile Phe Cys Gly Phe Ala Leu Leu Ser Tyr Asp Glu
                610                 615                 620
```

```
Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
            645                 650                 655

His Tyr Leu Leu Leu Thr Thr Asn Gly Thr Val Met Glu Ile Ala Gly
        660                 665                 670

Leu Tyr Glu Glu Arg Ala His Val Val Leu Ala Ile Ile Leu Tyr Phe
            675                 680                 685

Ile Ala Phe Ala Leu Gly Ile Phe Leu Val His Lys Ile Val Met Phe
        690                 695                 700

Phe Leu
705

<210> SEQ ID NO 17
<211> LENGTH: 137
<212> TYPE: PRT
<213> ORGANISM: Epstein-Barr virus

<400> SEQUENCE: 17

Met Arg Thr Val Gly Val Phe Leu Ala Thr Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
            85                  90                  95

Ser Ser Ala Leu Thr Gly His Leu Arg Glu Leu Leu Thr Thr Leu Glu
        100                 105                 110

Thr Leu Tyr Gly Ser Phe Ser Val Glu Asp Leu Phe Gly Ala Asn Leu
    115                 120                 125

Asn Arg Tyr Ala Trp His Arg Gly Gly
130                 135

<210> SEQ ID NO 18
<211> LENGTH: 857
<212> TYPE: PRT
<213> ORGANISM: Epstein-Barr virus

<400> SEQUENCE: 18

Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Pro Ala
            20                  25                  30

Thr Thr Val Gln Pro Thr Ala Thr Arg Gln Gln Thr Ser Phe Pro Phe
        35                  40                  45

Arg Val Cys Glu Leu Ser Ser His Gly Asp Leu Phe Arg Phe Ser Ser
    50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
            85                  90                  95
```

Arg Ser Tyr Thr Lys Ile Val Thr Asn Ile Leu Ile Tyr Asn Gly Trp
            100                 105                 110

Tyr Ala Asp Ser Val Thr Asn Arg His Glu Glu Lys Phe Ser Val Asp
            115                 120                 125

Ser Tyr Glu Thr Asp Gln Met Asp Thr Ile Tyr Gln Cys Tyr Asn Ala
            130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                    165                 170                 175

Gly Val Arg Arg Tyr Ala Ser Gln Thr Glu Leu Tyr Asp Ala Pro Gly
            180                 185                 190

Trp Leu Ile Trp Thr Tyr Arg Thr Arg Thr Thr Val Asn Cys Leu Ile
            195                 200                 205

Thr Asp Met Met Ala Lys Ser Asn Ser Pro Phe Asp Phe Val Thr
            210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                    245                 250                 255

Tyr Lys Ile Val Asp Tyr Asp Asn Arg Gly Thr Asn Pro Gln Gly Glu
            260                 265                 270

Arg Arg Ala Phe Leu Asp Lys Gly Thr Tyr Thr Leu Ser Trp Lys Leu
            275                 280                 285

Glu Asn Arg Thr Ala Tyr Cys Pro Leu Gln His Trp Gln Thr Phe Asp
            290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                    325                 330                 335

Pro Asp Ala Phe Lys Cys Ile Glu Glu Gln Val Asn Lys Thr Met His
            340                 345                 350

Glu Lys Tyr Glu Ala Val Gln Asp Arg Tyr Thr Lys Gly Gln Glu Ala
            355                 360                 365

Ile Thr Tyr Phe Ile Thr Ser Gly Gly Leu Leu Leu Ala Trp Leu Pro
            370                 375                 380

Leu Thr Pro Arg Ser Leu Ala Thr Val Lys Asn Leu Thr Glu Leu Thr
385                 390                 395                 400

Thr Pro Thr Ser Ser Pro Ser Ser Ser Pro Pro Ala Pro Pro
                    405                 410                 415

Ala Ala Arg Gly Ser Thr Ser Ala Ala Val Leu Arg Arg Arg Arg
            420                 425                 430

Asp Ala Gly Asn Ala Thr Thr Pro Val Pro Ala Ala Pro Gly Lys
            435                 440                 445

Ser Leu Gly Thr Leu Asn Asn Pro Ala Thr Val Gln Ile Gln Phe Ala
            450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                    485                 490                 495

Leu Thr Lys Ile Asn Pro Thr Thr Val Met Ser Ser Ile Tyr Gly Lys
            500                 505                 510

-continued

```
Ala Val Ala Ala Lys Arg Leu Gly Asp Val Ile Ser Val Ser Gln Cys
            515                 520                 525

Val Pro Val Asn Gln Ala Thr Val Thr Leu Arg Lys Ser Met Arg Val
530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
            580                 585                 590

Gln Tyr Tyr Phe Gln Ser Gly Asn Glu Ile His Val Tyr Asn Asp Tyr
        595                 600                 605

His His Phe Lys Thr Ile Glu Leu Asp Gly Ile Ala Thr Leu Gln Thr
    610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
            660                 665                 670

Gly Leu Arg Lys Asp Leu Asp Asn Ala Val Ser Asn Gly Arg Asn Gln
        675                 680                 685

Phe Val Asp Gly Leu Gly Glu Leu Met Asp Ser Leu Gly Ser Val Gly
    690                 695                 700

Gln Ser Ile Thr Asn Leu Val Ser Thr Val Gly Gly Leu Phe Ser Ser
705                 710                 715                 720

Leu Val Ser Gly Phe Ile Ser Phe Phe Lys Asn Pro Phe Gly Gly Met
                725                 730                 735

Leu Ile Leu Val Leu Val Ala Gly Val Val Ile Leu Val Ile Ser Leu
            740                 745                 750

Thr Arg Arg Thr Arg Gln Met Ser Gln Gln Pro Val Gln Met Leu Tyr
        755                 760                 765

Pro Gly Ile Asp Glu Leu Ala Gln Gln His Ala Ser Gly Glu Gly Pro
    770                 775                 780

Gly Ile Asn Pro Ile Ser Lys Thr Glu Leu Gln Ala Ile Met Leu Ala
785                 790                 795                 800

Leu His Glu Gln Asn Gln Glu Gln Lys Arg Ala Ala Gln Arg Ala Ala
                805                 810                 815

Gly Pro Ser Val Ala Ser Arg Ala Leu Gln Ala Ala Arg Asp Arg Phe
            820                 825                 830

Pro Gly Leu Arg Arg Arg Arg Tyr His Asp Pro Glu Thr Ala Ala Ala
        835                 840                 845

Leu Leu Gly Glu Ala Glu Thr Glu Phe
    850                 855
```

<210> SEQ ID NO 19
<211> LENGTH: 223
<212> TYPE: PRT
<213> ORGANISM: Epstein-Barr virus

<400> SEQUENCE: 19

```
Met Val Ser Phe Lys Gln Val Arg Val Pro Leu Phe Thr Ala Ile Ala
1               5                   10                  15

Leu Val Ile Val Leu Leu Leu Ala Tyr Phe Leu Pro Pro Arg Val Arg
            20                  25                  30
```

-continued

```
Gly Gly Gly Arg Val Ser Ala Ala Ile Thr Trp Val Pro Lys Pro
        35              40              45

Asn Val Glu Val Trp Pro Val Asp Pro Pro Pro Val Asn Phe Asn
    50              55              60

Lys Thr Ala Glu Gln Glu Tyr Gly Asp Lys Glu Ile Lys Leu Pro His
65              70              75              80

Trp Thr Pro Thr Leu His Thr Phe Gln Val Pro Lys Asn Tyr Thr Lys
                85              90              95

Ala Asn Cys Thr Tyr Cys Asn Thr Arg Glu Tyr Thr Phe Ser Tyr Lys
            100             105             110

Glu Arg Cys Phe Tyr Phe Thr Lys Lys Lys His Thr Trp Asn Gly Cys
        115             120             125

Phe Gln Ala Cys Ala Glu Leu Tyr Pro Cys Thr Tyr Phe Tyr Gly Pro
    130             135             140

Thr Pro Asp Ile Leu Pro Val Val Thr Arg Asn Leu Asn Ala Ile Glu
145             150             155             160

Ser Leu Trp Val Gly Val Tyr Arg Val Gly Glu Gly Asn Trp Thr Ser
                165             170             175

Leu Asp Gly Gly Thr Phe Lys Val Tyr Gln Ile Phe Gly Ser His Cys
            180             185             190

Thr Tyr Val Ser Lys Phe Ser Thr Val Pro Val Ser His His Glu Cys
        195             200             205

Ser Phe Leu Lys Pro Cys Leu Cys Val Ser Gln Arg Ser Asn Ser
    210             215             220
```

MULTIMERIC FUSION PROTEIN VACCINE AND IMMUNOTHERAPEUTIC

CROSS REFERENCE TO RELATED APPLICATIONS

This patent application is a continuation of U.S. Application No. 14/416,780, filed 23 Jan. 2015, which is a U.S. National Stage application of PCT/US2013/052270 filed 26 Jul. 2013, which claims priority to U.S. Provisional Application Ser. No. 61/675,948 filed 26 Jul. 2012, the entire disclosures of which are hereby incorporated herein by reference in their entireties.

GOVERNMENT INTEREST

This invention was made in part with Government support from the Uniformed Services University of the Health Services (Grant No. KM74LJ) and the NIH (Grant No. 1R21AI073627). The U.S. Government has certain rights in this invention.

SEQUENCE LISTING

The instant application contains a Sequence Listing which has been submitted in ASCII format via EFS-Web and is hereby incorporated by reference in its entirety. Said ASCII copy, created on Jul. 25, 2013, is named HMJ-134-PCT-_SL.txt and is 258,258 bytes in size.

BACKGROUND

Induction of humoral or T cell immunity to clinically relevant antigens is often hampered by the weak immunogenicity of these antigens. In order to enhance the immune response, exogenous adjuvants are commonly used. These adjuvants fall into many different categories but they all share the property of stimulating the immune response in an antigen-nonspecific manner (Schijns, V. E. 2000. *Curr. Opin. Immunology* 12: 456-463). Thus, their clinical use has been very limited because of the concern of stimulating unwanted inflammatory or autoimmune responses. Many of the newer, more potent adjuvants that stimulate the innate immune system via Toll-like receptors, non-specifically activate macrophages, dendritic cells and other innate immune cells with unwanted pro-inflammatory sequelae (van Duin et al., 2005. *Trends Immunol.*). Therefore, it would be extremely valuable to devise ways to augment the antigen-specific immune response in the absence of added adjuvants.

Protein aggregates are known to enhance immune responses (Rosenberg, 2006, The AAPS Journal, 8(3):E501-507). For example, protein antigens presented in a highly arrayed structure can induce highly potent antibody responses even in the absence of T helper cells. The mechanism by which protein aggregates mediate such potent antibody responses is not fully understood. However, it is believed that the potency is due, at least in part, to the ability of the multivalent protein to extensively cross link the cell surface immunoglobulins of B cells and activate the B cells.

Several factors can influence a protein aggregate's ability to induce an immune response, including molecular weight and solubility (Rosenberg, 2006, The AAPS Journal, 8(3): E501-507). Lower molecular weight aggregates, such as dimers and trimers generally are not as efficient at inducing immune responses as larger multimers. Multimerization, rather than size, appears to be an important immunogenicity factor because larger sized monomeric proteins are not necessarily more immunogenic than smaller monomeric proteins. In addition, particulate (insoluble) antigens are more rapidly endocytosed by antigen-presenting cells (APCs). The APCs, in turn, process the antigen and present it to T and/or B cells to induce an immune response. Other factors that can influence a protein aggregate's immunogenicity include product origin (foreign versus endogenous), the presence of product contaminants with immunomodulatory activity, the presence of neoepitopes (which may be created with fusion proteins), glycosylation patterns, frequency of administration, route of administration, the host immune status, activity of concomitant immunomodulators, and, for endogenous proteins, the strength of immunologic tolerance to the endogenous protein (Rosenberg, 2006, The AAPS Journal, 8(3):E501-507).

Others have attempted to take advantage of protein aggregation or multimeric targeting strategies in an effort to enhance immune responses. For example, Hultberg et al constructed multimers targeting different epitopes of three different viruses. Llama heavy chain antibody fragments (VHHs) against the trimeric envelope proteins of: 1) Respiratory Syncytial Virus, 2) Rabies virus glycoprotein, and 3) H5N1 Influenza virus were selected from libraries by phage display (Hultberg e al., 2011. *PloS ONE* 6: e17665). Neutralizing heavy chains recognizing the three different epitopes with affinities in the low nanomolar range were identified for all the three viruses by viral neutralization assays. By fusion with variable linker lengths, multimeric constructs were made that improved neutralization potencies up to 4,000-fold for RSV, 1,500-fold for Rabies virus and 75-fold for Influenza H5N1. The multimeric VHH constructs had increased neutralization activity and cross protection potency as compared to their monovalent counterparts, thus demonstrating that multimeric targeting strategies can enhance the potency of anti-viral molecules.

U.S. Pat. No. 6,749,857 describes a fusion protein with a single copy of a truncated flavivirus 80% E protein and a leucine zipper domain fused to the C terminus of the 80% E protein. When expressed in cells, the fusion proteins oligomerize to form a homodimeric polypeptide complex that mimics the homodimeric structure of the naturally occurring flavivirus 80% E protein. This approach was designed to increase the immune potency of the fusion protein by increasing the structural similarity to the native 80% E protein and by increasing the size and antigenic complexity of the immunogen. While the fusion proteins of U.S. Pat. No. 6,749,857 were designed in part to increase the antigenic complexity of the immunogen, the complexity of the construct was limited by a desire to mimic the structure of the native 80% protein. As such, the fusion protein constructs of U.S. Pat. No. 6,749,857 contained only a single copy of the 80% protein and the resulting polypeptide complex formed by the oligomerization of two fusion proteins contained only two copies of the 80% protein, limiting the size of the multimeric antigens formed through this strategy.

Even though protein aggregates are known to enhance immune responses, simple approaches to multimerize proteins in a defined and cost-effective manner for vaccine use, with direct validation of a resultant increase in immunogenicity, have been limited.

Other multi-component constructs have been designed to enhance immune responses by bringing two cells of interest into close proximity. For example, activation of T cells requires two signals. The first signal is initiated by T cell receptor binding to antigenic peptide presented by MHC molecules on antigen presenting cells (APC). The second, costimulatory signal, is mediated via CD28 on the T cell, upon binding to CD80 or CD86 on the APC. To selectively localize costimulatory activity to the surface of tumor cells and enhance activation of tumor-specific T cells, Asano et al. developed bi-specific costimulatory proteins with antibody-like structure (Asano et al., 2008. *J. Immunother.* 31: 752-761). Specifically, within a single polypeptide chain they assembled the IgV-like, CD28-binding domain of human CD86 together with hinge, CH2 and CH3 domains of human IgG1, and the scFv antibody fragment which recognizes the ErbB2 protooncogene present at high levels on the surface of many human tumor cells. Their results suggest that such multivalent soluble proteins which combine specific targeting to tumor cells with co-stimulatory activity may become useful tools to elicit and/or improve T-cell mediated, tumor-specific immune responses.

Another multi-component vaccine approach was designed to bring two different cell types into close proximity using a construct with components that allow simultaneous targeting of both cells (Asano et al., 2008. *J. Immunother.* 31: 752-761). Asano et al. produced a recombinant bi-specific antibody that co-targeted epidermal growth factor receptor on tumor cells and CD3 on T cells. The bi-specific and bi-valent IgG-like antibodies showed stronger binding to each target cell than did the monovalent diabody. The bi-specific construct mediated tumor cell cytotoxicity that was 10 times that of the monovalent constructs. Further the Fcc portion of the bi-specific construct further enhanced cytotoxicity via binding to Fc receptors on blood mononuclear cells for antibody-dependent cytotoxicity (ADCC). The growth-inhibition effects of this construct were superior to the approved therapeutic antibody cetuximab, which recognizes the same epidermal growth factor receptor antigen.

Miyata et al developed a multi-component vaccine strategy to enhance immune responses by creating genetic fusion proteins to target the antigen to specific APCs (Miyata et al., 2011. *Infect. Immun.* 79: 4260-4275). The fusion complex was composed of three physically linked molecular entities: 1) a vaccine antigen, 2) a multimeric α-helical coiled-coil core, and 3) an APC-targeting ligand linked to the core via a flexible linker. Immunization of mice with the tri-component complex as compared to the antigen only, induced an enhanced antibody response that conferred increased protection against lethal *Plasmodium yoelii* infection.

New and improved constructs for enhancing immune responses are needed, particularly constructs that can be used to enhance immune responses in the absence of added adjuvant.

SUMMARY

The present disclosure provides new and improved strategies for enhancing an immune response. These improved strategies involve fusion proteins that incorporate unique mechanisms for multimerizing antigens to enhance their immunogenicity. One mechanism for multimerizing antigens is using a linker sequence to separate two antigens in the fusion protein. Without intending to be bound by any theory, it is believed that such a linker sequence can allow the two antigens, whether they be the same or different, to undergo conformational folding and form a dimer or higher order multimer. Another mechanism for multimerizing antigens is using an oligomerization domain, such as a leucine zipper dimerization domain, a T4 bacteriophage fibritin motif trimerization domain, or a tetramerization domain. Combined with the linker sequence, the oligomerization domain permits the further multimerization of an antigen (e.g., tetramer, hexamer, octamer, etc). This approach can be used to multimerize a single antigen or to create multimers comprising two or more different antigens.

This multimerization strategy can also be used to multimerize two or more proteins of interest, such as two or more vaccine-related proteins. Thus, another aspect is directed to a fusion protein comprising a first protein, a linker sequence, a second protein, and an oligomerization domain, where the linker sequence joins the first protein to the second protein and wherein the first and second proteins are vaccine related proteins or peptides, such as a vaccine target protein, an adjuvanting protein, a cell surface targeting domain, a molecule that mediates immune suppression, or a cell surface target domain that binds to an activated cell.

Another aspect is an isolated nucleic acid encoding the fusion protein or oligomerized fusion protein. Yet another aspect is directed to methods of inducing an immune response in a subject by administering to the subject a vaccine composition comprising a fusion protein or nucleic acid encoding the fusion protein, where the fusion protein induces an immune response in the subject. In certain embodiments, the vaccine composition is used to induce an immune response in the subject without using an adjuvant.

BRIEF DESCRIPTION OF THE DRAWINGS

The accompanying drawings, which are incorporated in and constitute a part of this specification, illustrate certain embodiments, and together with the written description, serve to explain certain principles of the constructs and methods disclosed herein.

FIG. 7 shows that the TT-specific T cell epitopes in tetrameric gp350 do not contribute to the gp350-specific IgG response in naïve mice.

DETAILED DESCRIPTION

Figure 1:
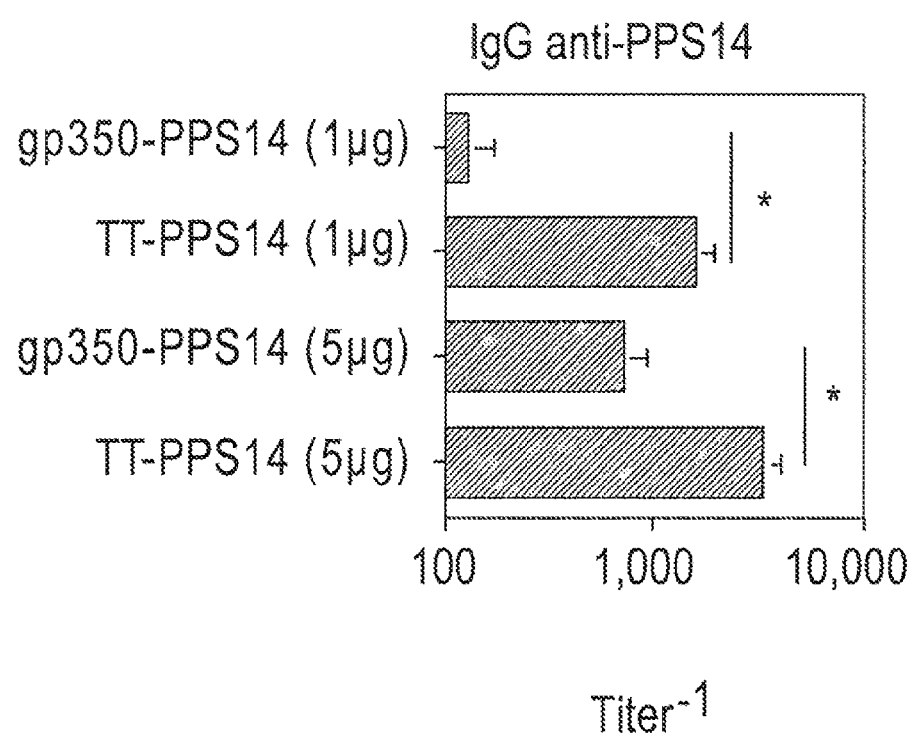
FIG. 1 shows that tetanus toxoid is a more potent carrier protein than gp350 for a pneumococcal polysaccharide conjugate vaccine. Mice were immunized i.p. with gp350-PPS14 or TT-PPS14 at 1 or 5 μg/mouse (5 mice per group) in alum+CpG-ODN, and boosted in a similar fashion on day 14. PPS14-specific IgG titers were measured by ELISA from sera obtained on day 21. *Significance, $p \leq 0.05$ between gp350-PPS14 and TT-PPS14.

It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "antibody" as used in this disclosure refers to an immunoglobulin or an antigen-binding fragment thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

The terms "antigen-binding domain" and "antigen-binding fragment" refer to a part of an antibody molecule that comprises amino acids responsible for the specific binding between the antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a F(ab')$_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a sc$F_v$ can be constructed. The sc$F_v$ contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ peptide (SEQ ID NO:3) may be used as a linker, but other linkers are known in the art. These antibody fragments are obtained using conventional techniques known to those with skill in the art; and the fragments are evaluated for function in the same manner as are intact antibodies.

The term "fusion protein" refers to a protein translated from a nucleic acid transcript generated by combining a first nucleic acid sequence that encodes a first protein and at least a second nucleic acid that encodes a second protein, where the fusion protein is not a naturally occurring protein. The nucleic acid construct may encode two or more proteins that are joined in the fusion protein.

The term "adjuvanting protein" refers to a protein that enhances the immune system's response to an antigen. An adjuvanting protein may accelerate, prolong, or enhance antigen-specific immune responses when used in combination with specific antigens. Exemplary adjuvanting proteins include, but are not limited to, flagellin, a heat shock protein, a toll like receptor ligand, or fragments or derivatives thereof that retain the adjuvanting property.

The term "cell surface targeting domain" refers to any moiety that will direct an antigen, vaccine, or specific cell to another specific cell type by binding to a specific cell surface receptor. Exemplary cell surface targeting domains, include, but not limited to, an antibody, or antigen-binding fragment thereof.

The term "cellular activation domain" refers to any moiety that can either specifically or non-specifically bind to a cell and induce cellular activation. Exemplary cellular activation domains include, but are not limited to, CD40 on B cells and CD28 on T cells.

The term "molecule mediating immune suppression" or "molecule that mediates immune suppression" refers to a molecule that upon binding to a cell induces suppression of cellular activation at any stage of activation including for example proliferation, differentiation, or secretion. Exemplary molecules that mediate immune suppression include, but are not limited to, B-7, CTLA-4, PD-1, Lag-3, Tim-3, CD200:CD200R, 2B4, CD160, PIR-B, BTLA, and GP49b.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived. The term also refers to preparations where the isolated polypeptide or nucleic acid is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The terms "polypeptide," "peptide," and "protein" are used interchangeably herein to refer to polymers of amino acids.

Fusion Proteins. The present disclosure relates to a new strategy for multimerizing protein antigens in vaccine-related or other immunotherapeutic constructs. The strategy involves creating nucleic acid constructs with oligomerization motifs and a linker sequence separating two or more antigens such that the encoded fusion protein can form a dimeric, trimeric, tetrameric, hexameric, heptameric, or octameric complex from a single nucleic acid construct. This strategy was tested first with a nucleic acid construct encoding two copies of a truncated EBV gp350 protein separated by a linker and a leucine zipper oligomerization domain. To enhance the immunogenicity of the construct, two potent T cell epitopes derived from the tetanus toxoid were included because it was believed that they would be necessary to recruit sufficient T cell help. With the leucine zipper domain, this construct formed a tetrameric gp350 complex when expressed. Compared to the traditional monomeric gp350, the tetramer showed an approximately 25-50-fold higher immunogenicity for specific antibody production both in the presence of weak and strong exogenous adjuvants. Surprisingly, however, the tetramer containing the tetanus toxoid T cell epitopes actually induced immune suppression in animals previously immunized with tetanus toxoid, a potential problem if used clinically. Based on these results, another nucleic acid construct was prepared without the tetanus toxoid epitopes. This construct encoded two copies of the truncated EBV gp350 protein separated by a linker and a leucine zipper oligomerization domain. The construct without the tetanus toxoid epitopes induced gp350-specific antibody responses that were comparable to the antibody responses induced by the construct containing the tetanus toxoid epitopes, unexpectedly showing that the tetanus toxoid epitopes were not required to achieve optimal immunogenicity in unprimed animals and in fact could be suppressive.

This strategy for multimerizing proteins can be exploited with proteins other than EBV gp350/220 proteins, including other viral, bacterial, parasitic, autoimmune, and tumor antigens. This platform can be used to create multimeric fusion proteins comprising multiple copies of a single antigen of interest, like an EBV gp350/220 antigen. For example, a bomodimer, homotrimer or tetramer can be created using two, three, or four copies of the same antigen with a dimerization, trimerization or tetramerization domain. When the oligomerization domains associate together, the construct will form a tetramer (if a dimerization domain is used) comprising four copies of the same antigen, a hexamer (if a trimerization domain is used) comprising six copies of the same antigen, or an octamer comprising eight copies of the same antigen (if a tetramerization domain is used).

Alternatively, this platform can be used to create multimeric fusion proteins comprising two or more different antigens of interest. For example, a heterodimer can be created with a first antigen linked to a second different, antigen (or a heterotrimer comprising two or three different antigens). When the oligomerization domains associate together, the construct will form a tetramer (if a dimerization domain is used) that is dimeric for both the first and second antigen, a hexamer (if a trimerization domain is used in the construct) that is dimeric for at least the first and second antigen or trimeric for the first, second, and third antigen, or an octamer (if a tetramerization domain is used). Alternatively a trimeric protein can be formed if the original protein is presented in monomeric form in association with the trimerization domain.

One aspect is directed to a fusion protein comprising a first antigen, a linker sequence, a second antigen, and an oligomerization domain, wherein the linker sequence joins the first antigen to the second antigen and wherein the fusion protein does not include a tetanus toxoid protein. In one embodiment, the first and second antigens are the same. In another embodiment, the first and second antigens are different. The first and second antigens can be viral antigens, bacterial antigens, parasite antigens, autoimmune antigens, or tumor antigens. In one embodiment, the first and second antigens comprise a polypeptide and/or a polysaccharide. In one embodiment, the fusion protein forms a multimeric protein when expressed in a host cell. In another embodiment, the first, second, and third antigens do not occur naturally as a multimeric protein.

The fusion protein may optionally further comprise a third protein and a second linker sequence, where the second linker sequence joins the second antigen to the third antigen, the first antigen, or the oligomerization domain. In other embodiments, the fusion protein comprises four or more proteins and additional linkers. In one embodiment, the fusion protein forms a multimeric protein when expressed in a host cell. In another embodiment, the first and second antigens do not occur naturally as a multimeric protein.

In certain embodiments, the oligomerization domain is a dimerization domain. In other embodiments, the oligomerization domain is a trimerization or tetrameric domain. In one embodiment, the dimerization domain is a leucine zipper domain, including but not limited to a yeast GCN4 leucine zipper domain or a derivative thereof. In another embodiment, the trimerization domain is a T4 bacteriophage fibritin motif or a eukaryotic GNC4 transcription factor motif or a derivative thereof. In other embodiments, the tetrameric domain is a modified eukaryotic GCN4 transcription factor motif or a derivative thereof. In embodiments with two antigens, the oligomerization domain can be located at the N terminus of the fusion protein before the first antigen, at the C terminus of the fusion protein after the second antigen, or between the first and second antigens. In embodiments where the fusion protein further comprises a third protein, the oligomerization domain can be located at the N terminus of the fusion protein before the first antigen, at the C terminus of the fusion protein after the third antigen, between the first and second antigens, or between the second antigen and the third protein. In embodiments where the fusion protein comprises four or more proteins, the oligomerization domain can be located at the N terminus of the fusion protein before the first antigen, at the C terminus of the fusion protein after the last antigen, or between any antigens in the fusion protein.

In one embodiment, the first and second antigen is an EBV antigen, including, but not limited to, a gp350/220 antigen, gH, gL, gB, or gp42. In one embodiment, the fusion protein comprises a homodimer or homotrimer of EBV gp350/220, gHl, gL, gB, or gp42. In another embodiment, the fusion protein comprises a heterodimer or heterotrimer of EBV antigens selected from gp350/220, gH, gL, gB, or gp42, such as a heterodimer of gH and gL, gB and gp42, gp350/220 and gB, gp350/220 and gp42, or a heterotrimer of gH, gL, and gB; gH, gL, and gp42; gp350/220, gH, and gL; or gp350/220, gB and gp42.

In another embodiment, the first and second antigen is a CMV antigen, including, but not limited to gB, gL, gH, or pp65. In yet another embodiment, the first antigen is an EBV antigen, including, but not limited to a gp350/220 antigen, and the second antigen is a CMV antigen, including, but not limited to gB, gL, gH, or pp65. In one embodiment, the fusion protein comprises a homodimer or homotrimer of gB, gL, gH, or pp65. In another embodiment, the fusion protein comprises a heterodimer or heterotrimer of CMV antigens selected from gB, gL, gH, and pp65, such as a heterodimer of gB and gL, gB and gH, gB and pp65, gL and gH, gL and pp65, or gH and pp65 or a heterotrimer of gB, gL, and gH, gB, gL, and pp65, gB, gH, and pp65, or gL, gH, and pp65.

In yet another embodiment, the first antigen is an EBV antigen, including, but not limited to, a gp350/220 antigen, gH, gL, gB, or gp42, and the second antigen is a CMV antigen, including, but not limited to gB, gL, gH, or pp65. In one embodiment, the first antigen is a gp350220 antigen and the second antigen is a CMV gB, gL, gH, or pp65.

In another embodiment, the first antigen is an EBV antigen, including, but not limited to a gp350/220 antigen, gH, gL, gB, or gp42, and the second antigen is an HIV antigen, including, but not limited to, Env (envelope protein, including, but not limited to gp160, gp140, gp20, and gp41gp140, gp120, or gp41), Gag (capsid protein), Pol (polymerase protein), Tat, Vif, Vpu, Vpr, Rev and Nef. Of course, these specific viral antigens are exemplary. In one embodiment, the first antigen is a gp350/220 antigen and the second antigen is an HIV Env (envelope protein, including, but not limited to gp160, gp140, gp120, and gp41gp140, gp120, or gp41), Gag (capsid protein), Pol (polymerase protein), Tat, Vif, Vpu, Vpr, Rev, or Nef. Given the disclosure of this application, one of skill in the art could substitute any antigen of interest into the fusion protein constructs described herein. Additional viral, bacterial, parasitic, autoimmune, and tumor antigens are discussed in more detail in other sections of the application.

Another aspect is directed to a fusion protein comprising a first protein, a linker sequence, a second protein, and an oligomerization domain, wherein the linker sequence joins the first protein to the second protein and wherein the first and second proteins are vaccine related proteins, such as a vaccine target protein, an adjuvanting protein, a cell surface targeting domain, a molecule that mediates immune suppression, or a cellular activating domain.

In one embodiment the fusion protein comprises a first protein, a linker sequence, a second protein, and an oligomerization domain, wherein the linker sequence joins the first protein to the second protein and wherein the first protein is a viral, bacterial, parasitic, autoimmune, tumor antigen, or other protein antigen and the second protein is an adjuvanting protein or comprises a cell surface targeting domain. In certain embodiments, the second protein is an adjuvanting protein, such as flagellin or a heat shock protein, or a toll like receptor (TLR) ligand. In certain embodiments, the cell surface targeting domain is specific for an antigen presenting cell, including, but not limited to a macrophage, a dendritic cell, or a B lymphocyte. In another embodiment, the first protein is a viral, bacterial, parasitic, autoimmune, or tumor antigen, the second protein comprises a cell surface targeting domain, and the fusion protein further comprises a third protein, wherein the third protein comprises a cellular activating domain. In this way, the fusion protein could be used to simultaneously target an antigen to a specific cell and activate the specific cell.

In another embodiment, the fusion protein comprises a first protein, a linker sequence, a second protein, and an oligomerization domain, wherein the linker sequence joins the first protein to the second protein and wherein the first protein comprises a first cell surface targeting domain and the second protein comprises a second cell surface targeting domain, wherein the first and second cell surface targeting domains target different cells. In this way, the fusion protein could be used to bring different types of cells into close proximity to each other, such as a natural killer cell or cytotoxic T lymphocyte and a tumor cell. In one embodiment, the first cell surface targeting domain binds to a ligand on a natural killer cell.

In another embodiment, the fusion protein comprises a first protein, a linker sequence, a second protein, and an oligomerization domain, wherein the linker sequence joins the first protein to the second protein and wherein the first protein is a molecule that mediates immune suppression and the second protein is a cell surface target domain that binds to an activated cell. In one embodiment, the molecule that mediates immune suppression binds to the Fc receptor of an antibody (e.g., Fc gamma receptor, Fc alpha receptor, or Fc epsilon receptor) and the cell surface target domain that binds to an activated cell binds to a ligand on a mast cell. In one embodiment, the Fc receptor is an Fc gamma receptor. In this way, the fusion protein construct could be used to suppress the activation of specific cells, for example, during an allergic reaction.

In yet another embodiment, the fusion protein comprises a first protein, a linker sequence, a second protein, and an oligomerization domain, wherein the linker sequence joins the first protein to the second protein and wherein the first and second proteins are HIV proteins. In one embodiment, the first and second proteins are selected from Env (envelope protein, including, but not limited to gp160, gp140, gp120, and gp41 gp140, gp120, or gp41), Gag (capsid protein), Pol (polymerase protein), Tat, Vif, Vpu, Vpr, Rev and Nef. In one embodiment, the first HIV protein is gp120 and the second HIV protein is gp41 and the oligomerization domain is a trimerization domain. In certain embodiments, the first and second proteins are HIV proteins, such as gp120 and gp41, the oligomerization domain is a trimerization domain, and the fusion protein further comprises a third protein and a second linker sequence and, optionally, a fourth protein and a third linker sequence. In one embodiment, the third protein is an EBV gp350/220 antigen. In another embodiment, the third protein and fourth protein are EBV gp350/220 antigens.

In certain embodiments, the oligomerization domain is a dimerization domain. In other embodiments, the oligomerization domain is a trimerization domain or tetrameric domain. In one embodiment, the dimerization domain is a leucine zipper domain, including but not limited to a yeast GCN4 llcucine zipper domain or a derivative thereof. In another embodiment, the trimerization domain is a T4 bacteriophage fibritin motif or a eukaryotic GNC4 transcription factor motif or a derivative thereof. In other embodiments, the tetrameric domain is a modified eukaryotic GNC4 transcription factor motif or a derivative thereof.

In embodiments with two proteins, the oligomerization domain can be located at the N terminus of the fusion protein before the first protein, at the C terminus of the fusion protein after the second protein, or between the first and second proteins. In embodiments with three proteins, the oligomerization domain can be located at the N terminus of the fusion protein before the first protein, at the C terminus of the fusion protein after the third protein, between the first and second proteins, or between the second and third proteins. In embodiments where the fusion protein comprises four or more proteins, the oligomerization domain can be located at the N terminus of the fusion protein before the first antigen, at the C terminus of the fusion protein after the last antigen, or between any antigens in the fusion protein.

Antigens. As used in this application, "antigen" means a protein or fragment thereof or a polysaccharide linked to a protein carrier that, when expressed in an animal or human cell or tissue, is capable of triggering an immune response. The protein or fragment thereof may be glycosylated or non-glycosylated. Examples include, but are not limited to, viral proteins, bacterial proteins, parasite proteins, autoimmune proteins, and tumor proteins. The antigen may be a wild-type protein, a truncated form of that protein, a mutated form of that protein or any other variant of that protein, in each case able to contribute to immune responses upon expression in the animal or human host to be vaccinated. In certain embodiments, the antigen is a polysaccharide, such as an antigenic polysaccharide from a pathogenic bacterium, that is linked to a protein carrier comprising a glycosylation consensus sequence, as described, for example, in the following published U.S. patent applications, the disclosures of which are hereby incorporated by reference in their entirety: US2011/0097357 and US2011/0274720.

The viral pathogens from which the viral antigens are derived include, but are not limited to: Orthomyxoviruses, such as influenza virus; Retroviruses, such as RSV, HTLV-I, and HTLV-II, Herpesviruses such as Epstein Barr Virus (EBV); cytomegalovirus (CMV) or herpes simplex virus; Lentiviruses, such as human immunodeficiency virus 1 (HIV-1) and HIV-2; Hepdnavirus, such as hepatitis B virus (HBV); Flavivirus, such as dengue fever virus; Rhabdoviruses, such as rabies virus; Picornaviruses, such as Poliovirus; Poxviruses, such as vaccinia virus; Rotavirus; and Parvoviruses, such as Adeno-Associated Viruses (AAV).

Examples of viral antigens can be found in the group including, but not limited to, the Human Immunodeficiency Virus (HIV) antigens Rev, Pol, Nef, Gag, Env, Tat, mutant derivatives of Tat, such as Tat-δ31-45, T- and B-cell epitopes of gp120, chimeric derivatives of HIV-1 Env and gp120, such as a fusion between gp120 and CD4, gp41, a truncated or modified HIV-1 Env, such as gp140 or derivatives of HIV-1 Env and/or gp140. Other examples are EBV envelope glycoproteins, such as Gp350/220; CMV antigens, such as gB, gL, gH, or pp65; hepatitis B surface antigen; rotavirus antigens, such as VP4 and VP7; influenza virus antigens, such as hemagglutinin, neuraminidase, M2, or nucleoprotein; flavivirus antigens, such as non-structural protein NSl; and herpes simplex virus antigens such as thymidine kinase. The EBBV Gp350/220 antigen is discussed in further detail below.

Examples of bacterial pathogens from which the bacterial antigens may be derived include, but are not limited to, *Streptococcus* spp. (including *S. pneumoniae*), *Enterococcus* spp., *Shigella* spp., *Salmonella* spp., *Mycobaterium* spp., *Clostridium* spp., *Rickettsia* spp., *Helicobacterpylori* spp., *Escherichia coli* spp., *Pseudomonas* spp., *Listeria* spp., *Legionella pneumonia*, *Borellia burgdorferi*, *Corynebacterium diphtheria*, *Bordetella pertussis*, *Chlamydia trachomitis*, *Haemophilus influenza*, *Neisseria meningitidis*, *Vibrio cholera*, *Listeria monocytogenes*, or *Bacillus anthracus*.

Examples of protective antigens of bacterial pathogens include the pneumolysin, PsaA, PspC, histidine triad proteins, and pilus proteins of *Streptococcus pneumoniae*; the somatic antigens of enterotoxigenic *E. coli*, such as the CFA/1 fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borelia burgdorferi*, protective paracrystalline-surface-layer proteins of *Rickettsia prowazekii* and *Rickettsia typhi*, the listeriolysin (also known as "Llo" and "Hly") and/or the superoxide dismutase (also known as "SOD" and "p60") of *Listeria monocytogenes*, urease of *Helicobacter pylori*, and the receptor-binding domain of lethal toxin and/or the protective antigen of *Bacillus* anthracus.

The parasitic pathogens from which the parasitic antigens are derived include, but are not limited to: *Plasmodium* spp. such as *Plasmodium falciparum*, *Trypanosome* spp. such as *Trypanosoma cruzi*, *Giardia* spp. such as *Giardia intestinalis*, *Boophilus* spp., *Babesia* spp. such as *Babesia microti*, *Entamoeba* spp. such as *Entamoeba histolytica*, *Eimeria* spp. such as *Eimeria maxima*, *Leishmania* spp., *Schistosome* spp., *Brugia* spp., Examples of protective antigens of parasitic pathogens include the circumsporozoite (CS) or Liver Stage Specific (LSA) antigens LSA-1 and LSA-3 of *Plasmodium* spp. such as those of *P. bergerii* or *P. falciparum*, or immunogenic mutants thereof; the merozoite surface antigen of *Plasmodium* spp., the galactose-specific lectin of *Entamoeba histolytica*, gp63 of *Leishmania* spp., gp46 of *Leishmania major*, paramyosin of *Brugia malayi*, the triose-phosphate isomerase of *Schistosoma mansoni*, the secreted globin-like protein of *Trichostrongylus colubriformis*, the glutathione-S-transferase of *Frasciola hepatica, Schistosoma bovis* and *S. japonicum*, and KLH of *Schistosoma bovis* and *S. japonicum*.

The fusion protein may also include host antigens, which may be any cellular protein expressed in the recipient cell including, but not limited to, tumor, transplantation, and autoimmune antigens. Examples of such antigens include, but are not limited to, prostate-specific antigen, mucin-1 (MUCI), gp100, HER2, AE37, E75, GP2, TAG-72, carcinoembryonic antigen (CEA), melanoma associated antigen 1 (MAGE-1), tyrosinase, CD3, and IAS beta chain.

Epstein Barr Virus. Epstein Barr virus (EBV), also known as human herpesvirus 4, is a major, global source of morbidity and mortality, responsible for such pathologic entities as Burkitt lymphoma, nasopharyngeal carcinoma, infectious mononucleosis, a subset of Hodgkin's disease, and the lymphoproliferative syndrome in immunosuppressed patients [1-3]. EBV has a double stranded, linear DNA genome. The nucleotide sequence of the EBV genome (SEQ ID NO: 15) and the amino acid sequences of the viral proteins encoded thereby are known and set forth under the NCBI Reference Number NC_009334, Version NC_009334.1, GI:139424470, which sequences are hereby incorporated by reference.

In the developing world, EBV seroconversion typically occurs in infancy, whereas in developed countries it is more likely contracted in adolescence. Infectious mononucleosis typically occurs only in this latter group [3]. The major human reservoir for latent EBV and EBV transmission is the resting memory B lymphocyte [4]. EBV is dependent upon the gp350-CD21 binding event for viral entry into the B cell [5, 6], an event that is critical for infectivity and B cell neoplastic transformation [2]. Gp350 is the major EBV outer membrane glycoprotein, while CD21, also known as complement receptor type 2 (CR2), is a receptor on the surface of B cells that binds to iC3b complement protein. Sera from patients with active EBV infection contain antibody that prevent EBV entry into B cells ("neutralizing" antibody). Adsorption of these sera with gp350, eliminates most of this neutralizing activity [7], indicating that gp350 serves as the major EBV antigen to which a protective humoral immune response is directed.

A number of studies have demonstrated that immunization of non-human primates with a subunit gp350 vaccine in adjuvant protects against experimental EBV-induced lymphoma or EBV replication. Thus, purified native gp350, injected into cottontop marmosets (CTM), in association with liposomes, ISCOM's, or muramyl dipeptide, protected against EBV-induced lymphoma [8, 9]. Recombinant gp350 in alum or muramyl dipeptide was similarly protective [10, 11]. Common marmosets also showed decreased viral replication after EBV challenge following immunization with recombinant gp350 in alum [12]. Non-human primate studies using gp350 expressed by adenoviral or vaccinia viral vectors have similarly shown protection against experimental EBV-induced lymphoma or EBV replication in CTM or common marmosets [13-15].

A pilot study in humans has also suggested a potential role for gp350 vaccination in host protection against EBV. In a study by Gu et al [16] a single dose of gp350/220 expressed by vaccinia virus (VV) was give by scarification to 1-3 year olds who were EBV-seronegative, and VV-seronegative. These children developed neutralizing antibodies to EBV (1:40-1:160). Whereas 10/10 unvaccinated controls became infected at 16 months of follow-up, only 3/9 vaccinated children became infected at this time. More recently, Phase I/II studies were conducted in which healthy EBV-seronegative adults were immunized with a recombinant monomeric $gp^{350}$ protein in alum+/-monophosphoryl lipid A [17, 18]. Following 3 doses, up to 82% of subjects had detectable neutralizing serum anti-gp350 antibody titers. The vaccine demonstrated an efficacy of 78.0% in preventing the development of infectious mononucleosis but not in preventing asymptomatic EBV infection. Finally, an additional phase I trial of recombinant monomeric gp350 protein in alum given to children with chronic kidney disease demonstrated only a minority of subjects developing detectable neutralizing serum anti-gp350 titers [19].

A monomeric protein, as used in phase I/II human clinical trials assessing gp350-induced IgG responses, is by itself a relatively weak immunogen relative to proteins that are expressed in a multimeric manner or that are aggregated [20-25]. Without intending to be bound by any theory, increased immunogenicity of multimeric proteins is most likely due, at least in part, to their more avid binding to, and crosslinking of the B cell receptor followed by more potent signaling and enhanced uptake of antigen by the B cell.

Gp350/220. The EBV glycoprotein gp350 and the related splice variant gp220 are responsible for attachment of EBV with high affinity to CR2 on B cells. Antibodies to gp350/220 that block EBV binding neutralize B-cell infection. gp350/220 is a highly glycosylated single-pass membrane protein. As a result of alternative splicing, the viral glycoprotein appears in two forms, with approximate masses of 350 and 220 kDa. The 200 kDa splice form lacks residues 500-757 of the full length gp350. Both gp350 and gp220 retain the CR2 binding domain at the amino terminus. A truncated version of gp350/220 having amino acids 1-470 of gp350 retains the ability to bind CR2 and can inhibit the binding of EBV to CR2 [29]. In addition, portions of the gp350/220 protein between amino acids 21-26 or between amino acids 372-378 of the gp350 sequence have been linked to CR2 binding. Tanner et al., Cell 203-213 (1987) and Nemerow et al. 61:1416-20 (1987). Thus, the term gp350/220 protein or gp350/220 antigen refers to the full length gp350 or gp220 proteins as well as fragments or modified versions thereof that retain the ability to bind the CR2.

The amino acid and nucleic acid sequence of gp350, set forth in GenBank under Accession Number M10593, Version M10593.1, GI 330360, is hereby incorporated by reference. The amino acid sequence of gp350 is:

```
                                                        (SEQ ID NO: 1)
MEAALLVCQY  TIQSLIHLTG  EDPGFFNVEI  PEFPFYPTCN  VCTADVNVTI        50

NFDVGGKKHQ  LDLDFGQLTP  HTKAVYQPRG  AFGGSENATN  LFLLELLGAG       100
```

-continued
```
ELALTMRSKK LPINVTTGEE QQVSLESVDV YFQDVFGTMW CHHAEMQNPV          150

YLIPETVPYI KWDNCNSTNI TAVVRAQGLD VTLPLSLPTS AQDSNFSVKT          200

EMLGNEIDIE CIMEDGEISQ VLPGDNKFNI TCSGYESHVP SGGILTSTSP          250

VATPIPGTGY AYSLRLTPRP VSRFLGNNSI LYVFYSGNGP KASGGDYCIQ          300

SNIVFSDEIP ASQDMPTNTT DITYVGDNAT YSVPMVTSED ANSPNVTVTA          350

FWAWPNNTET DFKCKWTLTS GTPSGCENIS GAFASNRTFD ITVSGLGTAP          400

KTLIITRTAT NATTTTHKVI FSKAPESTTT SPTLNTTGFA DPNTTTGLPS          450

STHVPTNLTA PASTGPTVST ADVTSPTPAG TTSGAGPVTP SPSPWDNGTE          500

SKAPDMTSST SPVTTPTPNA TSPTPAVTTP TPNATSPTPA VTTPTPNATS          550

PTLGKTSPTS AVTTPTPNAT SPTLGKTSPT SAVTTPTPNA TSPTLGKTSP          600

TSAVTTPTPN ATGPTVGETS PQANATNHTL GGTSPTPVVT SQPKNATSAV          650

TTGQHNITSS STSSMSLRPS SNPETLSPST SDNSTSHMPL LTSAHPTGGE          700

NITQVTPASI STHHVSTSSP EPRPGTTSQA SGPGNSSTST KPGEVNVTKG          750

TPPQNATSPQ APSGQKTAVP TVTSTGGKAN STTGGKHTTG HGARTSTEPT          800

TDYGGDSTTP RPRYNATTYL PPSTSSKLRP RWTFTSPPVT TAQATVPVPP          850

TSQPRFSNLS MLVLQSASLA VLTLLLLLVM ADCAFRRNLS TSHTYTTPPY          900

DDAETYV                                                        907
```

The amino acid sequence of gp220, set forth in GenBank under Accession Number M10593, Version M10593.1, GI 330360, and hereby incorporated by reference, is:

```
                                                (SEQ ID NO: 2)
MEAALLVCQY TIQSLIHLTG EDPGFFNVEI PEFPFYPTCN VCTADVNVTI           50

NFDVGGKKHQ LDLDFGQLTP HTKAVYQPRG AFGGSENATN LFLLELLGAG          100

ELALTMRSKK LPINVTTGEE QQVSLESVDV YFQDVFGTMW CHHAEMQNPV          150

YLIPETVPYI KWDNCNSTNI TAVVRAQGLD VTLPLSLPTS AQDSNFSVKT          200

EMLGNEIDIE CIMEDGEISQ VLPGDNKFNI TCSGYESHVP SGGILTSTSP          250

VATPIPGTGY AYSLRLTPRP VSRFLGNNSI LYVFYSGNGP KASGGDYCIQ          300

SNIVFSDEIP ASQDMPTNTT DITYVGDNAT YSVPMVTSED ANSPNVTVTA          350

FWAWPNNTET DFKCKSTLTS GTPSGCENIS GAFASNRTFD ITVSGLGTAP          400

KTLIITRTAT NATTTTHKVI FSKAPESTTT SPTLNTTGFA DPNTTTGLPS          450

STHVPTNLTA PASTGPTVST ADVTSPTPAG TTSGASPVTP SPSPWDNGTE          500

STPPQNATSP QAPSGQKTAV PTVTSTGGKA NSTTGGKHTT GHGARTSTEP          550

TTDYGGDSTT PRPRYNATTY LPPSTSSKLR PRWTFTSPPV TTAQATVPVP          600

PTSQPRFSNL SMLVLQWASL AVLTLLLLLV MADCAFRRNL STSHTYTTPP          650

YDDAETYV                                                       658
```

EBVgH, gL, gB, and gp42. EBV is an enveloped virus that gains entry into host cells by fusing its own lipid membrane with the host cell membrane. EBV can infect both B cells and epithelial cells. The minimal requirement for viral fusion with B cells includes EBV glycoproteins gH, gL, gB, and gp42. For infection of B cells, gp42 binds to the host cell MHC class II molecules to trigger viral cell membrane fusion. On the other hand, for infection of epithelial cells, gp42 is not required. Rather, the EB3V gHl, gL, and gB proteins are sufficient for viral fusion with epithelial cells. EBV gH/gL exists as a noncovalently associated complex. EBV gI, can be expressed independently of gH, but in order for EBV gHl to fold properly and traffic to the cell surface, gL must also be present.

The amino acid sequence of EBV gH is:

```
                                                       (SEQ ID NO: 16)
MQLLCVFCLV LLWEVGAASL SEVKLHLDIE GHASHYTIPW TELMAKVPGL        50

SPEALWREAN VTEDLASMLN RYKLIYKTSG TLGIALAEPV DIAPVSEGSM       100

QVDASKVHPG VISGLNSPAC MLSAPLEKQL FYYIGTMLPN TRPHSYVFYQ       150

LRCHLSYVAL SINGDKFQYT GAMTSKFLMG TYKRVTEKGD EHVLSLIFGK       200

TKDLPDLRGP FSYPSLTSAQ SGDYSLVIVT TFVHYANFHN YFVPNLKDMF       250

SRAVTMTAAS YARYVLQKLV LLEMKGGCRE PELDTETLTT MFEVSVAFEK       300

VGHAVGETGN GCVDLRWLAK SFFELTVLKD IIGICYGATV KGMQSYGLER       350

LAAVLMATVK MEELGHLTTE KQEYALRLAT VGYPKAGVYS GLIGGATSVL       400

LSAYNRHPLF QPLHTVMRET LFIGSHVVLR ELRLNVTTQG PNLALYQLLS       450

TALCSALEIG EVLRGLALGT ESGLFSPCYL SLRFDLTRDK LLSMAPQEAM       500

LDQAAVSNAV DGFLGRLSLE REDRDAWHLP AYKCVDRLDK VLMIIPLINV       550

TFIISSDREV RGSALYEAST TYLSSSLFLS PVIMNKCSQG AVAGEPRQIP       600

KIQNFTRTQK SCIFCGFALL SYDEKEGLET TTYITSQEVQ NSILSSNYFD       650

FDNLHVHYLL LTTNGTVMEI AGLYEERAHV VLAIILYFIA FALGIFLVHK       700

IVMFFL                                                      706
```

The amino acid sequence of EBV gL is:

```
                                                       (SEQ ID NO: 17)
MRTVGVFLAT CLVTIFVLPT WGNWAYPCCH VTQLRAQHLL ALENISDIYL        50

VSNQTCDGFS LASLNSPKNG SNQLVISRCA NGLNVVSFFI SILKRSSSAL       100

TGHLRELLTT LETLYGSFSV EDLFGANLNR YAWHRGG                    137
```

The amino acid sequence of EBV gB is:

```
                                                       (SEQ ID NO: 18)
MTRRRVLSVV VLLAALACRL GAQTPEQPAP PATTVQPTAT RQQTSFPFRV        50

CELSSHGDLF RFSSDIQCPS FGTRENHTEG LLMVFKDNII PYSFKVRSYT       100

KIVTNILIYN GWYADSVTNR HEEKFSVDSY ETDQMDTIYQ CYNAVKMTKD       150

GLTRVYVDRD GVNITVNLKP TGGLANGVRR YASQTELYDA PGWLIWTYRT       200

RTTVNCLITD MMAKSNSPFD FFVTTTGQTV EMSPFYDGKN KETFHERADS       250

FHVRTNYKIV DYDNRGTNPQ GERRAFLDKG TYTLSWKLEN RTAYCPLQHW       300

QTFDSTIATE TGKSIHFVTD EGTSSFVTNT TVGIELPDAF KCIEEQVNKT       350

MHEKYEAVQD RYTKGQEAIT YFITSGGLLL AQLPLTPRSL ATVKNLTELT       400

TPTSSPPSSP SPPAPPAARG STSAAVLRRR RRDAGNATTP VPPAAPGKSL       450

GTLNNPATVQ IQFAYDSLRR QINRMLGDLA RAWCLEQKRQ NMVLRELTKI       500

NPTTVMSSIY GKAVAAKRLG DVISVSQCVP VNQATVTLRK SMRVPGSETM       550

CYSRPLVSFS FINDTKTYEG QLGTDNEIFL TKKMTEVCQA TSQYYGQSGN       600

EIHVYNDYHH FKTIELDGIA TLQTFISLNT SLIENIDFAS LELYSRDEQR       650

ASNVFDLEGI FREYNFQAQN IAGLRKDLDN AVSNGRNQFV DGLGELMDSL       700

GSVGQSITNL VSTVGGLFSS LVSGFISFFK NPFGGMLILV LVAGVVILVI       750

SLTRRTRQMS QQPVQMLYPG IDELAQQHAS GEGPGINPIS KTELQAIMLA       800
```

```
                               -continued
LHEQNQEQKR AAQRAAGPSV ASRALQAARD RFPGLRRRRY HDPETAAALL       850

GEAETEF                                                     857
```

The amino acid sequence of EBV gp42 is:

```
                                                   (SEQ ID NO: 19)
MVSFKQVRVP LFTAIALVIV LLLAYFLPPR VRGGGRVSAA AITWVPKPNV        50

EVWPVDPPPP VNFNKTAEQE YGDKEIKLPH WTPTLHTFQV PKNYTKANCT       100

YCNTREYTFS YKERCFYFTK KKHTWNGCFQ ACAELYPCTY FYGPTPDILP       150

VVTRNLNAIE SLWVGVYRGV EGNWTSLDGG TFKVYQIFGS HCTYVSKFST       200

VPVSHHECSF LKPCLCVSQR SNS                                   223
```

Modified gp350/220 polypeptides that bind to CR2 include naturally-occurring or synthetically programmed variant polypeptides substantially identical to either the gp350 or gp220 polypeptides (e.g., SEQ ID Nos: 1 and 2), but which have an amino acid sequence different from that of gp350 or gp220 because of one or more deletions, insertions or substitutions. Some gp350/220 variant sequences have already been identified by sequencing the DNA of different strains of EBV, and are readily available to one of ordinary skill in the art (Beiscl et al., J. Viriol. 1985, 54(3):665-74). Similarly, modified gH, gL, gB, and gp42 polypeptides include naturally-occurring or synthetically programmed variant polypeptides substantially identical to either the gH, gL, gB, or gp42 polypeptides (e.g., SEQ ID Nos: 16, 17, 18, or 19), but which have an amino acid sequence different from that of gH, gL, gB, or gp42 because of one or more deletions, insertions or substitutions.

The variant amino acid sequence preferably is at least 60%, 65%, 70%, or 80%, identical to a gp350/220 polypeptide of SEQ ID Nos: 1 or 2 or a gH, gL, gB, or gp42 polypeptide of SEQ ID Nos: 16, 17, 18, or 19, more preferably at least 85% identical, still more preferably at least 90% identical, and most preferably at least 95% identical. The percent identity can be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Seauence and Structure, National Biomedical Research Foundation, pp. 353-358, 1979; (2) a penalty of 3.0 for each gap and an additional 0.10 penalty for each symbol in each gap; and (3) no penalty for end gaps.

Variant polypeptides can be obtained by mutation of nucleotide sequences encoding the gp350/220, gH, gL, gB, or gp42 polypeptides. Alterations of the amino acid sequence can occur naturally, or be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (Gene 42:133, 1986); Bauer et al. (Gene 37:73, 1985); Craik, (BioTechniques, Jan. 12-19, 1985); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987); and U.S. Pat. Nos. 4,518,584 and 4,737,462, all of which are incorporated by reference.

Oligomerization Domain. Oligomerization domains are polypeptides that cause polypeptides comprising them to oligomerize, i.e., to form covalent and/or non-covalent associations with another polypeptide comprising a corresponding oligomerization domain. Thus, two or more polypeptides are "oligomerized" if they are bound to each other via their oligomerization domains. Any oligomerization domain known in the art can be used. Examples include leucine zipper domains and fibritin domains. The polypeptides in an oligomer can have identical polypeptide sequences, similar polypeptide sequences, or different polypeptide sequences.

Homodimerization and homo-oligomerization refer to the association of the same polypeptide components to form dimers or oligomers. Heterodimerization and hetero-oligomerization refer to the association of different polypeptides to form dimers or oligomers. Homo-oligomers thus comprise an association of multiple copies of a particular polypeptide, while hetero-oligomers comprise an association of copies of different polypeptides. "Oligomcrization," "oligomerize," and "oligomer," with or without prefixes, are intended to encompass "dimerization," "dimerize," and "dimer." Thus, in one embodiment, the oligomerization domain is a dimerization domain that mediates the self-association of two fusion proteins. In another embodiment, the oligomcrization domain is a trimerization domain that mediates the self-association of three fusion proteins. In another embodiment, the oligomerization domain is a tetramerization domain that mediates the self-association of four fusion proteins. In one embodiment, the trimerization domain is fibritin motif or a eukaryotic GCN4 transcription factor motif or derivative thereof.

In one embodiment, the oligomerization domain comprises a leucine zipper domain. Leucine zipper domains are peptides that promote oligomerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize. For example, the yeast GCN4 leucine zipper can be used to dimerize polypeptides of interest [27, 28]. Other examples of leucine zipper domains suitable for producing soluble multimeric proteins are described in PCT application WO 94/10308, and the leucine zipper derived from lung surfactant protein D (SPD) described in Hoppe et al. FEBS Lett. 344:191, 1994. The use of a modified leucine zipper that allows for stable trimerization of a heterologous protein fused thereto is described in Fanslow et al., Semin. Immunol. 6:267, 1994.

In yet another embodiment, the oligomerization domain is a fibritin trimerization motif, particularly a bacteriophage fibritin trimerization motif, more particularly a fibritin trimerization domain from bacteriophage T4 or phage RB69 or phage AR1 or a derivative thereof. The T4 fibritin trimerization domain and variants thereof are described in U.S. Pat. No. 6,911,205; U.S. Pat. No. 8,147,843, and WO 01/19958, which are hereby incorporated by reference in their entirety.

Linker Sequences. Linker sequences are used in the fusion proteins to separate different components of the fusion protein. Thus, the amino terminal end of the linker sequence is joined by a peptide bond to a first polypeptide and the carboxy terminal end of the linker sequence is joined by a peptide bind to a second polypeptide. The first or second polypeptide may be an antigen, an oligomerization domain, an adjuvanting protein, a cell surface targeting domain, a molecule that mediates immune suppression, or a cellular activation domain. Such a linker sequence joins the first polypeptide and the second polypeptide, in contrast to a first polypeptide and a second polypeptide that are joined together without an intervening polypeptide sequence. Thus, the linker sequence can join two antigens, an antigen and an oligomerization domain, an antigen and an adjuvanting protein, an antigen and a cell surface targeting domain, an antigen and a molecule that mediates immune suppression, and an antigen and a cellular activation domain, an adjuvanting protein and an oligomerization domain, etc. It is understood that the linker sequence is not a sequence that naturally separates a first and second polypeptide, if the first and second polypeptide happen to naturally exist in combination together.

In one embodiment, the linker sequence is a polypeptide having 5-25 amino acids, particularly a length of 6, 7, 8, 9, 10, 11, 12, 13, 14, 15, 16, 17, 18, 19 or 20 amino acids. In another embodiment, the linker sequence is a polypeptide having 10-25 amino acids. The linker sequence preferably comprises glycine and serine amino acids. In one embodiment, the linker sequence is 15 amino acids in length and has the amino acid sequence $(Gly_4Ser)_3$ (SEQ ID NO:3).

Other suitable peptide linkers are those described in U.S. Pat. Nos. 4,751,180, 4,935,233, and 5,073,627, each of which is hereby incorporated by reference in its entirety. A DNA sequence encoding a desired linker sequence may be inserted between, and in the same reading frame as, for example, DNA sequences encoding the first and second polypeptide using conventional techniques known in the art. For example, a chemically synthesized oligonucleotide encoding the linker may be ligated between sequences encoding the first and second polypeptide.

Nucleic Acids, Cloning and Expression Systems. The present disclosure further provides isolated nucleic acids encoding the disclosed fusion proteins. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The present disclosure also provides constructs in the form of plasmids, vectors, phagemids, transcription or expression cassettes which comprise at least one nucleic acid encoding a fusion protein or a portion thereof. The disclosure further provides a host cell which comprises one or more constructs as above.

Also provided are methods of making the fusion proteins encoded by these nucleic acids. The fusion proteins may be produced using recombinant techniques. The production and expression of recombinant proteins is well known in the art and can be carried out using conventional procedures, such as those disclosed in Sambrook et al., *Molecular Cloning: A Laboratory Manual* (4th Ed. 2012), Cold Spring Harbor Press. For example, expression of the fusion protein may be achieved by culturing under appropriate conditions recombinant host cells containing the nucleic acid encoding the fusion protein. Following production by expression a fusion protein may be isolated and/or purified using any suitable technique, then used as appropriate.

Systems for cloning and expression of a polypeptide in a variety of different host cells are well known in the art. Any protein expression system compatible with the constructs disclosed in this application may be used to produce the disclosed fusion protein.

Suitable vectors can be chosen or constructed, so that they contain appropriate regulatory sequences, including promoter sequences, terminator sequences, polyadenylation sequences, enhancer sequences, marker genes and other sequences as appropriate.

A further aspect of the disclosure provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. These techniques are well known in the art. See e.g., Current Protocols in Molecular Biology, Ausubel et al. eds., John Wiley & Sons (2010). DNA introduction may be followed by a selection method (e.g., antibiotic resistance) to select cells that contain the vector.

Vaccine Compositions. The fusion proteins and nucleic acids encoding the same that are described in this application provide an improved platform for developing a vaccine that achieves enhanced immunogenicity in a subject.

Thus, one aspect is directed to a composition comprising the nucleic acid encoding the fusion protein or the fusion protein, at least one pharmaceutically acceptable excipient, and optionally an adjuvant (hereinafter referred to as "vaccine composition"). In certain embodiments, the vaccine composition does not include an adjuvant.

The pharmaceutically acceptable excipient can be chosen from, for example, diluents such as starch, microcrystalline cellulose, dicalcium phosphate, lactose, sorbitol, mannitol, sucrose, methyl dextrins; binders such as povidone, hydroxypropyl methylcellulose, dihydroxy propylcellulose, and sodium carboxylmethylcellulose; and disintegrants such as crospovidone, sodium starch glycolate, croscarmellose sodium, and mixtures of any of the foregoing. The pharmaceutically acceptable excipient can further be chosen from lubricants such as magnesium stearate, calcium stearate, stearic acid, glyceryl behenate, hygrogenated vegetable oil, glycerine fumerate and glidants such as colloidal silicon dioxide, and mixtures thereof. In some embodiments, the pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients can be intragranular, intergranular, or mixtures thereof.

The vaccine composition can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form. After formulation, the vaccine composition can be incorporated into a sterile container which is then sealed and stored at a low temperature (e.g., 4° C.), or it can be freeze dried.

The vaccine composition can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition can optionally comprise agents that enhance the protective efficacy of the vaccine, such as adjuvants. Adjuvants include any compound or compounds that act to increase an immune response to an antigen delivered by the fusion protein, thereby reducing the quantity of fusion protein (or nucleic acid encoding the same) necessary in the vaccine, and/or the frequency of administration necessary to generate a protective immune response. Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), Mycobacterialphlei (*M. phlei*) cell wall extract (MCWE) (U.S. Pat. No. 4,744,984), *M. phlei* DNA (M-DNA), and *M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (PCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof.

The vaccine composition can be prepared using techniques well known to those skilled in the art including, but not limited to, mixing, sonication and microfluidation. The adjuvant can comprise from about 10% to about 80% (v/v) of the vaccine composition, more preferably about 20% to about 50% (v/v), and more preferably about 20% to about 30% (v/v), or any integer within these ranges.

The vaccine composition can be administered to any animal, and preferably is a mammal such as a human, mouse, rat, hamster, guinea pig, rabbit, cat, dog, monkey, cow, horse, pig, and the like. Humans are most preferred.

Administration of the vaccine composition can be by infusion or injection (e.g., intravenously, intramuscularly, intracutaneously, subcutaneously, intrathecal, intraduodenally, intraperitoneally, and the like). The vaccine composition can also be administered intranasally, vaginally, rectally, orally, intratonsilar, or transdermally. Additionally, the vaccine composition can be administered by "needle-free" delivery systems.

The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art. Preferably, a therapeutically effective dose of the vaccine composition described herein will provide the therapeutic preventive benefit without causing substantial toxicity to the subject.

The vaccine composition can be administered to a patient on any schedule appropriate to induce and/or sustain an immune response against EBV Gp350/220 or any other protein of interest. For example, patients can be administered a vaccine composition as a primary immunization as described and exemplified herein, followed by administration of a secondary immunization, or booster, to bolster and/or maintain protective immunity.

The vaccine administration schedule, including primary immunization and booster administration, can continue as long as needed for the patient, for example, over the course of several years, to over the lifetime of the patient. The frequency of primary vaccine and booster administration and dose administered can be tailored and/or adjusted to meet the particular needs of individual patients, as determined by the administering physician according to any means suitable in the art.

The vaccine composition may be administered prophylactically (before exposure to the antigen or pathogen of interest) or therapeutically (after exposure to the antigen or pathogen of interest).

Methods of Inducing or Suppressing an Immune Response.

In another aspect, the vaccine composition comprising the fusion protein (or nucleic acid encoding the same) can be used in a method of inducing or suppressing an immune response. The immune response can be induced in a naïve subject who has not previously been exposed to EBV, CMV, or HIV (or some other foreign pathogen). Alternatively, the immune response can be induced or suppressed in a subject who has been previously exposed to EBV, CMV, or HIV (or some other foreign pathogen) and used to enhance an existing immune response.

In one embodiment, the method of enhancing or suppressing an immune response comprises administering to a subject a vaccine composition comprising a fusion protein, as described in this application, wherein the fusion protein induces or suppresses an immune response against an antigen in the fusion protein in the subject. In another embodiment, the method of enhancing or suppressing an immune response comprises administering to a subject a vaccine composition comprising a nucleic acid construct that encodes a fusion protein, as described in this application, wherein the fusion protein is expressed in the subject and induces or suppresses an immune response against an antigen in the fusion protein in the subject.

In these methods of inducing or suppressing an immune response, the immune response can be measured using routine methods in the art, such as those disclosed in this application. These routine methods include, but are not limited to, measuring an antibody response, such as an antibody response directed against a protein encoded by the recombinant vector, and measuring cellular proliferation, including, for example, by measuring tritiated thymidine incorporation or cytokine (e.g., IFN-γ) production.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

To test whether protein multimerization can provide a cost-effective and reproducible means for enhancing immune responses to target antigens of interest, a recombinant nucleic acid plasmid was designed to encode a fusion protein comprising a first and second antigen, separated by a linker sequence and an oligomerization domain. In the test construct prepared to validate the system, two identical gp350 sequences are separated by a $(Gly_4Ser)_3$ (SEQ ID NO:3) linker to allow for proper protein folding [26], followed by a *Saccharomyces cerevisiae* GCN4 leucine zipper sequence [27, 28] to mediate self-association of the gp350 dimer, and thus formation of a tetrameric gp350. Immunization of mice with either the plasmid DNA itself or the resulting tetrameric protein results in markedly higher titers of gp350-specific IgG relative to the gp350 monomer, even in the presence of a strong adjuvant. Most importantly, the gp350 subunits that comprise the tetrameric protein are conformationally intact and elicit serum titers of neutralizing antibody that are more than 19-fold higher than that induced by monomer. These data strongly suggest a promising, new prophylactic EBV vaccine for future clinical testing, as well as a more general approach to enhance the immunogenicity of other proteins of vaccine interest.

Materials and Methods

Construction of plasmids for production of monomeric and tetrameric gp350.

A gp350 cDNA fragment encoding amino acids 1-470 was cloned by PCR amplification of the DNA isolated from a recombinant baculovirus that expressed the truncated gp350 [29]. The following primer set was used:

```
                                           (SEQ ID NO: 4)
    forward    5'-CACCATGGAGGCAGCCTTGCTTGT-3'
    and (SEQ ID NO: 5)
    reverse    5'-AGATCTTTAGGATACAGTGGGGCCTGT GC-3',
``` denatured at 94° C. for 30 sec, annealed at 52° C. for 30 sec, extended at 68° C. for 2 min, total 25 cycles. The cDNA fragment was inserted into the pENTR/SD/D-TOPO directional cloning vector (Invitrogen, Grand Island, N.Y.) and verified by sequencing.

Gp350 Monomer Construct:

To make the construct expressing gp350 monomer, PCR amplification was performed under the conditions as described above using the primer sets designated

```
GF1:
                                           (SEQ ID NO: 6)
5'-GCCACCATGGAGACAGACACACTCCTGCTATGGGTACTGCTGCTCT

GGGTTCCAGGTTCCACTGGTGACGCGGCCCAGCCGGCCAGGCGCGCGCG

CCGTACGAAGCTCGCCCTT-3'
and

GR6:
                                           (SEQ ID NO: 7)
5'-TCAATGGTGATGGTGATGATGGGTGGATACAGTGGGGCCTGT-3'.
```

GF1 contained an IgGk leader sequence and GR6 contained the sequence coding for a $His_6$ tag (SEQ ID NO: 14). The PCR product was cloned into the pOptiVEC-TOPO vector (Invitrogen), and verified by sequencing.

G350 tetramer construct with TT epitopes:

The construct expressing gp350 tetramer was made by creating two separate gp350 units: gp350F1R1 and gp350F2R5, followed by ligating the two units together. The gp350F1R1 was made via PCR using the primer sets GF1 (as above) and GR1: 5'-CCATCGATGGCTAGCTAGCG-GTGGATACAGTGGGGCCTGT-3' (SEQ ID NO:8). GR1 contained a linker sequence $(Gly_4Ser)_3$ (SEQ ID NO:3) and sequences specific for the restriction enzymes Nhe I and Cla I. The PCR product was cloned into the pOptiVEC-TOPO vector, and was verified by sequencing. Gp350F2R5 contained sequences encoding the universal tetanus toxoid (TT)-specific CD4+ T cell epitopes $P_2$ and $P_{30}$ [30], a leucine zipper [27, 28] and a His6 tag (SEQ ID NO: 14), and was created by 3 rounds of PCR, adding the coding sequences sequentially. The first 2 rounds of PCR were done using the same forward primer designated GF: 5'-ATGGAGGCAGC-CTTGCTTGT-3' (SEQ ID NO:9) and reverse primers GR2: 5'-TCAACCAAAAGCTAACGTAAAATTATTAAATTT-TAGTTCAGTTATACCT ATAAATTTAGAATTGCTTT-TATATACTGGGTGGATACAGTGGGGCCTGT-3' (SEQ ID NO:10) and GR3: 5'-TTTGCTCAACAGCTCTTC-CACTTTATCTTCCAGCTGTTTCATG CGTTCTAAAT-GACTAGCAGATACTTAGGAACCCTCAAC-CAAAAGCTAACOGTA A-3' (SEQ ID NO: 1), respectively. The last PCR was performed using the forward primer designated GF2: 5'-CTAGCAGC GGT GGC GGA GGG AGT GGT GGC GGA GGG AGC GGT GC GGA GGG AGT ATGGAGGCAGCCTGCTTGT-3' (SEQ ID NO:12) and reverse primer GR5: 5'-CCATCGATTCAATG-GTGATGGTGATGATGGCTAGTGCGTTCGCCCAC-CAGC TTTTTCAGACGCGCCACTTCGTTTTCCAGAT-GATAGTTTTTGCTCAACAGCTCTTC C-3' (SEQ ID NO: 13). GF2 and GR5 contained the sequences for the restriction enzymes Nhe I and Cla I, respectively. The PCR product was cloned into the PCRII-TOPO vector (Invitrogen), and was verified by sequencing. The plasmids gp350F1R1 and gp350F2R5 were digested with Nhe I and Cla I, the fragments containing gp350 were gel-purified and ligated with T4 DNA ligase at 4° C. overnight, followed by transformation of "Top 10 F" E. coli (Invitrogen) with the ligation mixture. Two clones were selected for further study following verification by sequencing.

Gp350 Tetramer Construct without TT Epitope.

The plasmid was constructed using a similar approach as described above, but the sequences encoding $P_2$ and $P_{30}$ were deleted.

Transfection of Chinese Hamster Ovary (CHO) Cells (Clone DG44).

DG44 cells were maintained in "CD DG44" medium (Invitrogen), and $2\times10^7$ cells were used for transfection. 30 µg of gp350 monomeric or tetrameric construct was resuspended in 1.2 ml "OptiPro SFM" medium after linearization with PvuI, followed by adding 30 µl of "FreeStyle Max Reagent", mixed gently and incubated for 10 min at room temperature. The DNA-Freestyle Max Reagent complex was slowly added into the flask containing $2\times10^7$ DG44 cells with gentle shaking. The cells were incubated at 37° C., 5% $CO_2$ for 48 hours. Cells were centrifuged at 1,200 rpm and maintained in "CD OptiCHO" serum-free medium. Methotrexate (MTX, Sigma, St. Louis, Mo.) was used to select high recombinant protein-secreting cells, with the concentration of MTX gradually increased from 50 nM to 4 µM.

CHO Culture in Hollow Fiber Bioreactors and Purification of Recombinant Gp350 Proteins.

After MTX selection, gp350 monomer- and tetramer-expressing CHO cells were loaded into "Fibercell" cartridges ("C2008" [5 kD MW cut-off] and "C2011" [20 kD MW cut-off], respectively, FiberCell Systems, Inc., Frederick, Md.), and concentrated supernatants were collected daily. Supernatants were further concentrated by centrifugation at 3,000 rpm for 30 min using a "Centriprep Centrifugal Filter Unit", 30,000 MW cut-off (Thermo Scientific, Waltham, Mass.). Affinity purification was performed using a cobalt column (Thermo Scientific), according to manufacturer's instructions. Briefly, concentrated supernatants were mixed with an equal volume of equilibration buffer, and added to the cobalt purification column. The column was incubated with gentle agitation for 60 min at 4° C. and washed 3× with washing buffer. The gp350 recombinant proteins were eluted with elution buffer and analyzed by electrophoresis on 3-8% NuPAGE Tris-Acetate Mini Gels, under denaturing or native conditions, and stained with Simple Blue (Invitrogen). The gp350 proteins were also transferred onto nitrocellulose membranes and analyzed by Western Blot using anti-His antibody (Invitrogen). Gp350 proteins were further analyzed by immunoblotting with the g350-specific mAb, 72A1 [31], incubated overnight at 4° C. The nitrocellulose membranes were then incubated with HRP-labeled goat anti-mouse IgG, followed by development with chemiluminescent substrate (Thermo Scientific) for 10 min, and signal was detected on X-ray film. The 72A1 B cell hybridoma was a kind gift from Dr. Jonathan Hannan (University of Edinburgh, Edinburgh, UK). 72A1 mAb was purified on a protein G column from culture supernatant.

Mice.

Female BALB/c mice, purchased from the National Cancer Institute (Frederick, Md.) were used at 7-10 weeks of age for all protein immunizations. Female BALB/c mice purchased from Harlan Laboratories (Indianapolis, Ind.), were used at 4-6 weeks of age for all plasmid DNA vaccinations. These studies were conducted in accordance with the principles set forth in the *Guide for Care and Use of Laboratory Animals* (Institute of Laboratory Animal Resources, National Research Council, revised 1996), and were approved by the Uniformed Services University of the Health Sciences and the University of Washington Institutional Animal Care and Use Committees.

Antigens and Immunizations.

Purified pneumococcal capsular polysaccharide, type 14 (PPS14) was purchased from ATCC (Manassas, Va.). Gp350-PPS14 and TT-PPS14 conjugates were synthesized in a similar fashion, as previously described [32]. The molar ratios of gp350 and TT to PPS14 were about 8:1. Alum (Allhydrogel 2%) was obtained from Brenntag Biosector (Denmark). A stimulatory 30 mer CpG-containing oligodeoxynucleotide (CpG-ODN) was synthesized as previously described [33]. Mice were immunized i.p. with conjugates adsorbed on 13 µg of alum mixed with 25 µg of CpG-ODN. Monomeric and tetrameric Gp350 proteins were injected i.p. in alum+/−CpG-ODN. Serum samples for ELISA assay were obtained from blood taken from the tail vein.

Particle-Mediated Epidermal Delivery (PMED).

Mice were vaccinated by particle-mediated epidermal delivery (PMED) in the abdominal skin using the Powder-Joct XR-1 DNA vaccine delivery system as previously described [34]. Each immunization consisted of two tandem deliveries of 0.5 mg 1-3 µm-diameter gold particles coated with 1.0 µg DNA vaccine for a total dose of 4.0 µg DNA, formulated as previously described [34]. DNA vaccines were administered by PMED at a helium pressure of 350 psi at zero and four weeks.

Measurement of Serum Titers of Antigen-Specific IgG and IgG Isotypes by ELISA.

Immulon 4 ELISA plates (Dynex Technologies, Inc., Chantilly, Va.) were coated (50 µL/well) with monomeric gp350, TT, or PPSI4 (5 µg/ml) in PBS overnight at 4° C. Plates were washed 3× with PBS+0.1% Tween 20 and were blocked with PBS+1% BSA for 1 h at 37° C. Threefold dilutions of serum samples, starting at a 1/50 serum dilution, in PBS+1% BSA were then added overnight at 4° C. and plates were washed 3× with PBS+0.1% Tween 20. Alkaline phosphatase-conjugated polyclonal goat anti-mouse IgG, IgC3, IgG1, IgG2b, or IgG2a Abs (SouthernBiotech, Birmingham, Ala.) (200 ng/ml final concentration) in PBS+1% BSA were then added, and plates were incubated at 37° C. for 1 h. Plates were washed 5× with PBS+0.1% Tween 20. Substrate (p-nitrophenyl phosphate, disodium; Sigma) at 1 mg/ml in TM buffer (1 M Tris+0.3 mM $MgCl_2$, pH 9.8) was then added for color development. Color was read at an absorbance of 405 nm on a Multiskan Ascent ELISA reader (Labsystems, Finland).

Measurement of Serum Gp350-Specific Neutralizing Antibody.

Gp350 monomeric protein was labeled with Dylight 633 (Thermo Scientific). 25 µl of mouse serum from naïve or immunized mice, were incubated with 2.5 µl of DyLight 633-labeled gp350 monomer, for a final concentration of monomer of 1 µg/ml, for 30 min at room temperature. A pellet of $5\times10^5$ CR2M1α cells was resuspended in the serum/gp350 monomer mixture for 30 min on ice, washed 3× with 0.5% BSA-PBS, and fixed in 4% para-formaldehyde. The CR2M1α cell line was made by transfecting the K562 human erythroleukemia line with human CD21 [35]. To create a standard curve, varying concentrations of 72A1 mAb (final concentrations of 1-256 µg/ml) were incubated with Dylight 633-labeled monomeric gp350 (final concentration of 1 µg/ml) for 30 min at room temperature, followed by incubation with $5\times10^5$ CR2M1α cells as described above. CR2M1α cells were then analyzed on a BD LSRII Flow Cytometer Cell Analyzer.

Detection of Intracellular IL-4 and IL-5 by Flow Cytometry.

Spleen cells were isolated from mice, 21 d following i.p. immunization with gp350 monomer or tetramer in alum, and cultured for 5 h in 6-well plates at $2\times10^6$ cells/well in 1 ml of RPMI-1640+10% fetal calf serum, containing 10 U/ml rmIL-2 and 5 µg/ml of $P_2$ and $P_{30}$ TT-specific peptides. Golgi Stop (BD Biosciences, San Jose, Calif.) was added 1 h after initiation of culture. Cells were then stained with FTTC-rat IgG2b anti-mouse CD4 (clone GK1.5) in the presence of rat IgG2b anti-mouse CDl6/CD32 (clone 2.402) for 30 min on ice. Cells were washed, fixed, and permeabilized using cytofix/cytoperm solution (BD Biosciences). Following washing 2× in perm/wash buffer, cells were incubated with APC-labeled rat IgG2b anti-mouse IL-4 (clone BVD4-ID11) or PE-labeled rat IgG1 anti-mouse IL-5 (clone TRFKS) for 30 min on ice, followed by washing twice in perm/wash buffer. Cells were analyzed on a BD LSRII Flow Cytometer Cell Analyzer, using FlowJo software.

Binding of Monomeric and Tetrameric Gp350 Proteins to Human CD21.

CR2M1α cells were incubated for 30 min on ice with gp350 monomer or tetramer (0.05-30 µg/ml), washed 3× with 0.5% BSA-PBS and incubated further with mouse anti-gp350 mAb (2L10, Thermo Scientific) for 30 minutes. 2L10 mAb binds to a non-neutralizing epitope on gp350, distinct from the neutralizing epitope recognized by 72A1 [36, 37]. Cells were then washed 3× in 0.5% BSA-PBS, followed by incubation with DyLight 633-labeled goat anti-mouse IgG. Cells were fixed in 4% paraformaldehyde and analyzed on a BD LSRII Flow Cytometer Cell Analyzer.

Analysis of Human B Cell Activation.

Peripheral blood mononuclear cells (PBMC) were isolated by Ficoll-Hypaque (Roche, Indianapolis, Ind.) density gradient centrifugation from donor huffy coats (Blood Bank, National Institutes of Health, Bethesda, Md.) and washed twice in 1×PBS. B cells were purified from a starting population of $3\times10^8$ PBMC by magnetic bead cell separation (B cell isolation kit II, Miltenyi Biotec, Auburn, Calif.), yielding >94% purified CD19+ B cells as assessed by flow cytometry. Sorted B cells were resuspended at $1\times10^6$ cells/ml in complete RPMI 1640 medium (Lonza, Walkersville, Md.) containing 10% fetal calf serum (FCS, Lonza), 2 mM glutamine, and 100 U/ml each of penicillin and streptomycin (Invitrogen). B cells were aliquoted ($0.5$-$1\times10^6$ cells/well) in a 24 well plate and incubated for 24 or 72 h in a 37° C. incubator (5% $CO_2$) with monomeric or tetrameric gp350 (10 µg/ml), recombinant PspA (10 µg/ml), goat anti-human IgM F(ab')$_2$ (Jackson ImmunoResearch, West Grove, Pa., 20 µg/ml), or protein A from heat killed *Staphylococcus aureus* Cowan strain 1 (SAC, Sigma, St. Louis, Mo., 1:100 dilution)+recombinant human IL-2 (Peprotech, Rocky Hill, N.J., 200 IU/ml). Upregulation of cell surface activation markers was subsequently measured by staining cells with PE-conjugated anti-CD69 mAb (24 h post-stimulation) or PE-conjugated anti-CD25 mAb+FITC-conjugated anti-CD86 mAb (72 h post-stimulation). All antibodies were purchased from BD Biosciences. Cells ($3\times10^5$) were incubated with 5 µl of each antibody in 100 µl FACS buffer (1×PBS, 1% FCS, 0.1% sodium azide) for 30 min, washed in 2 ml FACS buffer, and collected on an LSR II flow cytometer (Becton Dickinson, Franklin Lakes, N.J.). Data analysis was performed using FlowJo software (TreeStar, Ashland, Oreg.).

Statistics.

Serum titers of antigen-specific Ig were expressed as the geometric means t SEM of the individual serum titers. Percentages of CD4+ T cells expressing cytoplasmic IL-4 or IL-5 were expressed as the arithmetic means+/−SEM of the individual samples. Significance was determined by the Student t test, p-values of ≤0.05 were considered statistically significant.

Example 1: DNA Plasmid and Production of a Tetrameric gp350 Protein Containing 77-Specific CD4+ T Cell Epitopes Optimal antibody responses to protein antigens require both dominant B and T cell epitopes. Although the EBV gp350 envelope protein is a potential target for an antibody-based prophylactic EBV vaccine, the relative strength and dominance of its T cell epitopes are unknown. Highly immunogenic carrier proteins, such as tetanus toxoid (TT), are utilized in polysaccharide conjugate vaccines to recruit CD4+ T cell help for the associated IgG anti-polysaccharide response. Initially, it was believed that adding TT to the EBV construct would help enhance and optimize the antibody response to the gp350 proteins. This initial belief was reinforced with early experiments comparing the relative ability of gp350 versus TT to promote an IgG response specific for pneumococcal polysaccharide, serotype 14 (PPS14), and thus indirectly to recruit CD4+ T cell help. Mice were immunized i.p. with either 1 or 5 µg of gp350-PPS14 or TT-PPS14 in alum+CpG-ODN as adjuvant and similarly boosted on day 14. Serum titers of PPSI4-specific IgG, measured on day 21, were significantly higher using TT-PPS14 relative to gp350-PPS14 using either 1 or 5 µg of conjugate (FIG. 1), strongly suggesting that TT contained more potent CD4+ T cell epitopes.

Figure 2:
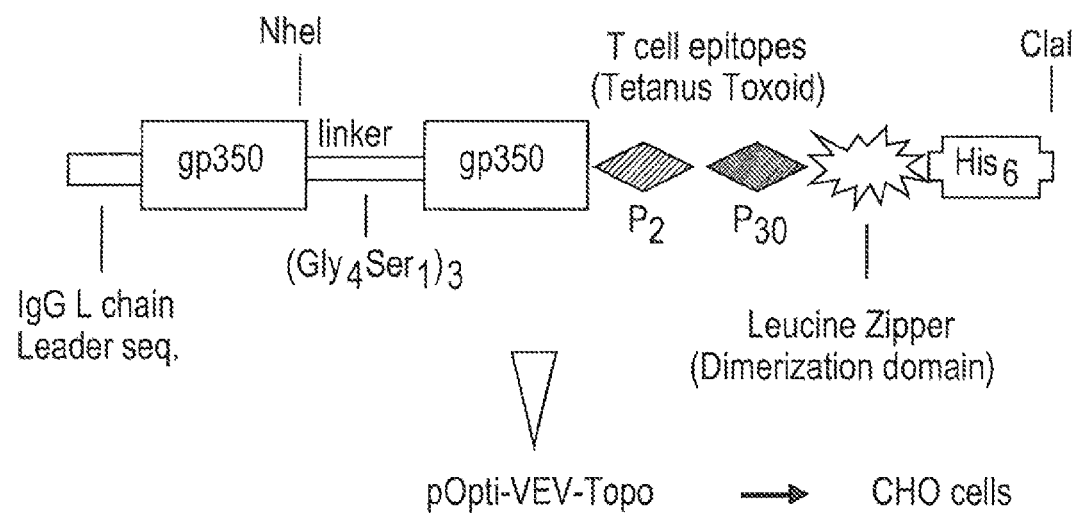
FIG. 2 shows a DNA plasmid map for production of tetrameric gp350 containing TT-specific CD4+ T cell epitopes. "$(Gly_4Ser_1)_3$" disclosed as SEQ ID NO: 3 and "$His_6$" disclosed as SEQ ID NO: 14, as well as production of a tetrameric gp350 protein containing TT-specific CD4+ T cell epitopes by SDS-PAGE (denatured) and PAGE (native) gels developed with 72A1 mAb.
Figure 2:
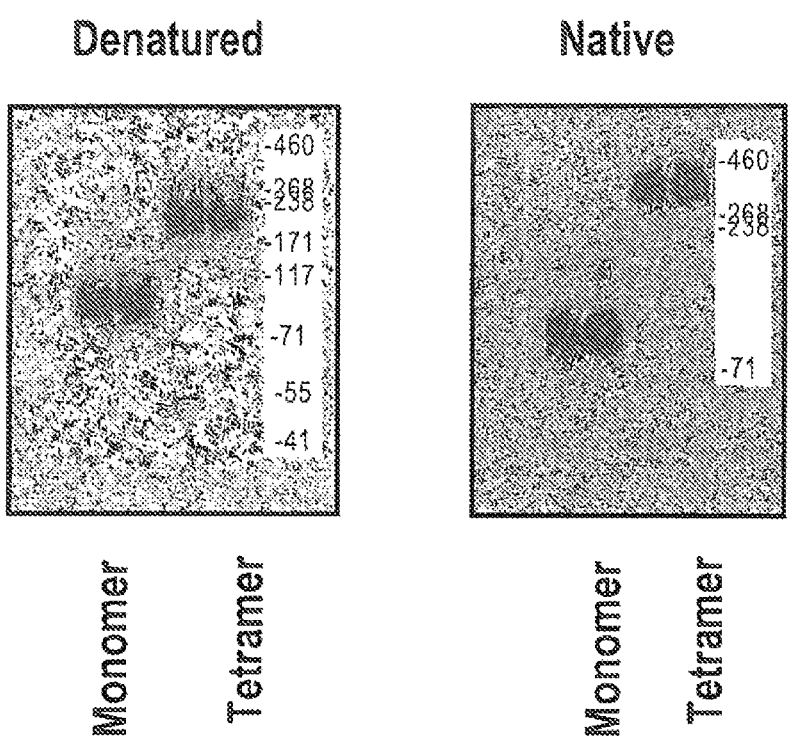

Multimerization of proteins can confer increased immunogenicity [21, 22, 25, 38, 39]. Therefore, a DNA construct that would direct the production of a tetrameric g350 was designed. EBV neutralizing antibody, required for a successful prophylactic vaccine, is specific for the conformational epitope of gp350 that mediates binding to CD21 on human B cells, mediating EBV entry. Thus, proper folding of the individual gp350 molecules in the tetramer was considered important. Given the known properties of TT as a potent inducer of CD4 T helper cells and the data illustrated in FIG. 1, two universal human TT-specific CD4+ T cell epitopes ($P_2$ and $P_{30}$) [30] were introduced into the construct to maximize recruitment of T cell help for the gp350-specific IgG response. The construct design is illustrated in FIG. 2A. Specifically, an IgG light chain leader sequence was introduced 5' to facilitate protein secretion, followed by two identical gp350 sequences separated by a $(Gly_4Ser)_3$ linker (SEQ ID NO:3) to allow for proper protein folding [26]. Sequences encoding $P_2$ and $P_{30}$ were introduced 3' to the second gp350 followed by a *Saccharomyces cerevisiae* GCN4 leucine zipper sequence [27, 28] to mediate self-association of the gp350 dimer, and thus formation of a tetrameric gp350. A $His_6$ tag (SEQ ID NO: 14) was positioned 3' of the leucine zipper for purposes of purification. A DNA construct encoding a monomeric gp350 lacking TT-specific epitopes was also produced for comparison.

To produce protein, Chinese hamster ovary (CHO) cells were stably transfected with either tetrameric or monomeric gp350 DNA, and high-producing CHO cells were selected using increasing concentrations of methotrexate in the culture medium. Protein was purified from culture supernatant and detected by SDS-PAGE (denaturing) and PAGE (native) using the gp350-specific 72A1 mAb that recognizes the CD21-binding, conformational epitope [31] (FIG. 2B). Under denaturing conditions, in which leucine zipper binding is disrupted, a single band of about 200 Kd was observed for the resulting gp350 dimer, whereas under native conditions a single band representing intact tetrameric gp350 of about 400 Kd was detected. In both cases, monomeric gp350 was detected as an approximately 100 Kd band. Of note, under denaturing conditions the concentration of 72A1 mAb required for development of a detectable band was 10-fold higher than that necessary under native conditions, likely reflecting loss of gp350 conformation in the former.

Figures 3A, 3B:
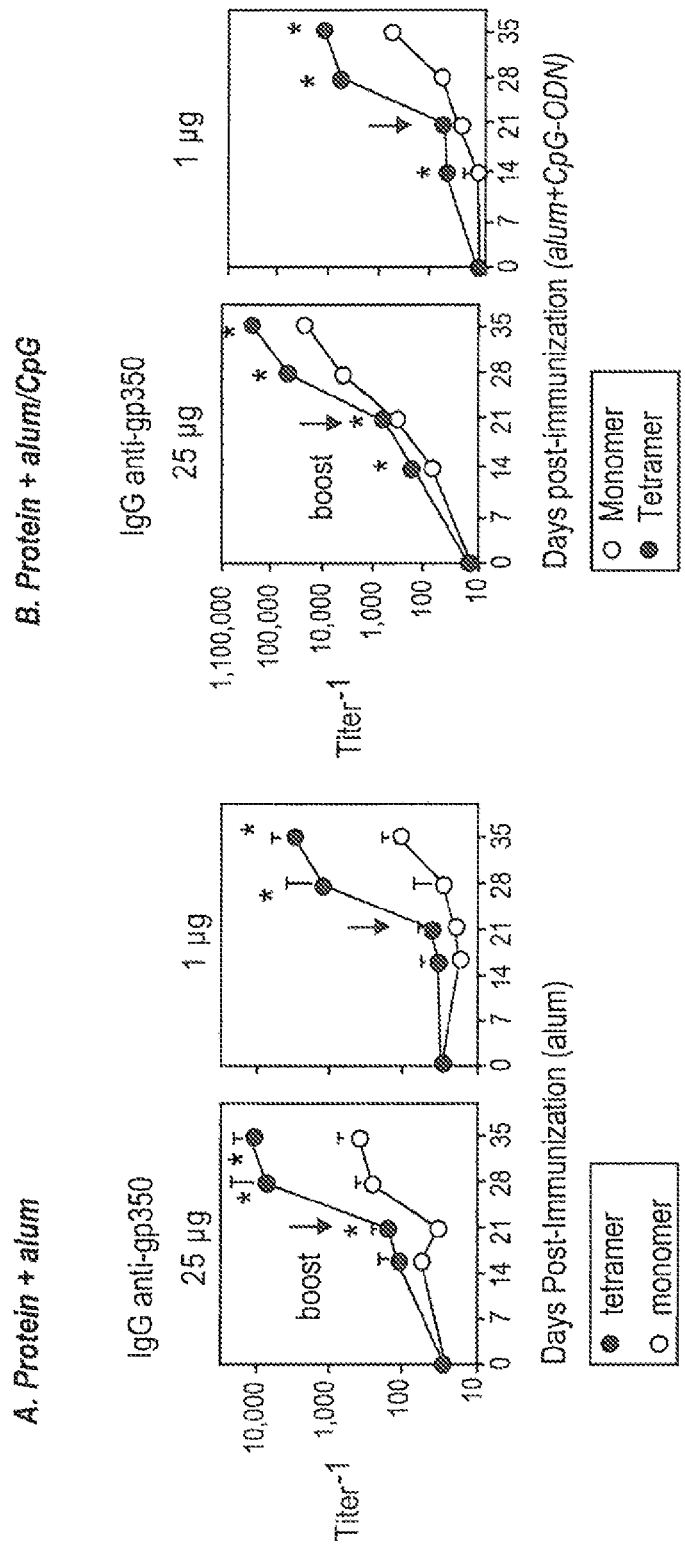
FIG. 3 shows that tetrameric gp350 is markedly more immunogenic than monomeric $gp^{350}$ protein whether administered in saline or with an adjuvant. DNA vaccination of these constructs also induced heightened immune responses. Mice (5 per group) were immunized i.p. with the indicated doses per mouse, of monomeric or tetrameric gp350 in (FIG. 3A) alum or (FIG. 3B) alum+CpG-ODN, and boosted in a similar manner on day 21. Mice (7 per group) were immunized in the abdominal skin with two tandem deliveries of 0.5 mg 1-3 μm-diameter gold particles coated with 1.0 μg DNA vaccine for a total dose of 4.0 μg DNA. Mice were boosted in a similar manner on week 4. Serum titers of gp350-specific IgG were determined by ELISA at the indicated times (FIG. 3C). Sera from tetramer-immunized mice: "A" and "B" (day 35, 25 μg dose) and "C" (week 6) were analyzed for serum titers of IgG isotypes (FIG. 3D). *Significance, $p \leq 0.05$ between tetramer and monomer.

Example 2: Tetrameric gp350 is Markedly More Immunogenic than Monomeric Gp350 Protein, Even in the Presence of a Strong Adjuvant and Following DNA Vaccination The relative ability of tetrameric versus monomeric gp350 to induce a gp350-specific IgG response was determined. Mice were injected i.p. with 25, 1.0, or 0.2 µg of tetrameric or monomeric gp350 per mouse in the presence of alum adjuvant and boosted in a similar fashion on day 21. Serum titers of gp350-specific IgG were measured by ELISA on the indicated days (FIG. 3A). Tetrameric gp350 induced 8-fold higher secondary serum gp350-specific IgG titers relative to monomeric gp350 at the higher dose (25 µg). Tetrameric gp350 at 1.0 µg induced serum titers that were comparable to mice receiving 25 µg of monomer, whereas tetramer at a dose of 0.2 µg/mouse elicited a barely detectable gp350-specific IgG response (data not shown). Thus, tetrameric gp350 exhibited about 25-fold higher immunogenicity on a per weight basis relative to monomer. In marked contrast to tetramer, monomer induced a barely detectable gp350-specific IgG response at 1.0 µg.

Next the effects of an adjuvant more potent than alum were tested to determine whether the differences observed between the immunogenicity of tetrameric and monomeric gp350 would still be manifest in the presence of the more potent adjuvant. Mice were immunized i.p. with 25 or 1.0 µg of tetrameric or monomeric gp350 per mouse in the presence of alum and 25 µg of a stimulatory 30-mer CpG-containing oligodeoxynuclcotide (CpG-ODN), a ligand for Toll-like receptor (TLR)9 [40]. Addition of CpG-ODN to alum resulted in a 21-fold enhancement in the secondary serum gp350-specific IgG titers in response to 25 µg of tetrameric gp350 relative to that observed using only alum as adjuvant (FIG. 3B). Similarly, CpG-ODN enhanced the response to 25 µg of monomeric gp350 by 54-fold. Nevertheless, at the 25 µg dose, tetrameric gp350 still induced 11-fold higher gp350-specific IgG titers relative to 25 µg of monomer. Of note, in the presence of alum+CpG-ODN, 1 µg of tetrameric gp350 induced responses that were comparable to mice receiving 25 µg of monomer. Even at the lower and much weaker immunogenic dose of 1 µg, tetrameric gp350 induced 21-fold higher serum titers of gp350-specific IgG relative to monomer. Thus, tetrameric gp350 is markedly more immunogenic than monomeric gp350 even in the presence of a relatively strong adjuvant.

Vaccination with plasmid DNA may confer a number of advantages over protein immunization [41], including the ability to elicit both humoral and cell-mediated immunity in a safe and cost-effective manner. Thus, the level of induction of gp350-specific IgG following primary immunization, and boost at 4 weeks, of equal amounts of DNA encoding monomer versus tetramer was compared. DNA was introduced into the epidermis on microscopic gold particles (i.e. particle-mediated epidermal delivery [PMED]) [42, 43]. Primary immunization with either plasmid induced minimal serum titers of gp350-specific IgG by 4 weeks (FIG. 3C). However, upon boosting, both plasmids induced a significant gp350-specific IgG response by week 6. Of note, the secondary gp350-specific IgG response to the DNA encoding tetrameric gp350 was 8-fold higher (p=0.0004) than that elicited by DNA encoding the monomer. Analysis of serum gp350-specific IgG isotype titers for tetrameric gp350 protein in alum+/−CpG-ODN (25 µg dose) and DNA encoding tetrameric gp350 were compared (FIG. 3D). As anticipated, gp350 protein in alum alone elicited a primarily IgG1 response. Addition of CpG-ODN significantly boosted the gp350-specific IgG1 response over that seen with alum alone, and further induced serum titers of gp350-specific IgG2b and IgG2a. DNA vaccination induced serum titers of gp350-specific IgG1 and IgG2a comparable to and lower (about 3-fold), respectively, to that observed for gp350 protein in alum+CpG-ODN, whereas no detectable IgG2b was observed in response to DNA (FIG. 3D). Minimal titers of gp350-specific IgG3 were produced in response to any of the 3 immunization groups.

Example 3: The Enhanced gp350-Specific IgG Response Requires Both Priming and Boosting with the Tetrameric Form of gp350

Figure 4:
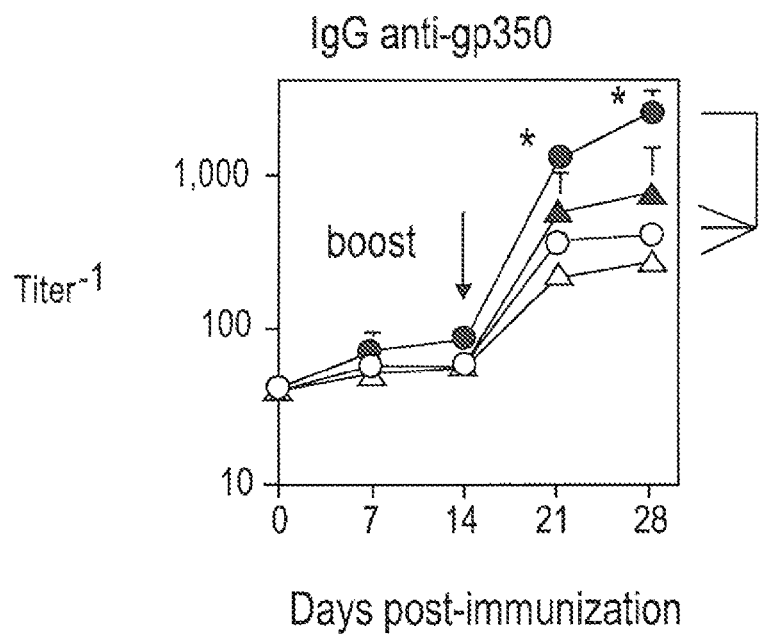
FIG. 4 shows that the enhanced gp350-specific IgG response requires both priming and boosting with tetrameric gp350. Mice (5 per group) were primed and boosted as indicated with tetrameric or monomeric gp350 in alum. Serum titers of gp350-specific IgG were determined by ELISA. *Significance, p≤0.05.

The stimulatory requirements for elicitation of a T cell-dependent secondary response are typically less stringent than that for induction of a primary [44, 45]. The substantially higher secondary gp350-specific IgG responses observed following priming and boosting with tetrameric gp350 relative to monomer, could have been caused by the tetrameric gp350 during the primary and/or secondary immunization. To determine this, four groups of mice were established in which various combinations of priming and boosting with tetrameric and monomer gp350 were performed, using alum as adjuvant. As illustrated in FIG. 4, only both priming and boosting with tetrameric gp350 resulted in significantly higher secondary serum titers of gp350-specific IgG relative to priming and boosting with monomer.

Figure 5:
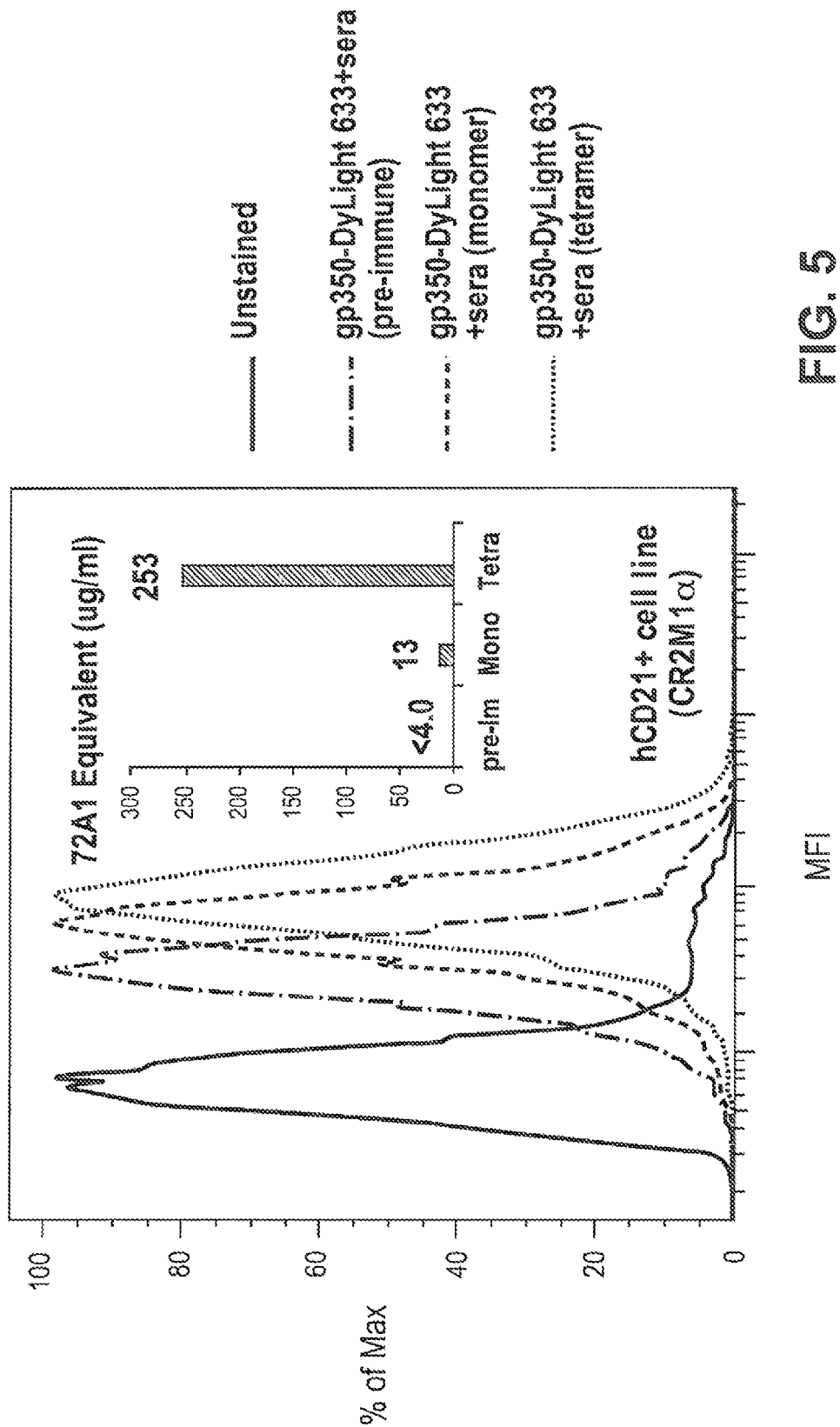
FIG. 5 shows that immunization of mice with tetrameric gp350 protein induces markedly higher levels of neutralizing gp350-specific antibodies relative to monomer. 25 µl of pooled mouse serum (5 mice each) from naïve or immunized mice (day 35, 25 µg monomeric or tetrameric gp350/mouse in alum, see FIG. 3A), were incubated with 2.5 µl of DyLight 633-labeled gp350 monomer. CR2M1α cells were then stained with these mixtures and analyzed by flow cytometry. Various concentrations of 72A1 mAb (neutralizing gp350-specific IgG) were used instead of serum to create a standard curved for quantitation.

Example 4: Immunization with Tetrameric Gp350 Protein Induces Markedly Higher Levels of Neutralizing Gp350-Specific Ig Relative to Monomer Binding of EBV gp350 to CD21 is necessary for viral entry into the B cell [5, 6], an event that is critical for infectivity and B cell neoplastic transformation [2]. Thus, elicitation of antibody that blocks this interaction (i.e. "neutralizing" antibody) [7] may serve as the basis for an effective prophylactic EBV vaccine [17, 18]. In this regard, a gp350-specific mAb was previously produced (clone 72A1), that can specifically block gp350 binding to human CD21 [31]. To measure the amount of neutralizing antibody in sera from gp350-immunized mice, an erythroleukemia cell line transfected with human CD21 (CR2M1α) was used. Initially, monomeric gp350 was directly labeled with the fluorochrome DyLight 633 and mixed with varying amounts of 72A1 mAb prior to incubation with CR2M1α cells. A standard neutralization curve was generated that related the amount of 72A1 mAb added with a fixed amount of gp350-DyLight 633, and the subsequent mean fluorescence intensity (MFI) of staining of CR2M1α cells. Monomeric gp350-DyLight 633 was then mixed with undiluted pre-immune sera or sera from mice following priming and boosting with 25 μg of tetrameric or monomeric gp350 and subsequently incubated with CR2M1α cells. As illustrated in FIG. 5, pre-immune sera contained <4.0 μg/ml of 72A1 mAb-equivalents of neutralizing activity. Whereas, monomeric gp350 induced 13 μg/ml of neutralizing activity, tetramer induced 253 μg/ml, a 19-fold greater level of activity than monomer. Of interest the difference in neutralizing activity between sera obtained from monomer-versus tetramer-immunized mice closely mirrored the difference observed for total (neutralizing and non-neutralizing) serum titers of gp350-specific IgG (see FIG. 3). These data indicate that tetrameric gp350 is a more effective EBV vaccine candidate than monomeric gp350, the latter already shown to be safe, and to have partial efficacy in reducing the incidence of infectious mononucleosis in phase I/II clinical trials [17, 18].

Example 5: Priming with TT Protein can Inhibit the Gp350-Specific IgG Response to Tetrameric, but not Monomeric Gp350

Figures 6A, 6B:
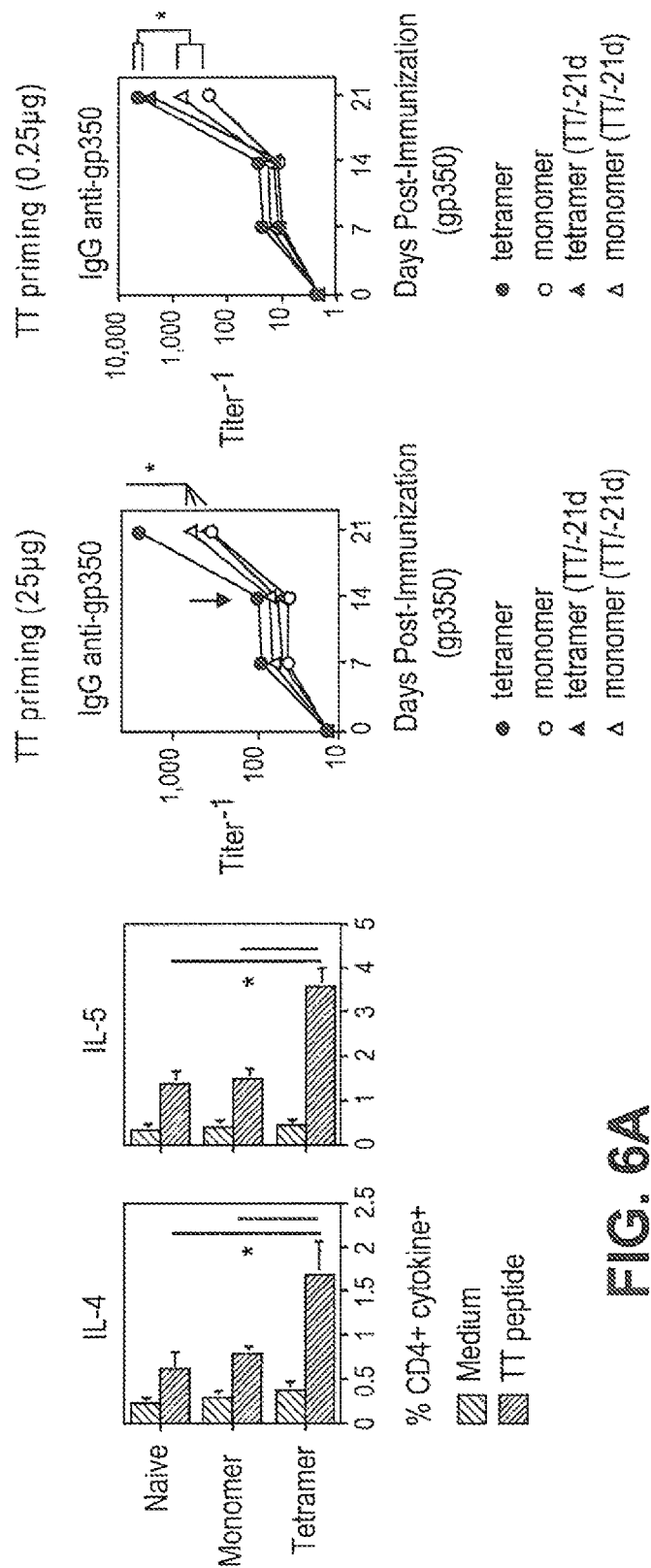
FIGS. 6A-B show that priming with TT protein inhibited the gp350-specific IgG response to tetrameric, but not monomeric gp350. For FIG. 6A, mice (5 per group) were immunized with 25 µg/mouse of monomeric or tetrameric gp350 in alum. Spleen cells were harvested from each mouse on day 21 and separately cultured for 5 h in medium containing 10 U/ml rmIL-2+/−5 µg/ml of $P_2$ and $P_{30}$ TT-specific peptides. Golgi Stop was added 1 h after initiation of culture. Cells were then stained for cytoplasmic IL-4 or IL-5 and analyzed by flow cytometry. The percentage of gated CD4+ cells staining positively for each cytokine is illustrated in FIG. 6A. *Significance, p≤0.05. For FIG. 6B, Mice (5 per group) were immunized with 25 µg/mouse or 0.25 µg/mouse of whole TT in alum for 14 days. Mice were then challenged with 25 µg of tetrameric or monomeric gp350 in alum and similarly boosted 14 days later. Serum titers of gp350-specific IgG were determined by ELISA. *Significance, p≤0.05.

Two universal TT-specific TT epitopes were introduced into the tetrameric gp350 vaccine with the expectation that this would contribute to the enhancement of the gp350-specific IgG response relative to monomeric gp350. In this regard, children typically receive TT as a vaccine for protection against *Clostridium tetani*, and thus are likely to have TT-primed CD4+ T cells. It has been demonstrated that pre-immunization of mice with TT suppressed a subsequent antibody response to synthetic peptides conjugated to TT [46] and that this was due to clonal dominance [47] and required CD4+ T cells for its induction [48]. Thus, it was first determined whether tetrameric gp350 primed TT-specific CD4+ T cells in vivo, and if initial priming of mice with whole TT protein would impact on the subsequent gp350-specific IgG response to tetramer. Mice were immunized with 25 μg of tetrameric or monomeric gp350 in alum. On day 21 spleen cells were isolated and cultured with the $P_2$ and $P_{30}$ TT peptides, followed by flow cytometric analysis of gated CD4+ T cells for intracytoplasmic expression of IL-4 and IL-5. CD4+ T cells from mice primed with tetrameric gp350, but not monomer-primed or naïve mice, exhibited a significant increase in CD4+ T cells expressing cytoplasmic IL-4 and IL-5 following elicitation with TT peptide in vitro, but not in the presence of medium alone (FIG. 6A). This indicated that tetrameric gp350 primed TT-specific CD4+ T cells in vivo. Next, naïve mice were immunized with 25 μg of whole TT protein in alum, with boosting in a similar fashion on day 14, resulting in readily detectable serum titers of TT-specific IgG by day 21 (data not shown). TT-primed and non-primed mice were then immunized with 25 μg of monomeric or tetrameric gp350 in alum and boosted in a similar fashion 14 days later. Non-primed mice immunized with tetrameric gp350 elicited a significantly higher gp350-specific IgG response relative to monomer (FIG. 6B), as demonstrated earlier (FIG. 3A). However, in TT-primed mice, the gp350-specific IgG response was inhibited in response to tetrameric, but not monomeric, grp350, so that no significant difference in serum titers was observed between the two groups. Utilizing a 100-fold lower dose of TT that induced about 3-fold lower secondary serum titers of TT-specific IgG than that observed using 25 μg of TT for priming (data not shown), no inhibition was observed, and no enhancement, of the gp350-specific IgG response to tetramer (FIG. 6C). The TT-specific IgG antibodies elicited in response to TT did not bind tetrameric gp350 as indicated by ELISA assay (data not shown), consistent with $P_2$ and $P_{30}$ being T cell, and not B cell, epitopes. Thus, TT priming, in a dose-dependent fashion, can result in inhibition of an antibody response to a protein antigen containing TT-specific T cell epitopes, consistent with earlier reports [46-48].

Figures 7A, 7B, 7C:
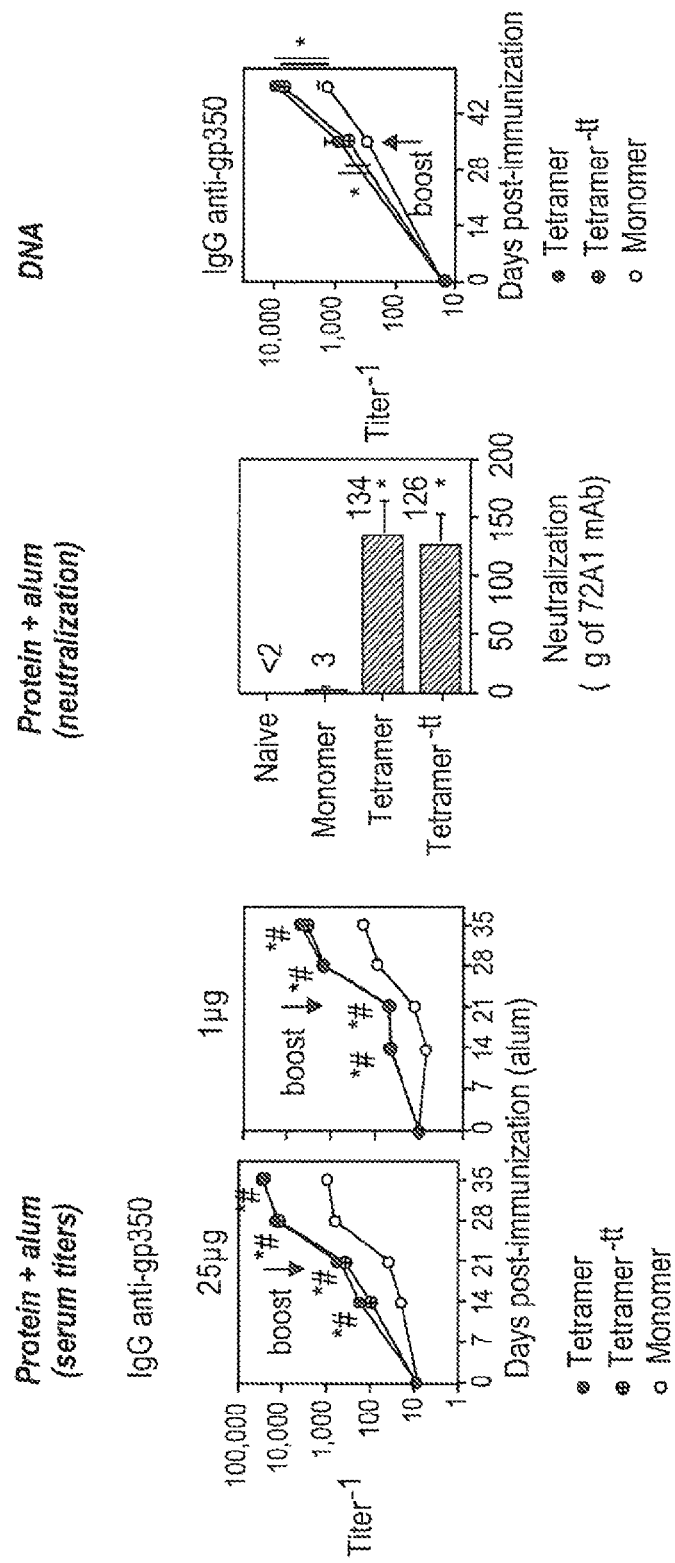
In FIG. 7A, mice (5 per group) were immunized with monomeric gp350 protein, tetrameric gp350 containing TT epitopes ("tetramer"), or tetrameric gp350 without TT epitopes ("tetramer$^{-tt}$") at either 25 µg or 1.0 µg per mouse in alum, and boosted in a similar manner on day 21. Serum titers of gp350-specific were measured by ELISA (FIG. 7A). *Significance, p≤0.05 between tetramer and monomer, #Significance, p≤0.05 between tetramer$^{-tt}$ and monomer.
FIG. 7B shows gp350-specific neutralization titers of sera from "A" (25 µg/mouse, day 35 as described in FIG. 5); *Significance, p≤0.05 between tetramer or tetramer$^{-tt}$ versus monomer.
FIG. 7C shows DNA immunization with plasmids encoding monomer, tetramer, and tetramer$^{-tt}$ as described in FIG. 3C; *Significance, p≤0.05 between tetramer or tetramer$^{-tt}$ versus monomer.

Example 6: The TT-Specific T Cell Epitopes in Tetrameric Gp350 do not Contribute to the Gp350-Specific IgG Response in Naïve Mice To determine the extent, if any, to which the TT epitopes contributed to the more potent immunogenicity of tetrameric versus monomeric gp350 in naïve mice, a new DNA plasmid was constructed in which the TT-specific T cell epitopes were deleted in the DNA encoding tetrameric TT (referred to as "tetramer$^{-tt}$"). The new plasmid was validated by sequencing, and immunoelectrophoresis of CHO cell-expressed protein using 72A1 mAb. A new set of mice were immunized with 25 or 1.0 μg of monomer, tetramer, or tetramer$^{-tt}$ in alum and boosted in a similar fashion on day 21. As illustrated in FIG. 7A, the tetramer and tetramer$^{-tt}$ induced dose-dependent gp350-specific IgG responses that were not significantly different from each other, but that were each about 25-fold higher than that elicited by monomer at each of the two doses. Again, in contrast to the robust gp350-specific IgG responses observed with 1 μg of tetramer or tetramer$^{-tt}$, 1 μg of monomer induced a barely detectable response. Similarly, tetramer and tetramer$^{-tt}$ elicited a similar gp350-specific neutralizing antibody response at the 25 μg dose, that was each greater than 40-fold higher than that elicited by monomer (FIG. 7B). Finally, immunization with plasmid DNA encoding tetramer and tetramer$^{-tt}$ elicited gp350-specific IgG responses that were similar, but about 8-fold higher than that observed using plasmid DNA encoding monomeric gp350 (FIG. 7C). These data strongly suggest that the marked enhancement in the gp350-specific TgG response to tetrameric versus monomeric gp350 is based exclusively on protein multimerization, and not to the provision of stronger T cell epitopes.

Example 7: Tetrameric Gp350 Binds More Avidly to Human CD21 than Monomer

Figure 8:
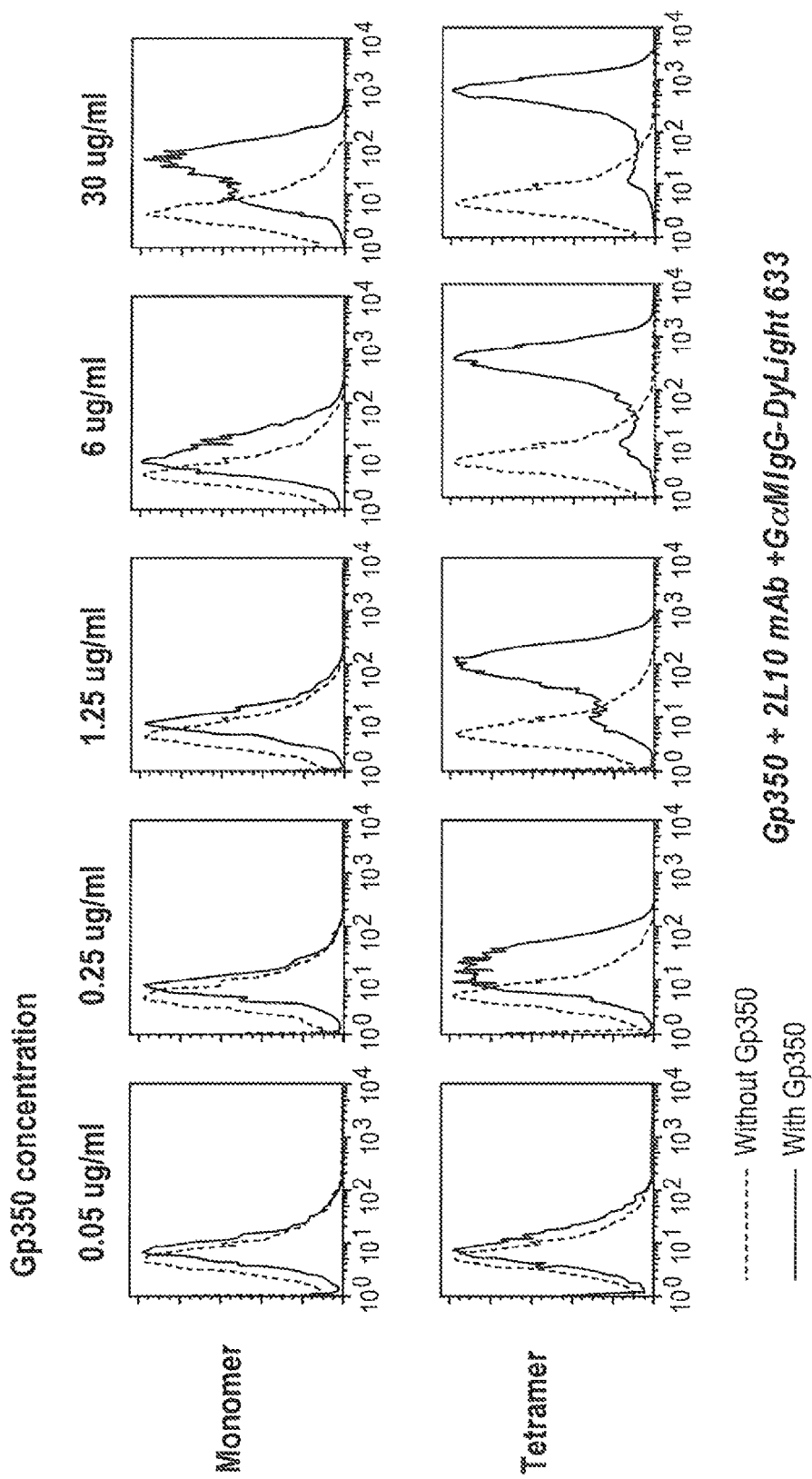
FIG. 8 shows that the tetrameric gp350 binds more avidly to human CD21 than monomer. CR2M1α cells were incubated for 30 min on ice with gp350 monomer or tetramer (0.05-30 µg/ml), washed, then incubated further with 2 L10 mAb (mouse IgG1 anti-gp350 mAb) for 30 min. Cells were then washed, followed by staining with DyLight 633-labeled goat anti-mouse IgG. Cells were analyzed by flow cytometry. Broken line: CR2M1α cells without gp350; solid line: with gp350.

The capacity of B cells to bind cognate antigen via their B cell receptor (BCR) and present the resulting peptide/MHC-II to CD4+ T cells is a critical event in the evolution of a T cell-dependent humoral immune response. In this regard, multimerization of antigen may boost immunogenicity, at least in part, by promoting more avid BCR binding to specific B cells. Gp350 is a ligand for human, although not mouse, CD21. Thus, human CD21, expressed by the CR2M1α, was used as a surrogate for BCR binding to gp350, to compare the efficiency of binding of tetrameric versus monomeric gp350. To accomplish this, CR2M1α cells were incubated with increasing concentrations of unlabeled monomer or tetramer (0.05-30 µg/ml), followed by unlabeled 2L10 mAb (mouse IgG anti-gp350). This mAb binds to gp350 at a site distinct from the CD21-binding site, and hence is not blocked upon gp350/CD21 binding. This was followed by staining with DyLight 633-labeled goat anti-mouse IgG and analysis by flow cytometry. Incubation of CR2M1α cells with increasing concentrations of monomeric and tetrameric gp350 resulted in a dose-dependent progressive increase in MFI staining in both cases (FIG. 8). Of note, staining using 1.25 µg/ml of tetrameric gp350 resulted in an MFI equivalent to 30 µg/ml of monomeric gp350, suggesting about 24-fold greater binding avidity of tetramer versus monomer. This degree of difference in apparent avidity of binding is similar to that observed for induction of gp350-specific IgG and neutralizing antibody in response to tetramer versus monomer. These data are consistent with the notion that greater BCR binding to tetrameric gp350 by gp350-specific B cells may account, at least in part, for its greater immunogenicity in vivo.

Figure 9:
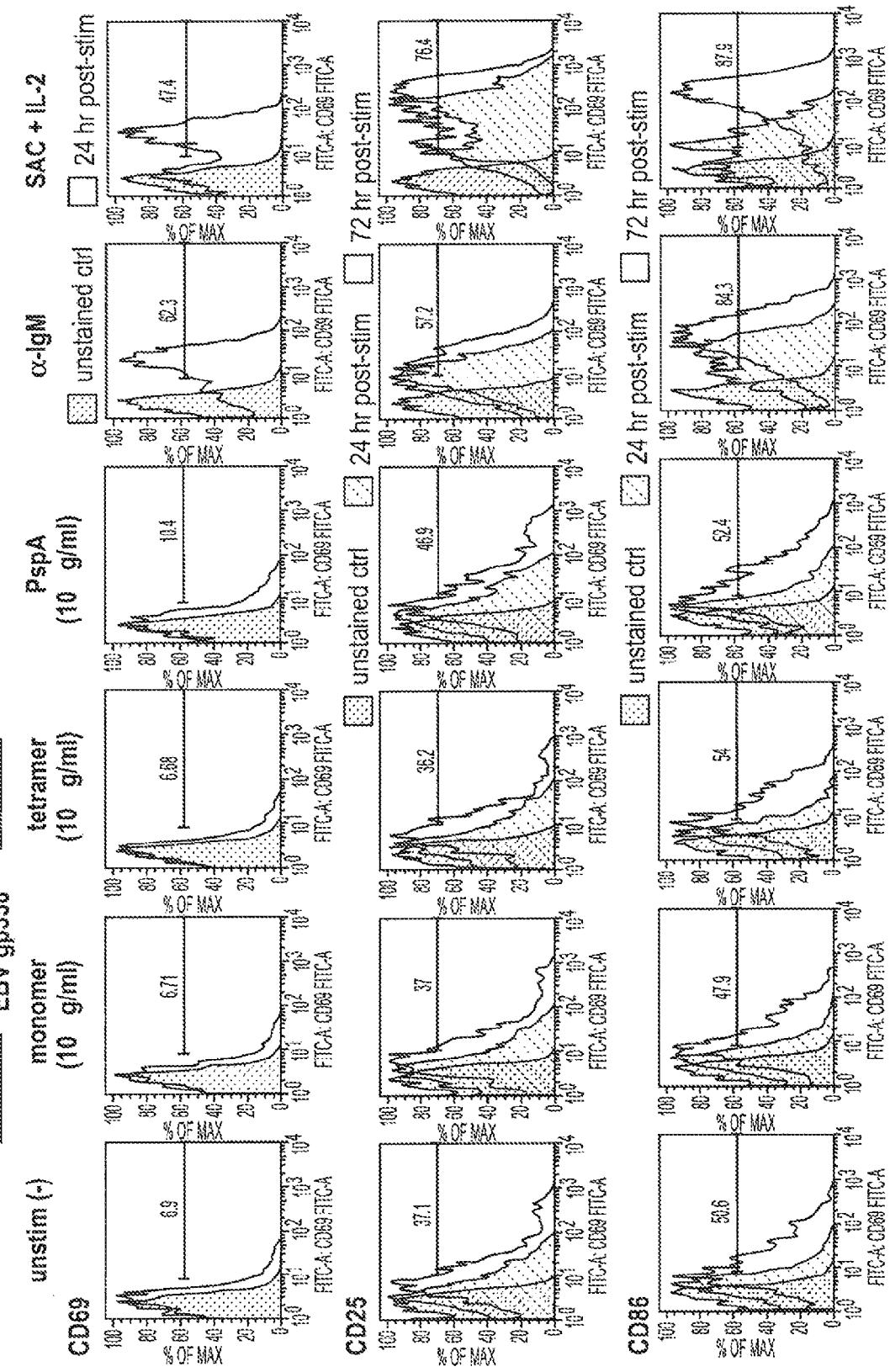
FIG. 9 shows that neither monomeric nor tetrameric gp350 polyclonally activates human B cells. Purified peripheral blood human B cells were cultured for 24 or 72 h with monomeric or tetrameric gp350 (10 µg/ml), recombinant PspA (10 µg/ml), goat anti-human IgM F(ab')$_2$ (20 ag/ml), or (SAC, 1:100 dilution)+recombinant human IL-2 (200 IU/ml). Cells were then stained with PE-conjugated anti-CD69 mAb (24 h post-stimulation) or PE-conjugated anti-CD25 mAb+FITC-conjugated anti-CD86 mAb (72 h post-stimulation) and analyzed by flow cytometry.

Example 8: Neither Monomeric Nor Tetrameric Gp350 Polyclonally Activates Human B Cells Purified, recombinant gp350 has been shown to upregulate IL-6 mRNA synthesis in human B cells in a CD21-dependent manner [49]. This suggests that tetrameric gp350, which is predicted to induce CD21 crosslinking on human B cells, could potentially act as a polyclonal B cell activator, with possible unwanted side-effects when used as a vaccine. To determine this, purified peripheral blood human B cells were incubated with 10 µg/ml of monomeric or tetrameric gp350, or a negative control protein (pneumococcal surface protein A [PspA]). As positive controls we used anti-IgM antibody or SAC+IL-2 for B cell activation. As illustrated in FIG. 9, neither monomeric nor tetrameric gp350, nor PspA, upregulated the activation markers CD69 (at 24 hrs) or CD25 (at 24 or 72 hrs), nor the costimulatory molecule CD86 (at 24 or 72 hrs). In contrast, anti-IgM or SAC+IL-2 strongly upregulated all 3 of these markers. Further, in contrast to anti-IgM or SAC+IL-2, neither monomeric nor tetrameric gp350 induced increases in B cell size (data not shown). These data are consistent with a previous report demonstrating that aggregated or latex-bound C3dg, which crosslink CD21, lack the ability to directly trigger G1 entry by resting human B cells [50]. These data strongly suggest that a tetrameric gp350 vaccine will not induce polyclonal B cell activation in vivo.

Example 9: Tetrameric Gp350 Immunization in a Permissive Rabbit Model

The rabbit, in contrast to the mouse, is a permissive model for EBV infection, and thus ideal for pre-clinical testing of an EBV vaccine [67]. This likely reflects, in part, our own observation that rabbit B cells, in contrast to mouse B cells, bind gp350, most likely by binding to B cell CD21. Thus, flow cytometric analysis using Dylight-labeled gp350 and FITC-anti-rabbit IgM mAb to stain B cells was conducted to determine whether gp350 binds to rabbit B cells. Both peripheral blood and splenic B cells, isolated from New Zealand white rabbits, showed strong double staining. No staining was observed using a negative control, Dylight-labeled pneumococcal surface protein A (PspA) (data not shown).

Figure 10:
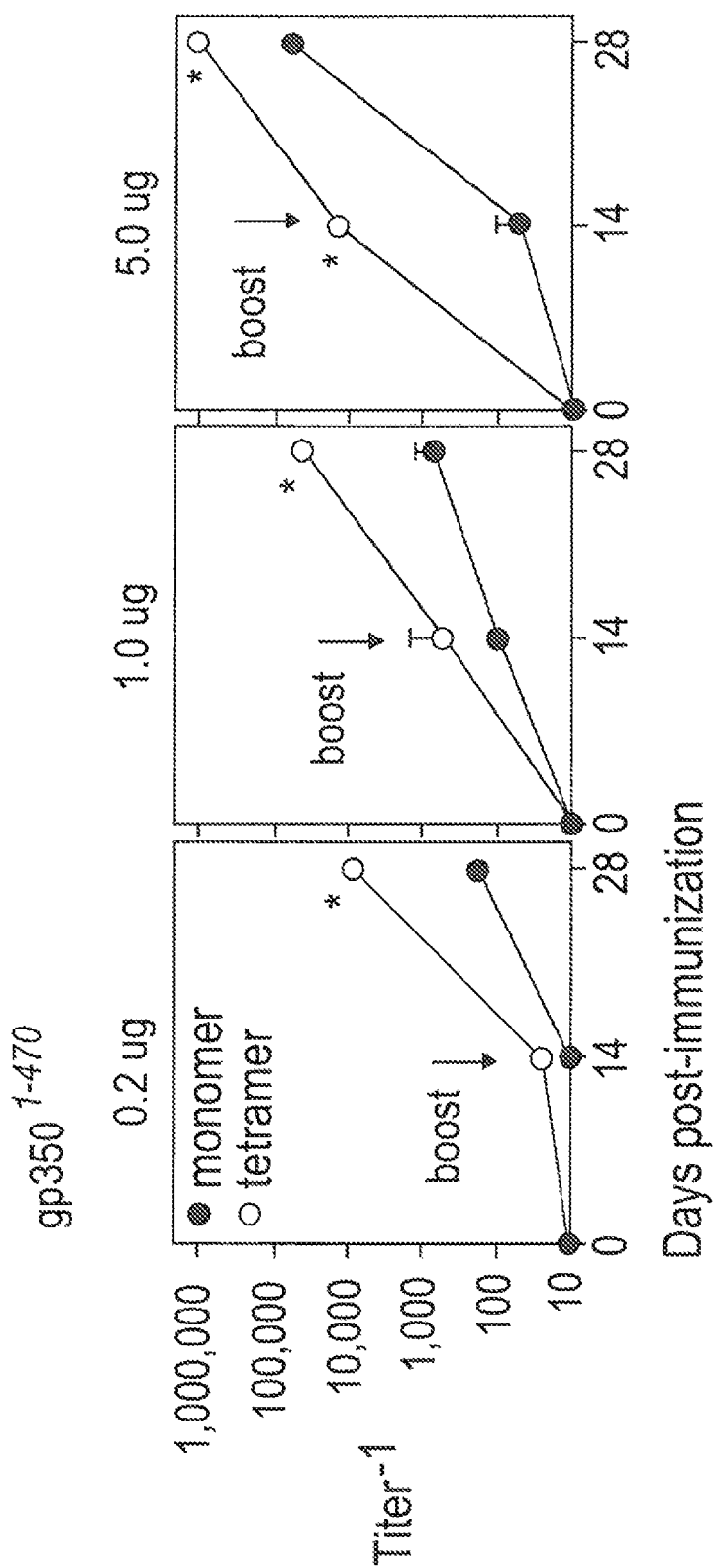
FIG. 10 shows that immunization of rabbits with tetrameric gp350 protein (0.2 µg, 1.0 µg, or 5.0 µg) induces markedly higher levels of neutralizing gp350-specific antibodies relative to monomer.

Next a series of dose response immunization studies of tetrameric versus monomeric gp350 were performed to determine the relative immunogenicity of monomeric gp350 and tetrameric gp350 in rabbits. Rabbits (4 per group) were immunized s.c. with 5.0, 1.0, or 0.2 jtg of monomeric or tetrameric gp350 in alum and boosted in a similar fashion on day 14. Sera were collected at day 0, 14, and 28 for measurement of gp350-specific IgG titers by ELISA (FIG. 10). As illustrated, tetrameric gp350 was markedly more immunogenic than monomeric gp350 at all doses. The difference in serum titers of gp350-specific IgG between tetramer and monomer in the rabbit were up to 100-fold, compared to the ~20-fold differences observed in the mouse. Since co-crosslinking of CD21 and the B cell receptor (BCR) induce synergistic B cell signaling, tetrameric gp350 may also act as an intramolecular adjuvant in rabbits (and by extension humans).

Example 10: Construction of Other EBV Multimeric Constructs

EBV infection and persistence is critically dependent upon viral entry into B cells and nasopharyngeal epithelial cells. B cell infection involves initial binding of EBV gp350 to B cell CD21 followed by binding of EBV gp42 to B cell MHC class II molecules. This results in viral fusion and entry mediated by EBV gH/gL heterodimer and gB. Epithelial cell infection by EBV also involves gH/gL and gB, but not gp350 or gp42. The multimerization technique described in this application has been used to produce an EBV gH/gL heterodimer with a trimerization domain. The multimerization techniques can be similarly used to produce multimeric gB or gp42 constructs.

Discussion:

In this study, a tetramer of the EBV envelope protein gp350 was created by constructing a plasmid in which two copies of a truncated gp350, containing the CD21-binding neutralization epitope, were separated by a linker, to allow for conformational folding. This dimeric gp350 underwent further dimerization to form a tetramer following translation within transfected CHO cells, via homotypic binding of 3' leucine zipper motifs. This protein multimerization strategy resulted in a marked enhancement in elicitation of gp350-specific IgG, including neutralizing antibody, relative to monomeric gp350. Enhanced immunogenicity of tetrameric versus monomeric gp350 was observed following direct immunization with plasmid, or with protein in the presence of even a strong adjuvant such as alum+CpG-ODN. Tetrameric gp350 bound much more efficiently to human CD21 but did not polyclonally activate human B cells. Furthermore, when the immunogenicity of the multimeric construct was tested in the permissive rabbit model, the difference in serum titers of gp350-specific IgG between tetramer and monomer in the rabbit were up to 100-fold, compared to the 20-fold differences observed in the mouse. Thus, these data support the value of testing tetrameric gp350 in clinical trials for its potential to elicit more protective immunity against such EBV-mediated diseases as infectious mononucleosis, and perhaps neoplastic transformation, as opposed to monomeric gp350 used in previous, small-scale human studies [16-19]. These data also support the use of this multimerization strategy to enhance humoral immune responses to other proteins of vaccine interest, in a reproducible and cost-effective manner.

Multimerization of proteins/peptides has been shown to enhance their immunogenicity. Thus, a plasmid encoding green fluorescent protein (GFP) fused to a long poly-glutamine tail that mediates aggregation, induced significantly higher serum GFP-specific Ig titers and enhanced GFP-specific CD8+CTL activity following prime/boost immunization in mice, relative to non-aggregating GFP [21]. Multimerization of bovine serum albumin (BSA) by covalent attachment of BSA or haptenated BSA to dextran at a ratio of 20-30 BSA/$2 \times 10^6$ MW dextran resulted in strong enhancements in elicited murine serum titers of BSA- or hapten-specific IgG1, respectively, relative to unconjugated protein [25]. Rabbits immunized with glutathione S-transferase (GST) fusion proteins with increasing copy number of a peptide epitope (M2e) of the influenza virus M2 protein elicited M2e-specific IgG in response to GST-(M2e)$_8$ with an average affinity constant ($K_A$) of up to two orders of magnitude greater than that induced by GST-(M2c)$_r$[20]. Covalent attachment of increasing copy number of peptides onto virus-like particles (VLPs) resulted in a positive correlation between epitope density and the magnitude of the peptide-specific murine IgG, although not IgM, response following immunization [23]. Higher epitope densities also allowed for efficient IgG responses in the absence of complement receptor type 2 (CD21). An unwanted consequence of protein multimerization has been observed with the use of therapeutic proteins such as human growth hormone, intravenous immune globulin (IVIG), human serum albumin, human interleukin-2, and human interferon-β in which aggregated proteins within the preparation preferentially induced immune responses, including neutralizing antibody that decreased therapeutic efficacy [22, 24]. Finally, alum, a commonly used adjuvant in clinical vaccines, itself forms aggregates that trap antigen at the site of injection [51]. Of note, in this study, tetrameric gp350 in alum with or without additional adjuvanting with CpG-ODN was nevertheless markedly more immunogenic than monomeric gp350 delivered in the same adjuvants. Although direct evidence in vivo is limited, and without intending to be bound by any theory, the increased immunogenicity of multimeric proteins likely arises from more efficient activation of complement, enhanced binding to the BCR, more efficient BCR-mediated signaling, enhanced B cell uptake and presentation of protein-derived peptide to CD4+ T cells and/or enhanced trapping of multimeric proteins on the surface of follicular dendritic cells [24, 52].

The presence of strong CD4+ T cell, in addition to B cell, epitopes is important for robust T cell-dependent (TD) IgG responses to protein antigens. In this regard, TT was shown to be a significantly more potent carrier protein than gp350 for eliciting a TD IgG response specific for a pneumococcal polysaccharide, as part of a conjugate vaccine. This strongly suggested that TT contained more potent CD4+ T cell epitopes than gp350 for delivery of helper function to B cells. Accordingly, the initial gp350 tetramer design incorporated two known universal TT-specific CD4+ T cell epitopes. However, the data in this study unexpectedly show that not only did the TT epitopes not contribute to the immunogenicity of the tetramer in naïve mice, but they actually mediated inhibition of antibody responses in TT-primed mice. This latter observation was relevant in light of the widespread use of TT as a clinical vaccine. In this regard, it has been demonstrated that pre-immunization of mice with TT suppressed a subsequent antibody response to synthetic peptides conjugated to TT [46] and that this was due to clonal dominance [47] and required CD4+ T cells for its induction [48]. However, it is possible that inclusion of other universal human CD4+ T cell epitopes such as N19 [53, 54] or PADRE [55, 56] might prove more successful.

EBV gp350 binds to human (and rabbit), but not mouse, CD21 [57]. Physiologically, CD21 expressed on B cells and follicular dendritic cells (FDC) binds the complement fragment C3d that in association with antigen, promotes immunogenicity [26, 58, 59]. This likely occurs via co-crosslinking of BCR and CD21, leading to highly synergistic B cell signaling [60], and trapping of antigen via CD21 on FDC to promote germinal center formation [61]. A previous study further demonstrated that gp350 could potentially substitute for C3d as an adjuvant, by promoting human B cell signaling via BCR/CD21 co-crosslinking [62]. Enhancement of antigen-specific antibody responses via C3d, involves at least 2 copies of C3d per molecule of antigen. Thus, in humans, gp350-specific B cells binding to tetrameric but not monomeric, gp350 via a single BCR would potentially have access to 2-3 gp350 molecules for CD21 binding, that could facilitate specific BCR/CD21 co-crosslinking and synergistic B cell signaling. In light of this data demonstrating a marked increase in the efficiency of binding of tetramer versus monomer to human CD21, we predict that tetrameric gp350 will also bind to specific BCR, as well CD21-expressing human FDC with greater avidity than monomeric gp350. Collectively, these observations strongly suggest that gp350, expressed as a tetramer, will act as both a molecular adjuvant as well as a specific target antigen for a clinical EBV vaccine. Importantly, tetrameric gp350 by itself did not polyclonally activate human B cells, thus obviating concerns for unwanted non-specific immune stimulation in vivo.

The molecular strategy described herein for creating tetrameric gp350 could also be applied to boost humoral immune responses to other proteins of vaccine interest, including other EBV proteins, such as gH/gL, gp42, and gB. Further, gp350 might be of value as a molecular adjuvant for another target protein, through creation of a heterodimer linked to a leucine zipper for dimerization, or a trimerization motif such as the T4 bacteriophage fibritin (FT) [63] or the eukaryotic GCN4 transcription factor motif (GCN4) [64]. Finally, heterodimers comprising a target protein and an additional protein possessing adjuvant activity, such as flagellin [65], or for example to an scFv fragment that targets an antigen-presenting cell or innate receptor [66], may generate additional, highly immunogenic multimeric proteins for vaccination.

REFERENCES

The following references are cited in the application and provide general information on the field of the invention and provide assays and other details discussed in the application. The following references are incorporated herein by reference in their entirety.

[1] Cohen J I. The biology of Epstein-Barr virus: lessons learned from the virus and the host. Current opinion in immunology 1999 August; 11(4):365-70.

[2] Thorley-Lawson D A. EBV the prototypical human tumor virus—just how bad is it? J Allergy Clin Immunol 2005 August; 116(2):251-61; quiz 62.

[3] Vetsika E K, Callan M. Infectious mononucleosis and Epstein-Barr virus. Expert Rev Mol Med 2004 Nov. 5; 6(23):1-16.

[4] Babcock G J, Decker L L, Volk M, Thorley-Lawson D A. EBV persistence in memory B cells in vivo. Immunity 1998 September; 9(3):395-404.

[5] Tanner J, Weis J, Fearon D, Whang Y, Kieff E. Epstein-Barr virus gp350/220 binding to the B lymphocyte C3d receptor mediates adsorption, capping, and endocytosis. Cell 1987 Jul. 17; 50(2):203-13.

[6] Tanner J, Whang Y, Sample J, Sears A, Kieff E. Soluble gp350/220 and deletion mutant glycoproteins block Epstein-Barr virus adsorption to lymphocytes. Journal of virology 1988; 62(12):4452-64.

[7] Thorley-Lawson D A, Poodry C A. Identification and isolation of the main component (gp350-gp220) of Epstein-Barr virus responsible for generating neutralizing antibodies in vivo. Journal of virology 1982 August; 43(2):730-6.

[8] Morgan A J, Epstein M A, North J R. Comparative immunogenicity studies on Epstein-Barr virus membrane antigen (MA) gp340 with novel adjuvants in mice, rabbits, and cottontop tamarins. J Med Virol 1984; 13(3): 281-92.

[9] Morgan A J, Allison A C, Finerty S, Scullion F T, Byars N E, Epstein M A. Validation of a first-generation Epstein-Barr virus vaccine preparation suitable for human use. J Med Virol 1989 September; 29(1):74-8.

[10] Finerty S, Tarlton J, Mackett M, Conway M, Arrand J R, Watkins P E, et al. Protective immunization against Epstein-Barr virus-induced disease in cottontop tamarins using the virus envelope glycoprotein gp340 produced from a bovine papillomavirus expression vector. J Gen Virol 1992 February; 73 (Pt 2):449-53.

[11] Finerty S, Mackett M, Arrand J R, Watkins P E, Tarlton 3, Morgan A J. Immunization of cottontop tamarins and rabbits with a candidate vaccine against the Epstein-Barr virus based on the major viral envelope glycoprotein gp340 and alum. Vaccine 1994 October; 12(13): 1180-4.

[12] Cox C, Naylor B A, Mackett M, Arrand J R, Griffin B E, Wedderburn N. Immunization of common marmosets with Epstein-Barr virus (EBV) envelope glycoprotein gp340: effect on viral shedding following EBV challenge. J Med Virol 1998 August; 55(4):255-61.

[13] Mackett M, Cox C, Pepper S D, Lees J F, Naylor B A, Wedderburn N, et al. Immunisation of common marmosets with vaccinia virus expressing Epstein-Barr virus (EBV) gp340 and challenge with EBV. J Med Virol 1996 November; 50(3):263-71.

[14] Ragot T, Finerty S, Watkins P E, Perricaudet M, Morgan A J. Replication-defective recombinant adenovirus expressing the Epstein-Barr virus (EBV) envelope glycoprotein gp340/220 induces protective immunity against EBV-induced lymphomas in the cottontop tamarin. J Gen Virol 1993 March; 74 (Pt 3):501-7.

[15] Morgan A J, Mackett M, Finerty S, Arrand J R, Scullion F T, Epstein M A. Recombinant vaccinia virus expressing Epstein-Barr virus glycoprotein gp340 protects cottontop tamarins against EB virus-induced malignant lymphomas. J Med Virol 1988 June; 25(2):189-95.

[16] Go S Y, Huang T M, Ruan L, Miao Y H, Lu H, Chu C M, et al. First EBV vaccine trial in humans using recombinant vaccinia virus expressing the major membrane antigen. Dcv Biol Stand 1995; 84:171-7.

[17] Sokal E M, Hoppenbrouwers K, Vandermeulen C, Moutscbhen M, Leonard P, Moreels A, et al. Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults. The Journal of infectious diseases 2007 Dec. 15; 196(12): 1749-53.

[18] Moutschen M, Leonard P, Sokal E M, Smets F, Haumont M, Mazzu P, et al. Phase/II studies to evaluate safety and immunogenicity of a recombinant gp350 Epstein-Barr virus vaccine in healthy adults. Vaccine 2007 Jun. 11; 25(24):4697-705.

[19] Rees L, Tizard E J, Morgan A J, Cubitt W D, Finerty S, Oyewole-Eletu T A, et al. A phase I trial of epstein-barr virus gp350 vaccine for children with chronic kidney disease awaiting transplantation. Transplantation 2009 Oct. 27; 88(8):1025-9.

[20] Liu W, Chen Y H. High epitope density in a single protein molecule significantly enhances antigenicity as well as immunogenicity: a novel strategy for modern vaccine development and a preliminary investigation about B cell discrimination of monomeric proteins. European journal of immunology 2005 February; 35(2):505-14.

[21] Ilyinskii P O, Thoidis G, Sherman M Y, Shneider A. Adjuvant potential of aggregate-forming polyglutamine domains. Vaccine 2008 Jun. 19; 26(26):3223-6.

[22] van Beers M M, Jiskoot W, Schellekens H. On the role of aggregates in the immunogenicity of recombinant human interferon beta in patients with multiple sclerosis. J Interferon Cytokine Res 2010 October; 30(10):767-75.

[23] Jegerlehner A, Stomi T, Lipowsky G, Schmid M, Pumpens P, Bachmann M F. Regulation of igG antibody responses by epitope density and CD21-mediated costimulation. European journal of immunology 2002 November; 32(11):3305-14.

[24] Rosenberg A S. Effects of protein aggregates: an immunologic perspective. AAPS J 2006; 8(3):E501-7.

[25] Lees A, Finkelman F, Inman J K, Witherspoon K, Johnson P, Kennedy J, et al. Enhanced immunogenicity of protein-dextran conjugates: I. Rapid stimulation of enhanced antibody responses to poorly immunogenic molecules. Vaccine 1994 October; 12(13): 1160-6.

[26] Dempsey P W, Allison M E, Akkaraju S, Goodnow C C, Fearon D T. C3d of complement as a molecular adjuvant: bridging innate and acquired immunity. Science 1996 Jan. 19; 271(5247):348-50.

[27] Czerwinski M, Siegel D L, Moore J S, Spitalnik P F, Spitalnik S L. Construction of bacteriophage expressing mouse monoclonal Fab fragments directed against the human MN glycophorin blood group antigens. Transfusion 1995 February; 35(2): 137-44.

[28] O'Shea E K, Rutkowski R, Kim P S. Evidence that the leucine zipper is a coiled coil. Science 1989 Jan. 27; 243(4890):538-42.

[29] Sarrias M R, Franchini S, Canziani G, Argyropoulos E, Moore W T, Sahu A, et al. Kinetic analysis of the interactions of complement receptor 2 (CR2, CD21) with its ligands C3d, iC3b, and the EBV glycoprotein gp350/220. J Immunol 2001 August; 167(3):1490-9.

[30] Valmori D, Pessi A, Bianchi E, Corradin G. Use of human universally antigenic tetanus toxin T cell epitopes as carriers for human vaccination. J Immunol 1992 Jul. 15; 149(2):717-21.

[31] Hoffman G J, Lazarowitz S G, Hayward S D. Monoclonal antibody against a 250,000-dalton glycoprotein of Epstein-Barr virus identifies a membrane antigen and a neutralizing antigen. Proceedings of the National Academy of Sciences of the United States of America 1980 May; 77(S):2979-83.

[32] Khan A Q, Lees A, Snapper C M. Differential regulation of IgG anti-capsular polysaccharide and antiprotein responses to intact *Streptococcus pneumoniae* in the presence of cognate CD4+ T cell help. J Immunol 2004 Jan. 1; 172(1):532-9.

[33] Sen G, Flora M, Chattopadhyay G, Klinman D M, Lees A, Mond J J, et al. The critical DNA flanking sequences of a CpG oligodeoxynucleotide, but not the 6 base CpG motif, can be replaced with RNA without quantitative or qualitative changes in Toll-like receptor 9-mediated activity. Cell Immunol 2004 November-December; 232(1-2): 64-74.

[34] Pertmer T M, Eisenbraun M D, McCabe D, Prayaga S K, Fuller D H, Haynes J R. Gene gun-based nucleic acid immunization: elicitation of humoral and cytotoxic T lymphocyte responses following epidermal delivery of nanogram quantities of DNA. Vaccine 1995; 13(15): 1427-30.

[35] Carel J C, Frazier B, Ley T J, Holers V M. Analysis of epitope expression and the functional repertoire of recombinant complement receptor 2 (CR2/CD21) in mouse and human cells. J Immunol 1989 Aug. 1; 143(3):923-30.

[36] Nemerow G R, Houghten R A, Moore M D, Cooper N R. Identification of an epitope in the major envelope protein of Epstein-Barr virus that mediates viral binding to the B lymphocyte EBV receptor (CR2). Cell 1989 Feb. 10; 56(3):369-77.

[37] Nemerow G R, Cooper N R. Early events in the infection of human B lymphocytes by Epstein-Barr virus: the internalization process. Virology 1984 Jan. 15; 132 (1):186-98.

[38] Zaborsky N, Brunner M, Wallner M, Himly M, Karl T, Schwarzenbacher R, et al. Antigen aggregation decides the fate of the allergic immune response. J Immunol 2010 Jan. 15; 184(2):725-35.

[39] Fradkin A H, Carpenter J F, Randolph T W. Immunogenicity of aggregates of recombinant human growth hormone in mouse models. J Pharm Sci 2009 September; 98(9):3247-64.

[40] Hemmi H, Takeuchi O, Kawai T, Kaisho T, Sato S, Sanjo H, et al. A Toll-like receptor recognizes bacterial DNA. Nature 2000; 408(6813):740-5.

[41] Ferraro B, Morrow M P, Hutnick N A, Shin T H, Lucke C E, Weiner D B. Clinical applications of DNA vaccines: current progress. Clinical infectious diseases: an official publication of the Infectious Diseases Society of America 2011 Aug. 1; 53(3):296-302.

[42] Yager E J, Dean H J, Fuller D H. Prospects for developing an effective particle-mediated DNA vaccine against influenza. Expert review of vaccines 2009 September; 8(9):1205-20.

[43] Roy M J, Wu M S, Barr L J, Fuller J T, Tussey L G, Speller S, et al. Induction of antigen-specific CD8+ T cells, T helper cells, and protective levels of antibody in humans by particle-mediated administration of a hepatitis B virus DNA vaccine. Vaccine 2000 Nov. 22; 19(7-8): 764-78.

[44] Luqman M, Bottomly K. Activation requirements for CD4+ T cells differing in CD45R expression. J Immunol 1992 Oct. 1; 149(7):2300-6.

[45] Ronchese F, Hausmann B. B lymphocytes in vivo fail to prime naïve T cells but can stimulate antigen-experienced T lymphocytes. The Journal of experimental medicine 1993 Mar. 1; 177(3):679-90.

[46] Schutze M P, Leclerc C, Jolivet M, Audibert F, Chedid L. Carrier-induced epitopic suppression, a major issue for future synthetic vaccines. J Immunol 1985 October; 135 (4):2319-22.

[47] Schutze M P, Deriaud E, Przewlocki G, LeClere C. Carrier-induced opitopic suppression is initiated through clonal dominance. J Immunol 1989 Apr. 15; 142(8):2635-40.

[48] Leclerc C, Schutze M P, Deriaud E, Przewlocki G. The in vivo elimination of CD4+ T cells prevents the induction but not the expression of carrier-induced epitopic suppression. J Immunol 1990 Sen 1:145(5: 1343-9.

[49] D'Addario M, Libermann T A, Xu J, Ahmad A, Menezes J. Epstein-Barr Virus and its glycoprotein-350 upregulate IL-6 in human B-lymphocytes via CD21, involving activation of NF-kappaB and different signaling pathways. Journal of molecular biology 2001; 308(3): 501-14.

[50] Bohnsack J F, Cooper N R. CR2 ligands modulate human B cell activation. J Immunol 1988 Oct. 15; 141 (8):2569-76.

[51] Shirodkar S, Hutchinson R L, Perry D L, White J L, Hem S L. Aluminum compounds used as adjuvants in vaccines. Pharmaceutical research 1990 December; 7(12):1282-8.

[52] Bachmann M F, Jennings G T. Vaccine delivery: a matter of size, geometry, kinetics and molecular patterns. Nature reviews Immunology 2010 November; 10(11): 787-96.

[53] Baraldo K, Mori E, Bartoloni A, Norelli F, Grandi G, Rappuoli R, et al. Combined conjugate vaccines: enhanced immunogenicity with the N19 polyepitope as a carrier protein. Infection and immunity 2005 September; 73(9):5835-41.

[54] Falugi F, Petracca R, Mariani M, Luzzi E, Mancianti S, Carinci V, et al. Rationally designed strings of promiscuous CD4(+) T cell epitopes provide help to *Haemophilus influenzae* type b oligosaccharide: a model for new conjugate vaccines. European journal of immunology 2001 December; 31(12):3816-24.

[55] del Guercio M F, Alexander J., Kubo R T, Arrhenius T, Maewal A, Appella E, et al. Potent immunogenic short linear peptide constructs composed of B cell epitopes and Pan D R T helper epitopes (PADRE) for antibody responses in vivo. Vaccine 1997 March; 15(4):441-8.

[56] Alexander J, del Guercio M F, Maewal A, Qiao L, Fikes J, Chesnut R W, et al. Linear PADRE T helper epitope and carbohydrate B cell epitope conjugates induce specific high titer IgG antibody responses. J Immunol 2000 Feb. 1; 164(3):1625-33.

[57] Martin D R, Yuryev A, Kalli K R, Fearon D T, Ahearn J M. Determination of the structural basis for selective binding of Epstein-Barr virus to human complement receptor type 2. The Journal of experimental medicine 1991 Dec. 1; 174(6):1299-311.

[58] Test S T, Mitsuyoshi J, Connolly C C, Lucas A H. Increased immunogenicity and induction of class switching by conjugation of complement C3d to pneumococcal serotype 14 capsular polysaccharide. Infection and immunity 2001 May; 69(5):3031-40.

[59] Ross T M, Xu Y, Bright R A, Robinson H L. C3d enhancement of antibodies to bemagglutinin accelerates protection against influenza virus challenge. Nature immunology 2000 August; 1(2):127-31.
[60] Fearon D T, Carter R H. The CDI9/CR2/TAPA-1 complex of B lymphocytes: linking natural to acquired immunity. Annual review of immunology 1995; 13:127-49.
[61] Allen C D, Cyster J G. Follicular dendritic cell networks of primary follicles and germinal centers: phenotype and function. Semin Immunol 2008 February; 20(1):14-25.
[62] Goeckeritz B E, Lees A, Vos Q. Tsokos G C, Kuhlbusch K, Mond J J. Enhanced and sustained activation of human B cells by anti-immunoglobulin conjugated to the EBV glycoprotein gp350. European journal of immunology 2000; 30(3):969-73.
[63] Bower J F, Yang X, Sodroski J, Ross T M. Elicitation of neutralizing antibodies with DNA vaccines expressing soluble stabilized human immunodeficiency virus type 1 envelope glycoprotein trimers conjugated to C3d. Journal of virology 2004 May; 78(9):4710-9.
[64] Zhang P F, Cham F, Dong M, Choudhary A, Bouma P, Zhang 7, et al. Extensively cross-reactive anti-HIV-1 neutralizing antibodies induced by gp140 immunization. Proceedings of the National Academy of Sciences of the United States of America 2007 Jun. 12; 104(24): 10193-8.
[65] McSorley S J, Ehst B D, Yu Y, Gewirtz A T. Bacterial flagellin is an effective adjuvant for CD4(+) T cells in vivo. J Immunol 2002 Oct. 1; 169(7):3914-9.
[66] Tunheim G, Thompson K M, Fredriksen A B, Espevik T, Schjetne K W, Bogen B. Human receptors of innate immunity (CDI4, TLR2) are promising targets for novel recombinant immunoglobulin-based vaccine candidates. Vaccine 2007 Jun. 11; 25(24):4723-34.
[67] Okuno K, et al., Epstein-Barr virus can infect rabbits by the intranasal or peroral route: an animal model for natural primary EBV infection in humans. J. Med. Virol. 2010 82: 977.

What is claimed:

1. A fusion protein comprising a first antigen, a linker sequence, a second antigen, and an oligomerization domain, wherein a first end of the linker sequence is joined to the first antigen and a second end of the linker sequence is joined to the second antigen, such that the linker sequence joins the first antigen to the second antigen and wherein the fusion protein does not include a tetanus toxoid protein, wherein the first and second antigens are viral antigens, wherein the linker sequence is a polypeptide having 5 to 25 amino acids, wherein the linker sequence comprises glycine and serine, and wherein the linker sequence allows the first and second antigens to undergo conformational folding and form a dimer or higher order multimer, and
    wherein the first and second antigens are HIV antigens or wherein the first and second antigens are herpesvirus antigens.
2. The fusion protein of claim 1, wherein the first and second antigens are the same.
3. The fusion protein of claim 1, wherein the first and second antigens are HIV antigens and wherein the first HIV antigen is gp120 and the second HIV antigen is gp41.
4. The fusion protein of claim 1, wherein the first and second antigens are herpesvirus antigens selected from gH, gL, and gB.
5. The fusion protein of claim 4, wherein the first and second antigens are herpes simplex virus antigens.
6. The fusion protein of claim 1, wherein the fusion protein forms a multimeric protein complex when expressed in a host cell.
7. The fusion protein of claim 1, wherein the first and second antigens do not occur naturally as a multimeric protein complex.
8. The fusion protein of claim 1, wherein the oligomerization domain is a dimerization domain, a trimerization domain, or a tetramerization domain.
9. The fusion protein of claim 8, wherein the dimerization domain is a GCN4 yeast leucine zipper domain or a derivative thereof.
10. The fusion protein of claim 8, wherein the trimerization domain is a T4 bacteriophage fibritin motif or a eukaryotic GNC4 transcription factor motif or a derivative thereof.
11. The fusion protein of claim 1, wherein the oligomerization domain is located at the C terminus or N terminus of the fusion protein.
12. The fusion protein of claim 1, wherein the linker sequence is a polypeptide comprising between 10-25 amino acids.
13. An isolated nucleic acid encoding the fusion protein of claim 1.
14. A method of inducing or suppressing an immune response in a subject, comprising administering to the subject a vaccine composition comprising the fusion protein claim 1, wherein the fusion protein induces or suppresses an immune response against the first antigen or the second antigen in the fusion protein in the subject.
15. The fusion protein of claim 1, wherein the linker sequence is 15 amino acids in length and has the amino acid sequence of SEQ ID NO:3.

* * * * *